United States Patent
Ikeda et al.

(10) Patent No.: US 12,280,118 B2
(45) Date of Patent: Apr. 22, 2025

(54) IL-2 VARIANT

(71) Applicant: Kyowa Kirin Co., Ltd., Tokyo (JP)

(72) Inventors: Masahiro Ikeda, Tokyo (JP); Shinpei Yamaguchi, Tokyo (JP); Masumi Murakami, Tokyo (JP); Hideyuki Onodera, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 1191 days.

(21) Appl. No.: 16/958,045

(22) PCT Filed: Dec. 27, 2018

(86) PCT No.: PCT/JP2018/048361
§ 371 (c)(1),
(2) Date: Jun. 25, 2020

(87) PCT Pub. No.: WO2019/131964
PCT Pub. Date: Jul. 4, 2019

(65) Prior Publication Data
US 2021/0060169 A1    Mar. 4, 2021

(30) Foreign Application Priority Data
Dec. 27, 2017    (JP) .................. 2017-252224

(51) Int. Cl.
*A61K 47/60* (2017.01)
*A61K 38/20* (2006.01)
*A61K 47/54* (2017.01)

(52) U.S. Cl.
CPC .......... *A61K 47/60* (2017.08); *A61K 38/2013* (2013.01); *A61K 47/545* (2017.08)

(58) Field of Classification Search
CPC ...................................... A61K 47/60
See application file for complete search history.

(56) References Cited

U.S. PATENT DOCUMENTS

| | | |
|---|---|---|
| 4,766,106 A | 8/1988 | Katre et al. |
| 4,902,502 A | 2/1990 | Nitecki et al. |

(Continued)

FOREIGN PATENT DOCUMENTS

| | | | | |
|---|---|---|---|---|
| AU | 2009244039 | | 11/2009 | |
| CA | 2296770 | * | 1/2000 | ........... C07K 14/475 |

(Continued)

OTHER PUBLICATIONS

Veronese, The Impact of PEGylation on Biological Therapies, Blodrugs, 2008, 22 (5), 315-329) (Year: 2008).*

(Continued)

*Primary Examiner* — Paul W Dickinson
(74) *Attorney, Agent, or Firm* — Wenderoth, Lind & Ponack, L.L.P.

(57) ABSTRACT

An object of the present invention is to provide a novel IL-2 variant which has improved selectivity for IL-2R$_{\alpha\beta\gamma}$ and selectively activates Tregs. The present invention relates to an IL-2 variant, a method for producing the IL-2 variant, a composition and a therapeutic agent for an immune disease, comprising the IL-2 variant, a method for increasing selectivity of IL-2 for IL-2R$\alpha\beta\gamma$, a method for improving an affinity of IL-2 for an IL-2R$\alpha$ subunit, a method of reducing an affinity of IL-2 for at least one of an IL-2R$\beta$ subunit and an IL-2R$\gamma$ subunit, and a method for selectively activating regulatory T cells.

Figure 1A:
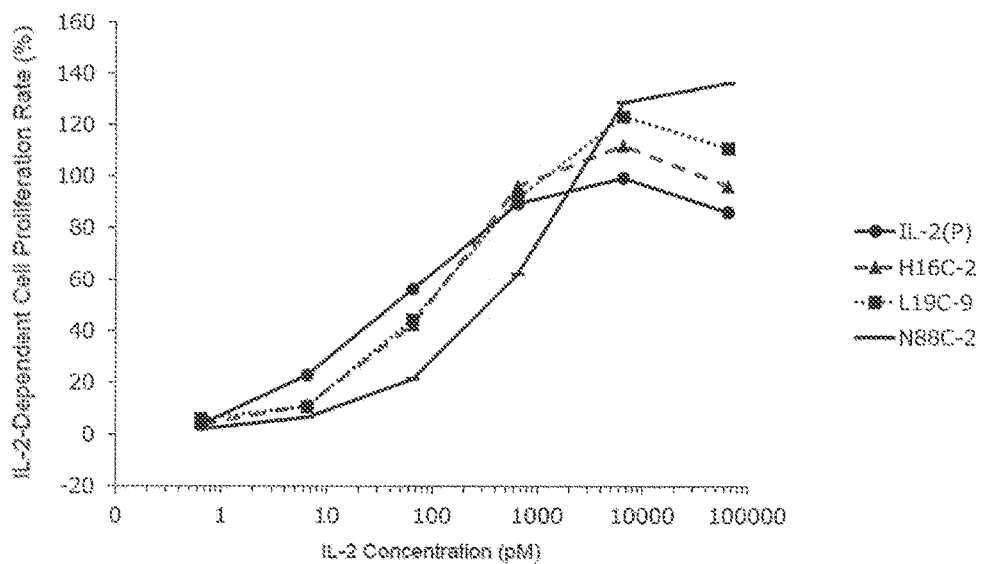

13 Claims, 10 Drawing Sheets
Specification includes a Sequence Listing.

(56) References Cited

U.S. PATENT DOCUMENTS

| | | | |
|---|---|---|---|
| 5,153,310 | A | 10/1992 | Mitchell et al. |
| 5,206,344 | A | 4/1993 | Katre et al. |
| 5,312,903 | A | 5/1994 | Linna et al. |
| 5,417,970 | A | 5/1995 | Roskam et al. |
| 7,186,804 | B2 | 3/2007 | Gillies et al. |
| 10,035,836 | B1 | 7/2018 | Greve |
| 2005/0142106 | A1 | 6/2005 | Wittrup et al. |
| 2011/0150826 | A1 | 6/2011 | Paulsen et al. |
| 2011/0274650 | A1 | 11/2011 | Gavin et al. |
| 2014/0286898 | A1 | 9/2014 | Gavin et al. |
| 2014/0328791 | A1 | 11/2014 | Bossard et al. |
| 2015/0374788 | A1 | 12/2015 | Paulsen et al. |
| 2017/0051029 | A1 | 2/2017 | Greve |
| 2018/0085468 | A1 | 3/2018 | Bossard et al. |
| 2019/0008978 | A1 | 1/2019 | Huang et al. |

FOREIGN PATENT DOCUMENTS

| | | |
|---|---|---|
| EP | 0 461 159 | 12/1991 |
| JP | 62-503171 | 12/1987 |
| JP | 4-503604 | 7/1992 |
| JP | 2011-519882 | 7/2011 |
| JP | 2012-515778 | 7/2012 |
| JP | 2014-506116 | 3/2014 |
| JP | 2016-518823 | 6/2016 |
| JP | 2016-202187 | 12/2016 |
| JP | 2017-528444 | 9/2017 |
| WO | 87/00056 | 1/1987 |
| WO | 90/10070 | 9/1990 |
| WO | 2005/007121 | 1/2005 |
| WO | 2010/085495 | 7/2010 |
| WO | 2012/065086 | 5/2012 |
| WO | 2014/028748 | 2/2014 |
| WO | 2014/153111 | 9/2014 |
| WO | 2015/109212 | 7/2015 |
| WO | 2016/025385 | 2/2016 |

OTHER PUBLICATIONS

Katre, Nandini V. et al., "Chemical modification of recombinant interleukin 2 by polyethylene glycol increases its potency in the murine Meth A sarcoma model", Proceedings of the National Academy of Sciences, 1987, vol. 84, No. 6, pp. 1487-1491, XP055272577.

Zhang, Bo et al., "Site-specific PEGylation of interleukin-2 enhances immunosuppression via the sustained activation of regulatory T cells", Nature Biomedical Engineering, 2021, pp. 1-26, XP055854571, https://doi.org/10.1038/s41551-021-00797-8.

Caridade et al., "Mechanisms underlying CD4CTreg immune regulation in the adult: from experiments to models", Frontiers in Immunology, 2013, vol. 4, Article 378, pp. 1-9.

Ramsdell et al., "FOXP3 and scurfy: how it all began", Nature Reviews Immunology, 2014, vol. 14, pp. 343-349.

Grant et al., "Regulatory T-cells in autoimmune diseases: Challenges, controversies and—yet—unanswered questions", Autoimmunity Reviews, 2015, vol. 14, pp. 105-116.

Malek, T. R. "The Biology of Interleukin-2", Annu. Rev. Immunol., 2008, vol. 26, pp. 453-479.

Liao et al., "Interleukin-2 at the Crossroads of Effector Responses, Tolerance, and Immunotherapy", Immunity, 2013, vol. 38, pp. 13-25.

Yu et al., "Selective IL-2 Responsiveness of Regulatory T Cells Through Multiple Intrinsic Mechanisms Supports the Use of Low-Dose IL-2 Therapy in Type 1 Diabetes", Diabetes, 2015, vol. 64, pp. 2172-2783.

Meyer et al., "Interaction of STAT5 Dimers on Two Low Affinity Binding Sites Mediates Interleukin 2 (IL-2) Stimulation of IL-2 Receptor a Gene Transcription*" The Journal of Biological Chemistry, 1997, vol. 272, No. 50, pp. 31821-31828.

Boyman et al., "The role of interleukin-2 during homeostasis and activation of the immune system", Nature Reviews Immunology, 2012, vol. 12, pp. 180-190.

Klatzmann et al., "The promise of low-dose interleukin-2 therapy for autoimmune and inflammatory diseases", Nature Reviews Immunology, 2015, vol. 15, pp. 283-294.

Sharfe et al., "Human immune disorder arising from mutation of the a chain of the interleukin-2 receptor", Proc. Natl. Acad. Sci. USA, 1997, vol. 94, pp. 3168-3171.

Tsokos, G. C., "Systemic Lupus Erythematosus", The New England Journal of Medicine, 2011, vol. 365, No. 22, pp. 2110-2121.

Rosenzwajg et al., "Interleukin 2 in the Pathogenesis and Therapy of Type 1 Diabetes", Curr Diab Rep, 2014, vol. 14, No. 553, pp. 1-7.

Mizui et al., "IL-2 Protects Lupus-Prone Mice from Multiple End-Organ Damage by Limiting CD4-CD8- IL-17-Producing T Cells", The Journal of Immunology, 2014, vol. 193, pp. 2168-2177.

Koreth et al., "Interleukin-2 and Regulatory T Cells in Graft-versus-Host Disease", The New England Journal of Medicine, 2011, vol. 365, No. 22, pp. 2055-2066.

Humrich et al., "Rapid induction of clinical remission by low-dose interleukin-2 in a patient with refractory SLE", Ann Rheum Dis, 2015, vol. 74, No. 4, pp. 791-792.

Van Gool et al., "Interleukin-5-producing group 2 innate lymphoid cells control eosinophilia induced by interleukin-2 therapy", Blood, 2014, vol. 124, No. 24, pp. 3572-3576.

Cassell et al., "Therapeutic Enhancement of IL-2 Through Molecular Design", Current Pharmaceutical Design, 2002, vol. 8, pp. 2171-2183.

Bell et al., "Sustained in vivo signaling by long-lived IL-2 induces prolonged increases of regulatory T cells", Journal of Autoimmunity, 2015, vol. 56, pp. 66-80.

Langowski et al., "NKTR-358: a selective, first-in-class IL-2 pathway agonist, which increases number and suppressive function of regulatory T cells for the treatment of immune inflammatory disorders", ACR/ARHP Annual Meeting Abstract, No. 2715, http://www.nektar.com/application/files/6315/1001/4171/NKTR-358_2017ACR_ABS2715.pdf.

Goodson et al., "Site-Directed Pegylation of Recombinant Interleukin-2 at its Glycosylation Site", Biotechnology, 1990, vol. 8, pp. 343-346.

International Search Report issued Feb. 5, 2019 in International (PCT) Application No. PCT/JP2018/048361, with English translation.

Written Opinion of the International Searching Authority issued Feb. 5, 2019 in International (PCT) Application No. PCT/JP2018/048361, with English translation.

International Preliminary Report on Patentability issued Jun. 30, 2020 in International (PCT) Application No. PCT/JP2018/048361.

Extended European Search Report issued Nov. 18, 2021 in corresponding European Patent Application No. 18897857.1.

Wu, Kefei et al., "Short-term intratracheal use of PEG-modified IL-2 and glucocorticoid persistently alleviates asthma in a mouse model", Scientific Reports, 2016, vol. 6, No. 1, pp. 1-12, XP055640972.

Charych, Deborah H. et al., "NKTR-214, an Engineered Cytokine with Biased IL2 Receptor Binding, Increased Tumor Exposure, and Marked Efficacy in Mouse Tumor Models", Clinical Cancer Research, 2016, vol. 22, No. 3, pp. 680-690, XP055432446.

Katre, Nandini V. et al., "Chemical modification of recombinant interleukin 2 by polyethylene glycol increases its potency in the urine Meth A sarcoma model", Proceedings of the National Academy of Sciences, 1987, vol. 84, No. 6, pp. 1487-1491, XP055272577.

Zhang, Bo ct al., "Site-specific PEGylation of interleukin-2 enhances immunosuppression via the sustained activation of regulatory T cells", Nature Biomedical Engineering, 2021, pp. 1-26, XP055854571, https://doi.org/10.1038/s41551-021-00797-8.

* cited by examiner

SEQUENCE LISTING

<160> NUMBER OF SEQ ID NOS: 52

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 142
<212> TYPE: PRT
<213> ORGANISM: Artificial Sequence
<220> FEATURE:
<223> OTHER INFORMATION: Description of the artificial sequence: amino
      acid sequence of 8His-IL-2

<400> SEQUENCE: 2

Met His His His His His His His His Ala Pro Thr Ser Ser Ser Thr
1               5                   10                  15

Lys Lys Thr Gln Leu Gln Leu Glu His Leu Leu Leu Asp Leu Gln Met
            20                  25                  30

Ile Leu Asn Gly Ile Asn Asn Tyr Lys Asn Pro Lys Leu Thr Arg Met
        35                  40                  45

```
Leu Thr Phe Lys Phe Tyr Met Pro Lys Lys Ala Thr Glu Leu Lys His
 50                  55                  60

Leu Gln Cys Leu Glu Glu Glu Leu Lys Pro Leu Glu Glu Val Leu Asn
 65                  70                  75                  80

Leu Ala Gln Ser Lys Asn Phe His Leu Arg Pro Arg Asp Leu Ile Ser
                 85                  90                  95

Asn Ile Asn Val Ile Val Leu Glu Leu Lys Gly Ser Glu Thr Thr Phe
            100                 105                 110

Met Cys Glu Tyr Ala Asp Glu Thr Ala Thr Ile Val Glu Phe Leu Asn
            115                 120                 125

Arg Trp Ile Thr Phe Ser Gln Ser Ile Ile Ser Thr Leu Thr
130                 135                 140

<210> SEQ ID NO 3
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-IL-2

<400> SEQUENCE: 3
atgcatcatc atcaccatca tcatcacgcc ccgaccagca gcagcaccaa aaagacccag      60
ctgcagctgg aacatctgct gctggatctg cagatgatcc tgaatggcat taacaactat     120
aaaaacccga agctgacccg catgctgacc tttaaatttt atatgccgaa aaaagccacc     180
gagctgaagc atctgcagtg cctggaagaa gaactgaaac cgctggaaga ggtgctgaac     240
ctggcccaga gcaaaaactt tcacctgcgc ccgcgtgacc tgatcagcaa catcaacgtg     300
atcgtgctgg aactgaaggg tagcgagacc accttcatgt gcgaatatgc cgacgagacc     360
gccaccatcg tggaattcct gaaccgctgg atcacctttt cccagagcat catcagtacc     420
ctgacc                                                                426

<210> SEQ ID NO 4
<211> LENGTH: 426
<212> TYPE: DNA
<213> ORGANISM: Artificial Sequence
<220> FEATURE:
<223> OTHER INFORMATION: Description of the artificial sequence: base
      sequence of S4 (o-Az-Z-Lys)

<400> SEQUENCE: 4
atgcatcatc atcaccatca tcatcacgcc ccgacctaga gcagcaccaa aaagacccag      60
ctgcagctgg aacatctgct gctggatctg cagatgatcc tgaatggcat taacaactat     120
aaaaacccga agctgacccg catgctgacc tttaaatttt atatgccgaa aaaagccacc     180
gagctgaagc atctgcagtg cctggaagaa gaactgaaac cgctggaaga ggtgctgaac     240
ctggcccaga gcaaaaactt tcacctgcgc ccgcgtgacc tgatcagcaa catcaacgtg     300
atcgtgctgg aactgaaggg tagcgagacc accttcatgt gcgaatatgc cgacgagacc     360
gccaccatcg tggaattcct gaaccgctgg atcacctttt cccagagcat catcagtacc     420
ctgacc                                                                426

<210> SEQ ID NO 5
<211> LENGTH: 426
<212> TYPE: DNA
<213> ORGANISM: Artificial Sequence
<220> FEATURE:
<223> OTHER INFORMATION: Description of the artificial sequence: base
``` sequence of S5 (o-Az-Z-Lys)

<400> SEQUENCE: 5

```
atgcatcatc atcaccatca tcatcacgcc ccgaccagct agagcaccaa aaagacccag      60
ctgcagctgg aacatctgct gctggatctg cagatgatcc tgaatggcat taacaactat    120
aaaaacccga agctgacccg catgctgacc tttaaattt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcaccttt cccagagcat catcagtacc    420
ctgacc                                                               426
```

<210> SEQ ID NO 6
<211> LENGTH: 426
<212> TYPE: DNA
<213> ORGANISM: Artificial Sequence
<220> FEATURE:
<223> OTHER INFORMATION: Description of the artificial sequence: base sequence of S6 (o-Az-Z-Lys)

<400> SEQUENCE: 6

```
atgcatcatc atcaccatca tcatcacgcc ccgaccagca gctagaccaa aaagacccag      60
ctgcagctgg aacatctgct gctggatctg cagatgatcc tgaatggcat taacaactat    120
aaaaacccga agctgacccg catgctgacc tttaaattt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcaccttt cccagagcat catcagtacc    420
ctgacc                                                               426
```

<210> SEQ ID NO 7
<211> LENGTH: 426
<212> TYPE: DNA
<213> ORGANISM: Artificial Sequence
<220> FEATURE:
<223> OTHER INFORMATION: Description of the artificial sequence: base sequence of T7 (o-Az-Z-Lys)

<400> SEQUENCE: 7

```
atgcatcatc atcaccatca tcatcacgcc ccgaccagca gcagctagaa aaagacccag      60
ctgcagctgg aacatctgct gctggatctg cagatgatcc tgaatggcat taacaactat    120
aaaaacccga agctgacccg catgctgacc tttaaattt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcaccttt cccagagcat catcagtacc    420
ctgacc                                                               426
```

<210> SEQ ID NO 8
<211> LENGTH: 426
<212> TYPE: DNA
<213> ORGANISM: Artificial Sequence
<220> FEATURE:
<223> OTHER INFORMATION: Description of the artificial sequence: base
      sequence of K8 (o-Az-Z-Lys)

<400> SEQUENCE: 8

```
atgcatcatc atcaccatca tcatcacgcc ccgaccagca gcagcaccta gaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaactt tcacctgcgc ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 9
<211> LENGTH: 426
<212> TYPE: DNA
<213> ORGANISM: Artificial Sequence
<220> FEATURE:
<223> OTHER INFORMATION: Description of the artificial sequence: base
      sequence of E60 (o-Az-Z-Lys)

<400> SEQUENCE: 9

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctgtaggaa gaactgaaac cgctggaaga ggtgctgaac   240
ctggcccaga gcaaaaactt tcacctgcgc ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 10
<211> LENGTH: 426
<212> TYPE: DNA
<213> ORGANISM: Artificial Sequence
<220> FEATURE:
<223> OTHER INFORMATION: Description of the artificial sequence: base
      sequence of F78 (o-Az-Z-Lys)

<400> SEQUENCE: 10

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaacta gcacctgcgc ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 11
<211> LENGTH: 426

<212> TYPE: DNA
<213> ORGANISM: Artificial Sequence
<220> FEATURE:
<223> OTHER INFORMATION: Description of the artificial sequence: base
      sequence of H79 (o-Az-Z-Lys)

<400> SEQUENCE: 11

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaactt ttagctgcgc ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 12
<211> LENGTH: 426
<212> TYPE: DNA
<213> ORGANISM: Artificial Sequence
<220> FEATURE:
<223> OTHER INFORMATION: Description of the artificial sequence: base
      sequence of R81 (o-Az-Z-Lys)

<400> SEQUENCE: 12

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaactt tcacctgtag ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 13
<211> LENGTH: 426
<212> TYPE: DNA
<213> ORGANISM: Artificial Sequence
<220> FEATURE:
<223> OTHER INFORMATION: Description of the artificial sequence: base
      sequence of L94 (o-Az-Z-Lys)

<400> SEQUENCE: 13

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaactt tcacctgcgc ccgcgtgacc tgatcagcaa catcaacgtg   300
atcgtgtagg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 14
<211> LENGTH: 426
<212> TYPE: DNA
<213> ORGANISM: Artificial Sequence
<220> FEATURE:
<223> OTHER INFORMATION: Description of the artificial sequence: base sequence of S99 (o-Az-Z-Lys)

<400> SEQUENCE: 14

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaaa cgctggaaga ggtgctgaac   240
ctggcccaga gcaaaaactt tcacctgcgc ccgcgtgacc tgatcagcaa catcaacgtg   300
atcgtgctgg aactgaaggg ttaggagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 15
<211> LENGTH: 426
<212> TYPE: DNA
<213> ORGANISM: Artificial Sequence
<220> FEATURE:
<223> OTHER INFORMATION: Description of the artificial sequence: base sequence of E100 (o-Az-Z-Lys)

<400> SEQUENCE: 15

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaaa cgctggaaga ggtgctgaac   240
ctggcccaga gcaaaaactt tcacctgcgc ccgcgtgacc tgatcagcaa catcaacgtg   300
atcgtgctgg aactgaaggg tagctagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 16
<211> LENGTH: 426
<212> TYPE: DNA
<213> ORGANISM: Artificial Sequence
<220> FEATURE:
<223> OTHER INFORMATION: Description of the artificial sequence: base sequence of T101 (o-Az-Z-Lys)

<400> SEQUENCE: 16

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaaa cgctggaaga ggtgctgaac   240
ctggcccaga gcaaaaactt tcacctgcgc ccgcgtgacc tgatcagcaa catcaacgtg   300
atcgtgctgg aactgaaggg tagcgagtag accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 17
<211> LENGTH: 426
<212> TYPE: DNA
<213> ORGANISM: Artificial Sequence
<220> FEATURE:
<223> OTHER INFORMATION: Description of the artificial sequence: base
      sequence of Q126 (o-Az-Z-Lys)

<400> SEQUENCE: 17

```
atgcatcatc atcaccatca tcatcacgcc ccgaccagca gcagcaccaa aaagacccag        60
ctgcagctgg aacatctgct gctggatctg cagatgatcc tgaatggcat taacaactat       120
aaaaacccga agctgacccg catgctgacc tttaaatttt atatgccgaa aaaagccacc       180
gagctgaagc atctgcagtg cctggaagaa gaactgaaac cgctggaaga ggtgctgaac       240
ctggcccaga gcaaaaactt tcacctgcgc ccgcgtgacc tgatcagcaa catcaacgtg       300
atcgtgctgg aactgaaggg tagcgagacc accttcatgt gcgaatatgc cgacgagacc       360
gccaccatcg tggaattcct gaaccgctgg atcacctttt cctagagcat catcagtacc       420
ctgacc                                                                  426
```

<210> SEQ ID NO 18
<211> LENGTH: 426
<212> TYPE: DNA
<213> ORGANISM: Artificial Sequence
<220> FEATURE:
<223> OTHER INFORMATION: Description of the artificial sequence: base
      sequence of I129 (o-Az-Z-Lys)

<400> SEQUENCE: 18

```
atgcatcatc atcaccatca tcatcacgcc ccgaccagca gcagcaccaa aaagacccag        60
ctgcagctgg aacatctgct gctggatctg cagatgatcc tgaatggcat taacaactat       120
aaaaacccga agctgacccg catgctgacc tttaaatttt atatgccgaa aaaagccacc       180
gagctgaagc atctgcagtg cctggaagaa gaactgaaac cgctggaaga ggtgctgaac       240
ctggcccaga gcaaaaactt tcacctgcgc ccgcgtgacc tgatcagcaa catcaacgtg       300
atcgtgctgg aactgaaggg tagcgagacc accttcatgt gcgaatatgc cgacgagacc       360
gccaccatcg tggaattcct gaaccgctgg atcacctttt cccagagcat ctagagtacc       420
ctgacc                                                                  426
```

<210> SEQ ID NO 19
<211> LENGTH: 1502
<212> TYPE: PRT
<213> ORGANISM: Artificial Sequence
<220> FEATURE:
<223> OTHER INFORMATION: Description of the artificial sequence: amino
      acid sequence of human IL-2abg-Azami green fusion

<400> SEQUENCE: 19

```
Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
```

```
                65                  70                  75                  80
        Gln Cys Thr Ser Ser Ala Thr Arg Asn Thr Thr Lys Gln Val Thr Pro
                        85                  90                  95
        Gln Pro Glu Glu Gln Lys Glu Arg Lys Thr Thr Glu Met Gln Ser Pro
                        100                 105                 110
        Met Gln Pro Val Asp Gln Ala Ser Leu Pro Gly His Cys Arg Glu Pro
                        115                 120                 125
        Pro Pro Trp Glu Asn Glu Ala Thr Glu Arg Ile Tyr His Phe Val Val
                        130                 135                 140
        Gly Gln Met Val Tyr Tyr Gln Cys Val Gln Gly Tyr Arg Ala Leu His
        145                 150                 155                 160
        Arg Gly Pro Ala Glu Ser Val Cys Lys Met Thr His Gly Lys Thr Arg
                        165                 170                 175
        Trp Thr Gln Pro Gln Leu Ile Cys Thr Gly Glu Met Glu Thr Ser Gln
                        180                 185                 190
        Phe Pro Gly Glu Glu Lys Pro Gln Ala Ser Pro Glu Gly Arg Pro Glu
                        195                 200                 205
        Ser Glu Thr Ser Cys Leu Val Thr Thr Thr Asp Phe Gln Ile Gln Thr
                        210                 215                 220
        Glu Met Ala Ala Thr Met Glu Thr Ser Ile Phe Thr Thr Glu Tyr Gln
        225                 230                 235                 240
        Val Ala Val Ala Gly Cys Val Phe Leu Leu Ile Ser Val Leu Leu Leu
                        245                 250                 255
        Ser Gly Leu Thr Trp Gln Arg Arg Gln Arg Lys Ser Arg Arg Thr Ile
                        260                 265                 270
        Arg Ala Lys Arg Ala Pro Val Lys Gln Thr Leu Asn Phe Asp Leu Leu
                        275                 280                 285
        Lys Leu Ala Gly Asp Val Glu Ser Asn Pro Gly Pro Met Ala Ala Pro
                        290                 295                 300
        Ala Leu Ser Trp Arg Leu Pro Leu Leu Ile Leu Leu Leu Pro Leu Ala
        305                 310                 315                 320
        Thr Ser Trp Ala Ser Ala Ala Val Asn Gly Thr Ser Gln Phe Thr Cys
                        325                 330                 335
        Phe Tyr Asn Ser Arg Ala Asn Ile Ser Cys Val Trp Ser Gln Asp Gly
                        340                 345                 350
        Ala Leu Gln Asp Thr Ser Cys Gln Val His Ala Trp Pro Asp Arg Arg
                        355                 360                 365
        Arg Trp Asn Gln Thr Cys Glu Leu Leu Pro Val Ser Gln Ala Ser Trp
                        370                 375                 380
        Ala Cys Asn Leu Ile Leu Gly Ala Pro Asp Ser Gln Lys Leu Thr Thr
        385                 390                 395                 400
        Val Asp Ile Val Thr Leu Arg Val Leu Cys Arg Glu Gly Val Arg Trp
                        405                 410                 415
        Arg Val Met Ala Ile Gln Asp Phe Lys Pro Phe Glu Asn Leu Arg Leu
                        420                 425                 430
        Met Ala Pro Ile Ser Leu Gln Val Val His Val Glu Thr His Arg Cys
                        435                 440                 445
        Asn Ile Ser Trp Glu Ile Ser Gln Ala Ser His Tyr Phe Glu Arg His
                        450                 455                 460
        Leu Glu Phe Glu Ala Arg Thr Leu Ser Pro Gly His Thr Trp Glu Glu
        465                 470                 475                 480
        Ala Pro Leu Leu Thr Leu Lys Gln Lys Gln Glu Trp Ile Cys Leu Glu
                        485                 490                 495
```

```
Thr Leu Thr Pro Asp Thr Gln Tyr Glu Phe Gln Val Arg Val Lys Pro
            500                 505                 510

Leu Gln Gly Glu Phe Thr Thr Trp Ser Pro Trp Ser Gln Pro Leu Ala
        515                 520                 525

Phe Arg Thr Lys Pro Ala Ala Leu Gly Lys Asp Thr Ile Pro Trp Leu
    530                 535                 540

Gly His Leu Leu Val Gly Leu Ser Gly Ala Phe Gly Phe Ile Ile Leu
545                 550                 555                 560

Val Tyr Leu Leu Ile Asn Cys Arg Asn Thr Gly Pro Trp Leu Lys Lys
                565                 570                 575

Val Leu Lys Cys Asn Thr Pro Asp Pro Ser Lys Phe Phe Ser Gln Leu
            580                 585                 590

Ser Ser Glu His Gly Gly Asp Val Gln Lys Trp Leu Ser Ser Pro Phe
        595                 600                 605

Pro Ser Ser Ser Phe Ser Pro Gly Gly Leu Ala Pro Glu Ile Ser Pro
    610                 615                 620

Leu Glu Val Leu Glu Arg Asp Lys Val Thr Gln Leu Leu Leu Gln Gln
625                 630                 635                 640

Asp Lys Val Pro Glu Pro Ala Ser Leu Ser Ser Asn His Ser Leu Thr
                645                 650                 655

Ser Cys Phe Thr Asn Gln Gly Tyr Phe Phe Phe His Leu Pro Asp Ala
            660                 665                 670

Leu Glu Ile Glu Ala Cys Gln Val Tyr Phe Thr Tyr Asp Pro Tyr Ser
        675                 680                 685

Glu Glu Asp Pro Asp Glu Gly Val Ala Gly Ala Pro Thr Gly Ser Ser
    690                 695                 700

Pro Gln Pro Leu Gln Pro Leu Ser Gly Glu Asp Asp Ala Tyr Cys Thr
705                 710                 715                 720

Phe Pro Ser Arg Asp Asp Leu Leu Phe Ser Pro Ser Leu Leu Gly
                725                 730                 735

Gly Pro Ser Pro Pro Ser Thr Ala Pro Gly Gly Ser Gly Ala Gly Glu
            740                 745                 750

Glu Arg Met Pro Pro Ser Leu Gln Glu Arg Val Pro Arg Asp Trp Asp
        755                 760                 765

Pro Gln Pro Leu Gly Pro Pro Thr Pro Gly Val Pro Asp Leu Val Asp
    770                 775                 780

Phe Gln Pro Pro Pro Glu Leu Val Leu Arg Glu Ala Gly Glu Glu Val
785                 790                 795                 800

Pro Asp Ala Gly Pro Arg Glu Gly Val Ser Phe Pro Trp Ser Arg Pro
                805                 810                 815

Pro Gly Gln Gly Glu Phe Arg Ala Leu Asn Ala Arg Leu Pro Leu Asn
            820                 825                 830

Thr Asp Ala Tyr Leu Ser Leu Gln Glu Leu Gln Gly Gln Asp Pro Thr
        835                 840                 845

His Leu Val Arg Ala Lys Arg Ala Pro Val Lys Gln Thr Leu Asn Phe
    850                 855                 860

Asp Leu Leu Lys Leu Ala Gly Asp Val Glu Ser Asn Pro Gly Pro Met
865                 870                 875                 880

Leu Lys Pro Ser Leu Pro Phe Thr Ser Leu Leu Phe Leu Gln Leu Pro
                885                 890                 895

Leu Leu Gly Val Gly Leu Asn Thr Thr Ile Leu Thr Pro Asn Gly Asn
            900                 905                 910
```

```
Glu Asp Thr Thr Ala Asp Phe Phe Leu Thr Thr Met Pro Thr Asp Ser
            915                 920                 925

Leu Ser Val Ser Thr Leu Pro Leu Pro Glu Val Gln Cys Phe Val Phe
    930                 935                 940

Asn Val Glu Tyr Met Asn Cys Thr Trp Asn Ser Ser Ser Glu Pro Gln
945                 950                 955                 960

Pro Thr Asn Leu Thr Leu His Tyr Trp Tyr Lys Asn Ser Asp Asn Asp
                965                 970                 975

Lys Val Gln Lys Cys Ser His Tyr Leu Phe Ser Glu Glu Ile Thr Ser
            980                 985                 990

Gly Cys Gln Leu Gln Lys Lys Glu Ile His Leu Tyr Gln Thr Phe Val
        995                 1000                1005

Val Gln Leu Gln Asp Pro Arg Glu Pro Arg Arg Gln Ala Thr Gln
    1010                1015                1020

Met Leu Lys Leu Gln Asn Leu Val Ile Pro Trp Ala Pro Glu Asn
    1025                1030                1035

Leu Thr Leu His Lys Leu Ser Glu Ser Gln Leu Glu Leu Asn Trp
    1040                1045                1050

Asn Asn Arg Phe Leu Asn His Cys Leu Glu His Leu Val Gln Tyr
    1055                1060                1065

Arg Thr Asp Trp Asp His Ser Trp Thr Glu Gln Ser Val Asp Tyr
    1070                1075                1080

Arg His Lys Phe Ser Leu Pro Ser Val Asp Gly Gln Lys Arg Tyr
    1085                1090                1095

Thr Phe Arg Val Arg Ser Arg Phe Asn Pro Leu Cys Gly Ser Ala
    1100                1105                1110

Gln His Trp Ser Glu Trp Ser His Pro Ile His Trp Gly Ser Asn
    1115                1120                1125

Thr Ser Lys Glu Asn Pro Phe Leu Phe Ala Leu Glu Ala Val Val
    1130                1135                1140

Ile Ser Val Gly Ser Met Gly Leu Ile Ile Ser Leu Leu Cys Val
    1145                1150                1155

Tyr Phe Trp Leu Glu Arg Thr Met Pro Arg Ile Pro Thr Leu Lys
    1160                1165                1170

Asn Leu Glu Asp Leu Val Thr Glu Tyr His Gly Asn Phe Ser Ala
    1175                1180                1185

Trp Ser Gly Val Ser Lys Gly Leu Ala Glu Ser Leu Gln Pro Asp
    1190                1195                1200

Tyr Ser Glu Arg Leu Cys Leu Val Ser Glu Ile Pro Pro Lys Gly
    1205                1210                1215

Gly Ala Leu Gly Glu Gly Pro Gly Ala Ser Pro Cys Asn Gln His
    1220                1225                1230

Ser Pro Tyr Trp Ala Pro Pro Cys Tyr Thr Leu Lys Pro Glu Thr
    1235                1240                1245

Arg Ala Lys Arg Ala Pro Val Lys Gln Thr Leu Asn Phe Asp Leu
    1250                1255                1260

Leu Lys Leu Ala Gly Asp Val Glu Ser Asn Pro Gly Pro Met Val
    1265                1270                1275

Ser Val Ile Lys Pro Glu Met Lys Ile Lys Leu Cys Met Arg Gly
    1280                1285                1290

Thr Val Asn Gly His Asn Phe Val Ile Glu Gly Glu Gly Lys Gly
    1295                1300                1305

Asn Pro Tyr Glu Gly Thr Gln Ile Leu Asp Leu Asn Val Thr Glu
```

| | | | | | | | | | | |
|---|---|---|---|---|---|---|---|---|---|---|
| | | 1310 | | | 1315 | | | 1320 | | |
| Gly | Ala | Pro | Leu | Pro | Phe | Ala | Tyr | Asp | Ile | Leu | Thr | Thr | Val | Phe |
| | 1325 | | | | 1330 | | | | 1335 | |
| Gln | Tyr | Gly | Asn | Arg | Ala | Phe | Thr | Lys | Tyr | Pro | Ala | Asp | Ile | Gln |
| | 1340 | | | | 1345 | | | | 1350 | |
| Asp | Tyr | Phe | Lys | Gln | Thr | Phe | Pro | Glu | Gly | Tyr | His | Trp | Glu | Arg |
| | 1355 | | | | 1360 | | | | 1365 | |
| Ser | Met | Thr | Tyr | Glu | Asp | Gln | Gly | Ile | Cys | Thr | Ala | Thr | Ser | Asn |
| | 1370 | | | | 1375 | | | | 1380 | |
| Ile | Ser | Met | Arg | Gly | Asp | Cys | Phe | Phe | Tyr | Asp | Ile | Arg | Phe | Asp |
| | 1385 | | | | 1390 | | | | 1395 | |
| Gly | Thr | Asn | Phe | Pro | Pro | Asn | Gly | Pro | Val | Met | Gln | Lys | Lys | Thr |
| | 1400 | | | | 1405 | | | | 1410 | |
| Leu | Lys | Trp | Glu | Pro | Ser | Thr | Glu | Lys | Met | Tyr | Val | Glu | Asp | Gly |
| | 1415 | | | | 1420 | | | | 1425 | |
| Val | Leu | Lys | Gly | Asp | Val | Asn | Met | Arg | Leu | Leu | Leu | Glu | Gly | Gly |
| | 1430 | | | | 1435 | | | | 1440 | |
| Gly | His | Tyr | Arg | Cys | Asp | Phe | Lys | Thr | Thr | Tyr | Lys | Ala | Lys | Lys |
| | 1445 | | | | 1450 | | | | 1455 | |
| Glu | Val | Arg | Leu | Pro | Asp | Ala | His | Lys | Ile | Asp | His | Arg | Ile | Glu |
| | 1460 | | | | 1465 | | | | 1470 | |
| Ile | Leu | Lys | His | Asp | Lys | Asp | Tyr | Asn | Lys | Val | Lys | Leu | Tyr | Glu |
| | 1475 | | | | 1480 | | | | 1485 | |
| Asn | Ala | Val | Ala | Arg | Tyr | Ser | Met | Leu | Pro | Ser | Gln | Ala | Lys |
| | 1490 | | | | 1495 | | | | 1500 | |

<210> SEQ ID NO 20
<211> LENGTH: 4506
<212> TYPE: DNA
<213> ORGANISM: Artificial Sequence
<220> FEATURE:
<223> OTHER INFORMATION: Description of the artificial sequence: base
      sequence of human IL-2Rabg-Azami green fusion

<400> SEQUENCE: 20

| | |
|---|---|
| atggattcat acctgcttat gtggggtctc ctcacctcca ttatggtccc cggatgtcaa | 60 |
| gccgagctct gtgacgatga tccacctgaa atccccatg caacttttaa ggccatggcc | 120 |
| tataaggaag gtaccatgct gaactgtgaa tgcaagcgtg gcttccgcag gattaagagc | 180 |
| ggctccctgt acatgctgtg caccgggaac tcttcccatt caagttggga caaccagtgt | 240 |
| cagtgtacct cctccgcaac aagaaatacc accaaacagg tgactcccca gccagaggag | 300 |
| cagaaggagc ggaagacaac agaaatgcaa agtccaatgc agcccgtgga tcaggccagc | 360 |
| ctcccaggcc actgtcggga accacccccct tgggaaaacg aggccacaga acggatatac | 420 |
| cacttcgttg tcggtcaaat ggtgtattat cagtgtgtgc agggctacag ggccctgcat | 480 |
| cgaggccccg cagaatcagt ctgcaaaatg actcacggca agactcgctg acccagcct | 540 |
| cagctgatat gtaccggaga gatggaaact ctccaattcc ccggggagga gaaaccccag | 600 |
| gcatctcctg aagggaggcc tgagtccgaa acctcttgtc tggttaccac aaccgacttc | 660 |
| cagatccaga ccgagatggc cgcaaccatg gaaacaagta ttttcactac agagtatcag | 720 |
| gtggccgtag caggctgtgt cttcctgttg atttccgtgc tgctgttgtc tgggctgacc | 780 |
| tggcaaagaa gacagagaaa gtctaggcgc actatccgag caaagcgggc tccagtgaag | 840 |
| cagacattga attttgatct gttgaaactt gccggcgacg ttgagtctaa ccctggcct | 900 |

```
atggctgcac cagccctgtc ctggcgtttg cctctcctta tattgctgct tcctcttgct    960
acctcttggg cttccgctgc agtgaatggg acctcccaat ttacatgctt ctacaacagt   1020
agagccaaca tttcatgtgt gtggagccag gatggcgctc tgcaagatac atcttgccag   1080
gtccacgcct ggccagatag acggcggtgg aatcagacct gtgagcttct gcccgtgtcc   1140
caggcaagtt gggcttgcaa ccttatactg ggcgctcccg atagtcagaa gctgaccact   1200
gtggacatcg tgaccctgcg ggtgctttgt agggagggcg tccggtggag agtcatggct   1260
atacaggatt ttaaaccctt cgagaacctt cgcctcatgg cccccatctc tctgcaagtc   1320
gtgcatgtag agacacatag gtgtaacatc tcttgggaaa tctctcaggc ttcacactac   1380
tttgagaggc acctggagtt tgaggcccgt actctgagcc caggacatac ttgggaggag   1440
gcaccectgc tcaccctcaa gcagaagcag gagtggatat gtctggagac tttgactccc   1500
gacactcagt atgagttcca ggtgagagtg aaaccectgc aggggagtt tacaacctgg   1560
tcaccatgga gtcagcccct tgcctttcga actaaacctg ccgccctcgg caaggacaca   1620
atccectggc tcggtcacct gcttgtcggc cttteeggeg cttttggttt tatcatcctg   1680
gtctaccttc tcatcaactg ccgcaatact gggccttggc tgaagaaagt ccttaagtgt   1740
aacaccccag atccaagtaa gttcttctct cagctgtcca gtgagcacgg tggcgatgtc   1800
cagaagtggt tgagcagtcc cttccectcc tccagtttca gccccggggg cctggctcca   1860
gagattagtc cccttgaggt gctggagcga gacaaggtaa ctcagctgtt gctgcagcaa   1920
gataaggtgc cagagcctgc atctctcagc agtaatcatt ccctgaccag ctgttttact   1980
aaccagggat acttctttt ccacctgcca gatgctctgg agattgaggc atgtcaagtc   2040
tattttacat acgaccccta cagtgaggaa gacccagatg agggggtcgc aggagctccc   2100
acaggttcat ccccacagcc actccagcct tgtcaggcg aggatgacgc atactgcaca   2160
tttccaagcc gcgatgatct ccttctgttc tcaccaagcc tgctgggggg acctagtcct   2220
cctagcaccg ctccaggagg gtctggcgca ggagaggaac gaatgcctcc aagtcttcag   2280
gagcgggtcc cccgggattg ggaccctcag cccctgggcc ccccacccc tggagtccct   2340
gacctcgtgg acttccaacc cccacccgag ttggtgctta gagaagccgg agaggaggtg   2400
cctgacgccg gccctagaga gggagtcagt tttccatgga gtcggccacc aggacagggc   2460
gaatttcgag ctctcaacgc tcgtctgcct ttgaacaccg atgcctattt gtctctccag   2520
gaactgcagg ggcaagatcc tacccacctc gtcagagcca aaagagctcc tgtgaagcag   2580
actctgaact ttgatttgct caaactggct ggcgacgtgg aatctaatcc aggcccaatg   2640
ctgaaaccca gtctgccatt caccctcttg ctcttcctgc agctccctct gttgggtgtc   2700
gggctgaaca caactattct gactccaaat gggaacgagg acaccaccgc cgatttcttc   2760
cttactacca tgcccaccga ctccctcagc gtgagtactt tgcccctccc agaagtgcag   2820
tgcttcgtct tcaacgtcga gtacatgaac tgtacttgga acagctcttc agagcctcag   2880
cctaccaacc tcacattgca ctattggtac aagaacagcg ataacgataa agtgcagaag   2940
tgctcccact atctgtttag tgaagagatc accagtgggt gccagctgca gaagaaggaa   3000
attcacctct atcagacttt tgtggtgcag ttgcaagatc cccgggagcc taggaggcag   3060
gccacccaaa tgcttaagct gcaaaatctc gttattcctt gggctcccga gaatctcaca   3120
ttgcacaagc tctccgagtc acagctcgaa ctgaattgga ataataggtt cctgaaccac   3180
tgcctcgagc acctggtgca gtaccggaca gactgggacc acagttggac tgagcaatct   3240
gtggactata gacataaatt ctccctgcct agcgtcgacg ggcagaaacg ttacacctt   3300
```

```
agggtgcggt ctcgttttaa tccactgtgt gggtctgccc agcactggtc agagtggtca    3360
caccctattc attggggtag taatacatct aaggagaatc cattcctctt cgccctcgag    3420
gctgtggtga tcagcgtggg aagtatgggc ctcatcattt ctctcctgtg cgtgtacttt    3480
tggctggaac ggactatgcc tcgtatccct acactcaaaa atctcgagga tctggtgact    3540
gagtatcacg gcaacttttc agcctggtca ggagtgtcaa agggattggc cgaatctctc    3600
cagcccgact atagtgagag ctttgtctg gtttccgaaa tccccccaaa aggcggagca    3660
ttgggtgagg gccccggagc ttcaccctgt aaccaacact ccccttactg ggcaccccct    3720
tgttacactc tgaagccaga aactagagca aagagggctc cagtgaaaca gactttgaat    3780
ttcgacctgc tgaagctggc aggtgacgta gagtcaaacc ccggcccat ggtgtctgtc     3840 attaagcctg aaatgaaaat taagctctgc atgaggggta ctgtgaacgg ccacaatttt    3900
gtgatcgagg gcgaaggaaa aggaaatccc tacgaaggga ctcagattct tgacctgaac    3960
gttactgaag gggctcctct cccctttgct tacgacatcc tgaccaccgt gtttcagtat    4020
ggtaaccgag cttttacaaa gtatcctgct gatatacagg actattttaa gcaaacattc    4080
ccagagggct accactggga gcggtctatg acctatgaag accaaggtat ttgcaccgct    4140
accagcaaca tctcaatgcg aggcgactgt ttctttacg atatcagatt cgatggaaca    4200
aacttccccc ccaacggacc cgttatgcaa aagaaaacac tgaaatggga acccagcaca    4260
gagaagatgt atgttgagga cggggttctg aaggggacg tgaatatgcg gctcttgctg    4320
gaaggcggag gccactatag atgtgatttc aagacaactt acaaggctaa gaaggaagtg    4380
aggttgcctg acgcccataa gatcgatcat cgaatcgaga ttttgaagca tgacaaggat    4440
tataataagg tgaaactgta cgagaacgcc gtggcccggt actccatgct ccccagtcaa    4500
gctaaa                                                              4506
```

<210> SEQ ID NO 21
<211> LENGTH: 1202
<212> TYPE: PRT
<213> ORGANISM: Artificial Sequence
<220> FEATURE:
<223> OTHER INFORMATION: Description of the artificial sequence: amino
      acid sequence of human IL-2bg-Azami green fusion

<400> SEQUENCE: 21

```
Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
                20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
        50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
                100                 105                 110

Gly Val Arg Trp Arg Val Met Ala Ile Gln Asp Phe Lys Pro Phe Glu
            115                 120                 125

Asn Leu Arg Leu Met Ala Pro Ile Ser Leu Gln Val Val His Val Glu
```

```
            130              135              140
Thr His Arg Cys Asn Ile Ser Trp Glu Ile Ser Gln Ala Ser His Tyr
145                  150                  155                  160

Phe Glu Arg His Leu Glu Phe Glu Ala Arg Thr Leu Ser Pro Gly His
                 165                  170                  175

Thr Trp Glu Glu Ala Pro Leu Leu Thr Leu Lys Gln Lys Gln Glu Trp
             180                  185                  190

Ile Cys Leu Glu Thr Leu Thr Pro Asp Thr Gln Tyr Glu Phe Gln Val
         195                  200                  205

Arg Val Lys Pro Leu Gln Gly Glu Phe Thr Thr Trp Ser Pro Trp Ser
210                  215                  220

Gln Pro Leu Ala Phe Arg Thr Lys Pro Ala Ala Leu Gly Lys Asp Thr
225                  230                  235                  240

Ile Pro Trp Leu Gly His Leu Leu Val Gly Leu Ser Gly Ala Phe Gly
                 245                  250                  255

Phe Ile Ile Leu Val Tyr Leu Leu Ile Asn Cys Arg Asn Thr Gly Pro
             260                  265                  270

Trp Leu Lys Lys Val Leu Lys Cys Asn Thr Pro Asp Pro Ser Lys Phe
         275                  280                  285

Phe Ser Gln Leu Ser Ser Glu His Gly Gly Asp Val Gln Lys Trp Leu
         290                  295                  300

Ser Ser Pro Phe Pro Ser Ser Ser Phe Ser Pro Gly Gly Leu Ala Pro
305                  310                  315                  320

Glu Ile Ser Pro Leu Glu Val Leu Glu Arg Asp Lys Val Thr Gln Leu
                 325                  330                  335

Leu Leu Gln Gln Asp Lys Val Pro Glu Pro Ala Ser Leu Ser Ser Asn
             340                  345                  350

His Ser Leu Thr Ser Cys Phe Thr Asn Gln Gly Tyr Phe Phe Phe His
         355                  360                  365

Leu Pro Asp Ala Leu Glu Ile Glu Ala Cys Gln Val Tyr Phe Thr Tyr
         370                  375                  380

Asp Pro Tyr Ser Glu Glu Asp Pro Asp Glu Gly Val Ala Gly Ala Pro
385                  390                  395                  400

Thr Gly Ser Ser Pro Gln Pro Leu Gln Pro Leu Ser Gly Glu Asp Asp
                 405                  410                  415

Ala Tyr Cys Thr Phe Pro Ser Arg Asp Asp Leu Leu Leu Phe Ser Pro
             420                  425                  430

Ser Leu Leu Gly Gly Pro Ser Pro Ser Thr Ala Pro Gly Gly Ser
         435                  440                  445

Gly Ala Gly Glu Glu Arg Met Pro Pro Ser Leu Gln Glu Arg Val Pro
450                  455                  460

Arg Asp Trp Asp Pro Gln Pro Leu Gly Pro Thr Pro Gly Val Pro
465                  470                  475                  480

Asp Leu Val Asp Phe Gln Pro Pro Glu Leu Val Leu Arg Glu Ala
                 485                  490                  495

Gly Glu Glu Val Pro Asp Ala Gly Pro Arg Glu Gly Val Ser Phe Pro
             500                  505                  510

Trp Ser Arg Pro Pro Gly Gln Gly Glu Phe Arg Ala Leu Asn Ala Arg
         515                  520                  525

Leu Pro Leu Asn Thr Asp Ala Tyr Leu Ser Leu Gln Glu Leu Gln Gly
         530                  535                  540

Gln Asp Pro Thr His Leu Val Arg Ala Lys Arg Ala Pro Val Lys Gln
545                  550                  555                  560
```

```
Thr Leu Asn Phe Asp Leu Leu Lys Leu Ala Gly Asp Val Glu Ser Asn
                565                 570                 575

Pro Gly Pro Met Leu Lys Pro Ser Leu Pro Phe Thr Ser Leu Leu Phe
            580                 585                 590

Leu Gln Leu Pro Leu Leu Gly Val Gly Leu Asn Thr Thr Ile Leu Thr
        595                 600                 605

Pro Asn Gly Asn Glu Asp Thr Thr Ala Asp Phe Phe Leu Thr Thr Met
    610                 615                 620

Pro Thr Asp Ser Leu Ser Val Ser Thr Leu Pro Leu Pro Glu Val Gln
625                 630                 635                 640

Cys Phe Val Phe Asn Val Glu Tyr Met Asn Cys Thr Trp Asn Ser Ser
                645                 650                 655

Ser Glu Pro Gln Pro Thr Asn Leu Thr Leu His Tyr Trp Tyr Lys Asn
            660                 665                 670

Ser Asp Asn Asp Lys Val Gln Lys Cys Ser His Tyr Leu Phe Ser Glu
        675                 680                 685

Glu Ile Thr Ser Gly Cys Gln Leu Gln Lys Lys Glu Ile His Leu Tyr
    690                 695                 700

Gln Thr Phe Val Val Gln Leu Gln Asp Pro Arg Glu Pro Arg Arg Gln
705                 710                 715                 720

Ala Thr Gln Met Leu Lys Leu Gln Asn Leu Val Ile Pro Trp Ala Pro
                725                 730                 735

Glu Asn Leu Thr Leu His Lys Leu Ser Glu Ser Gln Leu Glu Leu Asn
            740                 745                 750

Trp Asn Asn Arg Phe Leu Asn His Cys Leu Glu His Leu Val Gln Tyr
        755                 760                 765

Arg Thr Asp Trp Asp His Ser Trp Thr Glu Gln Ser Val Asp Tyr Arg
    770                 775                 780

His Lys Phe Ser Leu Pro Ser Val Asp Gly Gln Lys Arg Tyr Thr Phe
785                 790                 795                 800

Arg Val Arg Ser Arg Phe Asn Pro Leu Cys Gly Ser Ala Gln His Trp
                805                 810                 815

Ser Glu Trp Ser His Pro Ile His Trp Gly Ser Asn Thr Ser Lys Glu
            820                 825                 830

Asn Pro Phe Leu Phe Ala Leu Glu Ala Val Val Ile Ser Val Gly Ser
        835                 840                 845

Met Gly Leu Ile Ile Ser Leu Leu Cys Val Tyr Phe Trp Leu Glu Arg
    850                 855                 860

Thr Met Pro Arg Ile Pro Thr Leu Lys Asn Leu Glu Asp Leu Val Thr
865                 870                 875                 880

Glu Tyr His Gly Asn Phe Ser Ala Trp Ser Gly Val Ser Lys Gly Leu
                885                 890                 895

Ala Glu Ser Leu Gln Pro Asp Tyr Ser Glu Arg Leu Cys Leu Val Ser
            900                 905                 910

Glu Ile Pro Pro Lys Gly Gly Ala Leu Gly Glu Gly Pro Gly Ala Ser
        915                 920                 925

Pro Cys Asn Gln His Ser Pro Tyr Trp Ala Pro Pro Cys Tyr Thr Leu
    930                 935                 940

Lys Pro Glu Thr Arg Ala Lys Arg Ala Pro Val Lys Gln Thr Leu Asn
945                 950                 955                 960

Phe Asp Leu Leu Lys Leu Ala Gly Asp Val Glu Ser Asn Pro Gly Pro
                965                 970                 975
```

```
Met Val Ser Val Ile Lys Pro Glu Met Lys Ile Lys Leu Cys Met Arg
             980                 985                 990

Gly Thr Val Asn Gly His Asn Phe Val Ile Glu Gly Glu Gly Lys Gly
         995                1000                1005

Asn Pro Tyr Glu Gly Thr Gln Ile Leu Asp Leu Asn Val Thr Glu
    1010                1015                1020

Gly Ala Pro Leu Pro Phe Ala Tyr Asp Ile Leu Thr Thr Val Phe
    1025                1030                1035

Gln Tyr Gly Asn Arg Ala Phe Thr Lys Tyr Pro Ala Asp Ile Gln
    1040                1045                1050

Asp Tyr Phe Lys Gln Thr Phe Pro Glu Gly Tyr His Trp Glu Arg
    1055                1060                1065

Ser Met Thr Tyr Glu Asp Gln Gly Ile Cys Thr Ala Thr Ser Asn
    1070                1075                1080

Ile Ser Met Arg Gly Asp Cys Phe Phe Tyr Asp Ile Arg Phe Asp
    1085                1090                1095

Gly Thr Asn Phe Pro Pro Asn Gly Pro Val Met Gln Lys Lys Thr
    1100                1105                1110

Leu Lys Trp Glu Pro Ser Thr Glu Lys Met Tyr Val Glu Asp Gly
    1115                1120                1125

Val Leu Lys Gly Asp Val Asn Met Arg Leu Leu Leu Glu Gly Gly
    1130                1135                1140

Gly His Tyr Arg Cys Asp Phe Lys Thr Thr Tyr Lys Ala Lys Lys
    1145                1150                1155

Glu Val Arg Leu Pro Asp Ala His Lys Ile Asp His Arg Ile Glu
    1160                1165                1170

Ile Leu Lys His Asp Lys Asp Tyr Asn Lys Val Lys Leu Tyr Glu
    1175                1180                1185

Asn Ala Val Ala Arg Tyr Ser Met Leu Pro Ser Gln Ala Lys
    1190                1195                1200

<210> SEQ ID NO 22
<211> LENGTH: 3606
<212> TYPE: DNA
<213> ORGANISM: Artificial Sequence
<220> FEATURE:
<223> OTHER INFORMATION: Description of the artificial sequence: base
      sequence of human IL-2Rbg-Azami green fusion

<400> SEQUENCE: 22
atggctgcac cagccctgtc ctggcgtttg cctctcctta tattgctgct tcctcttgct     60
acctcttggg cttccgctgc agtgaatggg acctcccaat ttacatgctt ctacaacagt    120
agagccaaca tttcatgtgt gtggagccag gatggcgctc tgcaagatac atcttgccag    180
gtccacgcct ggccagatag acggcggtgg aatcagacct gtgagcttct gcccgtgtcc    240
caggcaagtt gggcttgcaa ccttatactg ggcgctcccg atagtcagaa gctgaccact    300
gtggacatcg tgaccctgcg ggtgcttgt agggagggcg tccggtggag agtcatggct    360
atacaggatt ttaaaccctt cgagaacctt cgcctcatgg ccccatctc tctgcaagtc    420 gtgcatgtag agacacatag tgtaacatc tcttgggaaa tctctcaggc ttcacactac    480
tttgagaggc acctggagtt tgaggcccgt actctgagcc aggacatac ttgggaggag    540 gcacccctgc tcaccctcaa gcagaagcag gagtggatat gtctggagac tttgactccc    600
gacactcagt atgagttcca ggtgagagtg aaacccctgc aggggagtt tacaacctgg    660 tcaccatgga gtcagcccct tgcctttcga actaaacctg ccgccctcgg caaggacaca    720
```

```
atcccctggc tcggtcacct gcttgtcggc ctttccggcg cttttggttt tatcatcctg    780
gtctaccttc tcatcaactg ccgcaatact gggccttggc tgaagaaagt ccttaagtgt    840
aacaccccag atccaagtaa gttcttctct cagctgtcca gtgagcacgg tggcgatgtc    900
cagaagtggt tgagcagtcc cttcccctcc tccagtttca gccccggggg cctggctcca    960
gagattagtc cccttgaggt gctggagcga gacaaggtaa ctcagctgtt gctgcagcaa   1020
gataaggtgc cagagcctgc atctctcagc agtaatcatt ccctgaccag ctgttttact   1080
aaccagggat acttcttttt ccacctgcca gatgctctgg agattgaggc atgtcaagtc   1140
tattttacat acgacccta cagtgaggaa gacccagatg agggggtcgc aggagctccc   1200
acaggttcat ccccacagcc actccagcct tgtcaggcg aggatgacgc atactgcaca    1260
tttccaagcc gcgatgatct ccttctgttc tcaccaagcc tgctggggg acctagtcct     1320 cctagcaccg ctccaggagg gtctggcgca ggagaggaac gaatgcctcc aagtcttcag   1380
gagcgggtcc cccgggattg ggaccctcag cccctgggcc cccccacccc tggagtccct   1440
gacctcgtgg acttccaacc cccacccgag ttggtgctta gagaagccgg agaggaggtg   1500
cctgacgccg gccctagaga gggagtcagt tttccatgga gtcggccacc aggacagggc   1560
gaatttcgag ctctcaacgc tcgtctgcct ttgaacaccg atgcctattt gtctctccag   1620
gaactgcagg ggcaagatcc tacccactc gtcagagcca aaagagctcc tgtgaagcag    1680
actctgaact ttgatttgct caaactggct ggcgacgtgg aatctaatcc aggcccaatg   1740
ctgaaaccca gtctgccatt caccctcttg ctcttcctgc agctccctct gttgggtgtc   1800
gggctgaaca caactattct gactccaaat gggaacgagg acaccaccgc cgatttcttc   1860
cttactacca tgcccaccga ctccctcagc gtgagtactt tgcccctccc agaagtgcag   1920
tgcttcgtct tcaacgtcga gtacatgaac tgtacttgga acagctcttc agagcctcag   1980
cctaccaacc tcacattgca ctattggtac aagaacagcg ataacgataa agtgcagaag   2040
tgctcccact atctgtttag tgaagagatc accagtgggt gccagctgca gaagaaggaa   2100
attcacctct atcagacttt tgtggtgcag ttgcaagatc cccggagcc taggaggcag   2160 gccacccaaa tgcttaagct gcaaaatctc gttattcctt gggctcccga gaatctcaca   2220
ttgcacaagc tctccgagtc acagctcgaa ctgaattgga ataataggtt cctgaaccac   2280
tgcctcgagc acctggtgca gtaccggaca gactgggacc acagttggac tgagcaatct   2340
gtggactata gacataaatt ctccctgcct agcgtcgacg ggcagaaacg ttacaccttt   2400
agggtgcggt ctcgttttaa tccactgtgt gggtctgccc agcactggtc agagtggtca   2460
caccctattc attggggtag taatacatct aaggagaatc cattcctctt cgccctcgag   2520
gctgtggtga tcagcgtggg aagtatgggc ctcatcattt ctctcctgtg cgtgtacttt   2580
tggctggaac ggactatgcc tcgtatccct acactcaaaa atctcgagga tctggtgact   2640
gagtatcacg gcaacttttc agcctggtca ggagtgtcaa agggattggc cgaatctctc   2700
cagcccgact atagtgagag gctttgtctg gtttccgaaa tccccccaaa aggcggagca   2760
ttgggtgagg ccccggagc ttcaccctgt aaccaacact ccccttactg ggcacccct     2820 tgttacactc tgaagccaga aactagagca aagagggctc cagtgaaaca gactttgaat   2880
ttcgacctgc tgaagctggc aggtgacgta gagtcaaacc ccggccccat ggtgtctgtc   2940
attaagcctg aaatgaaaat taagctctgc atgaggggta ctgtgaacgg ccacaatttt   3000
gtgatcgagg gcgaaggaaa aggaaatccc tacgaaggga ctcagattct tgacctgaac   3060
```

```
gttactgaag gggctcctct cccctttgct tacgacatcc tgaccaccgt gtttcagtat    3120
ggtaaccgag cttttacaaa gtatcctgct gatatacagg actattttaa gcaaacattc    3180
ccagagggct accactggga gcggtctatg acctatgaag accaaggtat ttgcaccgct    3240
accagcaaca tctcaatgcg aggcgactgt ttcttttacg atatcagatt cgatggaaca    3300
aacttccccc caacggacc cgttatgcaa agaaaacac tgaaatggga cccagcaca     3360 gagaagatgt atgttgagga cggggttctg aaggggacg tgaatatgcg gctcttgctg    3420
gaaggcggag gccactatag atgtgatttc aagacaactt acaaggctaa gaaggaagtg    3480
aggttgcctg acgcccataa gatcgatcat cgaatcgaga ttttgaagca tgacaaggat    3540
tataataagg tgaaactgta cgagaacgcc gtggcccggt actccatgct ccccagtcaa    3600
gctaaa                                                              3606
```

<210> SEQ ID NO 23
<211> LENGTH: 454
<212> TYPE: PRT
<213> ORGANISM: Artificial Sequence
<220> FEATURE:
<223> OTHER INFORMATION: Description of the artificial sequence: amino
      acid sequence of human CD25ECD-Fc-Avitag

<400> SEQUENCE: 23

```
Met Arg Val Leu Ile Leu Leu Trp Leu Phe Thr Ala Phe Pro Gly Ile
1               5                   10                  15

Leu Ser Glu Leu Cys Asp Asp Pro Pro Glu Ile Pro His Ala Thr
            20                  25                  30

Phe Lys Ala Met Ala Tyr Lys Glu Gly Thr Met Leu Asn Cys Glu Cys
        35                  40                  45

Lys Arg Gly Phe Arg Arg Ile Lys Ser Gly Ser Leu Tyr Met Leu Cys
    50                  55                  60

Thr Gly Asn Ser Ser His Ser Ser Trp Asp Asn Gln Cys Gln Cys Thr
65                  70                  75                  80

Ser Ser Ala Thr Arg Asn Thr Thr Lys Gln Val Thr Pro Gln Pro Glu
                85                  90                  95

Glu Gln Lys Glu Arg Lys Thr Thr Glu Met Gln Ser Pro Met Gln Pro
            100                 105                 110

Val Asp Gln Ala Ser Leu Pro Gly His Cys Arg Glu Pro Pro Pro Trp
        115                 120                 125

Glu Asn Glu Ala Thr Glu Arg Ile Tyr His Phe Val Val Gly Gln Met
    130                 135                 140

Val Tyr Tyr Gln Cys Val Gln Gly Tyr Arg Ala Leu His Arg Gly Pro
145                 150                 155                 160

Ala Glu Ser Val Cys Lys Met Thr His Gly Lys Thr Arg Trp Thr Gln
                165                 170                 175

Pro Gln Leu Ile Cys Thr Gly Glu Met Glu Thr Ser Gln Phe Pro Gly
            180                 185                 190

Glu Glu Lys Pro Gln Ala Ser Pro Glu Gly Arg Pro Glu Ser Glu Thr
        195                 200                 205

Ser Cys Leu Val Thr Thr Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255
```

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
            275                 280                 285

Gln Tyr Gly Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Leu Asn Asp Ile Phe Glu Ala Gln
            435                 440                 445

Lys Ile Glu Trp His Glu
    450

<210> SEQ ID NO 24
<211> LENGTH: 1362
<212> TYPE: DNA
<213> ORGANISM: Artificial Sequence
<220> FEATURE:
<223> OTHER INFORMATION: Description of the artificial sequence: base
      sequence of human CD25ECD-Fc-Avitag

<400> SEQUENCE: 24

```
atgagagtgc ttattttatt gtggctgttc acagcctttc ctggtattct tagtgagctc      60
tgtgacgatg acccgccaga gatcccacac gccacattca aagccatggc ctacaaggaa     120
ggaaccatgt tgaactgtga atgcaagaga ggtttccgca aataaaaag cgggtcactc     180 tatatgctct gtacaggaaa ctctagccac tcgtcctggg acaaccaatg tcaatgcaca     240
agctctgcca ctcggaacac aacgaaacaa gtgacacctc aacctgaaga acagaaagaa     300
aggaaaacca cagaaatgca aagtccaatg cagccagtgg accaagcgag ccttccaggt     360
cactgcaggg aacctccacc atgggaaaat gaagccacag agagaattta tcatttcgtg     420
gtggggcaga tggtttatta tcagtgcgtc cagggataca gggctctaca cagaggtcct     480
gctgagagcg tctgcaaaat gacccacggg aagacaaggt ggaccagcc ccagctcata     540 tgcacaggtg aaatggagac cagtcagttt ccaggtgaag agaagcctca ggcaagcccc     600
gaaggccgtc ctgagagtga gacttcctgc ctcgtcacaa cagacaaaac tcacacatgc     660
ccaccgtgcc cagcacctga actcctgggg ggaccgtcag tcttcctctt ccccccaaaa     720
cccaaggaca cctcatgat ctcccggacc cctgaggtca catgcgtggt ggtggacgtg     780
agccacgaag accctgaggt caagttcaac tggtacgtgg acggcgtgga ggtgcataat     840
gccaagacaa agccgcggga ggagcagtac ggagcacgt accgtgtggt cagcgtcctc     900
```

```
accgtcctgc accaggactg gctgaatggc aaggagtaca agtgcaaggt ctccaacaaa       960
gccctcccag cccccatcga gaaaaccatc tccaaagcca agggcagcc ccgagaacca      1020 caggtgtaca ccctgccccc atcccgggaa gagatgacca agaaccaggt cagcctgacc     1080
tgcctggtca aaggcttcta tcccagcgac atcgccgtgg agtgggagag caatgggcag     1140
ccggagaaca actacaagac cacgcctccc gtgctggact ccgacggctc cttcttcctc     1200
tacagcaagc tcaccgtgga caagagcagg tggcagcagg ggaacgtctt ctcatgctcc     1260
gtgatgcatg aggctctgca caaccactac acgcagaaga gcctctccct gtctccggga     1320
cttaacgaca tcttcgaagc acaaaagatc gaatggcacg ag                        1362
```

<210> SEQ ID NO 25
<211> LENGTH: 1010
<212> TYPE: PRT
<213> ORGANISM: Artificial Sequence
<220> FEATURE:
<223> OTHER INFORMATION: Description of the artificial sequence: amino
    acid sequence of human CD122ECD-Fc-Avitag-8His_human CD132ECD-Fc-
    FLAG

<400> SEQUENCE: 25

```
Met Arg Val Leu Ile Leu Leu Trp Leu Phe Thr Ala Phe Pro Gly Ile
1               5                   10                  15

Leu Ser Ala Val Asn Gly Thr Ser Gln Phe Thr Cys Phe Tyr Asn Ser
            20                  25                  30

Arg Ala Asn Ile Ser Cys Val Trp Ser Gln Asp Gly Ala Leu Gln Asp
        35                  40                  45

Thr Ser Cys Gln Val His Ala Trp Pro Asp Arg Arg Arg Trp Asn Gln
    50                  55                  60

Thr Cys Glu Leu Leu Pro Val Ser Gln Ala Ser Trp Ala Cys Asn Leu
65                  70                  75                  80

Ile Leu Gly Ala Pro Asp Ser Gln Lys Leu Thr Thr Val Asp Ile Val
                85                  90                  95

Thr Leu Arg Val Leu Cys Arg Glu Gly Val Arg Trp Arg Val Met Ala
            100                 105                 110

Ile Gln Asp Phe Lys Pro Phe Glu Asn Leu Arg Leu Met Ala Pro Ile
        115                 120                 125

Ser Leu Gln Val Val His Val Glu Thr His Arg Cys Asn Ile Ser Trp
    130                 135                 140

Glu Ile Ser Gln Ala Ser His Tyr Phe Glu Arg His Leu Glu Phe Glu
145                 150                 155                 160

Ala Arg Thr Leu Ser Pro Gly His Thr Trp Glu Glu Ala Pro Leu Leu
                165                 170                 175

Thr Leu Lys Gln Lys Gln Glu Trp Ile Cys Leu Glu Thr Leu Thr Pro
            180                 185                 190

Asp Thr Gln Tyr Glu Phe Gln Val Arg Val Lys Pro Leu Gln Gly Glu
        195                 200                 205

Phe Thr Thr Trp Ser Pro Trp Ser Gln Pro Leu Ala Phe Arg Thr Lys
    210                 215                 220

Pro Ala Ala Leu Gly Lys Asp Thr Gly Ala Gln Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Asp Val Ser His Glu Asp Pro Glu Val
            275                 280             285
Lys Phe Asn Trp Tyr Val Asp Gly Val Glu Val His Asn Ala Lys Thr
        290                 295             300
Lys Pro Arg Glu Glu Gln Tyr Asn Ser Thr Tyr Arg Val Val Ser Val
305                 310             315                 320
Leu Thr Val Leu His Gln Asp Trp Leu Asn Gly Lys Glu Tyr Lys Cys
                325             330                 335
Lys Val Ser Asn Lys Ala Leu Pro Ala Pro Ile Glu Lys Thr Ile Ser
            340             345             350
Lys Ala Lys Gly Gln Pro Arg Glu Pro Gln Val Cys Thr Leu Pro Pro
        355                 360             365
Ser Arg Asp Glu Leu Thr Lys Asn Gln Val Ser Leu Ser Cys Ala Val
370                 375             380
Lys Gly Phe Tyr Pro Ser Asp Ile Ala Val Glu Trp Glu Ser Asn Gly
385                 390             395                 400
Gln Pro Glu Asn Asn Tyr Lys Thr Thr Pro Pro Val Leu Asp Ser Asp
                405             410                 415
Gly Ser Phe Phe Leu Val Ser Lys Leu Thr Val Asp Lys Ser Arg Trp
            420             425             430
Gln Gln Gly Asn Val Phe Ser Cys Ser Val Met His Glu Ala Leu His
        435             440             445
Asn His Tyr Thr Gln Lys Ser Leu Ser Leu Ser Pro Gly Lys Gly Leu
            450             455             460
Asn Asp Ile Phe Glu Ala Gln Lys Ile Glu Trp His Glu His His His
465                 470             475                 480
His His His His His Arg Ala Lys Arg Ala Pro Val Lys Gln Thr Leu
                485             490             495
Asn Phe Asp Leu Leu Lys Leu Ala Gly Asp Val Glu Ser Asn Pro Gly
            500             505             510
Pro Met Asn Leu Gly Leu Ser Leu Ile Phe Leu Ala Leu Ile Leu Lys
        515             520             525
Gly Val Gln Cys Leu Asn Thr Thr Ile Leu Thr Pro Asn Gly Asn Glu
        530             535             540
Asp Thr Thr Ala Asp Phe Phe Leu Thr Thr Met Pro Thr Asp Ser Leu
545                 550             555                 560
Ser Val Ser Thr Leu Pro Leu Pro Glu Val Gln Cys Phe Val Phe Asn
                565             570                 575
Val Glu Tyr Met Asn Cys Thr Trp Asn Ser Ser Ser Glu Pro Gln Pro
                580             585             590
Thr Asn Leu Thr Leu His Tyr Trp Tyr Lys Asn Ser Asp Asn Asp Lys
        595             600             605
Val Gln Lys Cys Ser His Tyr Leu Phe Ser Glu Glu Ile Thr Ser Gly
        610             615             620
Cys Gln Leu Gln Lys Lys Glu Ile His Leu Tyr Gln Thr Phe Val Val
625                 630             635                 640
Gln Leu Gln Asp Pro Arg Glu Pro Arg Arg Gln Ala Thr Gln Met Leu
                645             650             655
Lys Leu Gln Asn Leu Val Ile Pro Trp Ala Pro Glu Asn Leu Thr Leu
            660             665             670
His Lys Leu Ser Glu Ser Gln Leu Glu Leu Asn Trp Asn Asn Arg Phe
        675             680             685
```

```
Leu Asn His Cys Leu Glu His Leu Val Gln Tyr Arg Thr Asp Trp Asp
    690                 695                 700
His Ser Trp Thr Glu Gln Ser Val Asp Tyr Arg His Lys Phe Ser Leu
705                 710                 715                 720
Pro Ser Val Asp Gly Gln Lys Arg Tyr Thr Phe Arg Val Arg Ser Arg
                725                 730                 735
Phe Asn Pro Leu Cys Gly Ser Ala Gln His Trp Ser Glu Trp Ser His
            740                 745                 750
Pro Ile His Trp Gly Ser Asn Thr Ser Lys Glu Asn Pro Phe Leu Phe
        755                 760                 765
Ala Leu Glu Ala Gly Ala Gln Asp Lys Thr His Thr Cys Pro Pro Cys
770                 775                 780
Pro Ala Pro Glu Leu Leu Gly Gly Pro Ser Val Phe Leu Phe Pro Pro
785                 790                 795                 800
Lys Pro Lys Asp Thr Leu Met Ile Ser Arg Thr Pro Glu Val Thr Cys
                805                 810                 815
Val Val Val Asp Val Ser His Glu Asp Pro Glu Val Lys Phe Asn Trp
            820                 825                 830
Tyr Val Asp Gly Val Glu Val His Asn Ala Lys Thr Lys Pro Arg Glu
        835                 840                 845
Glu Gln Tyr Asn Ser Thr Tyr Arg Val Val Ser Val Leu Thr Val Leu
850                 855                 860
His Gln Asp Trp Leu Asn Gly Lys Glu Tyr Lys Cys Lys Val Ser Asn
865                 870                 875                 880
Lys Ala Leu Pro Ala Pro Ile Glu Lys Thr Ile Ser Lys Ala Lys Gly
                885                 890                 895
Gln Pro Arg Glu Pro Gln Val Tyr Thr Leu Pro Pro Cys Arg Asp Glu
            900                 905                 910
Leu Thr Lys Asn Gln Val Ser Leu Trp Cys Leu Val Lys Gly Phe Tyr
        915                 920                 925
Pro Ser Asp Ile Ala Val Glu Trp Glu Ser Asn Gly Gln Pro Glu Asn
930                 935                 940
Asn Tyr Lys Thr Thr Pro Pro Val Leu Asp Ser Asp Gly Ser Phe Phe
945                 950                 955                 960
Leu Tyr Ser Lys Leu Thr Val Asp Lys Ser Arg Trp Gln Gln Gly Asn
                965                 970                 975
Val Phe Ser Cys Ser Val Met His Glu Ala Leu His Asn His Tyr Thr
            980                 985                 990
Gln Lys Ser Leu Ser Leu Ser Pro Gly Lys Asp Tyr Lys Asp Asp Asp
        995                 1000                1005
Asp Lys
    1010

<210> SEQ ID NO 26
<211> LENGTH: 3030
<212> TYPE: DNA
<213> ORGANISM: Artificial Sequence
<220> FEATURE:
<223> OTHER INFORMATION: Description of the artificial sequence: base
      sequence of human CD122ECD-Fc-Avitag-8His_human CD132ECD-Fc-FLAG

<400> SEQUENCE: 26
atgcgtgtgt tgatactcct ctggcttttc actgcttttc caggaattct ttcagccgta    60
aacggcacca gtcaatttac ctgcttctat aatagtcgcg ccaatatctc atgtgtttgg   120
agtcaagatg gcgctctgca ggacacaagt tgccaagtac acgcctggcc agatcgccgt   180
```

```
cggtggaacc agacttgtga gttgcttccc gtttctcagg catcctgggc ttgtaacctt    240
attctggggg ctcccgattc acagaagctg acaacagtgg atatcgttac cctcagagtc    300
ctttgtaggg agggcgtgag gtggcgtgtt atggccatcc aagacttcaa gccatttgaa    360
aacttgcgcc ttatggcccc aatttcattg caagtggttc atgtggagac acacaggtgc    420
aacatcagtt gggaaatttc tcaagcttct cactacttcg agaggcacct tgaatttgaa    480
gcccggaccc tctctcccgg acatacatgg aagaggctc cattgctgac tctgaagcag     540
aaacaggaat ggatttgcct tgagacattg accccagata cacaatacga attccaggtc    600
cgtgttaagc ctctccaggg ggagtttacc acatggagcc cttggagtca gccccttgct    660
ttccggacca aaccagctgc tctgggtaag acacaggggc tcaggacaa gacacacaca     720
tgtcctcctt gccccgctcc tgagctcctg ggcgggcctt cagtgtttct cttccctcca    780
aaacctaagg acaccttat gatatctcga acaccagaag tcacttgcgt tgtggtagac     840
gtgtcccatg aagaccctga ggtaaaattc aattggtatg ttgatggagt agaggtacac    900
aatgctaaga caaaacctcg agaggagcag tacaactcca cctatagggt tgtttctgta    960
cttaccgtct tgcatcagga ttggcttaac ggcaaggagt ataaatgtaa ggtgtctaat   1020
aaagcacttc ctgcccctat agaaaaaacc atatccaagg caaagggaca gcctcgtgaa   1080
cctcaggtct gtactctgcc cccatcccgg gacgaattga caaagaatca ggtaagcctc   1140
tcttgcgctg ttaaaggttt ctaccctcc gacatagccg tcgagtggga atccaatggc    1200
cagcccgaga ataattacaa aactactcct cccgtccttg atagcgatgg tagtttctt    1260
cttgtatcca agttgacagt ggacaagtca agatggcagc agggtaatgt atttagctgc   1320
tccgttatgc atgaggccct tcataaccat tacactcaga atccctctc actctcccct    1380
ggcaaaggac ttaacgacat cttcgaagca caaaagatcg aatggcacga gcaccaccac   1440
catcaccacc atcacaggc aaagcgggct ccagttaagc agaccttgaa ctttgatctt    1500
ctgaaactgg ccggtgacgt tgagtctaac cccggaccca tgaatttggg gctttccttg   1560
attttttctgg ccccttatcct taagggtg cagtgtttga acaccaccat tttgactccc   1620
aatgggaacg aagacacaac cgccgatttt tttctcacaa ccatgcctac cgatagcttg   1680
tccgttttcaa ctctgcctct tccagaagtt cagtgtttcg tgtttaatgt cgagtatatg   1740
aattgtacat ggaactcatc ttccgaacca caacctacca accttacttt gcactattgg   1800
tacaagaact ctgacaatga caaggtccag aagtgctctc actatttgtt ctctgaagag   1860
attacatctg gctgtcaatt gcaaaagaaa gagatccacc tttaccaaac cttcgtcgtc   1920
caattgcagg acccacgaga gccccgccgg caagctactc aaatgcttaa gctccagaat   1980
ctcgtcatcc cctgggcccc agagaacctg acacttcata gttgagtga aagtcagctt    2040
gagttgaact ggaacaatag atttctcaac cactgtctgg aacacctcgt ccaataccga   2100
accgactggg atcattcatg gaccgagcaa tctgttgact atcgccataa attctctttg   2160
ccatccgttg atgggcaaaa acgttacacc ttccgtgtcc gctcacgatt taatcctctc   2220
tgtggctccg cacagcattg gagcgagtgg agccaccca tacactgggg ttctaatact    2280
tctaaggaaa accctttcct ctttgcactt gaggccgggg cacaagataa gactcatact   2340
tgtcctccat gtccagcccc cgaattgctg ggtggaccca gcgtcttcct gttcccccca   2400
aagcccaaag acacactcat gataagtagg actcccgagg taacctgtgt cgtagtcgac   2460
gtaagtcatg aagatcctga ggtgaagttt aattggtatg tggatggggt tgaggttcac   2520
```

| aacgctaaaa ccaagccaag agaggagcaa tacaacagta cttatcgcgt cgtgagcgta | 2580 |
| ctcacagttc tgcatcaaga ttggctgaat ggcaaagagt acaaatgtaa agtaagcaat | 2640 |
| aaggcacttc ctgctcctat cgaaaagact atcagcaaag caaaaggcca accaagggag | 2700 |
| cctcaagtat atacactccc accttgtaga gatgagttga ctaagaatca ggtaagtctc | 2760 |
| tggtgtcttg tcaagggatt ttatccttca gatatagctg tggagtggga gtctaacggc | 2820 |
| caacctgaaa acaactataa gaccacccccc cctgtactgg atagcgatgg tagttttttc | 2880 |
| ctctactcca agctcaccgt ggacaagtct cgctggcaac aaggtaacgt gttttcctgc | 2940 |
| agcgttatgc acgaggcact tcataatcat tacacacaaa aatcactgtc tttgagtccc | 3000 |
| ggtaaagact acaaagacga cgatgacaag | 3030 |

<210> SEQ ID NO 27
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-S4(oAzZK) / F78(oAzZK)

<400> SEQUENCE: 27

| atgcatcatc atcaccatca tcatcacgcc ccgacctaga gcagcaccaa aaagacccag | 60 |
| ctgcagctgg aacatctgct gctggatctg cagatgatcc tgaatggcat taacaactat | 120 |
| aaaaacccga agctgacccg catgctgacc tttaaatttt atatgccgaa aaaagccacc | 180 |
| gagctgaagc atctgcagtg cctggaagaa gaactgaaac cgctggaaga ggtgctgaac | 240 |
| ctggcccaga gcaaaaacta gcacctgcgc ccgcgtgacc tgatcagcaa catcaacgtg | 300 |
| atcgtgctgg aactgaaggg tagcgagacc accttcatgt gcgaatatgc cgacgagacc | 360 |
| gccaccatcg tggaattcct gaaccgctgg atcacctttt cccagagcat catcagtacc | 420 |
| ctgacc | 426 |

<210> SEQ ID NO 28
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-S5(oAzZK) / F78(oAzZK)

<400> SEQUENCE: 28

| atgcatcatc atcaccatca tcatcacgcc ccgaccagct agagcaccaa aaagacccag | 60 |
| ctgcagctgg aacatctgct gctggatctg cagatgatcc tgaatggcat taacaactat | 120 |
| aaaaacccga agctgacccg catgctgacc tttaaatttt atatgccgaa aaaagccacc | 180 |
| gagctgaagc atctgcagtg cctggaagaa gaactgaaac cgctggaaga ggtgctgaac | 240 |
| ctggcccaga gcaaaaacta gcacctgcgc ccgcgtgacc tgatcagcaa catcaacgtg | 300 |
| atcgtgctgg aactgaaggg tagcgagacc accttcatgt gcgaatatgc cgacgagacc | 360 |
| gccaccatcg tggaattcct gaaccgctgg atcacctttt cccagagcat catcagtacc | 420 |
| ctgacc | 426 |

<210> SEQ ID NO 29
<211> LENGTH: 426
<212> TYPE: DNA
<213> ORGANISM: Artificial Sequence
<220> FEATURE:
<223> OTHER INFORMATION: Description of the artificial sequence: base sequence of 8His-K8(oAzZK) / F78(oAzZK)

<400> SEQUENCE: 29

```
atgcatcatc atcaccatca tcatcacgcc ccgaccagca gcagcaccta aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaacta gcacctgcgc ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 30
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-F78(oAzZK) / H79(oAzZK)

<400> SEQUENCE: 30

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaacta gtagctgcgc ccgcgtgacc tgatcagcaa catcaacgtg   300
atcgtgctgg aactgaaggg tagcgagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 31
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-F78(oAzZK) / S99(oAzZK)

<400> SEQUENCE: 31

```
atgcatcatc atcaccatca tcatcacgcc ccgaccagca gcagcaccaa aaagacccag    60
ctgcagctgg aacatctgct gctggatctg cagatgatcc tgaatggcat taacaactat   120
aaaaacccga agctgacccg catgctgacc tttaaatttt atatgccgaa aaaagccacc   180
gagctgaagc atctgcagtg cctggaagaa gaactgaaac cgctggaaga ggtgctgaac   240
ctggcccaga gcaaaaacta gcacctgcgc ccgcgtgacc tgatcagcaa catcaacgtg   300
atcgtgctgg aactgaaggg ttaggagacc accttcatgt gcgaatatgc cgacgagacc   360
gccaccatcg tggaattcct gaaccgctgg atcacctttt cccagagcat catcagtacc   420
ctgacc                                                              426
```

<210> SEQ ID NO 32
<211> LENGTH: 426
<212> TYPE: DNA
<213> ORGANISM: Artificial Sequence
<220> FEATURE:
<223> OTHER INFORMATION: Description of the artificial sequence: base
sequence of 8His-F78(oAzZK) / I129(oAzZK)

<400> SEQUENCE: 32

```
atgcatcatc atcaccatca tcatcacgcc ccgaccagca gcagcaccaa aaagacccag      60
ctgcagctgg aacatctgct gctggatctg cagatgatcc tgaatggcat taacaactat    120
aaaaacccga agctgacccg catgctgacc tttaaatttt atatgccgaa aaaagccacc    180
gagctgaagc atctgcagtg cctggaagaa gaactgaaac cgctggaaga ggtgctgaac    240
ctggcccaga gcaaaaacta gcacctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcacctttt cccagagcat ctagagtacc    420
ctgacc                                                                426
```

<210> SEQ ID NO 33
<211> LENGTH: 426
<212> TYPE: DNA
<213> ORGANISM: Artificial Sequence
<220> FEATURE:
<223> OTHER INFORMATION: Description of the artificial sequence: base
sequence of 8His-S4(oAzZK) / I129(oAzZK)

<400> SEQUENCE: 33

```
atgcatcatc atcaccatca tcatcacgcc ccgacctaga gcagcaccaa aaagacccag      60
ctgcagctgg aacatctgct gctggatctg cagatgatcc tgaatggcat taacaactat    120
aaaaacccga agctgacccg catgctgacc tttaaatttt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcacctttt cccagagcat ctagagtacc    420
ctgacc                                                                426
```

<210> SEQ ID NO 34
<211> LENGTH: 426
<212> TYPE: DNA
<213> ORGANISM: Artificial Sequence
<220> FEATURE:
<223> OTHER INFORMATION: Description of the artificial sequence: base
sequence of 8His-S5(oAzZK) / I129(oAzZK)

<400> SEQUENCE: 34

```
atgcatcatc atcaccatca tcatcacgcc ccgaccagct agagcaccaa aaagacccag      60
ctgcagctgg aacatctgct gctggatctg cagatgatcc tgaatggcat taacaactat    120
aaaaacccga agctgacccg catgctgacc tttaaatttt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcacctttt cccagagcat ctagagtacc    420
ctgacc                                                                426
```

<210> SEQ ID NO 35
<211> LENGTH: 426

```
<212> TYPE: DNA
<213> ORGANISM: Artificial Sequence
<220> FEATURE:
<223> OTHER INFORMATION: Description of the artificial sequence: base
      sequence of 8His-K8(oAzZK) / I129(oAzZK)

<400> SEQUENCE: 35
atgcatcatc atcaccatca tcatcacgcc ccgaccagca gcagcaccta gaagacccag      60
ctgcagctgg aacatctgct gctggatctg cagatgatcc tgaatggcat taacaactat    120
aaaaacccga agctgacccg catgctgacc tttaaatttt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaagggg tagcgagacc accttcatgt gcgaatatgc cgacgagacc    360
gccaccatcg tggaattcct gaaccgctgg atcacctttt cccagagcat ctagagtacc    420
ctgacc                                                                426

<210> SEQ ID NO 36
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-H79(oAzZK) / I129(oAzZK)

<400> SEQUENCE: 36
atgcatcatc atcaccatca tcatcacgcc ccgaccagca gcagcaccaa aaagacccag      60
ctgcagctgg aacatctgct gctggatctg cagatgatcc tgaatggcat taacaactat    120
aaaaacccga agctgacccg catgctgacc tttaaatttt atatgccgaa aaaagccacc    180
gagctgaagc atctgcagtg cctggaagaa gaactgaaac cgctggaaga ggtgctgaac    240
ctggcccaga gcaaaaactt ttagctgcgc ccgcgtgacc tgatcagcaa catcaacgtg    300
atcgtgctgg aactgaaggg tagcgagacc accttcatgt gcgaatatgc cgacgagacc    360
gccaccatcg tggaattcct gaaccgctgg atcacctttt cccagagcat ctagagtacc    420
ctgacc                                                                426

<210> SEQ ID NO 37
<211> LENGTH: 426
<212> TYPE: DNA
<213> ORGANISM: Artificial Sequence
<220> FEATURE:
<223> OTHER INFORMATION: Description of the artificial sequence: base
      sequence of 8His-S99(oAzZK) / I129(oAzZK)

<400> SEQUENCE: 37
atgcatcatc atcaccatca tcatcacgcc ccgaccagca gcagcaccaa aaagacccag      60
ctgcagctgg aacatctgct gctggatctg cagatgatcc tgaatggcat taacaactat    120
aaaaacccga agctgacccg catgctgacc tttaaatttt atatgccgaa aaaagccacc    180
gagctgaagc atctgcagtg cctggaagaa gaactgaaac cgctggaaga ggtgctgaac    240
ctggcccaga gcaaaaactt tcacctgcgc ccgcgtgacc tgatcagcaa catcaacgtg    300
atcgtgctgg aactgaaggg ttaggagacc accttcatgt gcgaatatgc cgacgagacc    360
gccaccatcg tggaattcct gaaccgctgg atcacctttt cccagagcat ctagagtacc    420
ctgacc                                                                426
```

<210> SEQ ID NO 38
<211> LENGTH: 134
<212> TYPE: PRT
<213> ORGANISM: Artificial Sequence
<220> FEATURE:
<223> OTHER INFORMATION: Description of the artificial sequence: amino
      acid sequence of IL-2 C125S Nter-Met

<400> SEQUENCE: 38

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ser Gln Ser
        115                 120                 125

Ile Ile Ser Thr Leu Thr
        130

<210> SEQ ID NO 39
<211> LENGTH: 402
<212> TYPE: DNA
<213> ORGANISM: Artificial Sequence
<220> FEATURE:
<223> OTHER INFORMATION: Description of the artificial sequence: base
      sequence of IL-2 C125S Nter-Met

<400> SEQUENCE: 39
atggcaccta cttcaagttc tacaaagaaa acacagctac aactggagca tttactgctg      60
gatttacaga tgattttgaa tggaattaat aattacaaga atcccaaact caccaggatg     120
ctcacattta gttttacat gcccaagaag gccacagaac tgaaacatct tcagtgtcta     180
gaagaagaac tcaaacctct ggaggaagtg ctaaatttag ctcaaagcaa aaactttcac     240
ttaagaccca gggacttaat cagcaatatc aacgtaatag ttctggaact aaagggatct     300
gaaacaacat tcatgtgtga atatgctgat gagacagcaa ccattgtaga atttctgaac     360
agatggatta ccttttcaca aagcatcatc tcaacactga ct                        402

<210> SEQ ID NO 40
<211> LENGTH: 133
<212> TYPE: PRT
<213> ORGANISM: Artificial Sequence
<220> FEATURE:
<223> OTHER INFORMATION: Description of the artificial sequence: amino
      acid sequence of desAla_IL-2 C125S

<400> SEQUENCE: 40

Met Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 41
<211> LENGTH: 399
<212> TYPE: DNA
<213> ORGANISM: Artificial Sequence
<220> FEATURE:
<223> OTHER INFORMATION: Description of the artificial sequence: base
      sequence of desAla_IL-2 C125S

<400> SEQUENCE: 41
atgcctactt caagtctac  aaagaaaaca cagctacaac tggagcattt actgctggat        60
ttacagatga ttttgaatgg aattaataat tacaagaatc ccaaactcac caggatgctc      120
acatttaagt tttacatgcc caagaaggcc acagaactga acatcttca gtgtctagaa       180 gaagaactca aacctctgga ggaagtgcta aatttagctc aaagcaaaaa ctttcactta      240
agacccaggg acttaatcag caatatcaac gtaatagttc tggaactaaa gggatctgaa      300
acaacattca tgtgtgaata tgctgatgag acagcaacca ttgtagaatt tctgaacaga      360
tggattacct tttcacaaag catcatctca acactgact                              399

<210> SEQ ID NO 42
<211> LENGTH: 402
<212> TYPE: DNA
<213> ORGANISM: Artificial Sequence
<220> FEATURE:
<223> OTHER INFORMATION: Description of the artificial sequence: base
      sequence of F78(oAzZK)

<400> SEQUENCE: 42
atggcaccta cttcaagttc tacaaagaaa acacagctac aactggagca tttactgctg        60
gatttacaga tgattttgaa tggaattaat aattacaaga tcccaaact caccaggatg      120 ctcacattta gttttacat gcccaagaag gccacagaac tgaaacatct tcagtgtcta      180
gaagaagaac tcaaacctct ggaggaagtg ctaaatttag ctcaaagcaa aaactagcac      240
ttaagaccca gggacttaat cagcaatatc aacgtaatag ttctggaact aaagggatct      300
gaaacaacat tcatgtgtga atatgctgat gagacagcaa ccattgtaga atttctgaac      360
agatggatta ccttttcaca aagcatcatc tcaacactga ct                          402

<210> SEQ ID NO 43
<211> LENGTH: 402
<212> TYPE: DNA
<213> ORGANISM: Artificial Sequence
<220> FEATURE:
<223> OTHER INFORMATION: Description of the artificial sequence: base
      sequence of I129(oAzZK)

<400> SEQUENCE: 43

```
atggcaccta cttcaagttc tacaaagaaa acacagctac aactggagca tttactgctg    60
gatttacaga tgattttgaa tggaattaat aattacaaga atcccaaact caccaggatg   120
ctcacattta agtttacat gcccaagaag gccacagaac tgaaacatct tcagtgtcta    180
gaagaagaac tcaaacctct ggaggaagtg ctaaatttag ctcaaagcaa aaactttcac   240
ttaagaccca gggacttaat cagcaatatc aacgtaatag ttctggaact aaagggatct   300
gaaacaacat tcatgtgtga atatgctgat gagacagcaa ccattgtaga atttctgaac   360
agatggatta ccttttcaca aagcatctag tcaacactga ct                      402
```

<210> SEQ ID NO 44
<211> LENGTH: 399
<212> TYPE: DNA
<213> ORGANISM: Artificial Sequence
<220> FEATURE:
<223> OTHER INFORMATION: Description of the artificial sequence: base sequence of desAla_I129(oAzZK)

<400> SEQUENCE: 44

```
atgcctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180
gaagaactca aacctctgga ggaagtgcta aatttagctc aaagcaaaaa ctttcactta   240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct tttcacaaag catctagtca acactgact                           399
```

<210> SEQ ID NO 45
<211> LENGTH: 402
<212> TYPE: DNA
<213> ORGANISM: Artificial Sequence
<220> FEATURE:
<223> OTHER INFORMATION: Description of the artificial sequence: base sequence of S4(oAzZK) / F78(oAzZK)

<400> SEQUENCE: 45

```
atggcaccta cttagagttc tacaaagaaa acacagctac aactggagca tttactgctg    60
gatttacaga tgattttgaa tggaattaat aattacaaga atcccaaact caccaggatg   120
ctcacattta agtttacat gcccaagaag gccacagaac tgaaacatct tcagtgtcta    180
gaagaagaac tcaaacctct ggaggaagtg ctaaatttag ctcaaagcaa aaactagcac   240
ttaagaccca gggacttaat cagcaatatc aacgtaatag ttctggaact aaagggatct   300
gaaacaacat tcatgtgtga atatgctgat gagacagcaa ccattgtaga atttctgaac   360
agatggatta ccttttcaca aagcatcatc tcaacactga ct                      402
```

<210> SEQ ID NO 46
<211> LENGTH: 402
<212> TYPE: DNA
<213> ORGANISM: Artificial Sequence
<220> FEATURE:
<223> OTHER INFORMATION: Description of the artificial sequence: base sequence of S5(oAzZK) / F78(oAzZK)

<400> SEQUENCE: 46

```
atggcaccta cttcatagtc tacaaagaaa acacagctac aactggagca tttactgctg    60
```

```
gatttacaga tgattttgaa tggaattaat aattacaaga atcccaaact caccaggatg      120
ctcacattta agttttacat gcccaagaag gccacagaac tgaaacatct tcagtgtcta      180
gaagaagaac tcaaacctct ggaggaagtg ctaaatttag ctcaaagcaa aaactagcac      240
ttaagaccca gggacttaat cagcaatatc aacgtaatag ttctggaact aaagggatct      300
gaaacaacat tcatgtgtga atatgctgat gagacagcaa ccattgtaga atttctgaac      360
agatggatta ccttttcaca aagcatcatc tcaacactga ct                        402
```

<210> SEQ ID NO 47
<211> LENGTH: 402
<212> TYPE: DNA
<213> ORGANISM: Artificial Sequence
<220> FEATURE:
<223> OTHER INFORMATION: Description of the artificial sequence: base
      sequence of K8(oAzZK) / F78(oAzZK)

<400> SEQUENCE: 47

```
atggcaccta cttcaagttc tacatagaaa acacagctac aactggagca tttactgctg       60
gatttacaga tgattttgaa tggaattaat aattacaaga atcccaaact caccaggatg      120
ctcacattta agttttacat gcccaagaag gccacagaac tgaaacatct tcagtgtcta      180
gaagaagaac tcaaacctct ggaggaagtg ctaaatttag ctcaaagcaa aaactagcac      240
ttaagaccca gggacttaat cagcaatatc aacgtaatag ttctggaact aaagggatct      300
gaaacaacat tcatgtgtga atatgctgat gagacagcaa ccattgtaga atttctgaac      360
agatggatta ccttttcaca aagcatcatc tcaacactga ct                        402
```

<210> SEQ ID NO 48
<211> LENGTH: 402
<212> TYPE: DNA
<213> ORGANISM: Artificial Sequence
<220> FEATURE:
<223> OTHER INFORMATION: Description of the artificial sequence: base
      sequence of S4(oAzZK) / I129(oAzZK)

<400> SEQUENCE: 48

```
atggcaccta cttagagttc tacaaagaaa acacagctac aactggagca tttactgctg       60
gatttacaga tgattttgaa tggaattaat aattacaaga atcccaaact caccaggatg      120
ctcacattta agttttacat gcccaagaag gccacagaac tgaaacatct tcagtgtcta      180
gaagaagaac tcaaacctct ggaggaagtg ctaaatttag ctcaaagcaa aaactttcac      240
ttaagaccca gggacttaat cagcaatatc aacgtaatag ttctggaact aaagggatct      300
gaaacaacat tcatgtgtga atatgctgat gagacagcaa ccattgtaga atttctgaac      360
agatggatta ccttttcaca aagcatctag tcaacactga ct                        402
```

<210> SEQ ID NO 49
<211> LENGTH: 402
<212> TYPE: DNA
<213> ORGANISM: Artificial Sequence
<220> FEATURE:
<223> OTHER INFORMATION: Description of the artificial sequence: base
      sequence of S5(oAzZK) / I129(oAzZK)

<400> SEQUENCE: 49

```
atggcaccta cttcatagtc tacaaagaaa acacagctac aactggagca tttactgctg       60
gatttacaga tgattttgaa tggaattaat aattacaaga atcccaaact caccaggatg      120
ctcacattta agttttacat gcccaagaag gccacagaac tgaaacatct tcagtgtcta      180
```

```
gaagaagaac tcaaacctct ggaggaagtg ctaaatttag ctcaaagcaa aaactttcac      240
ttaagaccca gggacttaat cagcaatatc aacgtaatag ttctggaact aaagggatct      300
gaaacaacat tcatgtgtga atatgctgat gagacagcaa ccattgtaga atttctgaac      360
agatggatta ccttttcaca aagcatctag tcaacactga ct                         402
```

<210> SEQ ID NO 50
<211> LENGTH: 402
<212> TYPE: DNA
<213> ORGANISM: Artificial Sequence
<220> FEATURE:
<223> OTHER INFORMATION: Description of the artificial sequence: base
      sequence of K8(oAzZK) / I129(oAzZK)

<400> SEQUENCE: 50

```
atggcaccta cttcaagttc tacatagaaa acacagctac aactggagca tttactgctg      60
gatttacaga tgattttgaa tggaattaat aattacaaga atcccaaact caccaggatg     120
ctcacattta agtttacat gcccaagaag gccacagaac tgaaacatct tcagtgtcta      180
gaagaagaac tcaaacctct ggaggaagtg ctaaatttag ctcaaagcaa aaactttcac      240
ttaagaccca gggacttaat cagcaatatc aacgtaatag ttctggaact aaagggatct      300
gaaacaacat tcatgtgtga atatgctgat gagacagcaa ccattgtaga atttctgaac      360
agatggatta ccttttcaca aagcatctag tcaacactga ct                         402
```

<210> SEQ ID NO 51
<211> LENGTH: 133
<212> TYPE: PRT
<213> ORGANISM: Artificial Sequence
<220> FEATURE:
<223> OTHER INFORMATION: Description of the artificial sequence: amino
      acid sequence of I129C

<400> SEQUENCE: 51

```
Met Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Cys Ser Thr Leu Thr
    130
```

```
<210> SEQ ID NO 52
<211> LENGTH: 399
<212> TYPE: DNA
<213> ORGANISM: Artificial Sequence
<220> FEATURE:
<223> OTHER INFORMATION: Description of the artificial sequence: base
      sequence of I129C

<400> SEQUENCE: 52
atgcctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga aacatcttca gtgtctagaa     180
gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
tggattacct tttcacaaag catctgttca acactgact                            399
```

IL-2 VARIANT

TECHNICAL FIELD

The present invention relates to an IL-2 variant, a method for producing the IL-2 variant, a composition and a therapeutic agent comprising the IL-2 variant, a method for improving an affinity of IL-2 for an IL-2Rα subunit, a method of reducing an affinity of IL-2 for at least one of an IL-2Rβ subunit and an IL-2Rγ subunit, and a method for selectively activating regulatory T cells.

BACKGROUND ART

Regulatory T cells (Tregs) are a subpopulation of CD4+ T cells, which express a transcription factor forkhead box P3 (Foxp3). Tregs inhibit activation of effector T cells (Teffs) by a variety of mechanisms such as production of inhibitory cytokines such as IL-10 or TGF-β, cytolysis through cytotoxic proteins such as Perforin or Granzyme, modulation of antigen-presenting cell activity through CTLA-4 or the like, and depletion of IL-2 by competitive use, and negatively regulate excessive immune responses. (Non-Patent Document 1).

Treg deficiency due to Foxp3 mutations leads to immune dysregulation, polyendocrinopathy, enteropathy, X-linked (IPEX) syndrome, which exhibits a severe systemic autoimmune response. In addition, since the amount and quality of Tregs are reduced in a plurality of autoimmune diseases, it is considered that disruption of Treg-mediated immune regulation contributes to onset of pathology (Non-Patent Documents 2 and 3).

Interleukin-2 (IL-2) is a cytokine mainly produced from activated T cells, and contributes to proliferation and activation of various immune cells. Human mature interleukin-2 has a molecular weight of about 15 kDa (133 residues) and has a four-helix bundle structure formed of four α-helices (Non-patent Document 4).

An IL-2 receptor (IL-2R) is formed of three molecules of CD25 (IL-2R$_\alpha$), CD122 (IL-2R$_\beta$) and CD132 ($\gamma_c$), and has a medium affinity ($K_D$) for IL-2. In a case where a heterotrimeric receptor (IL-2R$_{\alpha\beta\gamma}$) showing high affinity ($K_D \approx 10^{-11}$ M) with IL-2 or a heterodimeric receptor (IL-2R$_{\beta\gamma}$) showing intermediate affinity ($K_D \approx 10^{-9}$ M) with IL-2 is formed, a signal is transmitted. CD25 binds alone to IL-2 with low affinity ($K_D \approx 10^{-8}$ M), but cannot transmit a signal (Non-Patent Document 5).

An expression pattern of IL-2R differs among immune cells. In CD56$^{low}$NK cells or naive T cells, CD25 expression is extremely low, and IL-2R functions as IL-2R$_{\beta\gamma}$. On the other hand, in Tregs or CD56$^{high}$ NK cells, CD25 is expressed, and IL-2R functions as IL-2R$_{\alpha\beta\gamma}$ (Non-patent Document 6).

In binding between IL-2 and IL-2R$_{\alpha\beta\gamma}$, the IL-2 first binds to CD25 and then binds to CD122 and CD132 sequentially, thereby causing IL-2R to be trimerized. Dimerization of CD122 and CD132 by IL-2 promotes recruitment of JAK1 to a CD122 intracellular region and JAK3 to a CD132 intracellular region, and then causes STAT5 to be phosphorylated. The phosphorylated STAT5 (pSTAT5) translocates into the nucleus after forming a dimer and promotes transcription of a target gene (Non-Patent Documents 7 and 8).

An IL-2 signal plays an important role in maintaining homeostasis of Tregs. pSTAT5 generated by IL-2 stimulation directly promotes expression of Foxp3, thereby improving functions of promoting and stabilizing proliferation of Tregs and suppressing activation of Teff. Tregs express IL-2R$_{\alpha\beta\gamma}$ that is a high affinity receptor, and have high protein phosphatase 1 (PP1) and PP2A activities that positively regulate IL-2 signals. Therefore, phosphorylation of STAT5 in Tregs and gene expression on downstream thereof by the IL-2 stimulation are induced in a concentration range about 10 to 100 times lower than that of memory T cells (Non-Patent Documents 6 and 9).

Mice deficient in IL-2 gene or IL-2R gene exhibit reduced Tregs and a severe autoimmune response. Similarly, in humans, deficiency of the CD25 gene exhibits autoreactive T cell proliferation and symptoms similar to those of IPEX syndrome. In systemic lupus erythematosus (SLE) patients or Type I diabetic mellitus patients, a decrease in IL-2 production by T cells and a decrease in Tregs associated therewith are observed (Non-Patent Documents 10, 11, and 12).

Activation of the IL-2 signal enhances Treg function. Administration of IL-2 to MRL/lpr mice exhibiting SLE-like symptoms suppresses inflammatory response and ameliorates the pathology. In addition, administration of IL-2 to a graft-versus-host disease (GVHD) patient or an SLE patient promotes Treg amplification, and improves a pathological condition (Non-Patent Documents 13, 14, and 15).

However, administration of wild-type IL-2 often causes an increase of NK cells or eosinophils, thereby causes administration site reactions, fever, and flu-like symptoms. In addition, since half-life of IL-2 in blood is very short, about 1 hour, low-dose IL-2 therapy requires daily administration of IL-2 (Non-Patent Documents 14, 15, and 16).

To solve the above described problems, creation of an IL-2 variant that selectively activates Tregs and has an extended half-life in blood has been attempted.

An attempt to improve selectivity of IL-2 for IL-2R$_{\alpha\beta\gamma}$ is made. As one method, a method of introducing a mutation into an amino acid residue interacting with IL-2R$_{\beta\gamma}$ or forming an immune complex with an anti-IL-2 antibody is attempted (Patent Documents 1, 2, 3, 4, 5, and 6 and Non-Patent Document 17).

However, introduction of an amino acid mutation causes an increase in immunogenicity due to the mutation. In administration of an amino acid-mutated human IL-2 variant to cynomolgus monkeys, anti-drug antibodies are generated. Imparting IL-2R$_{\alpha\beta\gamma}$ selectivity to IL-2 by an anti-IL-2 antibody results in bell shaped activity (Patent Documents 2 and 6).

An attempt to improve half-life of IL-2 in blood is made. As one method, a method of adding an antibody-derived Fc sequence is attempted (Patent Documents 2, 4, and 7, and Non-Patent Document 18). As another method, a method of adding a non-toxic water-soluble polymer such as polyethylene glycol (PEG) is known (Patent Documents 8, 9, 10, and 11, and Non-Patent Documents 19 and 20). In addition, a method for introducing a saccharide is also attempted (Patent Documents 12, 13, and 14).

However, modification of IL-2 with polyethylene glycol causes a decrease in biological activity (Non-Patent Document 19).

RELATED ART

Patent Document

[Patent Document 1] International Publication No. WO2010/085495
[Patent Document 2] International Publication No. WO2014/153111

[Patent Document 3] US Application Publication No. 2015/0374788
[Patent Document 4] U.S. Pat. No. 7,186,804
[Patent Document 5] International Publication No. WO2014/028748
[Patent Document 6] International Publication No. WO2015/109212
[Patent Document 7] US Application Publication No. 2017/0051029
[Patent Document 8] International Publication No. WO2016/025385
[Patent Document 9] JP-A-2016-202187
[Patent Document 10] U.S. Pat. No. 4,902,502
[Patent Document 11] U.S. Pat. No. 5,206,344
[Patent Document 12] U.S. Pat. No. 5,153,310
[Patent Document 13] U.S. Pat. No. 5,312,903
[Patent Document 14] U.S. Pat. No. 5,417,970

Non-Patent Document

[Non-Patent Document 1] Front Immunol, 2013. 4 (378)
[Non-patent Document 2] Nat Rev Immunol, 2014. 14 (5): 343-349
[Non-Patent Document 3] Autoimmun Rev, 2015. 14 (2): 105-116
[Non-Patent Document 4] Annu Rev Immunol, 2008. 26: 453-479
[Non-Patent Document 5] Immunity, 2013. 38 (1): 13-25
[Non-Patent Document 6] Diabetes, 2015. 64 (6): 2172-2183
[Non-Patent Document 7] J Biol Chem, 1997. 272 (50): 31821-31828
[Non-Patent Document 8] Nat Rev Immunol. 2012 Feb. 17; 12 (3): 180-90
[Non-patent Document 9] Nat Rev Immunol. 2015 May; 15 (5): 283-94
[Non-Patent Document 10] Proc Natl Acad Sci USA, 1997. 94 (7): 3168-3171
[Non-Patent Document 11] N Engl J Med, 2011. 365 (22): 2110-2121
[Non-Patent Document 12] Curr Diab Rep, 2014. 14 (12): 553
[Non-Patent Document 13] J Immunol, 2014. 193 (5): 2168-2177
[Non-Patent Document 14] N Engl J Med, 2011. 365 (22): 2055-2066
[Non-Patent Document 15] Ann Rheum Dis, 2015. 74 (4): 791-792
[Non-Patent Document 16] Blood. 2014 Dec. 4; 124 (24): 3572-6.
[Non-Patent Document 17] Curr Pharm Des, 2002. 8 (24): 2171-83
[Non-Patent Document 18] J Autoimmun, 2015. 56: 66-80
[Non-Patent Document 19] American College of Rheumatology Annual Meeting, San Diego, Calif., 2017. Poster Abstract 2715: NKTR-358: A Selective, First-in-Class IL-2 Pathway Agonist Which Increases Number and Suppressive Function of Regulatory T Cells for the Treatment of Immune Inflammatory Disorders, Langowski, J., et al. http://www.nektar.com/application/files/6315/1001/4171/NKTR-358_2017ACR_ABS2715.pdf
[Non-Patent Document 20] Biotechnology (N Y), 1990. 8 (4): 343-346

DISCLOSURE OF INVENTION

Technical Problem

Problems to Be Solved by the Invention

An object of the present invention is to provide a novel IL-2 variant which has improved selectivity for IL-2R$_{\alpha\beta\gamma}$ and selectively activates Tregs.

Means for Solving the Problems

As a result of intensive studies on the above described problems, the present inventors found that the above described problems can be solved by an IL-2 variant modified by binding a saccharide or PEG to IL-2, and completed the present invention.

That is, the present invention is as follows.
(1) An Interleukin-2 (hereinafter abbreviated as IL-2) variant.
(2) The IL-2 variant according to (1), which is a saccharide-bound IL-2 variant and/or a polyethylene glycol (PEG)-bound IL-2 variant.
(3) The IL-2 variant according to (1) or (2), which has improved selectivity for an IL-2 receptor (hereinafter, IL-2R$_{\alpha\beta\gamma}$.
(4) The IL-2 variant according to (2) or (3), wherein a saccharide is bound to at least one amino acid residue selected from the group consisting of amino acid residues at positions 11, 12, 13, 15, 16, 18, 19, 20, 84, 87, 88, 91, 92, 108, 115, 119, 122, 123, and 130 in an amino acid sequence of IL-2.
(5) The IL-2 variant according to any one of (2) to (4), wherein the saccharide is at least one selected from saccharides comprising structures represented by (Formula 4) to (Formula 8), (Formula Y1), (Formula Y2), or (Formula Y3).

[Chem. 1]

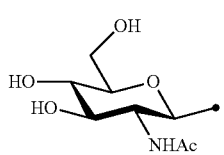

(Formula Y1)

[Chem. 2]

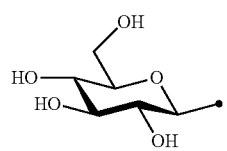

(Formula Y2)

[Chem. 3]
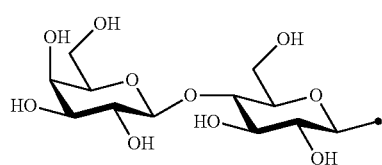
(Formula 4)
[Chem. 4]
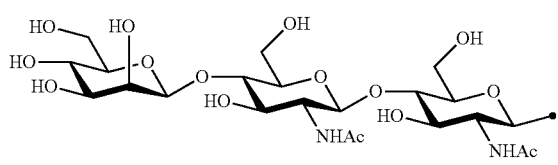
(Formula 5)
[Chem. 5]
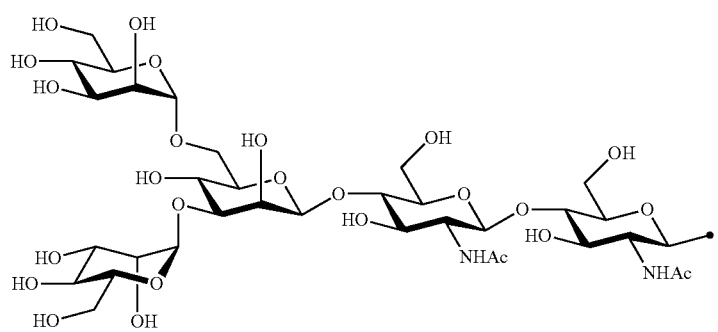
(Formula 6)
[Chem. 6]
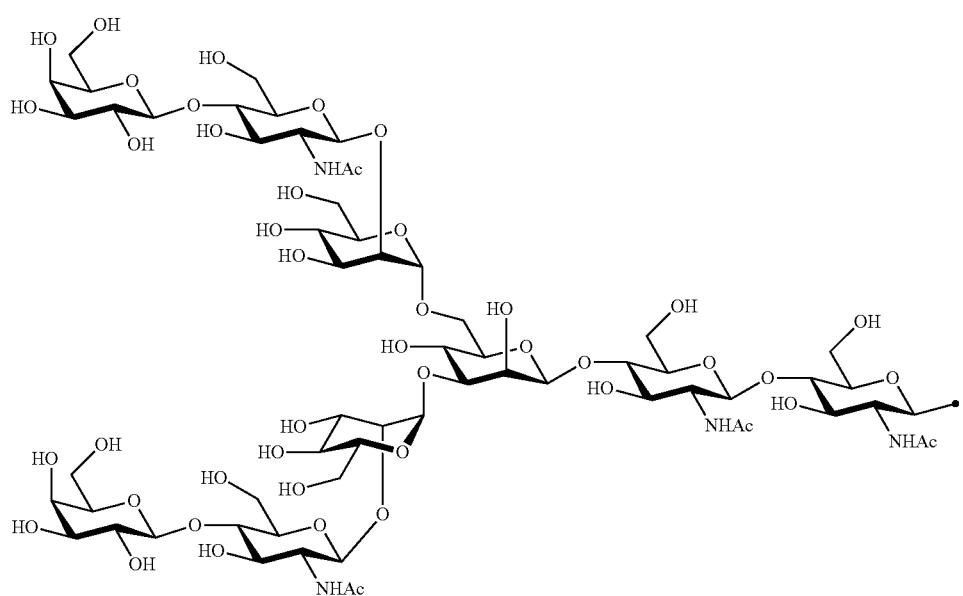
(Formula 7)

-continued
[Chem. 7]
(Formula 8)
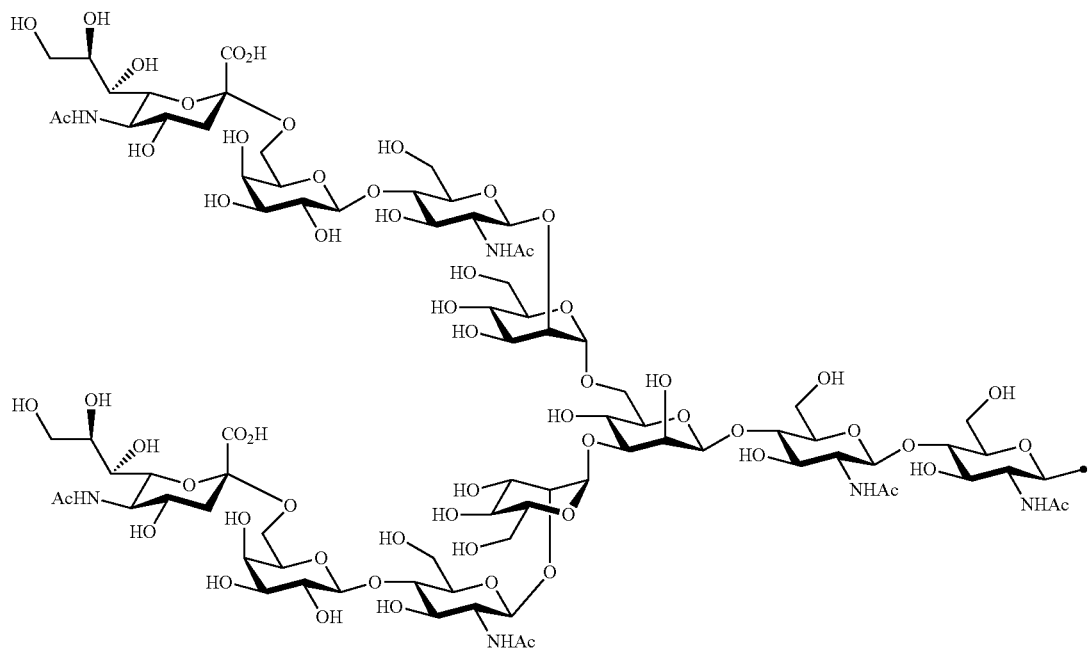
[Chem. 8]
(Formula Y3)
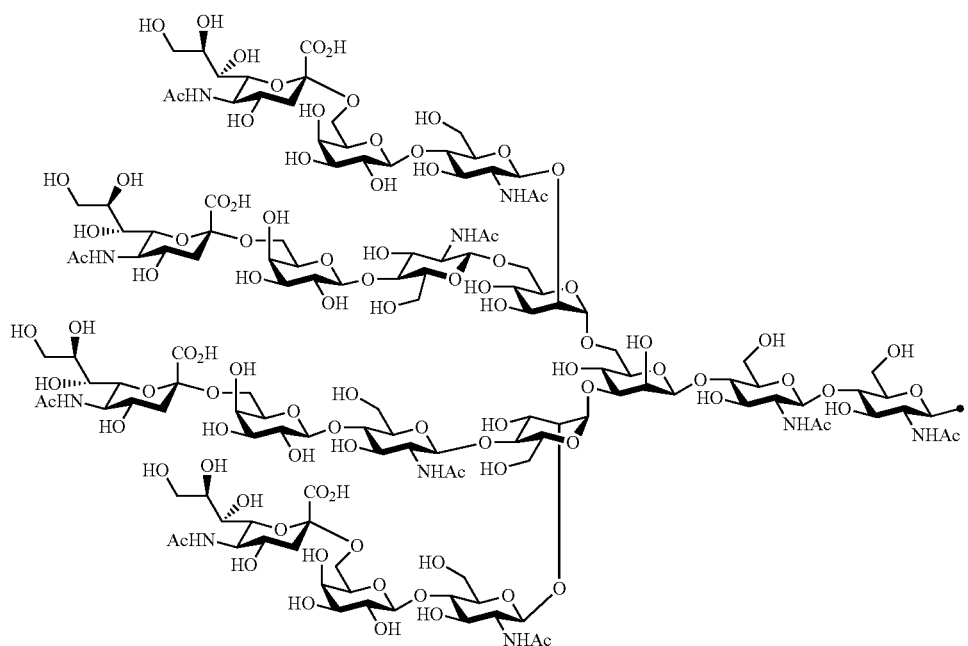

(6) The IL-2 variant according to any one of (2) to (5), which comprises an amino acid sequence in which at least one amino acid residue selected from the group consisting of amino acid residues at positions 11, 12, 13, 15, 16, 18, 19, 20, 84, 87, 88, 91, 92, 108, 115, 119, 122, 123, and 130 in an amino acid sequence represented by SEQ ID NO: 1 or an amino acid sequence in which an amino acid residue at position 125 in the amino acid sequence represented by SEQ ID NO: 1 is substituted with a serine residue is substituted with a saccharide-bound group derived from a cysteine residue or an asparagine residue.

(7) The IL-2 variant according to any one of (2) to (6), which comprises an amino acid sequence in which at least one amino acid residue selected from the group consisting of amino acid residues at positions 12, 15, 16, 19, 88, 91, and 119 in the amino acid sequence represented by SEQ ID NO: 1 or the amino acid sequence in which an amino acid residue at position 125 in the amino acid sequence represented by SEQ ID NO: 1 is substituted with a serine residue is substituted with the saccharide-bound group derived from the cysteine residue or the asparagine residue.

(8) The IL-2 variant according to (6) or (7), wherein the saccharide-bound group derived from the cysteine residue comprises a structure represented by (Formula 1),

[Chem. 9]

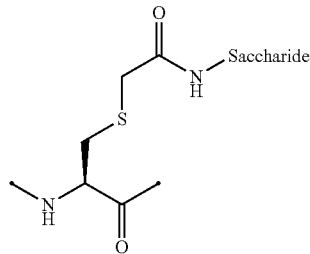

(Formula 1)

[in (Formula 1), Saccharide indicates a saccharide].

(9) The IL-2 variant according to (6) or (7), wherein the saccharide-bound group derived from the asparagine residue comprises a structure represented by (Formula 2),

[Chem. 10]

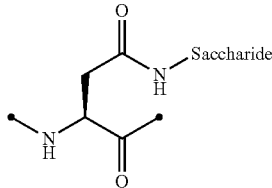

(Formula 2)

[in (Formula 2), Saccharide indicates a saccharide].

(10) The IL-2 variant according to any one of (2) to (9), which is an IL-2 variant in which PEG is further bound to the saccharide-bound IL-2 variant.

(11) The IL-2 variant according to any one of (2) to (10), which comprises an amino acid sequence in which at least one amino acid residue selected from the group consisting of amino acid residues at positions 1, 3, 51, and 78 in the amino acid sequence represented by SEQ ID NO: 1 or the amino acid sequence in which an amino acid residue at position 125 in the amino acid sequence represented by SEQ ID NO: 1 is substituted with a serine residue is substituted with with a PEGylated amino acid residue.

(12) The IL-2 variant according to (2) of (3), wherein PEG is bound to at least one amino acid residue selected from the group consisting of amino acid residues at positions 4, 5, 6, 7, 8, 60, 78, 79, 99, 100, 101, and 129 in the amino acid sequence of IL-2.

(13) The IL-2 variant according to any one of (2), (3) and (12), which comprises an amino acid sequence in which at least one amino acid residue selected from the group consisting of amino acid residues at positions 4, 5, 6, 7, 8, 60, 78, 79, 99, 100, 101, and 129 in the amino acid sequence represented by SEQ ID NO: 1 or the amino acid sequence in which an amino acid residue at position 125 in the amino acid sequence of SEQ ID NO: 1 is substituted with a serine residue is substituted with a PEGylated amino acid residue.

(14) The IL-2 variant according to any one of (2), (3), (12) and (13), wherein at least one amino acid residue selected from the group consisting of amino acid residues at positions 4, 5, 8, 78, and 129 in the amino acid sequence represented by SEQ ID NO: 1 or the amino acid sequence in which an amino acid residue at position 125 in the amino acid sequence represented by SEQ ID NO: 1 is substituted with a serine residue is substituted with a PEGylated amino acid residue.

(15) The IL-2 variant according to any one of (2), (3), and (12) to (14), wherein at least two amino acid residues selected from the group consisting of amino acid residues at positions 4, 5, 8, 78, and 129 in the amino acid sequence represented by SEQ ID NO: 1 or the amino acid sequence in which an amino acid residue at position 125 in the amino acid sequence represented by SEQ ID NO: 1 is substituted with a serine residue are substituted with a PEGylated amino acid residue.

(16) The IL-2 variant according to any one of (2), (3), and (12) to (15), wherein at least one amino acid residue selected from the group consisting of amino acid residues at positions 4, 5, and 8 and an amino acid residue at position 78 or 129 in the amino acid sequence represented by SEQ ID NO: 1 or the amino acid sequence in which an amino acid residue at position 125 in the amino acid sequence represented by SEQ ID NO: 1 is substituted with a serine residue are substituted with a PEGylated amino acid residue.

(17) The IL-2 variant according to any one of (2), (3), and (12) to (16), wherein a PEGylatedamino acid residue is a PEGylated non-natural amino acid residue.

(18) The IL-2 variant according to (17), wherein the PEGylated non-natural amino acid residue is a PEGylated group derived from an amino acid residue comprising a thiol group (—SH) or a PEGylated group derived from an amino acid residue comprising an azide group.

(19) The IL-2 variant according to (17) or (18), wherein the PEGylated non-natural amino acid residue is a group derived from an $N^6$-[{(o-azidobenzyl)oxy}carbonyl]-L-lysine(o-Az-Z-Lys) residue, a group derived from an $N^6$-[{(m-azidobenzyl)oxy}carbonyl]-L-lysine(m-Az-Z-Lys) residue, or a group derived from a cysteine residue.

(20) The IL-2 variant according to (19), wherein the PEGylated group derived from an o-Az-Z-Lys residue comprise a structure represented by (Formula 11) and/or (Formula 12).

[Chem. 11]
(Formula 11)
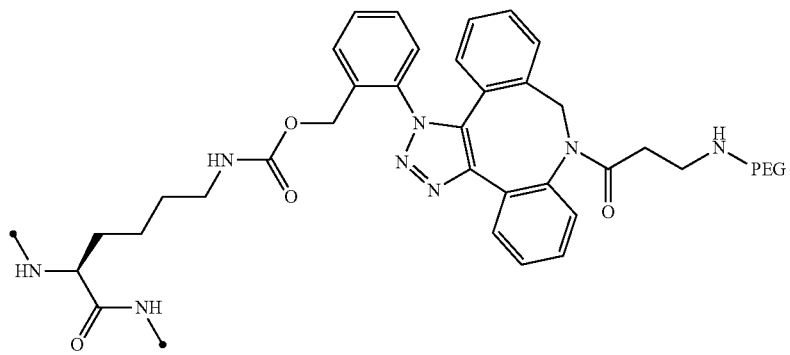
[Chem. 12]
(Formula 12)
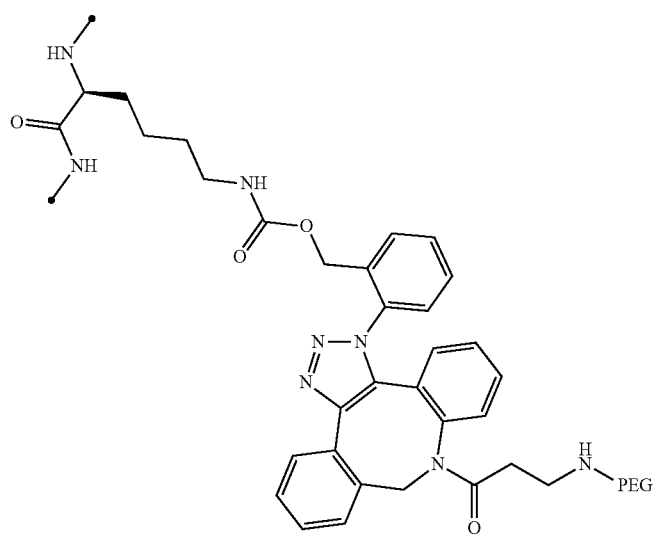
(21) The IL-2 variant according to (19), wherein the PEGylated group derived from an m-Az-Z-Lys residue comprises a structure represented by (Formula X4) and/or (Formula X5).

[Chem. 13]
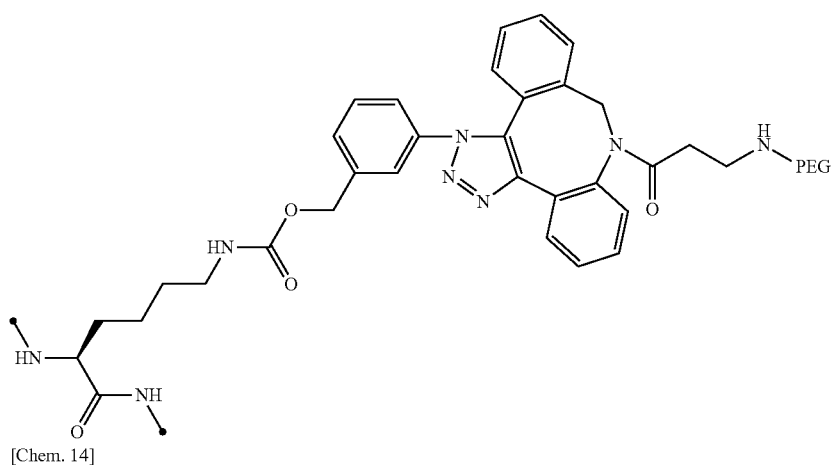
(Formula Y4)
[Chem. 14]
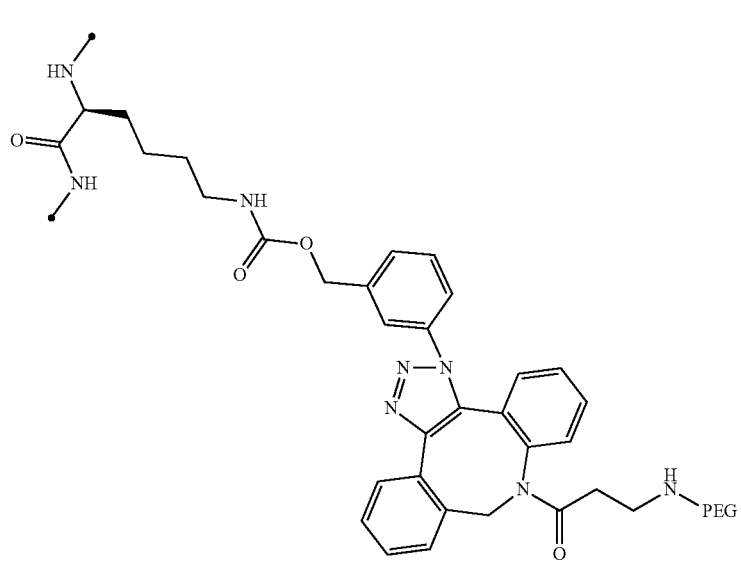
(Formula Y5)
(22) The IL-2 variant according to (19), wherein the PEGylated group derived from the cysteine residue comprises a structure represented by (Formula X11), and/or (Formula X12), and/or (Formula X13).
-continued
[Chem. 16]
[Chem. 15]
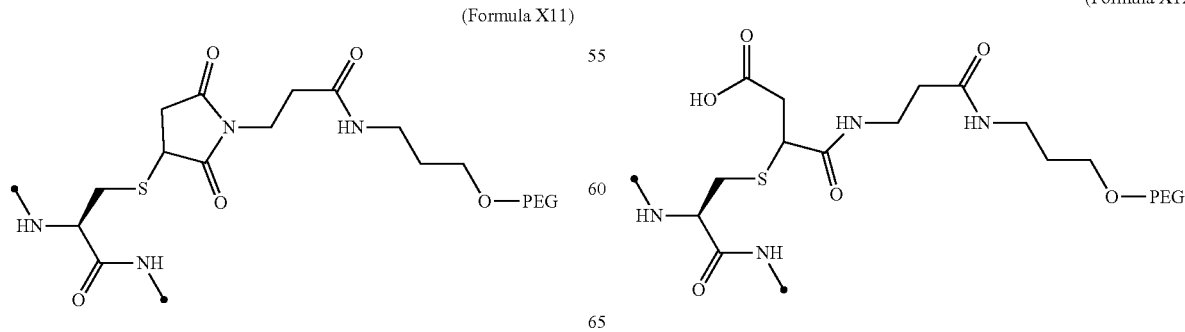
(Formula X11)
(Formula X12)

-continued

[Chem. 17]

(Formula X13)

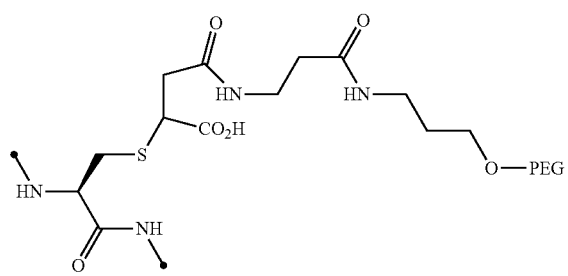

(23) The IL-2 variant according to any one of (2) and (10) to (22), wherein PEG is linear.
(24) The IL-2 variant according to any one of (2) and (10) to (22), wherein PEG is branched.
(25) The IL-2 variant according to any one of (2) and (10) to (24), wherein PEG has an average molecular weight of 10 kDa or more.
(26) The IL-2 variant according to any one of (2) and (10) to (25), wherein PEG has an average molecular weight of 10 kDa, 20 kDa, 30 kDa, 40 kDa, 50 kDa, 60 kDa, 70 kDa, or 80 kDa.
(27) The IL-2 variant according to any one of (2) and (10) to (26), wherein PEG comprises a structure represented by at least one formula of (Formula 13), (Formula 14), (Formula 15), (Formula 16), (Formula X7), (Formula X8), (Formula X9), (Formula X10), (Formula X11), (Formula X13), (Formula X14), or (Formula X15).

[Chem. 18]

(Formula 13)

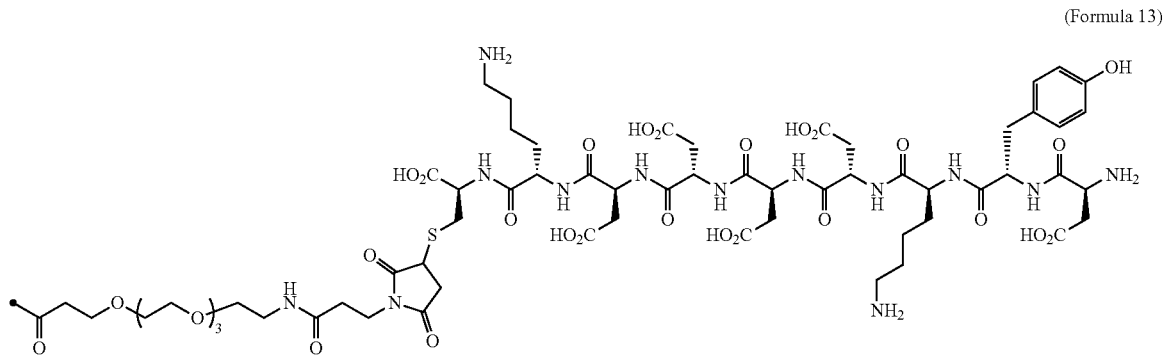

[Chem. 19]

(Formula 14)

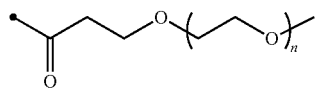

[Chem. 20]

(Formula X7)

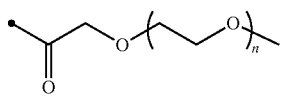

[Chem. 21]

(Formula 15)

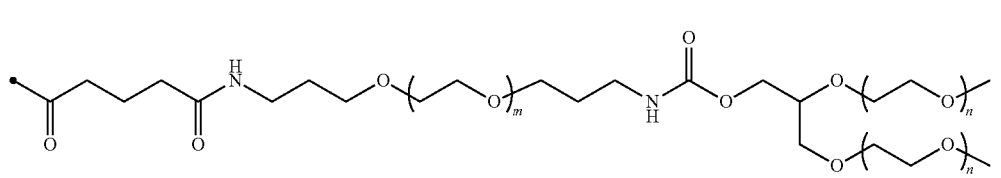

[Chem. 22]

(Formula 16)

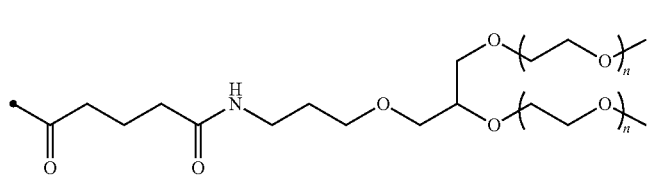

-continued

[Chem. 23]

(Formula X8)

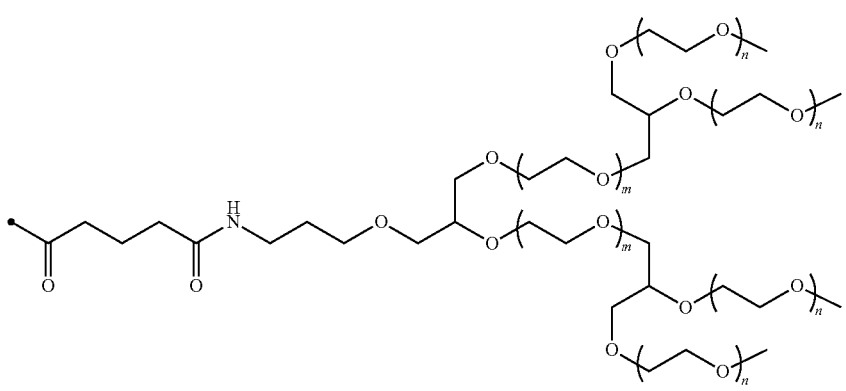

[Chem. 24]

(Formula X9)

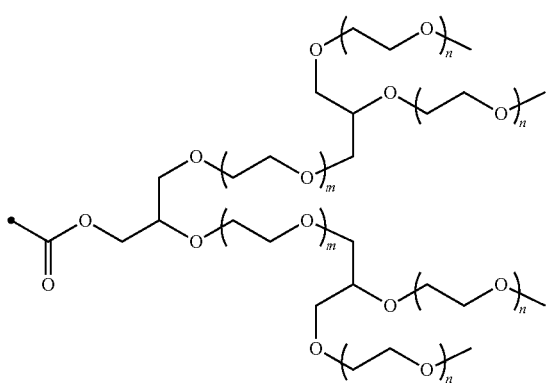

[Chem. 25]

(Formula X10)

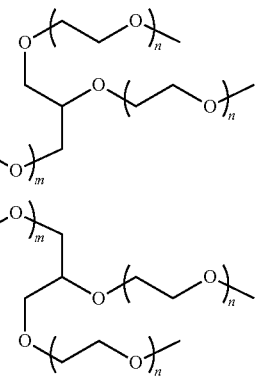

[Chem. 26]

(Formula X13)

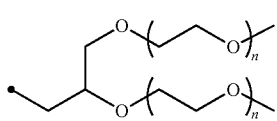

[Chem. 27]

(Formula X14)

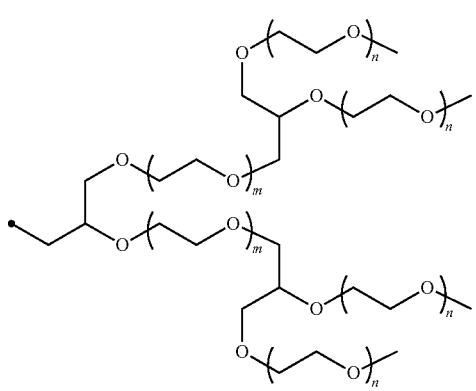

[Chem. 28]

(Formula X11)

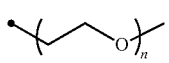

[Chem. 29]

(Formula X15)

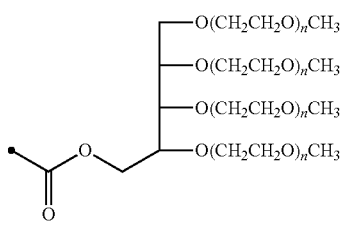

(28) The IL-2 variant according to any one of (1) to (27), wherein a methionine residue is further bound to an N-terminal of IL-2.

(29) The IL-2 variant according to any one of (1) to (28), wherein N-terminal alanine of IL-2 is deleted.

(30) The IL-2 variant according to any one of (1) to (29), wherein N-terminal alanine of IL-2 is deleted and further methionine is bonded.

(31) A method for producing the IL-2 variant according to any one of (1) to (30).

(32) A composition comprising the IL-2 variant according to any one of (1) to (30).

(33) A therapeutic agent for an immune disease, comprising the IL-2 variant according to any one of (1) to (30).

(34) A method for improving selectivity of IL-2 for IL-2R$_{\alpha\beta\gamma}$.

(35) The method according to (34), comprising binding a saccharide and/or PEG to IL-2.

(36) The method according to (35), comprising binding a saccharide to at least one amino acid residue selected from the group consisting of amino acid residues at positions 11, 12, 13, 15, 16, 18, 19, 20, 84, 87, 88, 91, 92, 108, 115, 119, 122, 123, and 130 in an amino acid sequence of the IL-2.

(37) The method according to (35) or (36), wherein the saccharide is at least one selected from saccharides comprising structures represented by (Formula 4) to (Formula 8), (Formula Y1), (Formula Y2), or (Formula Y3).

[Chem. 30]

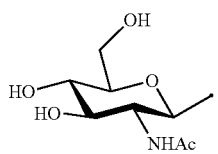

(Formula Y1)

[Chem. 31]

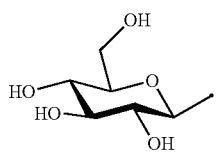

(Formula Y2)

[Chem. 32]

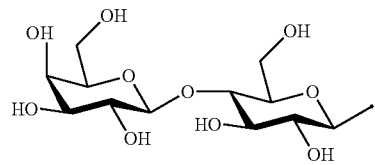

(Formula 4)

[Chem. 33]

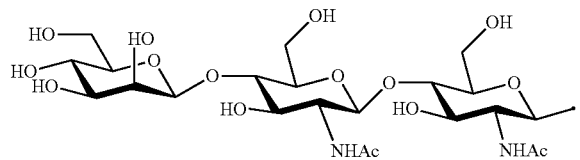

(Formula 5)

[Chem. 34]

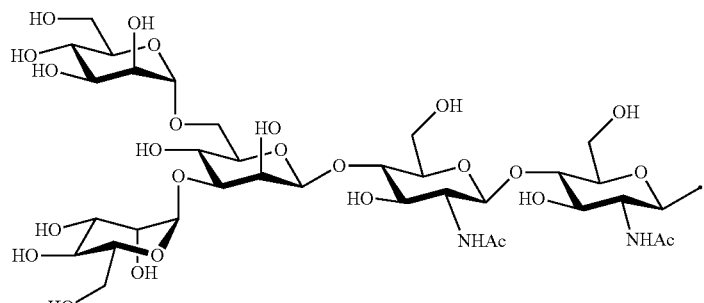

(Formula 6)

[Chem. 35]

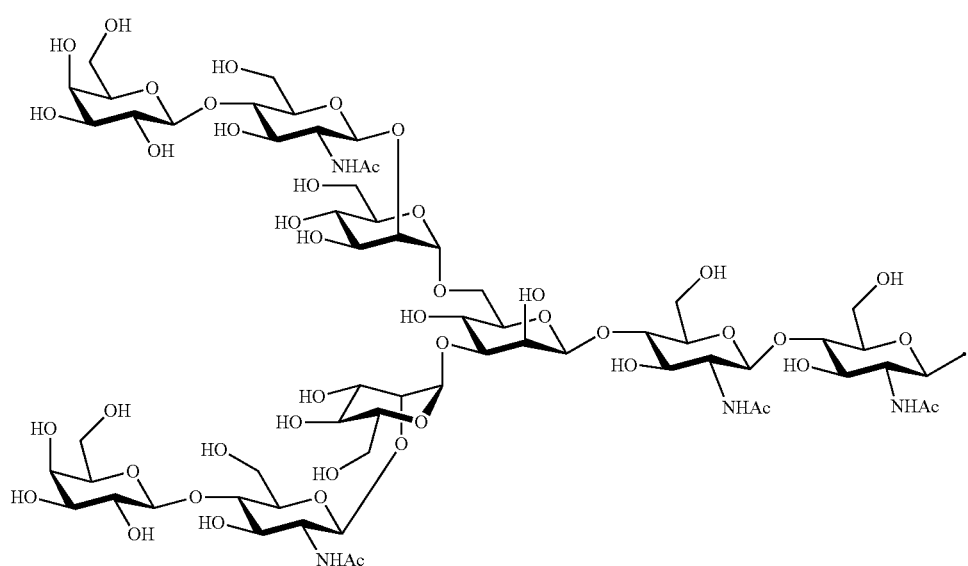

(Formula 7)

-continued
[Chem. 36]
(Formula 8)
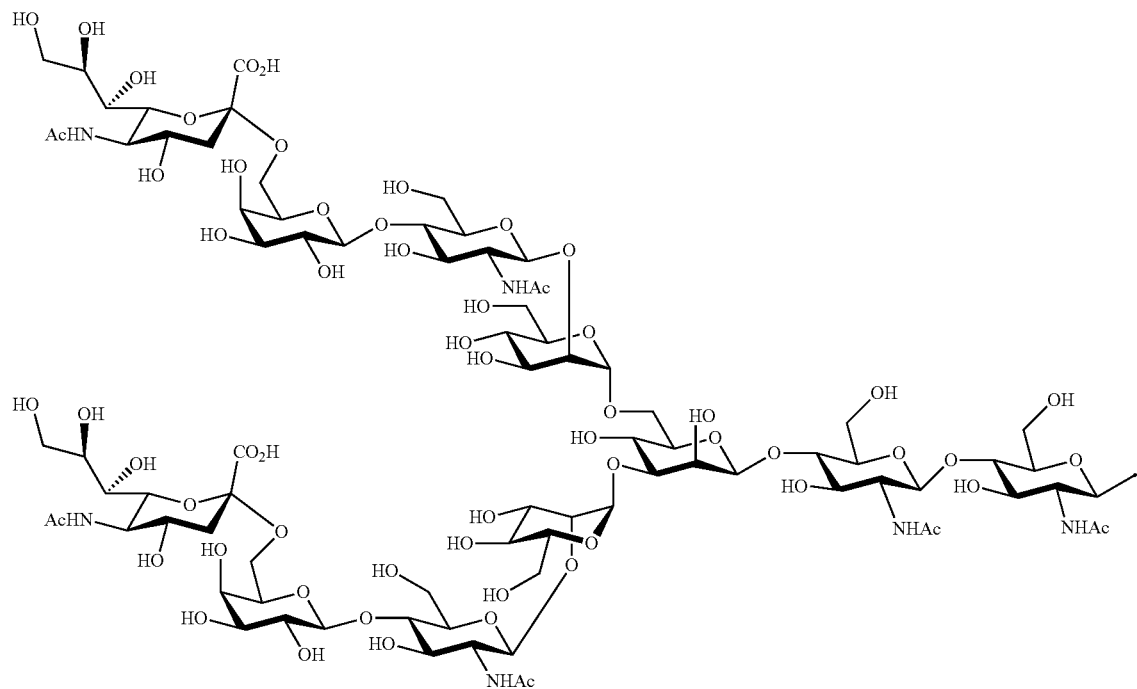
[Chem. 37]
(Formula Y3)
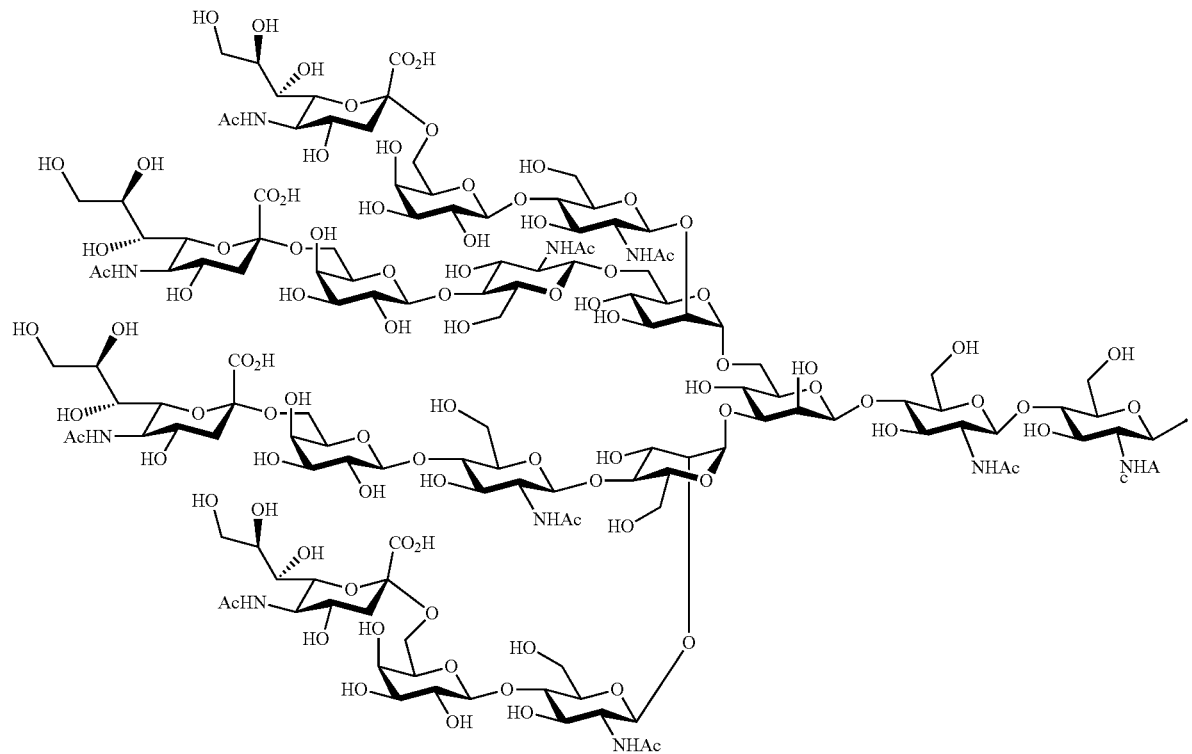

(38) The method according to any one of (35) to (37), comprising substituting at least one amino acid residue selected from the group consisting of amino acid residues at positions 11, 12, 13, 15, 16, 18, 19, 20, 84, 87, 88, 91, 92, 108, 115, 119, 122, 123, and 130 in IL-2 comprising an amino acid sequence represented by SEQ ID NO: 1 or an amino acid sequence in which an amino acid residue at position 125 in the amino acid sequence represented by SEQ ID NO: 1 is substituted with a serine residue, with a saccharide-bound group derived from a cysteine residue or an asparagine residue.

(39) The method according to any one of (35) to (38), comprising substituting at least one amino acid residue selected from the group consisting of amino acid residues at positions 12, 15, 16, 19, 88, 91, and 119 in an amino acid sequence represented by SEQ ID NO: 1 or an amino acid sequence in which an amino acid residue at position 125 in the amino acid sequence represented by SEQ ID NO: 1 is substituted with a serine residue, with a saccharide-bound group derived from a cysteine residue or an asparagine residue.

(40) The method according to (38) or (39), wherein the saccharide-bound group derived from the cysteine residue has a structure represented by (Formula 1),

[Chem. 38]

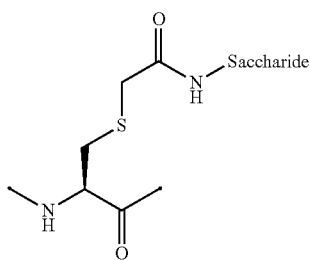

(Formula 1)

[in (Formula 1), Saccharide indicates a saccharide].

(41) The method according to (38) or (39), wherein the saccharide-bound group derived from the asparagine residue has a structure represented by (Formula 2),

[Chem. 39]

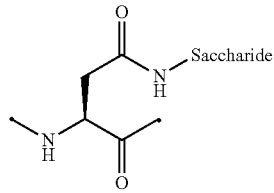

(Formula 2)

[in (Formula 2), Saccharide indicates a saccharide].

(42) The method according to any one of (35) to (41), further comprising binding the PEG to a saccharide-bound IL-2 variant.

(43) The method according to (42), which comprises an amino acid sequence in which at least one amino acid residue selected from the group consisting of amino acid residues at positions 1, 3, 51, and 78 in the amino acid sequence represented by SEQ ID NO: 1 or an amino acid sequence in which an amino acid residue at position 125 in the amino acid sequence represented by SEQ ID NO: 1 is substituted with a serine residue is substituted with a PEGylated amino acid residue.

(44) The method according to (35), wherein the PEG is bound to at least one amino acid residue selected from the group consisting of amino acid residues at positions 4, 5, 6, 7, 8, 60, 78, 79, 99, 100, 101, and 129 in an amino acid sequence of the IL-2.

(45) The method according to (35) or (44), which comprises an amino acid sequence in which at least one amino acid residue selected from the group consisting of amino acid residues at positions 4, 5, 6, 7, 8, 60, 78, 79, 99, 100, 101, and 129 in the amino acid sequence represented by SEQ ID NO: 1 or the amino acid sequence in which an amino acid residue at position 125 in the amino acid sequence of SEQ ID NO: 1 is substituted with a serine residue is substituted with a PEGylated amino acid residue.

(46) The method according to any one of (35), (44) and (45), wherein at least one amino acid residue selected from amino acid residues at positions 4, 5, 8, 78, and 129 in the amino acid sequence represented by SEQ ID NO: 1 or the amino acid sequence in which an amino acid residue at position 125 in the amino acid sequence represented by SEQ ID NO: 1 is substituted with a serine residue is substituted with a PEGylate amino acid residue.

(47) The method according to any one of (35) and (44) to (46), wherein at least two amino acid residues selected from amino acid residues at positions 4, 5, 8, 78, and 129 in the amino acid sequence represented by SEQ ID NO: 1 or the amino acid sequence in which an amino acid residue at position 125 in the amino acid sequence represented by SEQ ID NO: 1 is substituted with a serine residue are substituted with PEGylated amino acid residues.

(48) The method according to any one of (35) and (42) to (47), wherein a PEGylated amino acid residue is a PEGylated non-natural amino acid residue.

(49) The method according to (48), wherein the PEGylated non-natural amino acid residue is a PEGylated group derived from an amino acid residue comprising a thiol group (—SH) or a PEGylated group derived from an amino acid residue comprising an azide group.

(50) The method according to (48) or (49), wherein the PEGylated non-natural amino acid residue is a group derived from an $N^6$-[{(o-azidobenzyl)oxy}carbonyl]-lysine (o-Az-Z-Lys) residue, a group derived from an $N^6$-[{(m-azidobenzyl)oxy}carbonyl]-L-lysine(m-Az-Z-Lys) residue, or a group derived from a cysteine residue.

(51) The method according to (50), wherein the PEGylated group derived from an o-Az-Z-Lys residue comprises a structure represented by (Formula 11) and/or (Formula 12).

[Chem. 40]
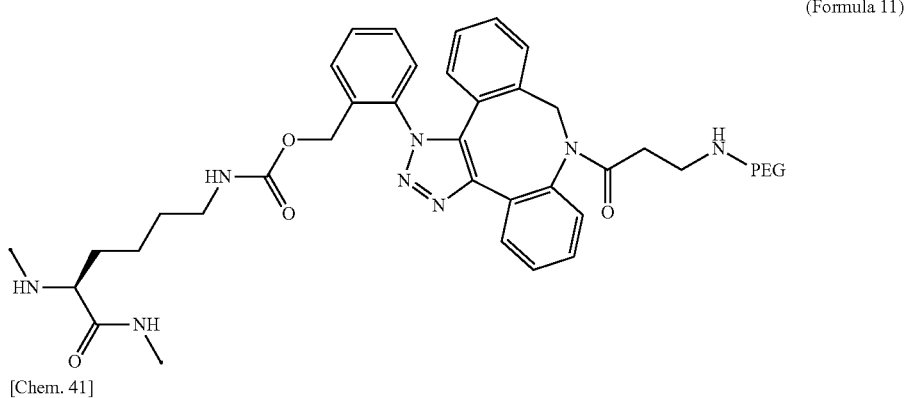
(Formula 11)
[Chem. 41]
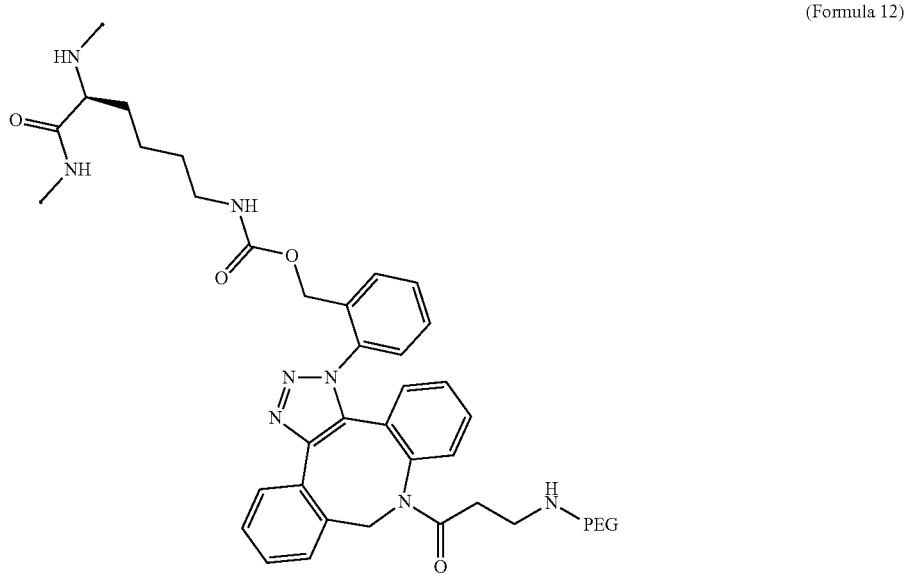
(Formula 12)
(52) The method according to (50), wherein the PEGylated group derived from an m-Az-Z-Lys residue comprises a structure represented by (Formula X4) and/or (Formula X5).
[Chem. 42]
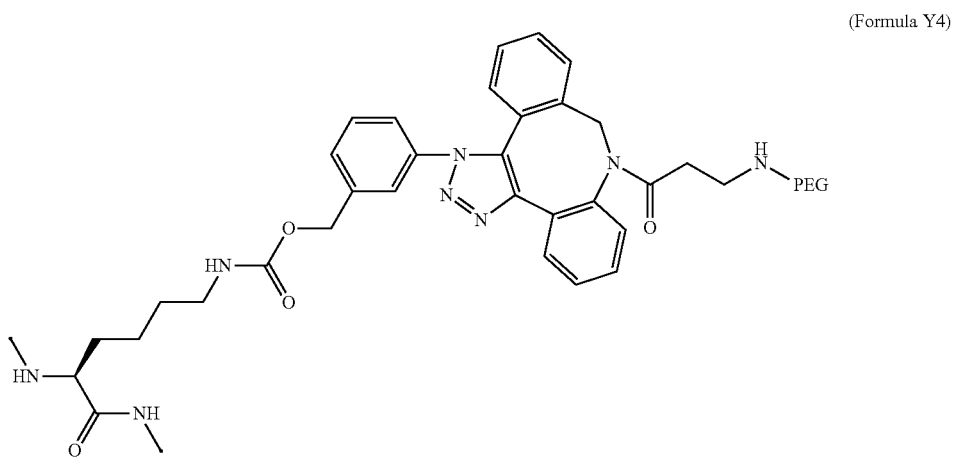
(Formula Y4)

[Chem. 43]

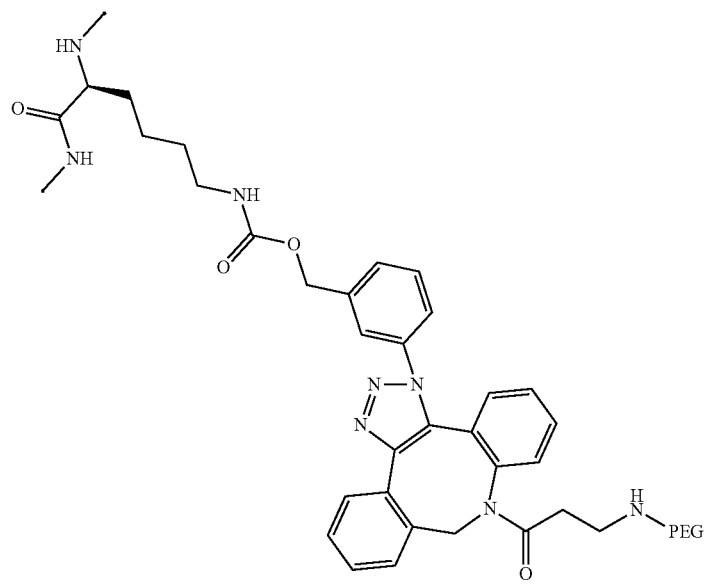
(Formula Y5)

(53) The method according to (50), wherein the PEGylated group derived from the cysteine residue comprises a structure represented by (Formula X11), and/or (Formula X12), and/or (Formula X13).

[Chem. 44]

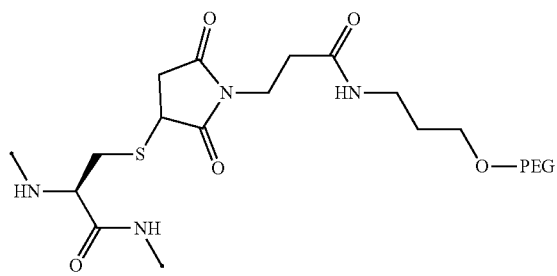
(Formula X11)

[Chem. 45]

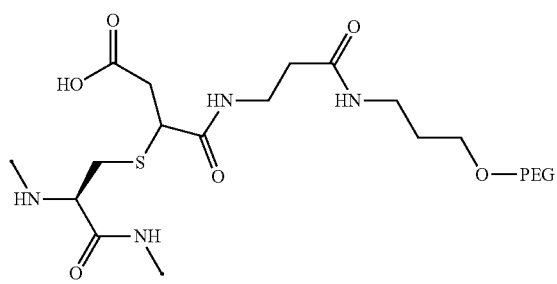
(Formula X12)

[Chem. 46]

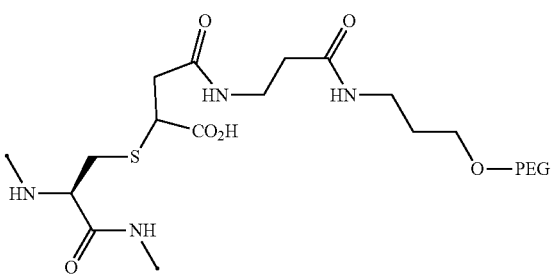
(Formula X13)

(54) The method according to any one of (35) and (42) to (53), wherein the PEG is linear.

(55) The method according to any one of (35) and (42) to (53), wherein the PEG is branched.

(56) The method according to any one of (35) and (42) to (55), wherein the PEG has an average molecular weight of 10 kDa or more.

(57) The method according to any one of (35) and (42) to (56), wherein the PEG has an average molecular weight of 10 kDa, 20 kDa, 30 kDa, 40 kDa, 50 kDa, 60 kDa, 70 kDa, or 80 kDa.

(58) The method according to any one of (35) and (42) to (57), wherein the PEG comprises a structure represented by at least one formula of (Formula 13), (Formula 14), (Formula 15), (Formula 16), (Formula X7), (Formula X8), (Formula X9), (Formula X10), (Formula X11), (Formula X13), (Formula X14), or (Formula X15).

[Chem. 47]
(Formula 13)
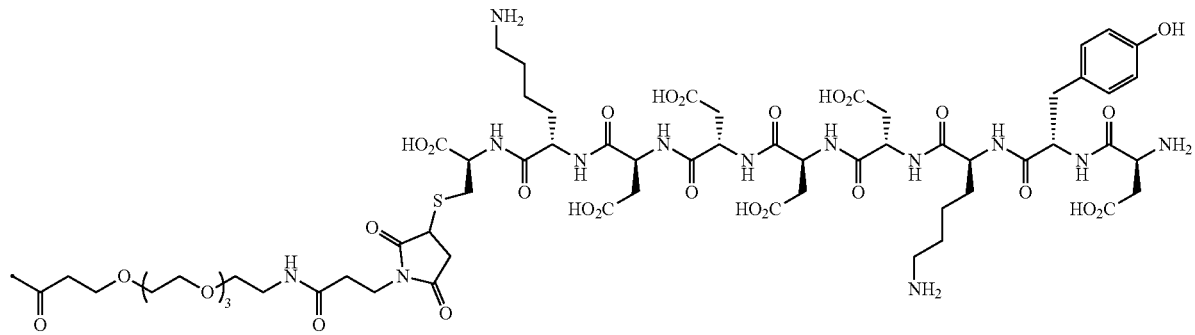
[Chem. 48]
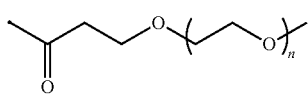
(Formula 14)
[Chem. 49]
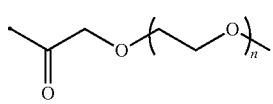
(Formula X7)
[Chem. 50]
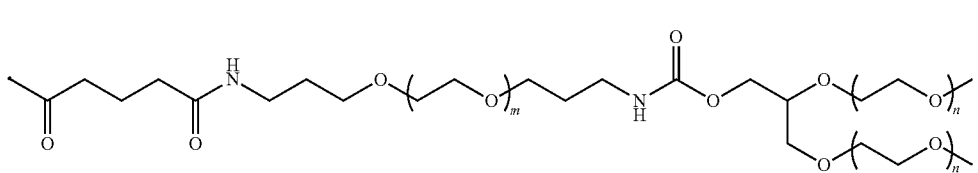
(Formula 15)
[Chem. 51]
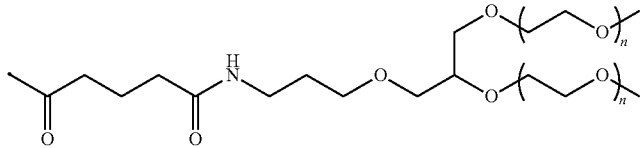
(Formula 16)
[Chem. 52]
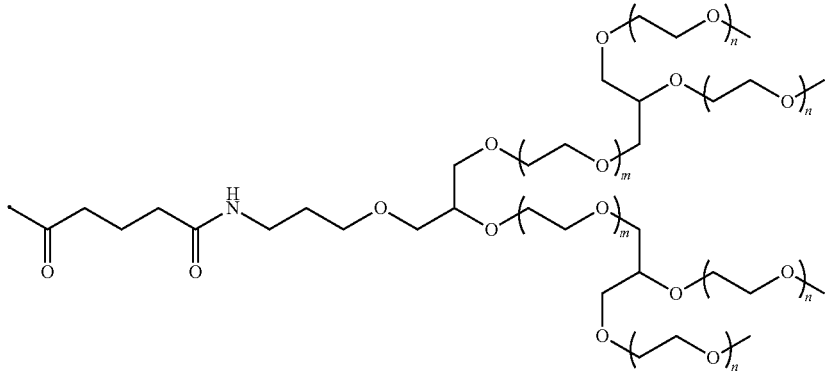
(Formula X8)

[Chem. 53]

(Formula X9)

[Chem. 54]

(Formula X10)

[Chem. 55]

(Formula X13)

[Chem. 56]

(Formula X14)

[Chem. 57]

(Formula X11)

[Chem. 58]

(Formula X15)

[Chem. 56]

(59) The method according to any one of (34) to (58), wherein a methionine residue is further bound to an N-terminal of the IL-2.
(60) The method according to any one of (34) to (59), wherein N-terminal alanine of the IL-2 is deleted.
(61) The method according to any one of (34) to (59), wherein N-terminal alanine of the IL-2 is deleted, and further methione is bonded.
(62) A method for selectively activating regulatory T cells.
(63) A method for reducing an affinity of IL-2 for at least one of an IL-2Rβ subunit and an IL-2Rγ subunit.
(64) A method for improving an affinity of IL-2 for an IL-2Rα subunit.

EFFECTS OF THE INVENTION

An IL-2 variant of the present invention selectively binds to IL-2R$_{\alpha\beta\gamma}$ highly expressed on Tregs and selectively activates Tregs. According to the present invention, it is possible to provide an IL-2 variant, a method for producing the IL-2 variant, a composition and a therapeutic agent for an immune disease comprising the IL-2 variant, a method for increasing selectivity of IL-2 for IL-2R$_{\alpha\beta\gamma}$, a method for improving an affinity of IL-2 for an IL-2Rα subunit, a method of reducing an affinity of IL-2 for at least one of an IL-2Rβ subunit and an IL-2Rγ subunit, and a method for selectively activating regulatory T cells.

FIG. 1A is a graph showing Treg proliferation promoting activities of various glycosylated IL-2 variants. The black circles indicate an activity of IL-2 produced by Peprotech (hereinafter referred to as IL-2 (P)), black triangles indicate an activity of H16C-2, black squares indicate an activity of L19C-9, and black horizontal bars indicate an activity of N88C-2. A horizontal axis indicates an IL-2 concentration (pM), and a vertical axis indicates an IL-2-dependent cell proliferation rate (%).

Figure 1B:
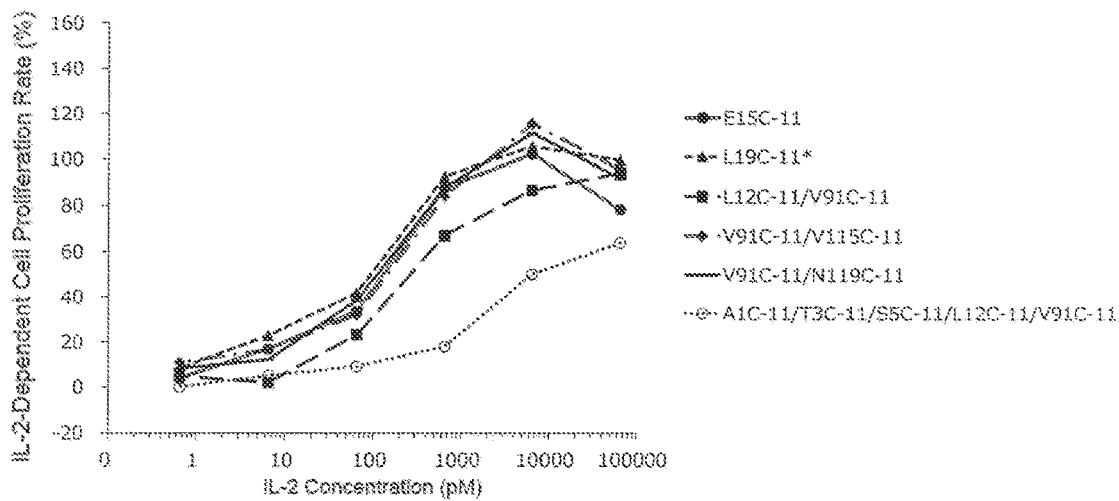

FIG. 1B is a graph showing Treg proliferation promoting activities of various glycosylated IL-2 variants. Black circles indicate an activity of E15C-11, black triangles indicate an activity of L19C-11*, black squares indicate an activity of L12C-11/V91C-11, black diamonds indicate an activity of V91C-11/V115C-11, black horizontal bars indicate an activity of V91C-11N119C-11, and white circles indicate an activity of A1C-11/T3C-11/S5C-11/L12C-11/V91C-11. A horizontal axis indicates an IL-2 concentration (pM), and a vertical axis indicates an IL-2-dependent cell proliferation rate (%).

Figure 1C:
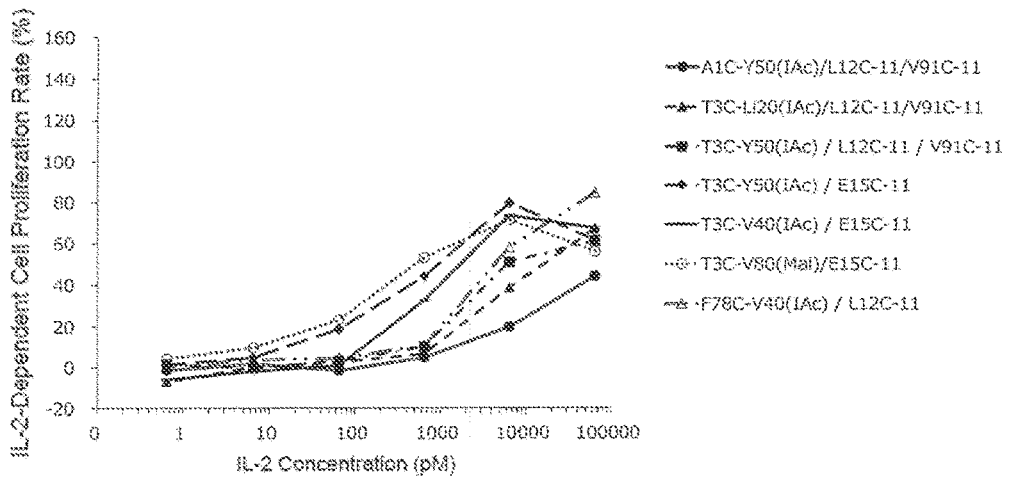

FIG. 1C is a graph showing Treg proliferation promoting activities of various Cys-PEGylated and glycosylated IL-2 variants. Black circles indicate an activity of A1C-Y50 (IAc)/L12C-11/V91C-11, black triangles indicate an activity of T3C-Li20(IAc)/L12C-11/V91C-11, and black squares indicate an activity of T3C-Y50(IAc)/L12C-11/V91C-11, black diamonds indicate an activity of T3C-Y50(IAc)/E15C-11, black bars indicate an activity of T3C-V40(IAc)/E15C-11, white circles indicate an activity of T3C-V80 (Mal)/E15C-11, and white triangles indicate an activity of F78C-V40(IAc)/L12C-11. A horizontal axis indicates an IL-2 concentration (pM), and a vertical axis indicates an IL-2-dependent cell proliferation rate (%).

Figure 1D:
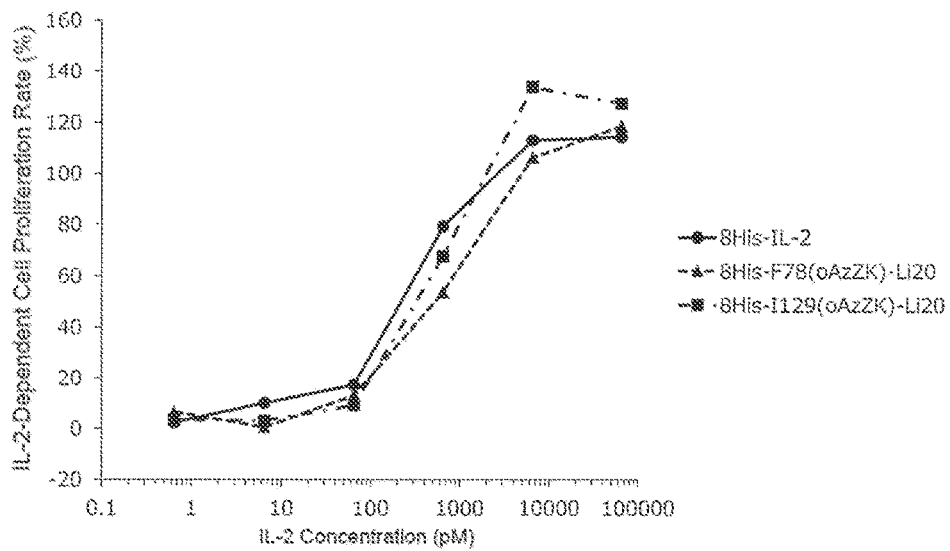

FIG. 1D is a graph showing Treg proliferation promoting activities of various PEGylated IL-2 variants. Black circles indicate an activity of 8His-IL-2, black triangles indicate an activity of 8His-F78(oAzZK)-Li20, and black squares indicate an activity of 8His-I129(oAzZK)-Li20. A horizontal axis indicates an IL-2 concentration (pM), and a vertical axis indicates an IL-2-dependent cell proliferation rate (%).

Figure 1E:
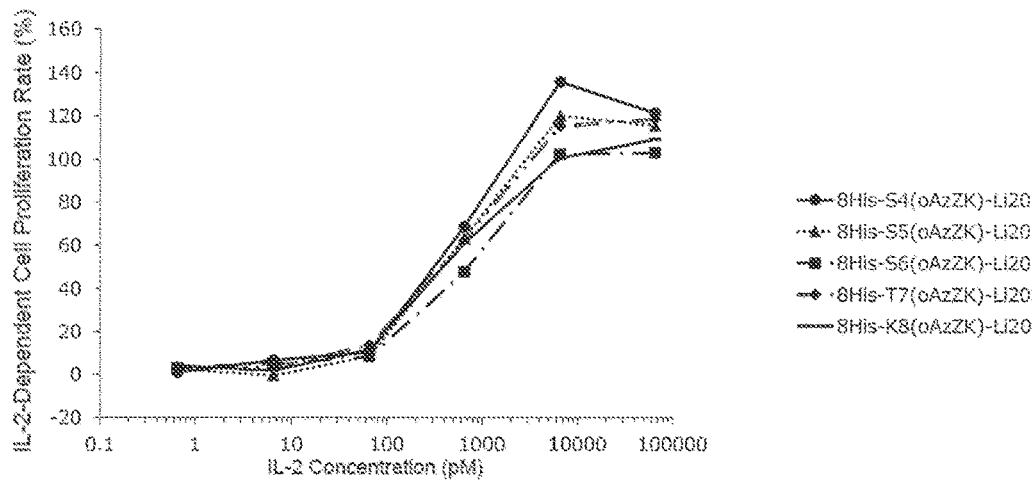

FIG. 1E is a graph showing Treg proliferation promoting activities of various PEGylated IL-2 variants. Black circles indicate an activity of 8His-S4(oAzZK)-Li20, black triangles indicate an activity of 8His-S5(oAzZK)-Li20, black squares indicate an activity of 8His-S6(oAzZK)-Li20, black diamonds indicate an activity of 8His-T7(oAzZK)-Li20, and black horizontal bars indicate an activity of 8His-K8(oAzZK)-Li20. A horizontal axis indicates an IL-2 concentration (pM), and a vertical axis indicates an IL-2-dependent cell proliferation rate (%).

Figure 1F:
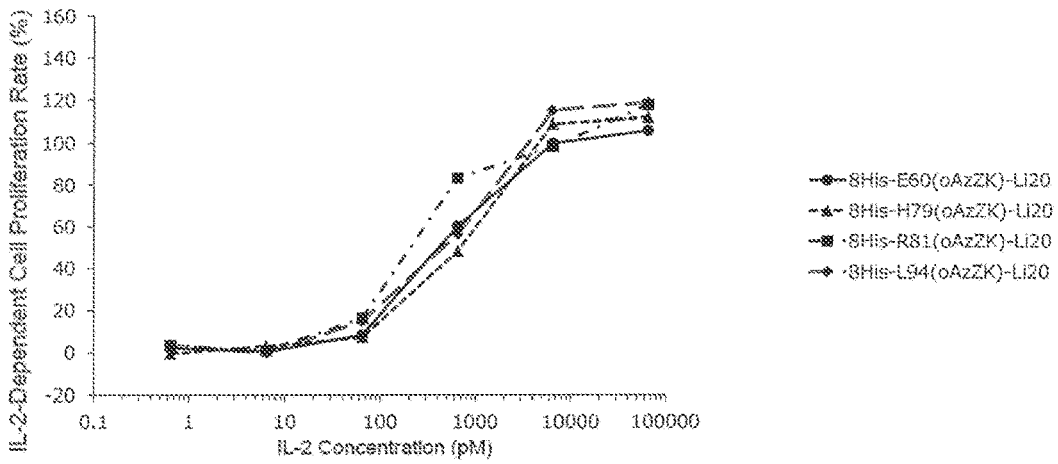

FIG. 1F is a graph showing Treg proliferation promoting activities of various PEGylated IL-2 variants. Black circles indicate an activity of 8His-E60(oAzZK)-Li20, black triangles indicate an activity of 8His-H79(oAzZK)-Li20, black squares indicate an activity of 8His-R81(oAzZK)-Li20, and black diamonds indicate an activity of 8His-L94(oAzZK)-Li20. A horizontal axis indicates an IL-2 concentration (pM), and a vertical axis indicates an IL-2-dependent cell proliferation rate (%).

Figure 1G:
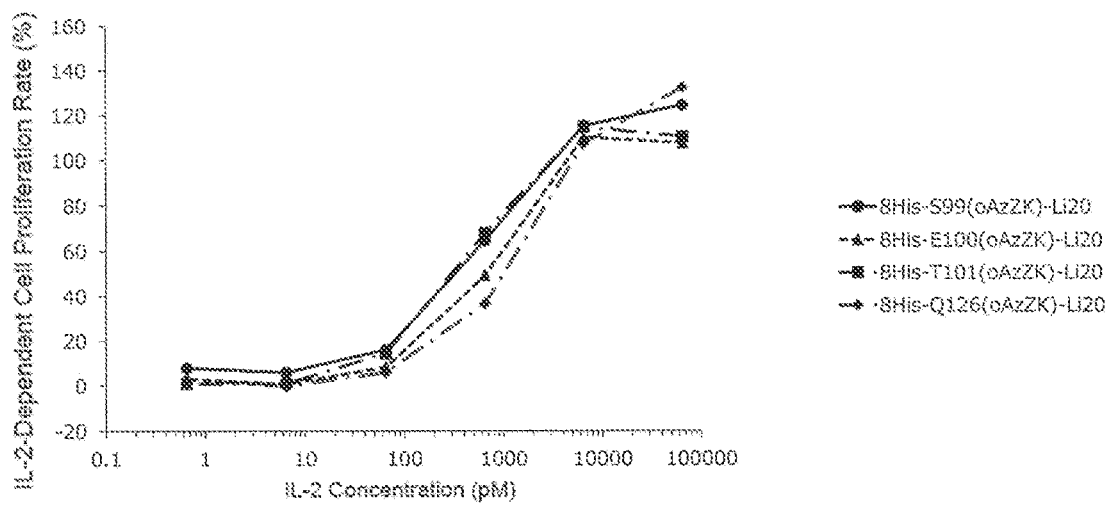

FIG. 1G is a graph showing Treg proliferation promoting activities of various PEGylated IL-2 variants. Black circles indicate an activity of 8His-S99(oAzZK)-Li20, black triangles indicate an activity of 8His-E100(oAzZK)-Li20, black squares indicate an activity of 8His-T101(oAzZK)-Li20, and black diamonds indicate an activity of 8His-Q126(oAzZK)-Li20. A horizontal axis indicates an IL-2 concentration (pM), and a vertical axis indicates an IL-2-dependent cell proliferation rate (%).

Figure 1H:
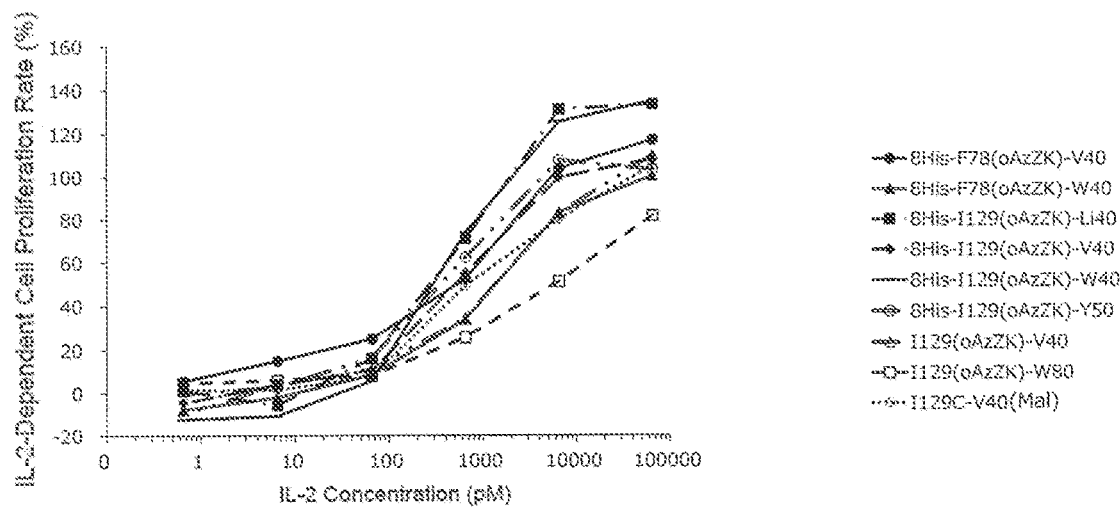

FIG. 1H is a graph showing Treg proliferation promoting activities of various PEGylated IL-2 variants. Black circles indicate an activity of 8His-F78(oAzZK)-V40, black triangles indicate an activity of 8His-F78(oAzZK)-W40, black squares indicate an activity of 8His-I129(oAzZK)-Li40, black diamonds indicate an activity of 8His-I129(oAzZK)-V40, black bars indicate an activity of 8His-I129(oAzZK)-W40, white circles indicate an activity of 8His-I129(oAzZK)-Y50, white triangles indicate an activity of I129(oAzZK)-V40, white squares indicate an activity of I129(oAzZK)-W80, and white diamonds indicate an activity of I129C-V40(Mal). A horizontal axis indicates an IL-2 concentration (pM), and a vertical axis indicates an IL-2-dependent cell proliferation rate (%).

Figure 1I:
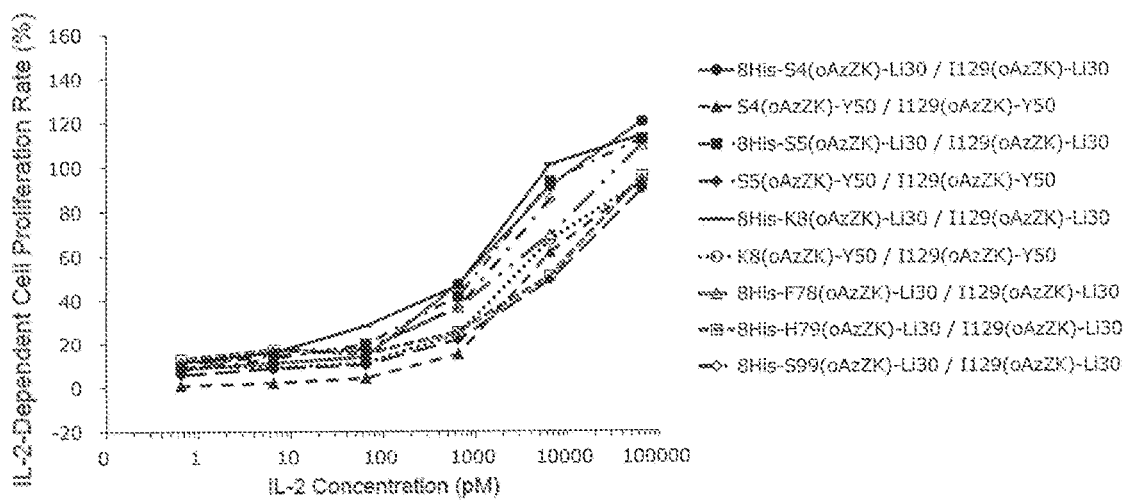

FIG. 1I is a graph showing Treg proliferation promoting activities of various PEGylated IL-2 variants. Black circles indicate an activity of 8His-S4(oAzZK)-Li30/4129(oAzZK)-Li30, black triangles indicate an activity of S4(oAzZK)-Y50/I129(oAzZK)-Y50, black squares indicate an activity of 8His-S5(oAzZK)-Li30/I129(oAzZK)-Li30, black diamonds indicate an activity of S5(oAzZK)-Y50/I129 (oAzZK)-Y50, black bars indicate an activity of 8His-K8(oAzZK)-Li30/4129(oAzZK)-Li30, white circles indicate an activity of K8(oAzZK)-Y50/I129(oAzZK)-Y50, white triangles indicate an activity of 8His-F78(oAzZK)-Li30/I129 (oAzZK)-Li30, white squares indicate an activity of 8His-H79(oAzZK)-Li30/I129(oAzZK)-Li30, and white diamonds indicate an activity of 8His-S99(oAzZK)-Li30/I129(oAzZK)-Li30. A horizontal axis indicates an IL-2 concentration (pM), and a vertical axis indicates an IL-2-dependent cell proliferation rate (%).

Figure 1J:
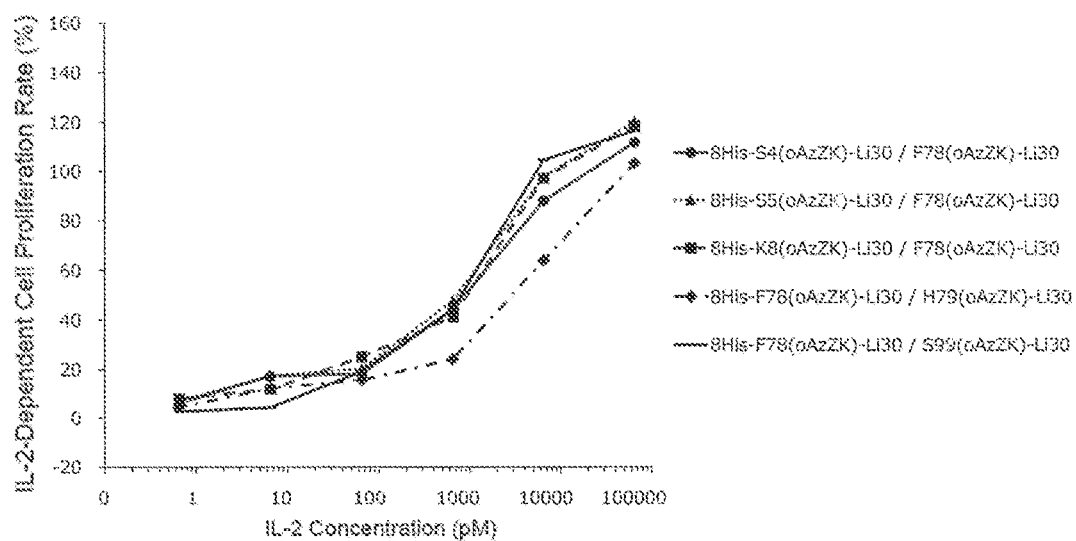

FIG. 1J is a graph showing Treg proliferation promoting activities of various PEGylated IL-2 variants. Black circles indicate an activity of 8His-S4(oAzZK)-Li30/F78(oAzZK)-Li30, black triangles indicate an activity of 8His-S5(oAzZK)-Li30/F78(oAzZK)-Li30, black squares indicate an activity of 8His-K8(oAzZK)-Li30/F78(oAzZK)-Li30, black diamonds indicate an activity of 8His-F78(oAzZK)-Li30/H79(oAzZK)-Li30, and black bars indicate an activity of 8His-F78(oAzZK)-Li30/S99(oAzZK)-Li30. A horizontal axis indicates an IL-2 concentration (pM), and a vertical axis indicates an IL-2-dependent cell proliferation rate (%).

Figure 2A:
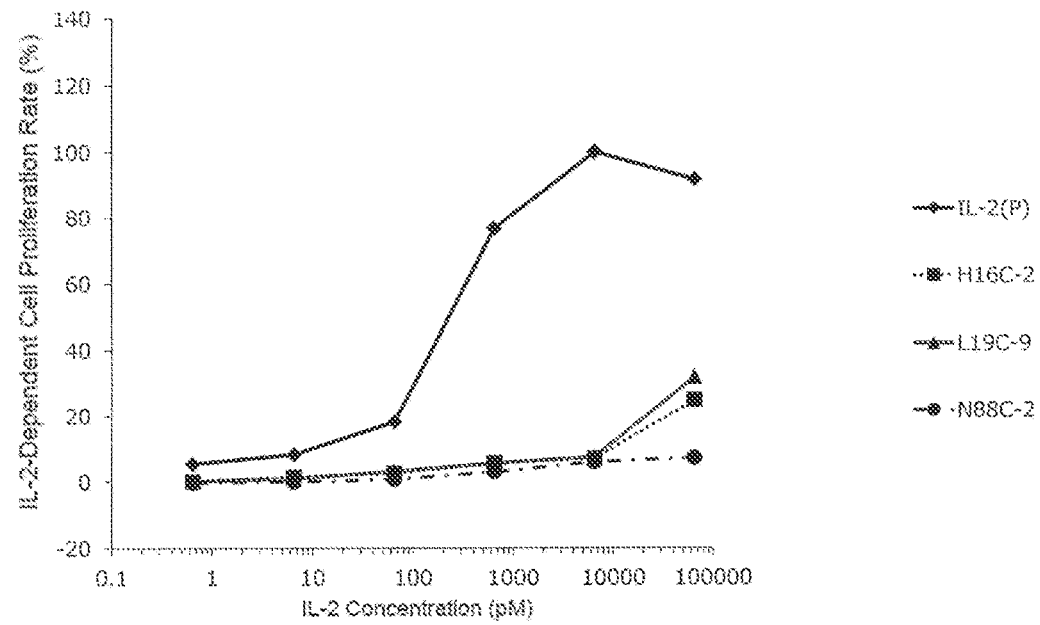

FIG. 2A is a graph showing NK cell proliferation promoting activities of various glycosylated IL-2 variants. Black diamonds indicate an activity of IL-2(P), black squares indicate an activity of H16C-2, black triangles indicate an activity of L19C-9, and black circles indicate an activity of N88C-2. A horizontal axis indicates an IL-2 concentration (pM), and a vertical axis indicates an IL-2-dependent cell proliferation rate (%).

Figure 2B:
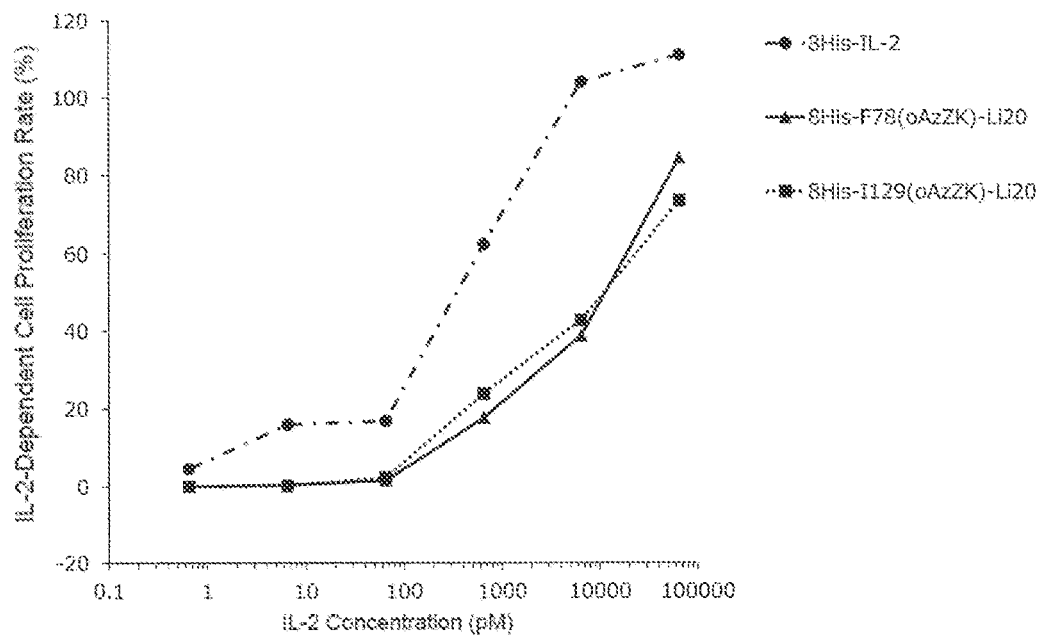

FIG. 2B is a graph showing NK cell proliferation promoting activities of various PEGylated IL-2 variants. Black circles indicate an activity of 8His-IL-2, black triangles indicate an activity of 8His-F78(oAzZK)-Li20, and black squares indicate an activity of 8His-I129(oAzZK)-Li20. A horizontal axis indicates an IL-2 concentration (pM), and a vertical axis indicates an IL-2-dependent cell proliferation rate (%).

Figure 2C:
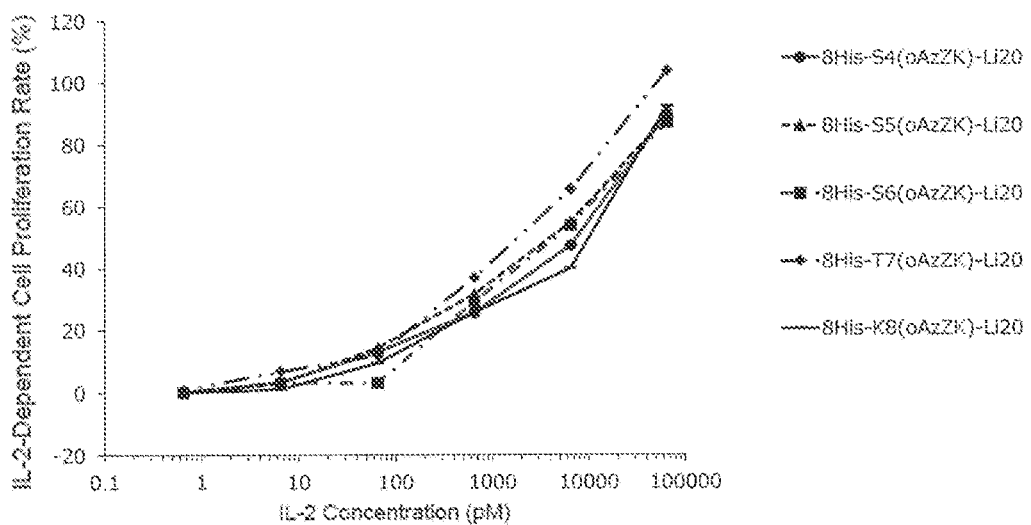

FIG. 2C is a graph showing NK cell proliferation promoting activities of various PEGylated IL-2 variants. Black circles indicate an activity of 8His-S4(oAzZK)-Li20, black triangles indicate an activity of 8His-S5(oAzZK)-Li20, black squares indicate an activity of 8His-S6(oAzZK)-Li20, black diamonds indicate an activity of 8His-T7(oAzZK)-Li20, and black horizontal bars indicate an activity of 8His-K8(oAzZK)-Li20. A horizontal axis indicates an IL-2 concentration (pM), and a vertical axis indicates an IL-2-dependent cell proliferation rate (%).

Figure 2D:
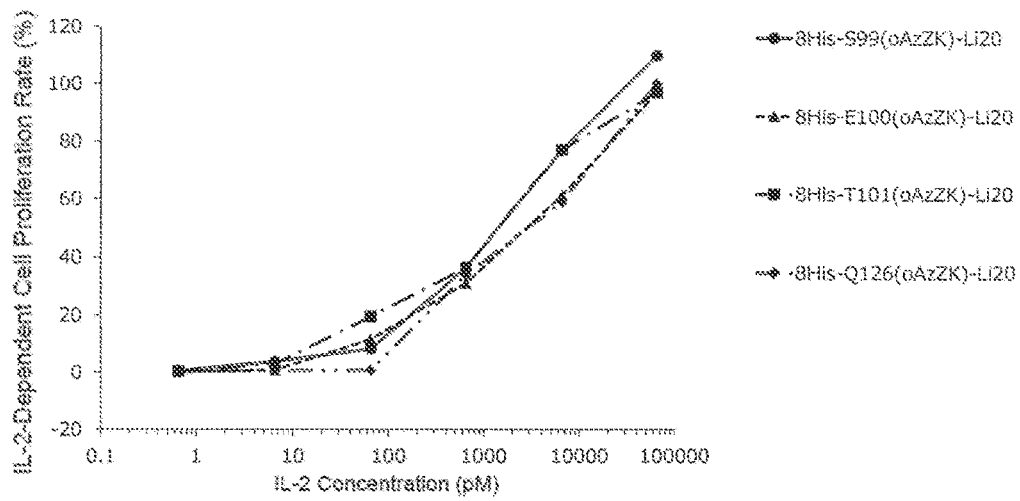

FIG. 2D is a graph showing NK cell proliferation promoting activities of various PEGylated IL-2 variants. Black circles indicate an activity of 8His-S99(oAzZK)-Li20, black triangles indicate an activity of 8His-E100(oAzZK)-Li20, black squares indicate an activity of 8His-T101(oAzZK)-Li20, and black diamonds indicate an activity of 8His-Q126(oAzZK)-Li20. A horizontal axis indicates an IL-2 concentration (pM), and a vertical axis indicates an IL-2-dependent cell proliferation rate (%).

Figure 2E:
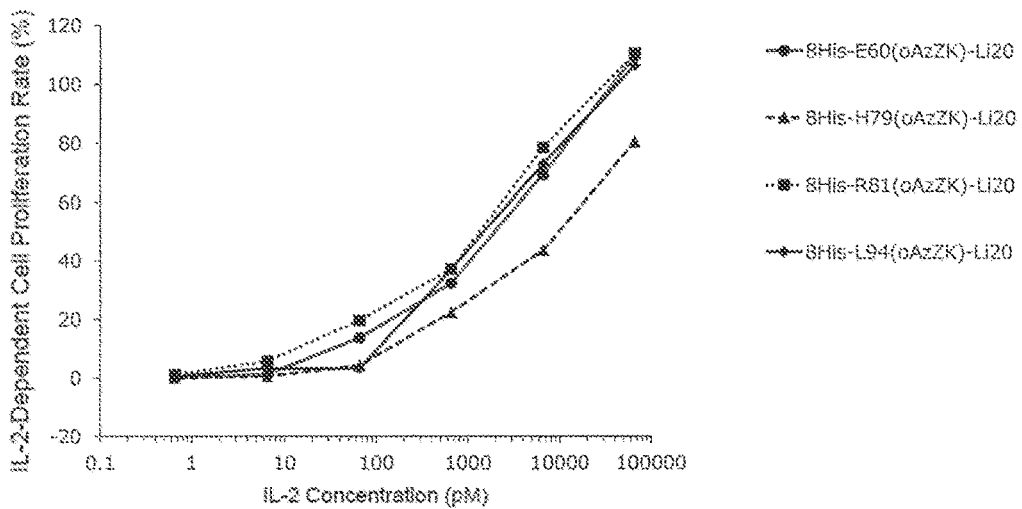

FIG. 2E is a graph showing NK cell proliferation promoting activities of various PEGylated IL-2 variants. Black circles indicate an activity of 8His-E60(oAzZK)-Li20, black triangles indicate an activity of 8His-H79(oAzZK)-Li20, black squares indicate an activity of 8His-R81(oAzZK)-Li20, and black diamonds indicate an activity of 8His-L94(oAzZK)-Li20. A horizontal axis indicates an IL-2 concentration (pM), and a vertical axis indicates an IL-2-dependent cell proliferation rate (%).

Figure 2F:
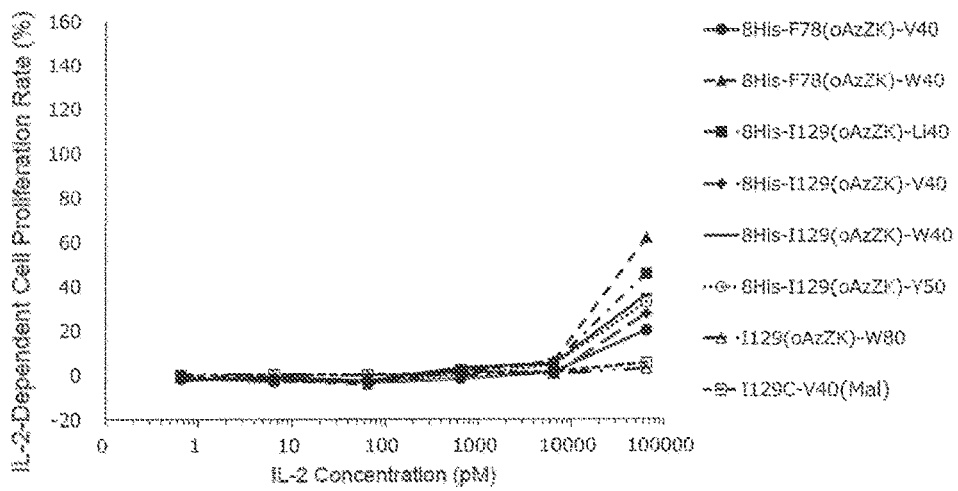

FIG. 2F is a graph showing NK cell proliferation promoting activities of various PEGylated IL-2 variants. Black circles indicate an activity of 8His-F78(oAzZK)-V40, black triangles indicate an activity of 8His-F78(oAzZK)-W40, black squares indicate an activity of 8His-I129(oAzZK)-Li40, black diamonds indicate an activity of 8His-I129(oAzZK)-V40, black horizontal bars indicate an activity of 8His-I129(oAzZK)-W40, white circles indicate an activity of 8His-I129(oAzZK)-Y50, white triangles indicate an activity of I129(oAzZK)-W80, and white squares indicate an activity of I129C-V40(Mal). A horizontal axis indicates an IL-2 concentration (pM), and a vertical axis indicates an IL-2-dependent cell proliferation rate (%).

Figure 2G:
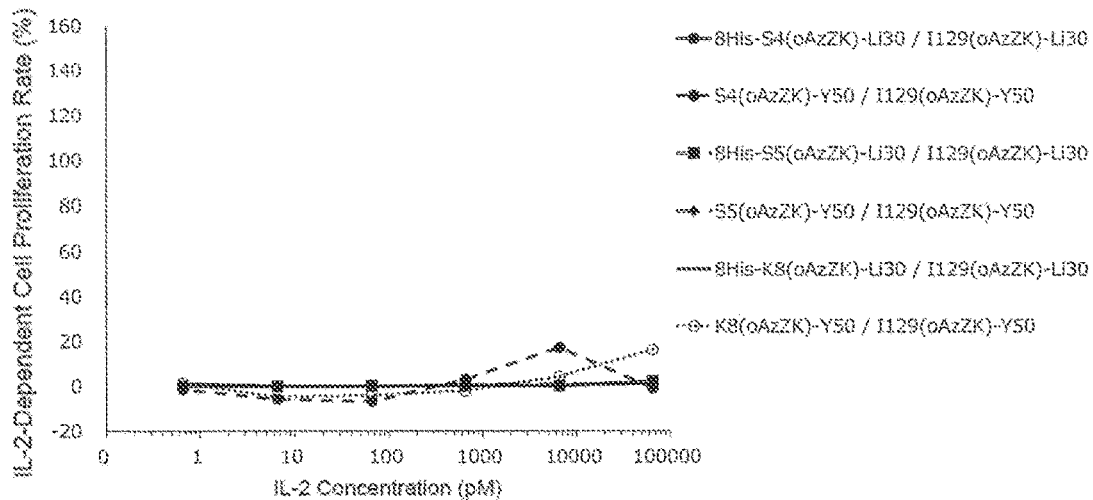

FIG. 2G is a graph showing NK cell proliferation promoting activities of various PEGylated IL-2 variants. Black circles indicate an activity of 8His-S4(oAzZK)-Li30/I129(oAzZK)-Li30, black triangles indicate an activity of S4(oAzZK)-Y50/I129(oAzZK)-Y50, black squares indicate an activity of 8His-S5(oAzZK)-Li30/I129(oAzZK)-Li30, black diamonds indicate an activity of S5(oAzZK)-Y50/I129(oAzZK)-Y50, black horizontal bars indicate an activity of 8His-K8(oAzZK)-Li304129(oAzZK)-Li30, and white circles indicate an activity of K8(oAzZK)-Y50/I129(oAzZK)-Y50. A horizontal axis indicates an IL-2 concentration (pM), and a vertical axis indicates an IL-2-dependent cell proliferation rate (%).

Figure 2H:
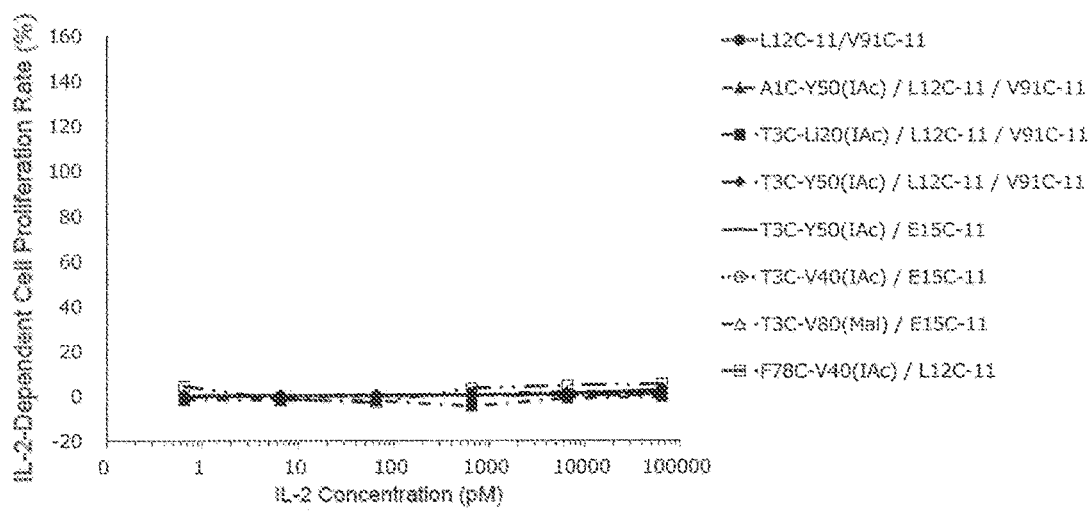

FIG. 2H is a graph showing NK cell proliferation promoting activities of various glycosylated IL-2 variants and various Cys-PEGylated and glycosylated IL-2 variants. Black circles indicate an activity of L12C-11/V91C-11, black triangles indicate an activity of A1C-Y50(IAc)/L12C-11N91C-11, black squares indicate an activity of T3C-Li20(IAc)/L12C-11/V91C-11, black diamonds indicate an activity of T3C-Y50(IAc)/L12C-11/V91C-11, black bars indicate an activity of T3C-Y50(IAc)/E15C-11, white circles indicate an activity of T3C-V40(IAc)/E15C-11, white triangles indicate an activity of T3C-V80(Mal)/E15C-11, and white squares indicate an activity of F78C-V40(IAc)/L12C-11. A horizontal axis indicates an IL-2 concentration (pM), and a vertical axis indicates an IL-2-dependent cell proliferation rate (%).

Figure 2I:
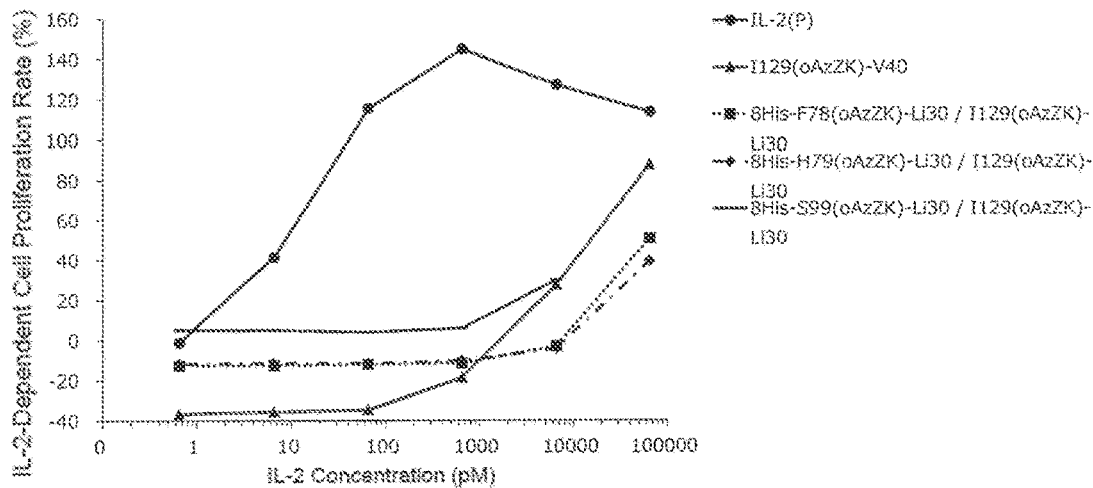

FIG. 2I is a graph showing NK cell proliferation promoting activities of various PEGylated IL-2 variants. Black circles indicate an activity of IL-2(P), black triangles indicate an activity of I129(oAzZK)-V40, black squares indicate an activity of 8His-F78(oAzZK)-Li30/I129(oAzZK)-Li30, black diamonds indicate an activity of 8His-H79(oAzZK)-Li30/I129(oAzZK)-Li30, and black bars indicate an activity of 8His-S99(oAzZK)-Li30/I129(oAzZK)-Li30. A horizontal axis indicates an IL-2 concentration (pM), and a vertical axis indicates an IL-2-dependent cell proliferation rate (%).

Figure 2J:
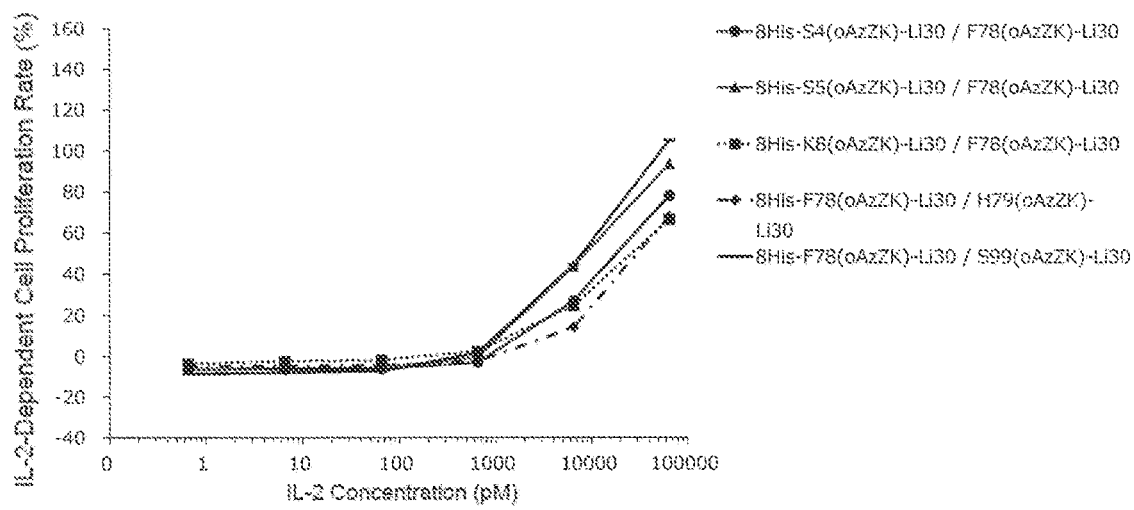

FIG. 2J is a graph showing NK cell proliferation promoting activities of various PEGylated IL-2 variants. Black circles indicate an activity of 8His-S4(oAzZK)-Li30/F78(oAzZK)-Li30, black triangles indicate an activity of 8His-S5(oAzZK)-Li30/F78(oAzZK)-Li30, black squares indicate an activity of 8His-K8(oAzZK)-Li30/F78(oAzZK)-Li30, black diamonds indicate an activity of 8His-F78(oAzZK)-Li30/H79(oAzZK)-Li30, and black bars indicate an activity of 8His-F78(oAzZK)-Li30/S99(oAzZK)-Li30. A horizontal axis indicates an IL-2 concentration (pM), and a vertical axis indicates an IL-2-dependent cell proliferation rate (%).

Figure 2K:
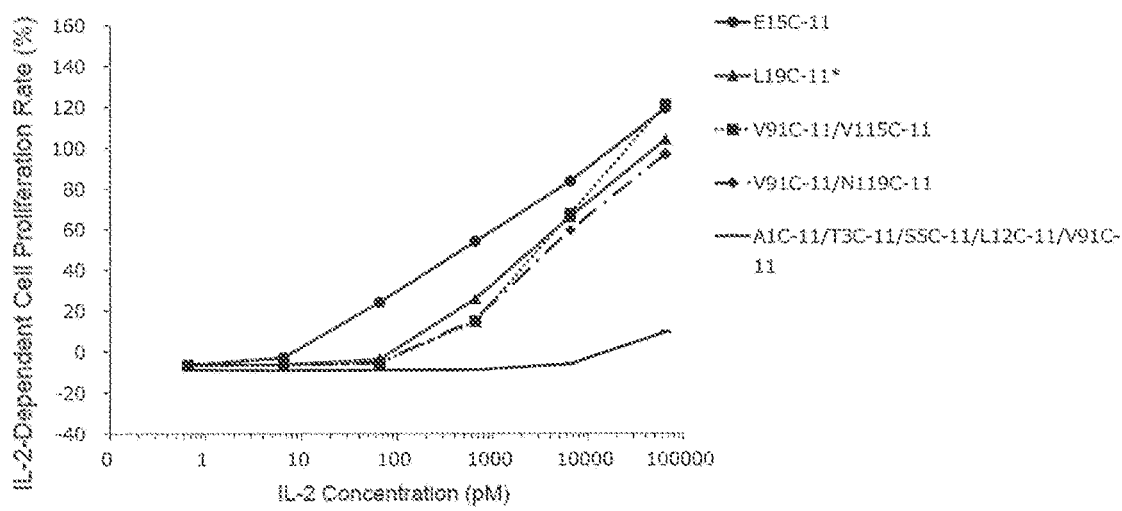

FIG. 2K is a graph showing NK cell proliferation promoting activities of various glycosylated IL-2 variants. Black circles indicate an activity of E15C-11, black triangles indicate an activity of L19C-11*, black squares indicate an activity of V91C-11/V115C-11, black diamonds indicate an activity of V91C-11/N119C-11, and black bars indicate an activity of A1C-11/T3C-11/S5C-11/L12C-11/V91C-11. A horizontal axis indicates an IL-2 concentration (pM), and a vertical axis indicates an IL-2-dependent cell proliferation rate (%).

Figure 3:
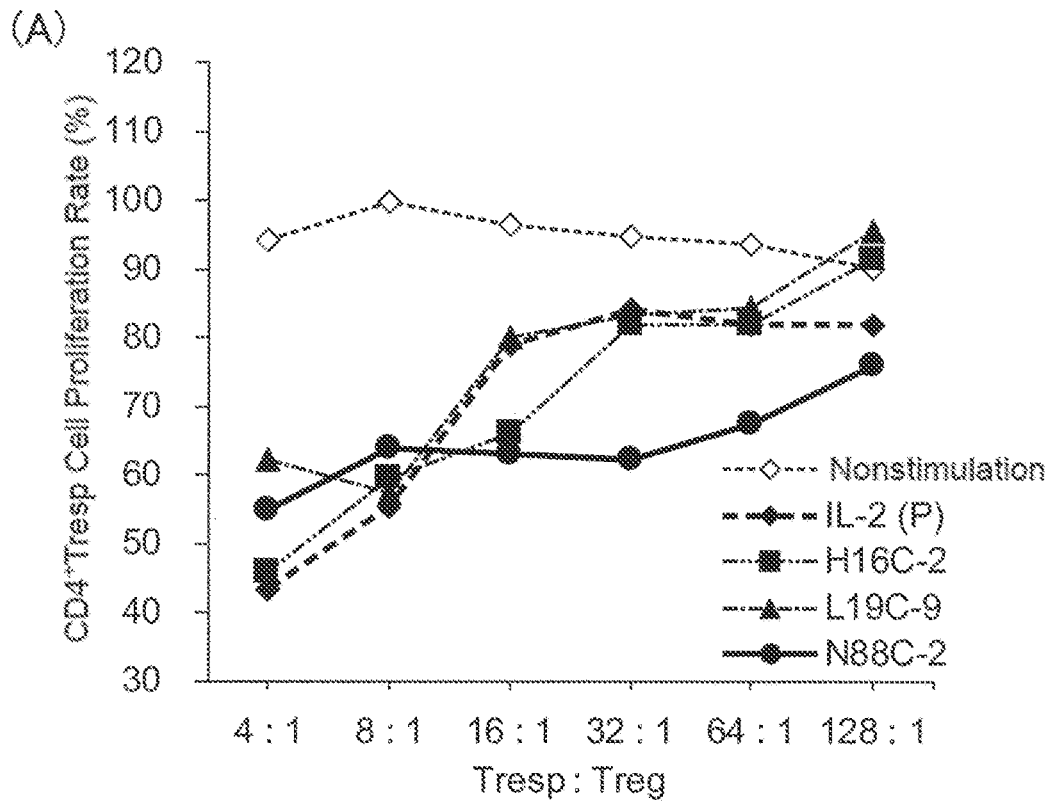
Figure 3:
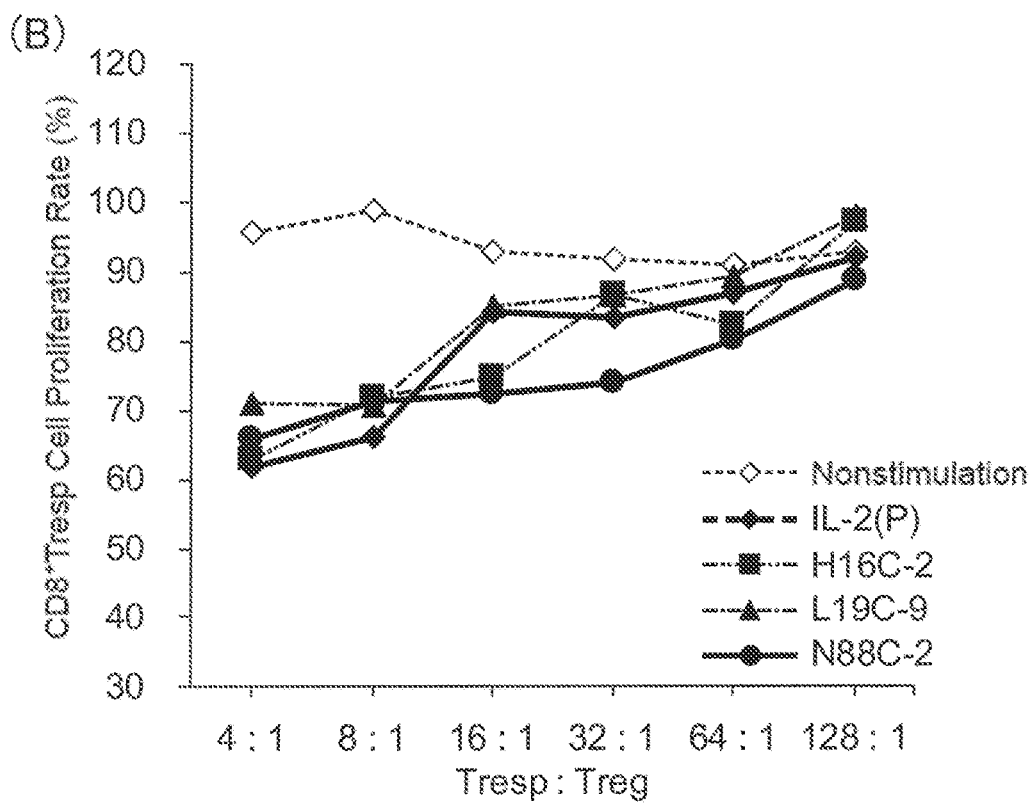

FIG. 3 shows graphs showing a proliferation rate of responder T cells (Tresp) in the presence of unstimulated Tregs or various IL-2 variant-stimulated Tregs. FIG. 3(A) shows a proliferation rate of CD4-positive Tresp, and FIG. 3(B) shows a proliferation rate of CD8-positive Tresp. In each figure, a horizontal axis indicates an abundance ratio between Tresp and Treg, and a vertical axis indicates a proliferation rate (%) of Tresp. White diamonds indicate nonstimulation, black diamonds indicate IL-2(P), black squares indicate H16C-2, black triangles indicate L19C-9, and black circles indicate N88C-2.

Figure 4:
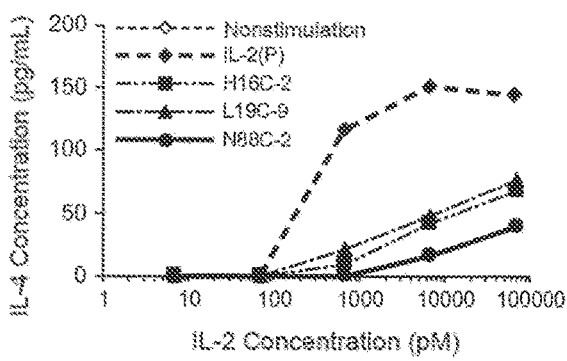
Figure 4:
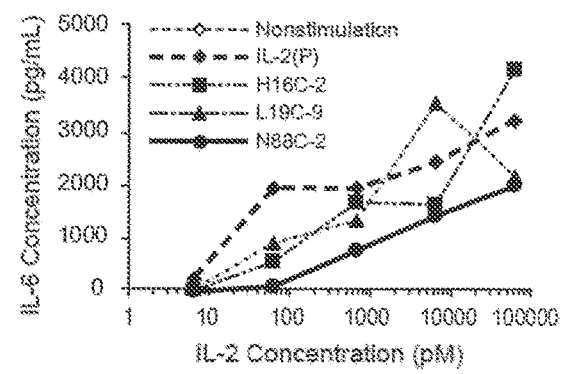
Figure 4:
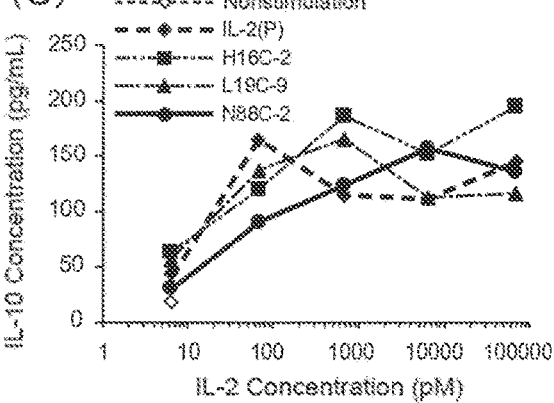
Figure 4:
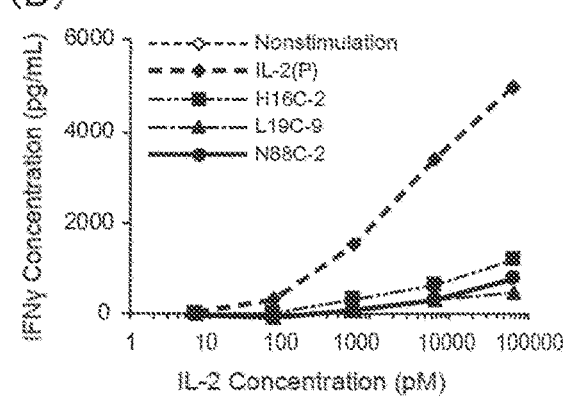
Figure 4:
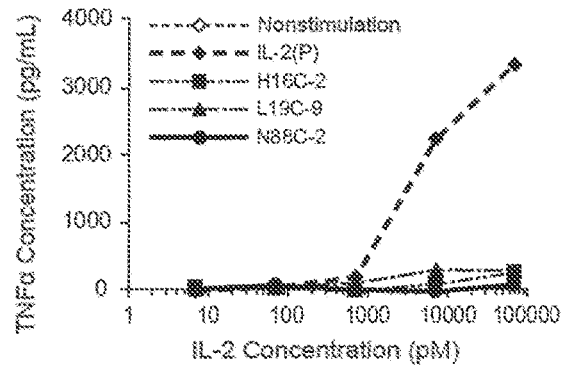
Figure 4:
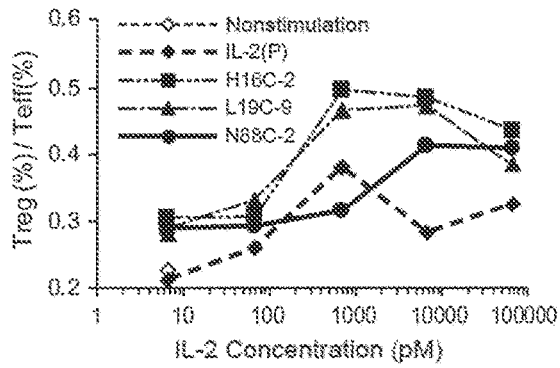

FIG. 4. (A) to (E) show graphs showing cytokine concentrations in a culture supernatant, when various IL-2 variants are added to human PBMC reconstituted with autologous plasma, and cultured. FIG. 4(A) shows an IL-4 concentration, FIG. 4(B) shows an IL-6 concentration, FIG. 4(C) shows an IL-10 concentration, FIG. 4(D) shows an IFNγ concentration, and FIG. 4(E) shows a TNFα concentration. In each figure, a horizontal axis indicates an added IL-2 concentration (pM), and a vertical axis indicates a production amount of cytokine (pg/mL). FIG. 4(F) is a graph showing results of evaluating Treg-selective proliferation activity. A vertical axis indicates a ratio [Treg (%)/Teff (%)], when a $CD25^+$ $Foxp3^{high}$ fraction is Treg and a $CD25^+$ $Foxp3^{low}$ fraction is effector T cells (Teff) in the CD4-positive fractions. A horizontal axis indicates an added IL-2 concentration. In each figure, white diamonds indicate nonstimulation, black diamonds indicate IL-2(P), black squares indicate H16C-2, black triangles indicate L19C-9, and black circles indicate N88C-2.

EMBODIMENTS FOR CARRYING OUT THE INVENTION

Hereinafter, the present invention will be described in detail.

"Treg" or "Treg cells" refers to regulatory T cells. Regulatory T cells are a class of T cells that suppress an activity of other immune cells and are defined by cell marker phenotype $CD4^+$ $CD25^+$ $FOXP3^+$ using flow cytometry.

Since FOXP3 is an intracellular protein and requires fixation and permeabilization of cells for staining, cell surface phenotype $CD4^+CD25^+$ $CD127^{low}$ can be used in order to define viable Tregs.

Tregs also include various Treg subclasses, such as tTreg (derived from thymus) and pTreg (derived from the periphery and differentiated from peripheral naive T cells). Although all Tregs express IL-$2R_{\alpha\beta\gamma}$ and proliferate in an IL-2-dependent manner, an IL-2 variant of the present invention is capable of selectively activating at least one Treg subclass, and preferably capable of selectively activating any subclass.

"IL-2" may be either wild-type IL-2 or an IL-2 variant. The "wild-type IL-2" includes any IL-2 of 1) to 3) below.
1) A human-derived wild-type mature IL-2 consisting of an amino acid sequence represented by SEQ ID NO: 1.
2) IL-2 comprising an amino acid modification that can be added when producing a genetic recombinant of the above 1).
3) IL-2 in which an amino acid residue at N-terminal of IL-2 of the above 1) and 2) is deleted.

The amino acid modification of the above 2) is, for example, a modification of binding a methionine residue encoded by an initiation codon to an N-terminal of the amino acid sequence represented by SEQ ID NO: 1 in order to express IL-2 in *Escherichia coli*, a modification of binding an amino acid sequence represented by MHHHHHHHH (methionine-bound polyhistidine) to the N-terminal of the amino acid sequence represented by SEQ ID NO: 1 in order to express IL-2 in *Escherichia coli* and easily purify the IL-2, or a modification of substituting an amino acid residue at position 125 of human-derived wild-type mature IL-2 with an alanine residue or a serine residue in order to improve physical properties of IL-2.

Examples of the IL-2 of the above 3) in which an N-terminal amino acid residue of IL-2 is deleted include an IL-2 comprising an amino acid sequence in which an alanine residue or an alanine residue and a proline residue at N-terminal of amino acid sequence represented by SEQ ID NO: 1 are deleted.

Specific examples of the wild-type IL-2 include an IL-2 consisting of an amino acid sequence represented by SEQ ID NO: 1, an amino acid sequence in which a methionine residue is bound to an N-terminal of the amino acid sequence represented by SEQ ID NO: 1, an amino acid sequence in which an amino acid sequence represented by MHHHHHHHH is bound to the N-terminal of the amino acid sequence represented by SEQ ID NO: 1, an amino acid sequence in which an N-terminal alanine residue of the amino acid sequence represented by SEQ ID NO: 1 is deleted, an amino acid sequence in which the N-terminal alanine residue of the amino acid sequence represented by SEQ ID NO: 1 is deleted and methionine is bound thereto, an amino acid sequence in which an alanine residue and a proline residue at the N-terminal of the amino acid sequence represented by SEQ ID NO: 1 are deleted. Moreover, specific examples of the wild-type IL-2 include an IL-2 comprising an amino acid sequence in which in the amino acid sequence represented by SEQ ID NO: 1, the amino acid sequence in which a methionine residue is bound to an N-terminal of the amino acid sequence represented by SEQ ID NO: 1, the amino acid sequence in which an amino acid sequence represented by MHHHHHHHH is bound to the N-terminal of the amino acid sequence represented by SEQ ID NO: 1, the amino acid sequence in which an N-terminal alanine residue of the amino acid sequence represented by SEQ ID NO: 1 is deleted, the amino acid sequence in which the N-terminal alanine residue of the amino acid sequence represented by SEQ ID NO: 1 is deleted and methionine is bound thereto, or the amino acid sequence in which an alanine residue and a proline residue at the N-terminal of the amino acid sequence represented by SEQ ID NO: 1 are deleted, wherein an amino acid residue at position 125 is substituted with a serine residue or an alanine residue. The amino acid sequence on the N-terminal side and the serine residue at position 125 in the amino acid sequence represented by SEQ ID NO: 1 described above are variations of an amino acid sequence which is allowed from a viewpoint of protein expression or protein stability without affecting an activity of IL-2. In the IL-2 variant of the present invention, variations of these amino acid sequences are also included.

Note that all the numbers of the amino acid residues of IL-2 described in the present invention indicate the numbers (positions) of the amino acid residues with reference to the amino acid sequence of IL-2 represented by SEQ ID NO: 1. Therefore, in the amino acid sequence represented by SEQ ID NO: 1, the N-terminal alanine residue is defined as position 1, the proline residue is defined as position 2, and the methionine residue bound to the N-terminal is defined as position −1.

The "IL-2 variant" includes all proteins which are produced by adding any modifications to the wild-type IL-2, and has a function of wild-type IL-2. Examples of the variants include an IL-2 variant in which the wild-type IL-2 is modified by an amino acid modification (for example, substitution, deletion, or addition), an IL-2 variant in which the wild-type IL-2 is modified by saccharide modification, and IL-2 variant in which the wild-type IL-2 is modified by chemical modification. The modifications include both naturally occurring modifications and artificial modifications.

The "function of wild-type IL-2" refers to at least one function selected from binding to IL-2Rαβγ, binding to IL-2Rβγ, activating intracellular signaling pathways through intracellular regions of CD122 and CD132, phosphorylation of JAK1, phosphorylation of JAK3, phosphorylation of STAT5, phosphorylation of STAT3, phosphorylation of PI3K, phosphorylation of MEK, promotion of Foxp3 expression, promotion of expression of genes whose transcription is controlled by Foxp3, promotion of DNA demethylation in a region of Treg-specific demethylation region (TSDR) of Foxp3 gene, promotion of proliferation and survival of immune cells expressing IL-2R$_{\beta\gamma}$, promotion of cytokine production by immune cells expressing IL-2R$_{\beta\gamma}$, promotion of proliferation and survival of immune cells expressing IL-2R$_{\alpha\beta\gamma}$, promotion of cytokine production by immune cells expressing IL-2R$_{\alpha\beta\gamma}$, promotion of Treg proliferation and survival, and improvement of ability of Treg to suppress Teff activation.

Examples of the IL-2 variant according to one embodiment of the present invention include an IL-2 variant in which a saccharide is bound to a predetermined region(s) of IL-2, an IL-2 variant in which PEG is bound to a predetermined region(s) of IL-2, and an IL-2 variant in which a saccharide and PEG are bound to a predetermined region(s) of IL-2. Examples of the bond include a covalent bond and a non-covalent bond, but a bonding mode does not matter.

The "amino acid residue" may be either a natural amino acid residue or a non-natural amino acid residue.

Examples of the "natural amino acid residue" include selenocysteine residue and the following 20 α-amino acid residues: an alanine residue, an asparagine residue, an aspartic acid residues, a glutamine residue, a glutamic acid residue, a glycine residues, a histidine residue, an isoleucine residue, a leucine residue, a lysine residue, a methionine residue, a phenylalanine residue, a proline residue, a serine residue, a threonine residue, a tryptophan residues, a tyrosine residue, a valine residue, or a cysteine residue. The natural amino acid residues include both L-form and D-form, and the L-form is preferred for humans.

The "non-natural amino acid residue" refers to all amino acid residues other than the natural amino acid residues. Examples of the non-natural amino acid residue include an amino acid residue obtained by modifying the natural amino acid residue and an artificially designed amino acid residue.

The "modification" includes any modification, such as chemical modification or post-translational modification.

Examples of the IL-2 variant according to one embodiment of the present invention include an IL-2 variant having improved selectivity for IL-2R$_{\alpha\beta\gamma}$. Tregs that express IL-2R$_{\alpha\beta\gamma}$ can be selectively activated by the IL-2 variant having improved selectivity for IL-2R$_{\alpha\beta\gamma}$.

The "selectivity for IL-2R$_{\alpha\beta\gamma}$" refers to a property that IL-2 selectively binds to IL-2R$_{\alpha\beta\gamma}$ rather than IL-2R$_{\beta\gamma}$. In addition, the expression "having improved selectivity for IL-2R$_{\alpha\beta\gamma}$" means that the selectivity of the IL-2 variant for IL-2R$_{\alpha\beta\gamma}$ is improved as compared with the wild-type IL-2.

The selectivity for IL-2R$_{\alpha\beta\gamma}$ or the improved selectivity for IL-2R$_{\alpha\beta\gamma}$ can be determined, for example, by a method described below.

(1) For each type of IL-2, an EC$_{50}$ value of a binding activity to IL-2R$_{\alpha\beta\gamma}$ and an EC$_{50}$ value of a binding activity to IL-2R$_{\beta\gamma}$ are measured. when the EC$_{50}$ of IL-2R$_{\alpha\beta\gamma}$ is smaller than the EC$_{50}$ of IL-2R$_{\beta\gamma}$, or when an EC$_{50}$ ratio value (EC$_{50}$ of IL-2R$_{\beta\gamma}$/EC$_{50}$ of IL-2R$_{\alpha\beta\gamma}$) is greater than 1, it can be determined that the IL-2 has selectivity for IL-2R$_{\alpha\beta\gamma}$.

In addition, in a case where the EC$_{50}$ ratio value of the IL-2 variant is greater than the EC$_{50}$ ratio value of the wild-type IL-2, or in a case where a standardized EC$_{50}$ ratio value (EC$_{50}$ ratio value of IL-2 variant/EC$_{50}$ ratio value of wild-type IL-2) is greater than 1, it can be determined that the IL-2 variant has improved selectivity for IL-2R$_{\alpha\beta\gamma}$. The standardized EC$_{50}$ ratio value is preferable in the order that greater than 1, 5 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more. Instead of the wild-type IL-2, an IL-2 variant having an EC$_{50}$ ratio value equivalent to that of the wild-type IL-2 may be used.

Specific examples of a method of measuring the EC$_{50}$ value include a method according to procedures (A) to (C) below. More specific examples of the method include a method to be described later in Examples.

(A) Human IL-2R$_{\alpha\beta\gamma}$ or human IL-2R$_{\beta\gamma}$ is expressed in mammalian cells to prepare a human IL-2-dependent viable cell line, and each cell line is seeded in a 96-well plate.

(B) Assuming that a relative fluorescence units (RLU) value of wells to which control IL-2 was added at 1000 ng/ml is 100% and the RLU value of wells to which a medium without containing IL-2 was added is 0%, the IL-2-dependent cell proliferation rate of the test substance IL-2 variant is calculated.

(C) Based on data obtained in (B), an EC$_{50}$ value is calculated using statistical analysis software (for example, XLfit5 version 5.3.1.3 manufactured by IBDS).

(2) An affinity of each of the wild-type IL-2 and the IL-2 variant for CD25 ECD-Fc and IL-2R$_{\beta\gamma}$ ECD-Fc, which are IL-2R extracellular domain (ECD)-Fc fusion proteins, is measured with Biacore. When a K$_D$ value for CD25 ECD-Fc is smaller and/or a K$_D$ value for IL-2R$_{\beta\gamma}$ ECD-Fc is larger in the IL-2 variant than in the wild-type, it can be determined that the IL-2 variant has improved selectivity for IL-2R$_{\alpha\beta\gamma}$. In addition, when a relative value of the K$_D$ value for IL-2R$_{\beta\gamma}$ ECD-Fc to the K$_D$ value for CD25 ECD-Fc increases at the IL-2 variant than at the wild-type, it can be determined that the IL-2 variant has improved selectivity for IL-2R$_{\alpha\beta\gamma}$.

The expression "selectively activating Tregs" refers to at least one of (a) to (c) below.

(a) The IL-2 variant has higher Treg proliferation activity and/or lower NK cell proliferation activity than those of the wild-type IL-2.

(b) A ratio of a proportion of Tregs to a proportion of effector T cells (Teff) [Treg (%)/Teff (%)] in a cell population is higher for the IL-2 variant than for the wild-type IL-2.

(c) Production amount of inflammatory cytokines is lower and/or production amount of anti-inflammatory cytokines increases for the IL-2 variant comparing to the wild-type IL-2.

In any of the cases (a) to (c), an IL-2 variant having an activity equivalent to that of the wild-type IL-2 may be used instead of the wild-type IL-2.

The Treg proliferation activity and the NK cell proliferation activity can be measured, for example, by methods described below. Treg or NK cells are seeded in a 96-well plate, and assuming that a RLU value of wells to which control IL-2 was added is 100% and a RLU value of wells to which a medium without containing IL-2 was added is 0%, the Treg proliferation rate or NK cell proliferation rate of the test substance IL-2 variant is calculated. More specific examples of the method include a method to be described later in Examples.

Treg (%)/Teff (%) can be measured, for example, by a method described below. Human peripheral blood mononuclear cells (hereinafter, also abbreviated as PBMC) are suspended in autologous plasma, and an anti-CD3 antibody OKT3 is added thereto. A 96-well plate is seeded with the PBMCs, and then each IL-2 is added thereto, and cultured. After reacting the obtained human PBMCs with a fluorescently labeled anti-human CD4 antibody, a fluorescently labeled CD25 antibody, and a fluorescently labeled anti-Foxp3 antibody, various fluorescence intensities are measured with a flow cytometer (for example, LSRFortessa manufactured by BD Biosciences).

The obtained data is analyzed using data analysis software (for example, FLowJo, version 7.6.5, manufactured by TreeStar Inc). Among the CD4 positive fractions, assuming that a CD25$^+$Foxp3$^{high}$ fraction is Treg and the CD25$^+$Foxp3$^{low}$ fraction is effector T cells (Teff), an abundance ratio therebetween [Treg (%)/Teff (%)] is calculated. More specific examples of the method include a method to be described later in Examples.

A production amount of each cytokine can be measured, for example, by a method described below. Human PBMCs are suspended in autologous plasma, and anti-CD3 antibody OKT3 is added thereto. A 96-well plate is seeded with the PBMCs, and then each IL-2 is added thereto, and cultured. The production amount of cytokine in a supernatant is quantified. More specific examples of the method include a method to be described later in Examples.

Examples of the IL-2 variant according to one embodiment of the present invention include an IL-2 variant modified by binding a saccharide to IL-2 (hereinafter, also abbreviated as a glycosylated IL-2 variant) and an IL-2 variant modified by binding PEG to IL-2 (hereinafter, also abbreviated as a PEGylated IL-2 variant). Hereinafter, each variant will be described.

[Saccharide-Bound (Glycosylated) IL-2 Variant]

As the IL-2 variant according to one embodiment of the present invention, an IL-2 variant in which a saccharide is bound to at least one amino acid residue selected from amino acid residues at positions 11, 12, 13, 15, 16, 18, 19, 20, 84, 87, 88, 91, 92, 108, 115, 119, 122, 123, and 130 in an amino acid sequence of IL-2 is preferred.

In the present specification, the "saccharide" refers to a monosaccharide or a saccharidein which two or more monosaccharides bind via a glycoside bond, and any saccharide can be used.

Specific examples of the saccharide to be bound to IL-2 include at least one selected from the group consisting of saccharides comprising structures represented by (Formula 4) to (Formula 8) and (Formula Y1) to (Formula Y3). When the saccharide is bound to the amino acid residue in the amino acid sequence of IL-2, it is possible to improve the selectivity for IL-2$R_{\alpha\beta\gamma}$. In addition, for the saccharide of the IL-2 variant of the present invention, a saccharide in which one N-acetylglucosamine (GlcNAc) is bound to Mannose (Man) of each of an α1-6 arm and an α1-3 arm of (Formula 6), a saccharide in which one Galactose (Gal) is removed from Man-GlcNAc of each of an α1-6 arm and an α1-3 arm of (Formula 7) (G1), a saccharide in which one Sialic acid (Sial) at a non-reducing terminal is removed from (Formula 8), and a saccharide in which 1 to 4 Sials at a non-reducing terminal are removed from (Formula Y3) can also be used.

[Chem. 59]

(Formula Y1)

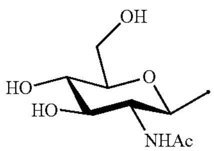

[Chem. 60]

(Formula Y2)

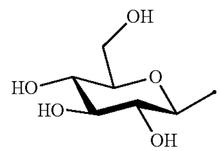

[Chem. 61]

(Formula 4)

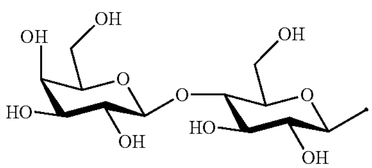

[Chem. 62]

(Formula 5)

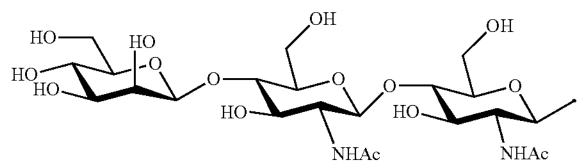

[Chem. 63]

(Formula 6)

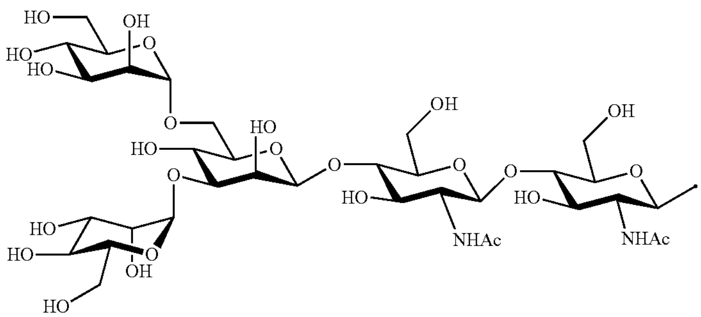

[Chem. 64]

(Formula 7)

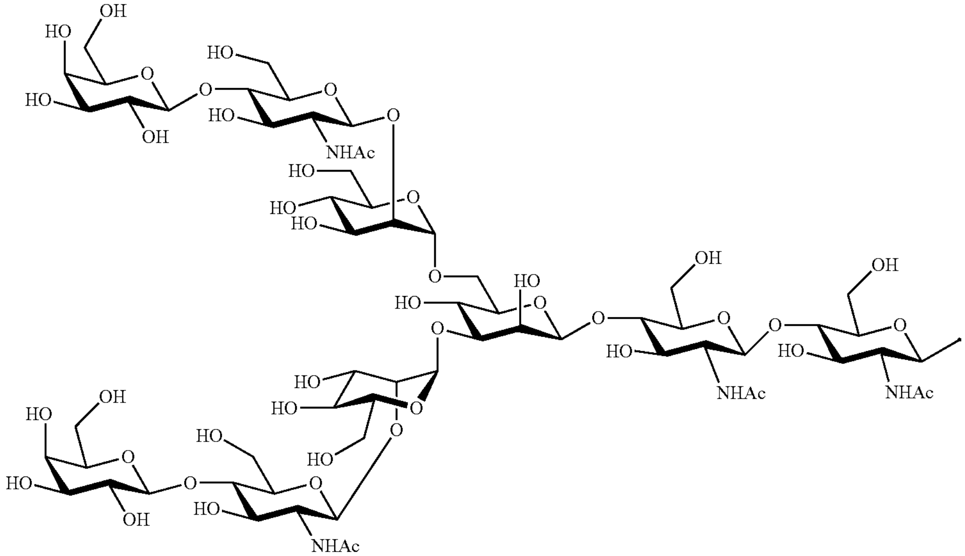

[Chem. 65]
(Formula 8)
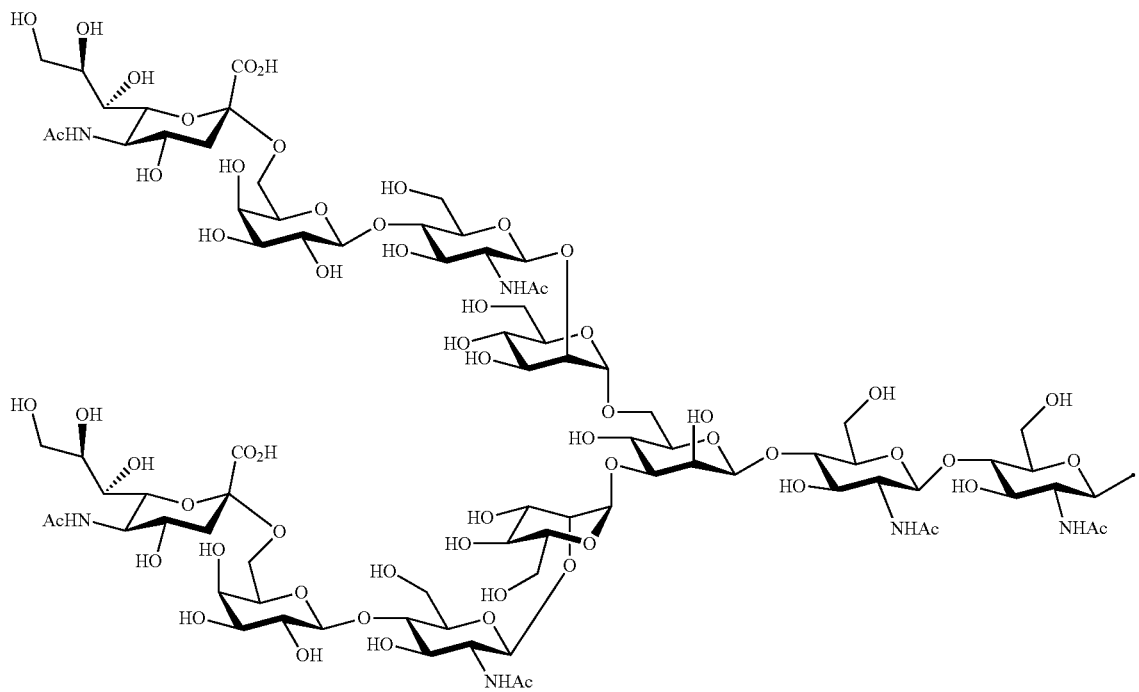
[Chem. 66]
(Formula Y3)
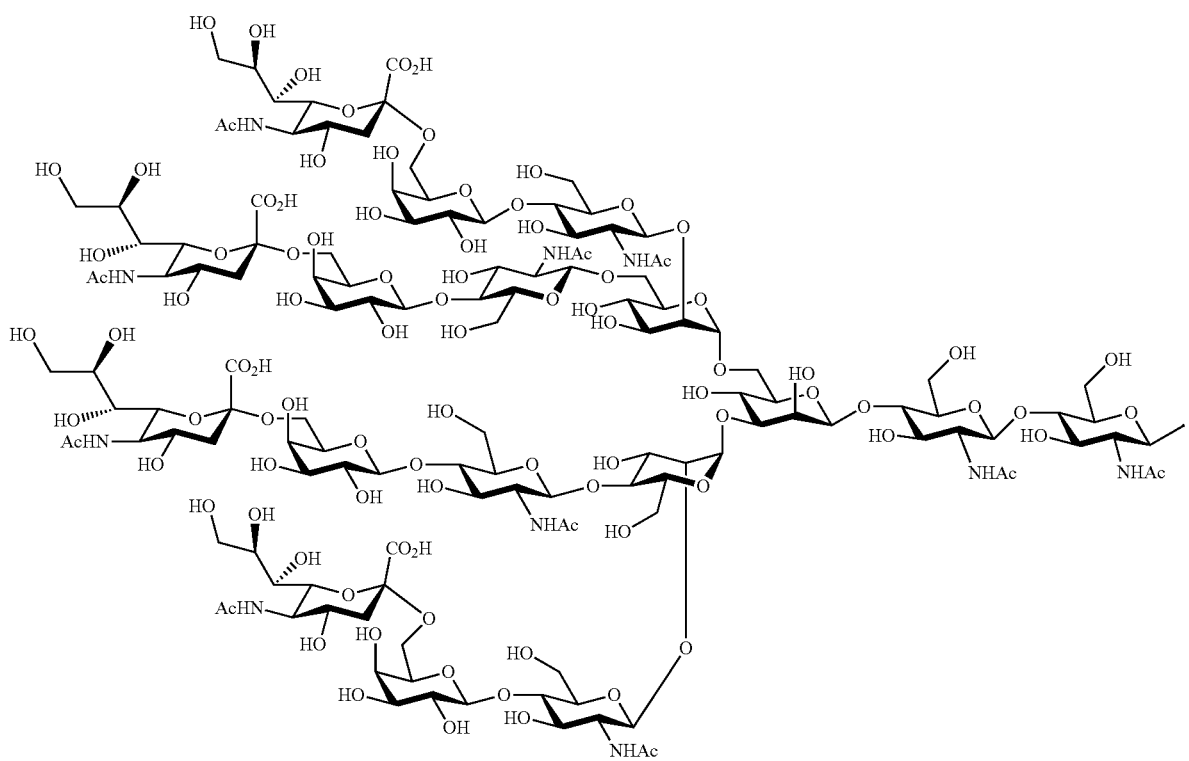
As the IL-2 variant according to one embodiment of the present invention, an IL-2 variant comprising an amino acid sequence in which at least one amino acid residue selected from the group consisting of amino acid residues at positions 11, 12, 13, 15, 16, 18, 19, 20, 84, 87, 88, 91, 92, 108, 115, 119, 122, 123, and 130 in an amino acid sequence of wild-type IL-2 is substituted with a glycosylated group derived from a cysteine residue or an asparagine residue is preferred, and an IL-2 variant comprising an amino acid sequence in which at least one amino acid residue selected from the group consisting of amino acid residues at positions 12, 13, 15, 16, 19, 88, 91, and 119 in an amino acid sequence of wild-type IL-2 is substituted with a glycosylated group derived from a cysteine residue or an asparagine residue is more preferred.

In the present embodiment, as the amino acid sequence of the wild-type IL-2, an amino acid sequence represented by SEQ ID NO: 1 or an amino acid sequence in which an amino acid residue at position 125 in the amino acid sequence represented by SEQ ID NO: 1 is substituted with a serine residue or an alanine residue is more preferred.

The group derived from a cysteine residue or an asparagine residue refers to a group in which either a side chain thiol of the cysteine residue or a side chain amide of the asparagine residue is modified.

The glycosylated group derived from a cysteine residue or an asparagine residue refers to a group in which a saccharide is bound to a side chain thiol of the cysteine residue or a side chain amide of the asparagine residue by chemical modification. The group derived from a cysteine residue or an asparagine residue may be modified with a linker or the like, or in the group, the cysteine residue or the asparagine residue and the saccharide may be bound to each other via a linker.

Examples of the glycosylated group derived from a cysteine residue include an amino acid residue comprising a structure in which a saccharide is bound to a side chain thiol of the cysteine residue via a CH$_2$CONH linker, as shown in (Formula 1) below. The side chain thiol of the cysteine residue and the saccharide may be bound to each other without a linker.

[Chem. 67]

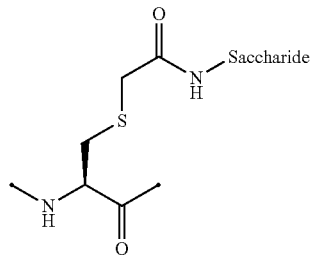

(Formula 1)

In the above (Formula 1), "Saccharide" represents a saccharide.

Examples of the glycosylated group derived from an asparagine residue include a structure in which a saccharide is bound to a side chain amide of the asparagine residue by chemical modification, as shown in (Formula 2) below. The side chain amide of the asparagine residue and the saccharide may be bound via a linker.

[Chem. 68]

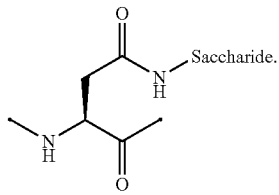

(Formula 2)

In the above (Formula 2), "Saccharide" represents a saccharide.

Examples of the IL-2 variant according to one embodiment of the present invention include an IL-2 variant in which at least one amino acid residue selected from the group consisting of amino acid residues at positions 11, 12, 13, 15, 16, 18, 19, 20, 84, 87, 88, 91, 92, 108, 115, 119, 122, 123, and 130 in the amino acid sequence of the wild-type IL-2 is substituted with a glycosylated amino acid residue.

Examples of an IL-2 variant in which one saccharide is bound to the wild-type IL-2 include those described below.

An IL-2 variant in which an amino acid residue at position 11 in an amino acid sequence of wild-type IL-2 is substituted with a glycosylated amino acid residue.

An IL-2 variant in which an amino acid residue at position 12 in an amino acid sequence of wild-type IL-2 is substituted with a glycosylated amino acid residue.

An IL-2 variant in which an amino acid residue at position 13 in an amino acid sequence of wild-type IL-2 is substituted with a glycosylated amino acid residue.

An IL-2 variant in which an amino acid residue at position 15 in an amino acid sequence of wild-type IL-2 is substituted with a glycosylated amino acid residue.

An IL-2 variant in which an amino acid residue at position 16 in an amino acid sequence of wild-type IL-2 is substituted with a glycosylated amino acid residue.

An IL-2 variant in which an amino acid residue at position 18 in an amino acid sequence of wild-type IL-2 is substituted with a glycosylated amino acid residue.

An IL-2 variant in which an amino acid residue at position 19 in an amino acid sequence of wild-type IL-2 is substituted with a glycosylated amino acid residue.

An IL-2 variant in which an amino acid residue at position 20 in an amino acid sequence of wild-type IL-2 is substituted with a glycosylated amino acid residue.

An IL-2 variant in which an amino acid residue at position 84 in an amino acid sequence of wild-type IL-2 is substituted with a glycosylated amino acid residue.

An IL-2 variant in which an amino acid residue at position 87 in an amino acid sequence of wild-type IL-2 is substituted with a glycosylated amino acid residue.

An IL-2 variant in which an amino acid residue at position 88 in an amino acid sequence of wild-type IL-2 is substituted with a glycosylated amino acid residue.

An IL-2 variant in which an amino acid residue at position 91 in an amino acid sequence of wild-type IL-2 is substituted with a glycosylated amino acid residue.

An IL-2 variant in which an amino acid residue at position 92 in an amino acid sequence of wild-type IL-2 is substituted with a glycosylated amino acid residue.

An IL-2 variant in which an amino acid residue at position 108 in an amino acid sequence of wild-type IL-2 is substituted with a glycosylated amino acid residue.

An IL-2 variant in which an amino acid residue at position 115 in an amino acid sequence of wild-type IL-2 is substituted with a glycosylated amino acid residue.

An IL-2 variant in which an amino acid residue at position 119 in an amino acid sequence of wild-type IL-2 is substituted with a glycosylated amino acid residue.

An IL-2 variant in which an amino acid residue at position 122 in an amino acid sequence of wild-type IL-2 is substituted with a glycosylated amino acid residue.

An IL-2 variant in which an amino acid residue at position 123 in an amino acid sequence of wild-type IL-2 is substituted with a glycosylated amino acid residue.

An IL-2 variant in which an amino acid residue at position 130 in an amino acid sequence of wild-type IL-2 is substituted with a glycosylated amino acid residue.

In the IL-2 variants described above, the saccharide to be bound may be any saccharide, and examples thereof include a saccharide comprising a structure represented by (Formula 4), (Formula 5), (Formula 6), (Formula 7), (Formula 8), or (Formula Y3).

An IL-2 variant in which an amino acid residue at position 11 in an amino acid sequence of wild-type IL-2 is substituted with a glycosylated group shown in (Formula 1) derived from a cysteine residue, and a structure of "Saccharide" in (Formula 1) is a structure represented by (Formula 8).

An IL-2 variant in which an amino acid residue at position 12 in an amino acid sequence of wild-type IL-2 is substituted with a glycosylated group shown in (Formula 1) derived from a cysteine residue, and a structure of "Saccharide" in (Formula 1) is a structure represented by (Formula 7) or (Formula 8).

An IL-2 variant in which an amino acid residue at position 13 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 8).

An IL-2 variant in which an amino acid residue at position 15 in an amino acid sequence of wild-type IL-2 is substituted with a glycosylated group shown in (Formula 1) derived from a cysteine residue, and a structure of "Saccharide" in (Formula 1) is a structure represented by (Formula 4), (Formula 8), or (Formula Y3).

An IL-2 variant in which an amino acid residue at position 16 in an amino acid sequence of wild-type IL-2 is substituted with a glycosylated group shown in (Formula 1) derived from a cysteine residue, and a structure of "Saccharide" in (Formula 1) is a structure represented by (Formula 4), (Formula 5), (Formula 6), or (Formula 7).

An IL-2 variant in which an amino acid residue at position 18 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 8).

An IL-2 variant in which an amino acid residue at position 19 in an amino acid sequence of wild-type IL-2 is substituted with a glycosylated group shown in (Formula 1) derived from a cysteine residue, and a structure of "Saccharide" in (Formula 1) is a structure represented by (Formula 4), (Formula 7), (Formula 8), or (Formula Y3).

An IL-2 variant in which an amino acid residue at position 20 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 8).

An IL-2 variant in which an amino acid residue at position 84 in an amino acid sequence of wild-type IL-2 is substituted with a glycosylated group shown in (Formula 1) derived from a cysteine residue, and a structure of "Saccharide" in (Formula 1) is a structure represented by (Formula 4).

An IL-2 variant in which an amino acid residue at position 87 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 8).

An IL-2 variant in which an amino acid residue at position 88 in an amino acid sequence of wild-type IL-2 is substituted with a glycosylated group shown in (Formula 1) derived from a cysteine residue, and a structure of "Saccharide" in (Formula 1) is a structure represented by (Formula 4), (Formula 7), or (Formula 8).

An IL-2 variant in which an amino acid residue at position 91 in an amino acid sequence of wild-type IL-2 is substituted with a glycosylated group shown in (Formula 1) derived from a cysteine residue, and a structure of "Saccharide" in (Formula 1) is a structure represented by (Formula 4), (Formula 7), or (Formula 8).

An IL-2 variant in which an amino acid residue at position 92 in an amino acid sequence of wild-type IL-2 is substituted with a glycosylated group shown in (Formula 1) derived from a cysteine residue, and a structure of "Saccharide" in (Formula 1) is a structure represented by (Formula 4).

An IL-2 variant in which an amino acid residue at position 108 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 7).

An IL-2 variant in which an amino acid residue at position 115 in an amino acid sequence of wild-type IL-2 is substituted with a glycosylated group shown in (Formula 1) derived from a cysteine residue, and a structure of "Saccharide" in (Formula 1) is a structure represented by (Formula 4).

An IL-2 variant in which an amino acid residue at position 119 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 7).

An IL-2 variant in which an amino acid residue at position 122 in an amino acid sequence of wild-type IL-2 is substituted with a glycosylated group shown in (Formula 1) derived from a cysteine residue, and a structure of "Saccharide" in (Formula 1) is a structure represented by (Formula 4).

An IL-2 variant in which an amino acid residue at position 123 in an amino acid sequence of wild-type IL-2 is substituted with a glycosylated group shown in (Formula 1) derived from a cysteine residue, and a structure of "Saccharide" in (Formula 1) is a structure represented by (Formula 8).

An IL-2 variant in which an amino acid residue at position 130 in an amino acid sequence of wild-type IL-2 is substituted with a glycosylated group shown in (Formula 1) derived from a cysteine residue, and a structure of "Saccharide" in (Formula 1) is a structure represented by (Formula 4) or (Formula 7).

One embodiment of the present invention also includes an IL-2 variant in which at least two saccharides are bound to wild-type IL-2. Examples of the IL-2 variant in which two saccharides are bound to wild-type IL-2 include an IL-2 variant comprising an amino acid sequence in which at least two amino acid residues selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 are substituted with a glycosylated group derived from a cysteine residue or an asparagine residue.

As an example of the IL-2 variant in which two saccharides are bound to wild-type IL-2, an IL-2 variant comprising an amino acid sequence in which one amino acid residue selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 and one amino acid residue selected from the group consisting of amino acid residues at positions 11, 12, 18, 20, 84, 87, 88, 91, 108, 115, 119, 122, and 123 in the amino acid sequence are substituted with a glycosylated group derived from a cysteine residue or an asparagine residue is preferred.

Specific examples of the IL-2 variant according to one embodiment of the present invention include those shown below.

An IL-2 variant in which each of amino acid residues at positions 8 and 19 in an amino acid sequence of wild-type IL-2 is substituted with a glycosylated amino acid residue.

An IL-2 variant in which each of amino acid residues at positions 12 and 16 in an amino acid sequence of wild-type IL-2 is substituted with a glycosylated amino acid residue.

An IL-2 variant in which each of amino acid residues at positions 15 and 119 in an amino acid sequence of wild-type IL-2 is substituted with a glycosylated amino acid residue.

An IL-2 variant in which each of amino acid residues at positions 19 and 23 in an amino acid sequence of wild-type IL-2 is substituted with a glycosylated amino acid residue.

An IL-2 variant in which each of amino acid residues at positions 12 and 91 in an amino acid sequence of wild-type IL-2 is substituted with a glycosylated amino acid residue.

An IL-2 variant in which each of amino acid residues at positions 12 and 115 in an amino acid sequence of wild-type IL-2 is substituted with a glycosylated amino acid residue.

An IL-2 variant in which each of amino acid residues at positions 12 and 119 in an amino acid sequence of wild-type IL-2 is substituted with a glycosylated amino acid residue.

An IL-2 variant in which each of amino acid residues at positions 13 and 91 in an amino acid sequence of wild-type IL-2 is substituted with a glycosylated amino acid residue.

An IL-2 variant in which each of amino acid residues at positions 13 and 115 in an amino acid sequence of wild-type IL-2 is substituted with a glycosylated amino acid residue.

An IL-2 variant in which each of amino acid residues at positions 13 and 119 in an amino acid sequence of wild-type IL-2 is substituted with a glycosylated amino acid residue.

An IL-2 variant in which each of amino acid residues at positions 19 and 115 in an amino acid sequence of wild-type IL-2 is substituted with a glycosylated amino acid residue.

An IL-2 variant in which each of amino acid residues at positions 91 and 115 in an amino acid sequence of wild-type IL-2 is substituted with a glycosylated amino acid residue.

An IL-2 variant in which each of amino acid residues at positions 91 and 119 in an amino acid sequence of wild-type IL-2 is substituted with a glycosylated amino acid residue.

In the IL-2 variants described above, the saccharide to be bound may be any saccharide, and examples thereof include a saccharide comprising a structure represented by (Formula 4) or (Formula 8).

In addition, specific examples of the IL-2 variant according to one embodiment of the present invention also include those shown below.

An IL-2 variant in which amino acid residues at positions 8 and 19 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 12 and 16 in an amino acid sequence of wild-type IL-2 are substituted with a glycosylated group shown in (Formula 1) derived from a cysteine residue, a structure of "Saccharide" in (Formula 1) to be bound position 12 is represented by (Formula 8), and a structure of "Saccharide" in (Formula 1) to be bound position 16 is represented by (Formula 4).

An IL-2 variant in which amino acid residues at positions 15 and 119 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 19 and 23 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 12 and 91 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 12 and 115 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 12 and 119 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 13 and 91 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 13 and 115 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 13 and 119 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 19 and 115 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 91 and 115 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 91 and 119 in an amino acid sequence of wild-type IL-2 are substituted with a glycosylated group shown in (Formula 1) derived from a cysteine residue, and a structure of "Saccharide" in (Formula 1) is represented by (Formula 8).

One embodiment of the present invention also includes an IL-2 variant in which at least three saccharides are bound to wild-type IL-2. Examples of the IL-2 variant in which three saccharides are bound to wild-type IL-2 include an IL-2 variant comprising an amino acid sequence in which at least three amino acid residues selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 are substituted with a glycosylated group derived from a cysteine residue or an asparagine residue.

In addition, as an example of the IL-2 variant in which three saccharides are bound to wild-type IL-2, an IL-2 variant comprising an amino acid sequence in which at least one amino acid residue selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 and at least one amino acid residue selected from the group consisting of amino acid residues at positions 11, 12, 18, 20, 84, 87, 88, 91, 108, 115, 119, 122, and 123 in the amino acid sequence are substituted with a glycosylated group derived from a cysteine residue or an asparagine residue is more preferred.

One embodiment of the present invention also includes an IL-2 variant in which at least four saccharides are bound to wild-type IL-2. Examples of the IL-2 variant in which four saccharides are bound to wild-type IL-2 include an IL-2 variant comprising an amino acid sequence in which at least four amino acid residues selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 are substituted with a glycosylated group derived from a cysteine residue or an asparagine residue.

In addition, as an example of the IL-2 variant in which four saccharides are bound to wild-type IL-2, an IL-2 variant comprising an amino acid sequence in which at least one amino acid residue selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 and at least one amino acid residue selected from the group consisting of amino acid residues at positions 11, 12, 18, 20, 84, 87, 88, 91, 108, 115, 119, 122, and 123 in the amino acid sequence are substituted with a glycosylated group derived from a cysteine residue or an asparagine residue is more preferred.

One embodiment of the present invention also includes an IL-2 variant in which at least five saccharides are bound to wild-type IL-2. Examples of the IL-2 variant in which five saccharides are bound to wild-type IL-2 include an IL-2 variant comprising an amino acid sequence in which five amino acid residues selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 are substituted with a glycosylated group derived from a cysteine residue or an asparagine residue.

In addition, as an example of the IL-2 variant in which five saccharides are bound to wild-type IL-2, an IL-2 variant comprising an amino acid sequence in which at least one amino acid residue selected from the group consisting of amino acid residues at positions 1, 3, 4, 5, 8, 11, 12, 13, 15, 16, 18, 19, 20, 23, 32, 38, 51, 76, 84, 87, 88, 91, 92, 100, 102, 104, 108, 115, 119, 122, 123, 127, and 130 in an amino acid sequence of wild-type IL-2 and at least one amino acid residue selected from the group consisting of amino acid residues at positions 1, 3, 5, 12, 32, 51, 76, 91, 100, 102, and 104 in the amino acid sequence are substituted with a glycosylated group derived from a cysteine residue or an asparagine residue is more preferred.

Examples of the IL-2 variant according to one embodiment of the present invention include those shown below.

An IL-2 variant in which each of amino acid residues at positions 3, 12, 32, 76, and 91 in an amino acid sequence of wild-type IL-2 is substituted with a glycosylated amino acid residue.

An IL-2 variant in which each of amino acid residues at positions 1, 3, 5, 12, and 91 in an amino acid sequence of wild-type IL-2 is substituted with a glycosylated amino acid residue.

An IL-2 variant in which each of amino acid residues at positions 3, 12, 51, 91, and 100 in an amino acid sequence of wild-type IL-2 is substituted with a glycosylated amino acid residue.

An IL-2 variant in which each of amino acid residues at positions 3, 12, 76, 91, and 100 in an amino acid sequence of wild-type IL-2 is substituted with a glycosylated amino acid residue.

An IL-2 variant in which each of amino acid residues at positions 12, 91, 100, 102, and 104 in an amino acid sequence of wild-type IL-2 is substituted with a glycosylated amino acid residue.

In the IL-2 variants described above, the saccharide to be bound may be any saccharide, and examples thereof include a saccharide comprising a structure represented by (Formula 8).

In addition, examples of the IL-2 variant according to one embodiment of the present invention also include those shown below.

An IL-2 variant in which amino acid residues at positions 3, 12, 32, 76, and 91 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 1, 3, 5, 12, and 91 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 3, 12, 51, 91, and 100 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 3, 12, 76, 91, and 100 in an amino acid sequence of wild-type IL-2 are substituted with a glycosylated group shown in (Formula 1) derived from a cysteine residue, and a structure of "Saccharide" in (Formula 1) is represented by (Formula 8).

An IL-2 variant in which amino acid residues at positions 12, 91, 100, 102, and 104 in an amino acid sequence of wild-type IL-2 are substituted with a glycosylated group shown in (Formula 1) derived from a cysteine residue, and a structure of "Saccharide" in (Formula 1) is represented by (Formula 8).

In the present embodiment, as the amino acid sequence of the wild-type IL-2, an amino acid sequence represented by SEQ ID NO: 1 or an amino acid sequence in which an amino acid residue at position 125 in the amino acid sequence represented by SEQ ID NO: 1 is substituted with a serine residue or an alanine residue is more preferred.

[Method for Producing Glycosylated IL-2 Variant]

Examples of a method for producing the glycosylated IL-2 variant include a method of chemically synthesizing a glycosylated peptide and then folding the same (chemical synthesis method) or a method in which an IL-2 variant in which an amino acid residue at a saccharide introduction position in an amino acid sequence of wild-type IL-2 is substituted with an amino acid residue to which the saccharide can be bound is expressed by a host cell such as *Escherichia coli*, and then a saccharide is bound to the amino acid residue to which the saccharide can be bound (expression method).

In the present specification, the "peptide" refers to a peptide in which a plurality of amino acid residues are linked via peptide bonds to form a chain. Unless otherwise specified, a side chain of each amino acid residue may contain a protective group, and an N-terminal amino group and a C-terminal carboxyl group may be modified.

The glycosylated IL-2 variant may be produced by a combination of the chemical synthesis method and the expression method. Hereinafter, each method will be described.

(Production of Glycosylated IL-2 Variant by Chemical Synthesis Method)

In the chemical synthesis method, it is preferable to produce a glycosylated IL-2 variant by sequentially joining at least one glycosylated peptide fragments and a peptide fragment and then folding the peptide fragments.

A total number of the peptide fragment and glycosylated peptide fragments to be joined is preferably 2 to 15 fragments, more preferably 2 to 5 fragments. The glycosylated peptide fragments and the peptide fragment may be thioesterified to obtain glycosylated peptide thioesters and a peptide thioester, and these may be joined.

Examples of a method for synthesizing the peptide fragment and a peptide thioester include a method commonly used in peptide synthesis [for example, method described in Fifth Edition, Experimental Chemistry Course 16, Synthesis of Organic Compounds IV: Carboxylic acid/Amino acid/Peptide (edited by The Chemical Society of Japan, Maruzen, 2005), Chemical Ligation: Tools for Biomolecule Synthesis and Modification (Luca D. DiAndrea et al., Wiley, 2017), and the like].

In this case, in order to improve solubility of peptides or the like, pseudoproline (J. Am. Chem. Soc., 1996, 118, 9218-9227) or isopeptide (Angew. Chem. Int. Ed., 2015, 54, 8226-8230) can also be used instead of two amino acids.

In addition, examples of a method for synthesizing peptide fragments and peptide thioesters include a liquid phase synthesis method such as Ajiphase technology (Tetrahedron Lett., 2012, 53, 1936.) developed by Takahashi et al. and Molecular Hiving technology (J. Org. Chem., 2013, 78, 320-327) developed by Okada et al., instead of a peptide solid phase synthesis method.

In addition, examples of the method for synthesizing peptide fragment include a method known in the related art, such as a production method using a recombinant DNA method including polymerase chain amplification reaction (PCR), preparation of plasmid DNA, cleavage of DNA by a restriction enzyme, preparation of oligonucleotides, DNA ligation, mRNA isolation, acquisition of a transformant by introducing DNA into an appropriate host cell, and culture of the transformant, a method described in cell-free protein expression method (Current Opinion in Biotechnology 2002, 13: 297-303) or the like. Examples of a method for synthesizing the peptide thioester include a method described in (Proc Natl Acad Sci USA 1998, 95: 6705-6710).

As a method of binding a saccharide to a peptide fragment, a peptide thioester, or the like, for example, in a case where a saccharide is bound to a side chain thiol of a cysteine residue of the peptide fragment, there is a method described in Japanese Patent No. 4607017. In addition, for example, in a case where a saccharide is bound to a side chain amide of an asparagine residue of the peptide fragment, there is a method described in Japanese Patent No. 4119428 or the like. In addition, examples of a method for producing a saccharide include a method described in International Publication No. WO 03/008431.

Examples of a method for joining the peptide fragments and/or the glycosylated peptide fragment include a method commonly used in peptide synthesis [for example, method described in Fifth Edition, Experimental Chemistry Course 16, Synthesis of Organic Compounds IV: Carboxylic acid/Amino acid/Peptide (edited by The Chemical Society of Japan, Maruzen, 2005), Chemical Ligation: Tools for Biomolecule Synthesis and Modification (Luca D. DiAndrea et al., Wiley, 2017), Chemoselective and Bioorthogonal Ligation Reactions Volume 1, 2 (W. Russ Algar et al. Wiley, 2017), or the like], and a native chemical ligation (NCL) method of a peptide fragment comprising a thioester at a C-terminal and another peptide fragment comprising a cysteine residue at an N-terminal is preferred.

The peptide fragment and/or the glycosylated peptide fragment can be joined at any position. However, in a case where the NCL method is used, as the N-terminal amino acid residue of a peptide fragment on a C-terminal side, a cysteine residue and an alanine residue are preferred, and the cysteine residue are more preferred.

As a method for joining the peptide fragment and/or the glycosylated peptide fragment, specifically, for example, in a case where an alanine residue is used as the N-terminal amino acid residue of the fragment on the C-terminal side, there is a method in which a C-terminal peptide fragment in which an alanine residue is substituted with a cysteine residue and an N-terminal peptide thioester fragment are joined by the NCL method, and then the cysteine residue is converted to an alanine residue by a desulfurization reaction, in accordance with a conventional method [Chemical Ligation: Tools for Biomolecule Synthesis and Modification (Luca D. DiAndrea et al., Wiley, 2017) and the like].

Examples of a method for folding the glycosylated peptide include a method commonly used in peptide folding [for example, method described in Fifth Edition, Experimental Chemistry Course 16, Synthesis of Organic Compounds IV: Carboxylic acid/Amino acid/Peptide (edited by The Chemical Society of Japan, Maruzen, 2005), Chemical Ligation: Tools for Biomolecule Synthesis and Modification (Luca D. DiAndrea et al., Wiley, 2017), and the like].

(Production of Glycosylated IL-2 Variant by Expression Method)

In the expression method, a glycosylated IL-2 variant can be produced in accordance with a method known in the related art. For example, the glycosylated IL-2 variant can be produced by a recombinant DNA method including polymerase chain amplification reaction (PCR), preparation of plasmid DNA, cleavage of DNA by a restriction enzyme, preparation of oligonucleotides, DNA ligation, mRNA isolation, acquisition of a transformant by introducing DNA into an appropriate host cell, and culture of the transformant and saccharide introduction by chemical modification.

Regarding the glycosylated IL-2 variant, for example, in an amino acid sequence of wild-type IL-2, an expression cassette containing a nucleotide sequence encoding a mutation-introduced amino acid sequence to include an amino acid residue to which a saccharide can be bound is incorporated into an appropriate expression vector, and the expression vector is introduced into host cells, a saccharide is bound to the obtained protein by chemical modification, whereby it is possible to obtain the glycosylated IL-2 variant.

Examples of the nucleotide sequence encoding wild-type IL-2 used for preparing the expression vector include a nucleotide sequence obtained by removing a nucleotide sequence encoding a signal sequence from a nucleotide sequence represented by NCBI Accession No. NM_000586 and a nucleotide sequence encoding an amino acid sequence represented by SEQ ID NO: 1.

The nucleotide sequence encoding IL-2 can be obtained by artificial gene synthesis or by designing appropriate primers from sequences registered in gene banks such as the Japan DNA Data Bank (DDBJ) and performing RT-PCR by mRNA extracted from cells or tissues of the animal.

In addition, the glycosylated IL-2 variant can also be obtained by introducing the expression vector described above into host cells capable of biosynthesizing a objective saccharide.

Specifically, regarding the expression vector, for example, the expression vector can be obtained by joining to downstream of a promoter in a vector suitable for expression in which the nucleotide sequence encoding the mutation-introduced IL-2 is incorporated in a desired position (for example, 5' terminal). The expression vector may have a secretion signal depending on the host.

As a method for introducing site-specific mutation into an amino acid sequence of wild-type IL-2 so as to include an amino acid residue to which a saccharide can be bound, known methods can be used (US Application Publication No. 2004/0171154); Storici et al, 2001, Nature Biotechnology, 19, p. 773-776: Kren et al, 1998, Nat. Med., Vol. 4, p. 285-290; and Calissano and Macino, 1996, Fungal Genet. News lett., Vol. 43, p. 15-16). In addition, commercially available kit may be used to introduce the site-specific mutation.

Specifically, for example, in a case where a cysteine residue is used as the amino acid residue to which a saccharide can be bound, an IL-2 variant in which an amino acid residue of wild-type IL-2 is substituted with a cysteine residue can be prepared in accordance with a method described in U.S. Pat. No. 5,206,344, International Publication No. WO 2016/025385 or the like, and the sacchariden can be bound to the IL-2 variant in accordance with a method described in Japanese Patent No. 4607017.

A region containing the nucleotide sequence encoding IL-2 may have a translation initiation codon at the 5' terminal and also may have a translation termination codon at a 3' terminal. In addition, in order to express the nucleotide sequence encoding IL-2, it is preferable to connect the promoter upstream thereof.

The promoter is not particularly limited as long as it is a promoter corresponding to a host used for gene expression. In a case in which the host to be transformed is *Bacillus subtilis*, examples of the promoter include SP01, SP02, and PenP promoters. In a case where the host is yeast, examples of the promoter include PH05, PGK, GAP, and ADH promoters. In a case where the host is *Escherichia coli*, examples of the promoter include a trp promoter (Ptrp) and a lac promoter. In a case where the host is an animal cell, examples of the promoter include an SV40-derived promoter and a retrovirus promoter.

IL-2 protein can also be expressed without a signal sequence in *Escherichia coli*, and the protein can be collected from inclusion bodies and refolded into an active form. Such an expression system is described in U.S. Pat. No. 7,105,653.

When using a signal sequence, it is possible to facilitate expression of the IL-2 protein. Examples of the signal sequence of a mammalian cell include a natural human IL-2 signal sequence, a signal sequence homologous to a TCR coding sequence, and a signal sequence homologous to a mouse IL-2 coding sequence. In addition, examples of another suitable signal sequence/host cell pairs include a *B. subtilis* sacB signal sequence for secretion in *B. subtilis*, and Saccharomyces cerevisiae a conjugation inducing factor signal sequence or *P. pastoris* acid phosphatase phol signal sequence, for secretion by *P. pastoris*. The signal sequence can be directly connected to a protein encoding sequence via a sequence encoding a signal peptidase cleavage site, or can be connected via a short nucleotide bridge.

Elements may be used for enhancing transcription and translation of eukaryotic protein expression systems. For example, when placing a cauliflower mosaic virus (CaMV) promoter at position 1000 bp on both sides of a heterologous promoter, it is possible to increase the transcription level in plant cells by a factor of 10 to 400.

The host cell is not particularly limited, and examples thereof include prokaryotic cells and eukaryotic cells. Preferred examples of the host cells include the prokaryotic cells such as *E. coli* and *Bacillus subtillus*, animal cells such as HEK, J558, NSO, SP2-O, CHO, COS, KB, NIH3T3, BALB/c3T3, and umbilical vein endothelial cells, yeast strains such as *S. cerevisiae* and *Pichia pastoris*, and insect cells such as SD or Tn.

The host cell may be modified so that the objective saccharide can be biosynthesized.

Transformation of the host may be performed by a method generally used for each host or an adaptable method. For example, when the host is *Escherichia coli* or yeast, an expression vector containing the recombinant DNA is introduced into a competent cell prepared by a lithium method or the like, by a temperature shock method or an electroporation method. when the host is an animal cell, an expression vector containing the recombinant DNA is introduced into a cell in a proliferation phase or the like by a calcium phosphate method, a lipofection method, or an electroporation method.

The transformant obtained in this manner is cultured in a medium generally used for each host or in an applicable culture solution to express the protein, and if necessary, a saccharide is further bound thereto by chemical modification. Accordingly, a glycosylated IL-2 protein can be produced. Examples of the culture solution include a culture solution such as an LB medium when the host is *Escherichia coli*, a culture solution such as a YPD medium when the host is yeast, and a culture solution in which fetal bovine serum is added to Dulbecco's MEM when the host is an animal cell.

The culture may be performed under conditions generally used for each host or under applicable conditions. For example, when the host is yeast, culture is performed at about 25° C. to 37° C. for about 12 hours to 2 weeks, and if necessary, aeration and stirring can be applied. In a case where the host is an animal cell, culture is performed at 37° C. under the conditions of 5% carbon dioxide gas and 100% humidity, for about 24 hours to 2 weeks, and if necessary, the gas phase conditions may be changed or stirred.

[PEGylated IL-2 Variant]

As the IL-2 variant according to one embodiment of the present invention, a variant in which PEG is bound to at least one amino acid residue selected from the group consisting of amino acid residues at positions 4, 5, 6, 7, 8, 60, 78, 79, 99, 100, 101, and 129 in an amino acid sequence of IL-2 is preferred, and an IL-2 variant in which PEG is bound to at least one of amino acid residues at positions 78 and 129 in the amino acid sequence is more preferred.

As the IL-2 variant according to one embodiment of the present invention, an IL-2 variant comprising an amino acid sequence in which at least one amino acid residue selected from the group consisting of amino acid residues at positions 4, 5, 6, 7, 8, 60, 78, 79, 99, 100, 101, and 129 in an amino acid sequence of wild-type IL-2 is substituted with a PEGylated amino acid residue is preferred, and an IL-2 variant comprising an amino acid sequence in which at least one of amino acid residues at positions 78 and 129 is substituted with a PEGylated amino acid residue is more preferred.

In the present embodiment, as the amino acid sequence of wild-type IL-2, an amino acid sequence represented by SEQ ID NO: 1, an amino acid sequence in which a methionine residue is bound to the N-terminal of the amino acid sequence represented by SEQ ID NO: 1, an amino acid sequence in which the N-terminal alanine residue of the amino acid sequence represented by SEQ ID NO: 1 has been deleted, an amino acid sequence in which the N-terminal alanine residue of the amino acid sequence represented by SEQ ID NO: 1 has been deleted and a methionine residue has been bound, or the amino acid sequence represented by SEQ ID NO: 1, the amino acid sequence in which a methionine residue is bound to the N-terminal of the amino acid sequence represented by SEQ ID NO: 1, the amino acid sequence in which the N-terminal alanine residue of the amino acid sequence represented by SEQ ID NO: 1 has been deleted, or the amino acid sequence in which the N-terminal alanine residue of the amino acid sequence represented by SEQ ID NO: 1 has been deleted and a methionine residue has been bound, wherein an amino acid residue at position 125 in these amino acid sequences is substituted with a serine residue or an alanine residue is more preferred.

The "PEG" is a poly (ethylene glycol) molecule that is a water-soluble polymer comprising a structure in which ethylene glycol represented by "—$(CH_2CH_2O)_n$-" (n is 2 or more) is polymerized. As the PEG, PEG4 having an average molecular weight of 10 kDa or more is preferred. For example, the average molecular weight is 10 kDa, 20 kDa, 30 kDa, 40 kDa, 50 kDa, 60 kDa, 70 kDa, 80 kDa, 90 kDa, 100 kDa, 200 kDa, or the like, and is not particularly limited. In addition, a shape of PEG may be linear or branched, and is not limited thereto. When chemically binding the PEG to the amino acid residue in the amino acid sequence of IL-2, it is possible to improve selectivity for IL-2$R_{\alpha\beta\gamma}$. Tregs can be selectively activated by the IL-2 variant having improved selectivity for IL-2$R_{\alpha\beta\gamma}$.

Examples of the PEGylated amino acid residue include a PEGylated cysteine residue and a PEGylated non-natural amino acid residue.

Examples of the PEGylated non-natural amino acid residue include a PEGylated group derived from an amino acid residue comprising a thiol group and a PEGylated group derived from an amino acid residue comprising an azide group. Specific examples of the amino acid residue comprising a thiol group include acetylcysteine and homocysteine, but are not limited thereto. Specific examples of the amino acid residue comprising an azide group include an o-Az-Z-Lys residue, an m-Az-Z-Lys residue, $N^6$-diazolidine, and p-azidophenylalanine, and are not limited thereto. Other examples of the non-natural amino acid residue may include non-natural amino acid residues described in International Publication No. WO 2017/030156, [Nature. 2017 Nov. 29; 551 (7682): 644-647.], International Publication No. WO 2013/068874, US Application Publication No. 2014-0046030, [Bioconj. Chem., 2014, 25 (2), pp 351-361], International Publication No. WO 2014/044872, [Bioconj. Chem. 2015 Nov. 18; 26 (11): 2249-60], International Publication No. WO 2014/124258, [Proc Natl Acad Sci US A. 2011 Jun. 28; 108 (26): 10437-42] and the like. The PEG and the non-natural amino acid residue may be bound to each other via a linker. The linker can be appropriately changed depending on the type of the PEG or the non-natural amino acid residue.

The o-Az-Z-Lys residue is an amino acid residue comprising a structure represented by (Formula 10) below.

[Chem. 69]

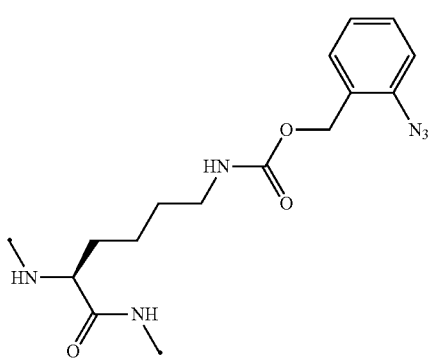

(Formula 10)

The m-Az-Z-Lys residue is an amino acid residue comprising a structure represented by (Formula XX1) below.

[Chem. 70]

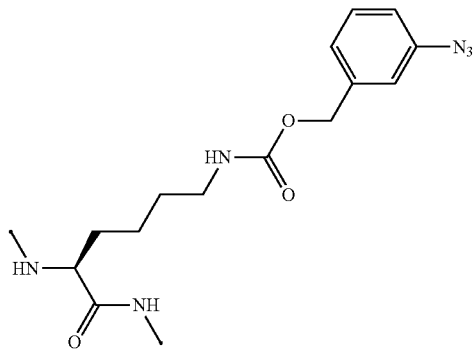

(Formula XX1)

Examples of the PEGylated group derived from an o-Az-Z-Lys residue or the PEGylated group derived from an m-Az-Z-Lys residue include a structure in which PEG is bound to the o-Az-Z-Lys residue or an amide group of the m-Az-Z-Lys via a linker by reacting acetylene. Examples of the acetylene include Dibenzylcyclooctyne (DBCO) and Bicyclo [6.1.0] nonyne (BCN). In addition, a structure in which the PEG is bound via amide bond instead of the acetylene, according to a method described in [J. Am. Chem. Soc. 2006, 128, pp 8820], [Org. Lett. 2000, 2, pp 2141], [Org. Lett. 2000, 2, pp 1939.], or the like is exemplified, but not limited thereto.

Specific examples of the PEGylated group derived from the o-Az-Z-Lys residue or the PEGylated group derived from the m-Az-Z-Lys residue include a structure represented by (Formula 11) and/or (Formula 12) or (Formula Y4) and/or (Formula Y5) below.

[Chem. 71]

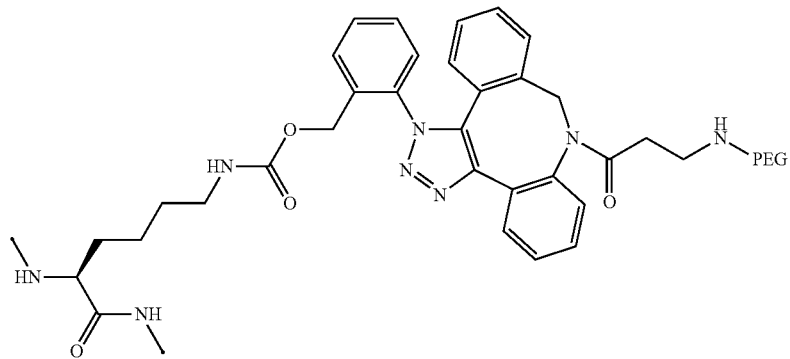

(Formula 11)

[Chem. 72]
(Formula 12)
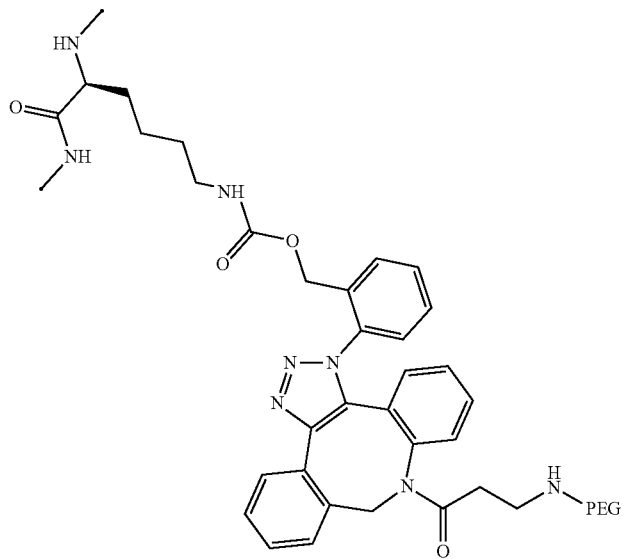
[Chem. 73]
(Formula Y4)
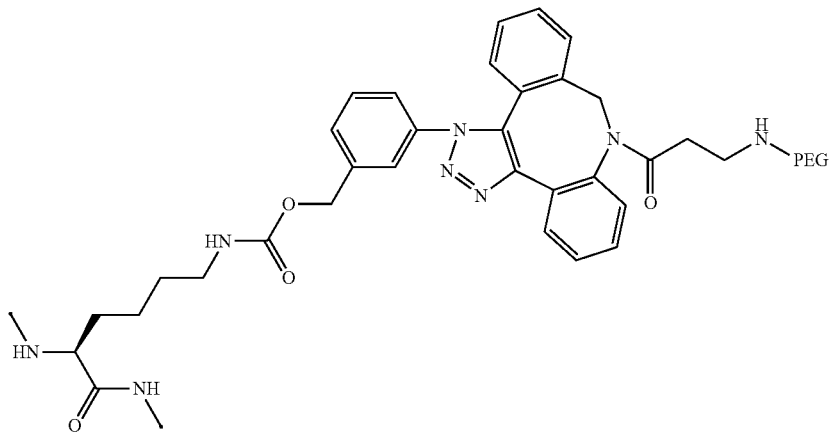

[Chem. 74]

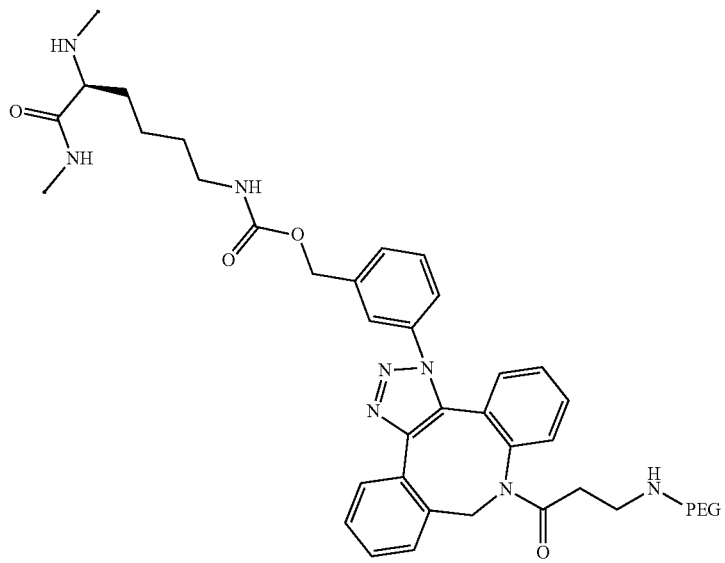

(Formula Y5)

As PEG in the formula, various PEGs can be used with various average molecular weight or a structure of PEG. Specific examples of the PEG include structures represented by (Formula 13) below, Formula (14) below in a case where the average molecular weight is 20 kDa, Formula (14) below in a case where the average molecular weight is 30 kDa, (Formula X0) below in a case where the average molecular weight is 40 kDa, (Formula 15) below in a case where the average molecular weight is 50 kDa, (Formula 16) below in a case where the average molecular weight is 40 kDa, (Formula 16) below in a case where the average molecular weight is 80 kDa, (Formula X1) below in a case where the average molecular weight is 40 kDa, (Formula X2) below in a case where the average molecular weight is 80 kDa, and (Formula X3) below in a case where the average molecular weight is 40 kDa, and are not limited thereto. In addition, in a case where PEG in the formula is represented by (Formula X3) below, not only the 4-branched chain of $O(CH_2CH_2O)_nCH_3$ but also a 2-branched or 3-branched chain thereof can be used in the same manner.

[Chem. 75]

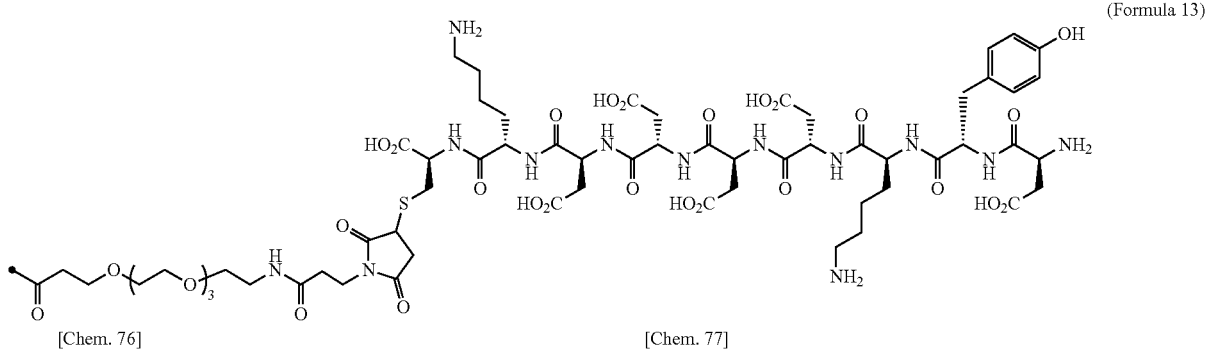

(Formula 13)

[Chem. 76]

(Formula 14)

[Chem. 77]

(Formula X0)

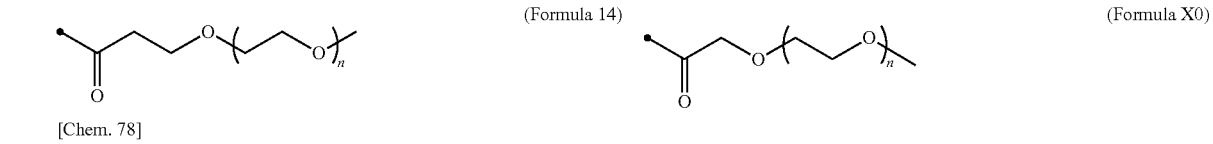

[Chem. 78]

(Formula 15)

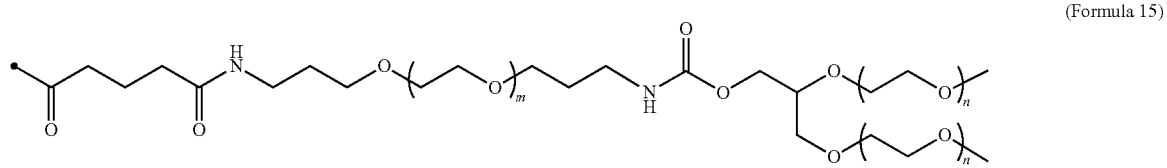

[Chem. 79]
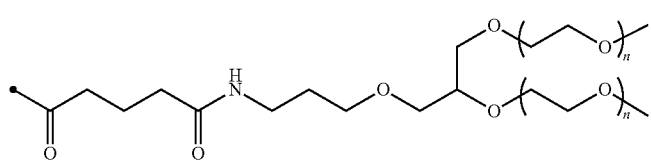
(Formula 16)
[Chem. 80]
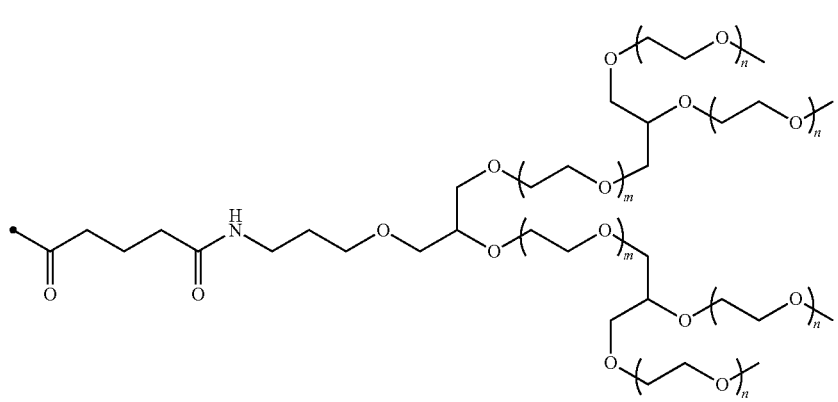
(Formula X1)
[Chem. 81]
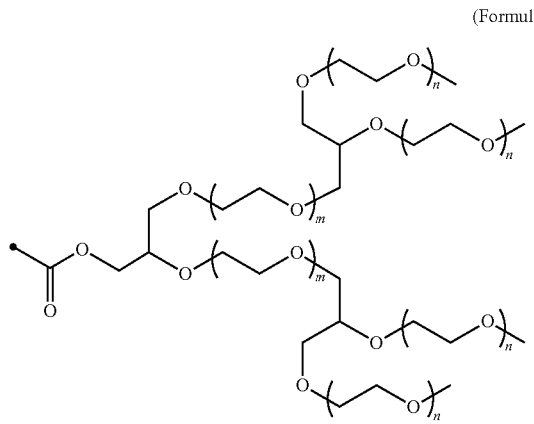
(Formula X2)
[Chem. 82]
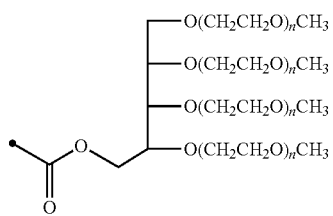
(Formula X3)

Specific examples of the PEGylated group derived from a cysteine residue include a structure represented by (Formula Y6), (Formula Y7), and/or (Formula Y8) below in which the PEG is bound to a thiol group of the cysteine residue via a linker formed by reacting maleimide, a structure represented by (Formula Y9) below in which the PEG is bound to a thiol group of the cysteine residue via a linker formed by reacting a haloacetyl group, and the like, and are not limited thereto.

[Chem. 83]

(Formula Y6)

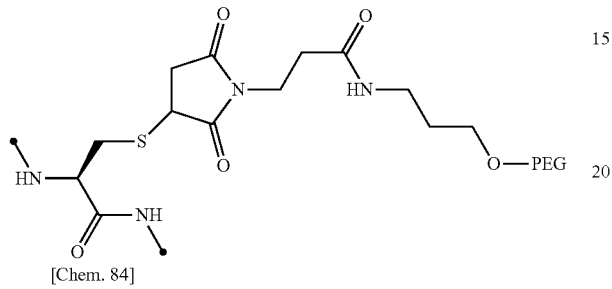

[Chem. 84]

(Formula Y7)

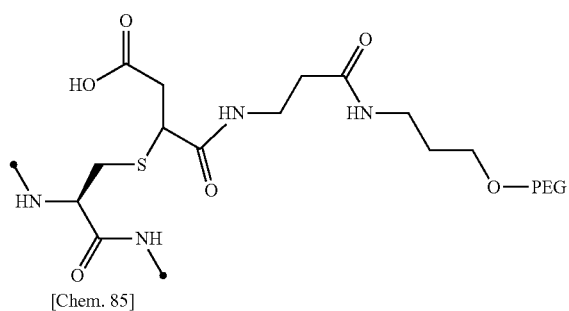

[Chem. 85]

(Formula Y8)

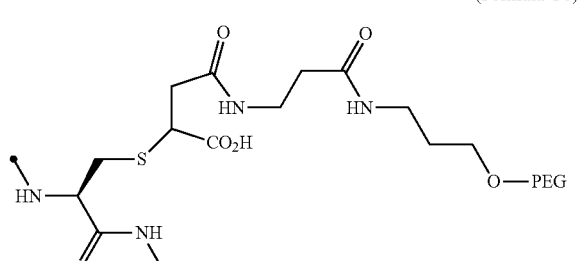

[Chem. 86]

(Formula Y9)

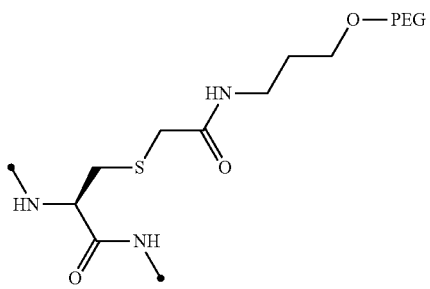

In the formula, specific examples of the PEG include a structure represented by (Formula X7) below in a case where the average molecular weight is 40 kDa, (Formula X7) below in a case where the average molecular weight is 80 kDa, or (Formula X8) below in a case where the average molecular weight is 80 kDa, and are not limited thereto.

[Chem. 87]

(Formula X7)

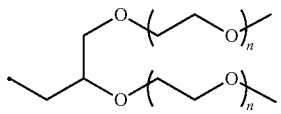

[Chem. 88]

(Formula X8)

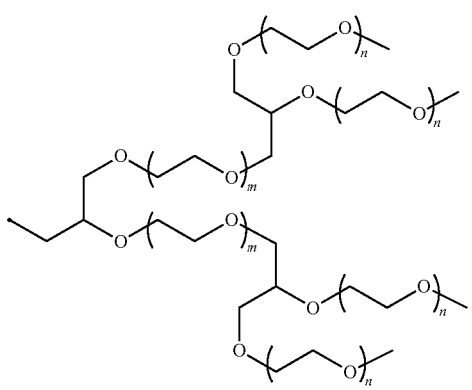

As the IL-2 variant according to one embodiment of the present invention, IL-2 variants to be described below are preferred.

Examples of the IL-2 variant according to one embodiment of the present invention include IL-2 variants to be described below, in which one PEG is bound to IL-2.

An IL-2 variant in which an amino acid residue at position 4 in an amino acid sequence of wild-type IL-2 is substituted with a PEGylated amino acid residue.

An IL-2 variant in which an amino acid residue at position 5 in an amino acid sequence of wild-type IL-2 is substituted with a PEGylated amino acid residue.

An IL-2 variant in which an amino acid residue at position 6 in an amino acid sequence of wild-type IL-2 is substituted with a PEGylated amino acid residue.

An IL-2 variant in which an amino acid residue at position 7 in an amino acid sequence of wild-type IL-2 is substituted with a PEGylated amino acid residue.

An IL-2 variant in which an amino acid residue at position 8 in an amino acid sequence of wild-type IL-2 is substituted with a PEGylated amino acid residue.

An IL-2 variant in which an amino acid residue at position 60 in an amino acid sequence of wild-type IL-2 is substituted with a PEGylated amino acid residue.

An IL-2 variant in which an amino acid residue at position 78 in an amino acid sequence of wild-type IL-2 is substituted with a PEGylated amino acid residue.

An IL-2 variant in which an amino acid residue at position 79 in an amino acid sequence of wild-type IL-2 is substituted with a PEGylated amino acid residue.

An IL-2 variant in which an amino acid residue at position 99 in an amino acid sequence of wild-type IL-2 is substituted with a PEGylated amino acid residue.

An IL-2 variant in which an amino acid residue at position 100 in an amino acid sequence of wild-type IL-2 is substituted with a PEGylated amino acid residue.

An IL-2 variant in which an amino acid residue at position 101 in an amino acid sequence of wild-type IL-2 is substituted with a PEGylated amino acid residue.

An IL-2 variant in which an amino acid residue at position 129 in an amino acid sequence of wild-type IL-2 is substituted with a PEGylated amino acid residue.

In the IL-2 variants described above, regarding a size of the PEG to be bound, PEG having an average molecular weight of 20 kDa or more is preferred. Examples thereof include PEG having an average molecular weight of 20, 30, 40, 50, 60, 70, or 80 kDa.

Examples of the IL-2 variant according to one embodiment of the present invention also include IL-2 variants to be described below, in which one PEG is bound to IL-2.

An IL-2 variant in which an amino acid residue at position 4 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa.

An IL-2 variant in which an amino acid residue at position 5 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa.

An IL-2 variant in which an amino acid residue at position 6 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa.

An IL-2 variant in which an amino acid residue at position 7 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which an amino acid residue at position 8 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa.

An IL-2 variant in which an amino acid residue at position 60 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which an amino acid residue at position 78 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa, (Formula X0) in a case where the average molecular weight is 40 kDa, (Formula 15) in a case where the average molecular weight is 50 kDa, (Formula 16) in a case where the average molecular weight is 40 kDa or 80 kDa, (Formula X1) in a case where the average molecular weight is 40 kDa, (Formula X2) in a case where the average molecular weight is 80 kDa, or (Formula X3) in a case where the average molecular weight is 40 kDa.

An IL-2 variant in which an amino acid residue at position 79 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa.

An IL-2 variant in which an amino acid residue at position 99 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which an amino acid residue at position 100 in an amino acid sequence of wild-type IL-2 is substituted with a PEGylated group derived from an o-Az-Z-Lys residue, in which the PEG is represented by (Formula 14) in a case where the average molecular weight is 20 kDa.

An IL-2 variant in which an amino acid residue at position 101 in an amino acid sequence of wild-type IL-2 is substituted with a PEGylated group derived from an o-Az-Z-Lys residue, in which the PEG is represented by (Formula 14) in a case where the average molecular weight is 20 kDa or the average molecular weight is 30 kDa.

An IL-2 variant in which an amino acid residue at position 129 in an amino acid sequence of wild-type IL-2 is substituted with a PEGylated group derived from an o-Az-Z-Lys residue, in which the PEG is represented by (Formula 13), (Formula 14) in a case where the average molecular weight is 20 kDa or the average molecular weight is 30 kDa, (Formula X0) in a case where the average molecular weight is 40 kDa, (Formula 16) in a case where the average molecular weight is 40 kDa or 80 kDa, (Formula X1) in a case where the average molecular weight is 40 kDa, (Formula X2) in a case where the average molecular weight is 80 kDa, (Formula 15) in a case where the average molecular weight is 50 kDa, or (Formula X3) in a case where the average molecular weight is 40 kDa.

An IL-2 variant in which an amino acid residue at position 129 in an amino acid sequence of wild-type IL-2 is substituted with a PEGylated group derived from an o-Az-Z-Lys residue, in which the PEG is represented by (Formula 16) in a case of 40 kDa.

An IL-2 variant in which an amino acid residue at position 129 in an amino acid sequence of wild-type IL-2 is substituted with a PEGylated group derived from a cysteine residue, in which the PEG is represented by (Formula X7) and/or (Formula X8) in a case where the average molecular weight is 40 kDa or 80 kDa.

As the IL-2 variant according to one embodiment of the present invention, IL-2 variants to be described below in which at least two PEGs are bound to IL-2 is preferred.

An IL-2 variant in which each of amino acid residues at positions 4 and 78 in an amino acid sequence of wild-type IL-2 is substituted with a PEGylated amino acid residue.

An IL-2 variant in which each of amino acid residues at positions 5 and 78 in an amino acid sequence of wild-type IL-2 is substituted with a PEGylated amino acid residue.

An IL-2 variant in which each of amino acid residues at positions 8 and 78 in an amino acid sequence of wild-type IL-2 is substituted with a PEGylated amino acid residue.

An IL-2 variant in which each of amino acid residues at positions 78 and 79 in an amino acid sequence of wild-type IL-2 is substituted with a PEGylated amino acid residue.

An IL-2 variant in which each of amino acid residues at positions 78 and 99 in an amino acid sequence of wild-type IL-2 is substituted with a PEGylated amino acid residue.

An IL-2 variant in which each of amino acid residues at positions 78 and 129 in an amino acid sequence of wild-type IL-2 is substituted with a PEGylated amino acid residue.

An IL-2 variant in which each of amino acid residues at positions 4 and 129 in an amino acid sequence of wild-type IL-2 is substituted with a PEGylated amino acid residue.

An IL-2 variant in which each of amino acid residues at positions 5 and 129 in an amino acid sequence of wild-type IL-2 is substituted with a PEGylated amino acid residue.

An IL-2 variant in which each of amino acid residues at positions 8 and 129 in an amino acid sequence of wild-type IL-2 is substituted with a PEGylated amino acid residue.

An IL-2 variant in which each of amino acid residues at positions 79 and 129 in an amino acid sequence of wild-type IL-2 is substituted with a PEGylated amino acid residue.

An IL-2 variant in which each of amino acid residues at positions 99 and 129 in an amino acid sequence of wild-type IL-2 is substituted with a PEGylated amino acid residue.

In the IL-2 variants described above, regarding the size of the PEG to be bound, PEG having an average molecular weight of 20 kDa or more is preferred. Examples thereof include PEG having an average molecular weight of 20, 30, 40, 50, 60, 70, or 80 kDa.

As the IL-2 variant according to one embodiment of the present invention, IL-2 variants to be described below in which at least two PEGs are bound to IL-2 is also preferred.

An IL-2 variant in which each of amino acid residues at position 4 and 78 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which each of amino acid residues at position 4 and 78 in an amino acid sequence of wild-type IL-2 is substituted with a PEGylated group derived from an o-Az-Z-Lys residue, in which the PEG is represented by (Formula X0) in a case where the average molecular weight is 40 kDa.

An IL-2 variant in which each of amino acid residues at position 4 and 78 in an amino acid sequence of wild-type IL-2 is substituted with a PEGylated group derived from an o-Az-Z-Lys residue, in which the PEG is represented by (Formula 15) in a case where the average molecular weight is 50 kDa.

An IL-2 variant in which each of amino acid residues at position 5 and 78 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which each of amino acid residues at position 5 and 78 in an amino acid sequence of wild-type IL-2 is substituted with a PEGylated group derived from an o-Az-Z-Lys residue, in which the PEG is represented by (Formula X0) in a case where the average molecular weight is 40 kDa.

An IL-2 variant in which each of amino acid residues at position 8 and 78 in an amino acid sequence of wild-type IL-2 is substituted with a PEGylated group derived from an o-Az-Z-Lys residue, in which the PEG is represented by (Formula 14) in a case where the average molecular weight is 30 kDa or (Formula X0) in a case where the average molecular weight is 40 kDa.

An IL-2 variant in which each of amino acid residues at position 78 and 79 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which each of amino acid residues at position 78 and 99 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which each of amino acid residues at position 78 and 129 in an amino acid sequence of wild-type IL-2 is substituted with a PEGylated group derived from an o-Az-Z-Lys residue, in which the PEG is represented by (Formula 14) in a case where the average molecular weight is 30 kDa.

An IL-2 variant in which each of amino acid residues at position 4 and 129 in an amino acid sequence of wild-type IL-2 is substituted with a PEGylated group derived from an o-Az-Z-Lys residue, in which the PEG is represented by (Formula 14) in a case where the average molecular weight is 30 kDa, (Formula X0) in a case where the average molecular weight is 40 kDa, or (Formula 15) in a case where the average molecular weight is 50 kDa.

An IL-2 variant in which each of amino acid residues at position 5 and 129 in an amino acid sequence of wild-type IL-2 is substituted with a PEGylated group derived from an o-Az-Z-Lys residue, in which the PEG is represented by (Formula 14) in a case where the average molecular weight is 30 kDa, (Formula X0) in a case where the average molecular weight is 40 kDa, or (Formula 15) in a case where the average molecular weight is 50 kDa.

An IL-2 variant in which each of amino acid residues at position 8 and 129 in an amino acid sequence of wild-type IL-2 is substituted with a PEGylated group derived from an o-Az-Z-Lys residue, in which the PEG is represented by (Formula 14) in a case where the average molecular weight is 30 kDa, (Formula X0) in a case where the average molecular weight is 40 kDa, or (Formula 15) in a case where the average molecular weight is 50 kDa.

An IL-2 variant in which each of amino acid residues at position 79 and 129 in an amino acid sequence of wild-type IL-2 are substituted with a PEGylated group derived from an o-Az-Z-Lys residue, in which the PEG is represented by (Formula 14) in a case where the average molecular weight is 30 kDa.

An IL-2 variant in which each of amino acid residues at position 99 and 129 in an amino acid sequence of wild-type IL-2 are substituted with a PEGylated group derived from an o-Az-Z-Lys residue, in which the PEG is represented by (Formula 14) in a case where the average molecular weight is 30 kDa.

In the present embodiment, as the amino acid sequence of wild-type IL-2, an amino acid sequence represented by SEQ ID NO: 1, an amino acid sequence in which a methionine residue is bound to the N-terminal of the amino acid sequence represented by SEQ ID NO: 1, an amino acid sequence in which the N-terminal alanine residue of the amino acid sequence represented by SEQ ID NO: 1 has been deleted, an amino acid sequence in which the N-terminal alanine residue of the amino acid sequence represented by SEQ ID NO: 1 has been deleted and a methionine residue has been bound, or the amino acid sequence represented by SEQ ID NO: 1, the amino acid sequence in which a methionine residue is bound to the N-terminal of the amino acid sequence represented by SEQ ID NO: 1, the amino acid sequence in which the N-terminal alanine residue of the amino acid sequence represented by SEQ ID NO: 1 has been deleted, or the amino acid sequence in which the N-terminal alanine residue of the amino acid sequence represented by SEQ ID NO: 1 has been deleted and a methionine residue has been bound, wherein an amino acid residue at position 125 of these amino acid sequences is substituted with a serine residue or an alanine residue, is preferred.

[Method for Producing PEGylated IL-2 Variant]

Examples of a method for producing the PEGylated IL-2 variant include a chemical synthesis method and an expression method. The PEGylated IL-2 variant may be produced by a combination of the chemical synthesis method and the expression method. Hereinafter, each method will be described.

(Production of PEGylated IL-2 Variant by Chemical Synthesis Method)

Examples of a method for producing the PEGylated IL-2 variant by the chemical synthesis method include a method in which the PEG is bound to an IL-2 variant obtained by chemically synthesizing a peptide in which an amino acid residue at a PEGylation position in the amino acid sequence of wild-type IL-2 has been substituted with an amino acid residue having chemical reactivity that enables site-specific PEGylation of protein and then folding to produce the PEGylated IL-2 variant, and a method in which PEGylated peptide fragment is chemically synthesized and then folded to produce the PEGylated IL-2 variant.

The PEGylated peptide fragment can be produced by a method of PEGylation of the amino acid residue having chemical reactivity that enables site-specific PEGylation of protein in the peptide fragment.

Examples of the method of folding after chemically synthesizing the PEGylated peptide fragment include a method of sequentially joining at least one or more PEGylated peptide fragments and the peptide fragment and then folding, or a method of folding after PEGylation of a chemically synthesized IL-2 full-length peptide fragment.

Examples of a method for synthesizing the peptide fragment and a method for sequentially joining and then folding a peptide fragment include a method similar to the method described in the section of (Production of glycosylated IL-2 variant by chemical synthesis).

Examples of a method of PEGylation of the IL-2 variant obtained by synthesizing the peptide in which an amino acid residue at a PEGylation position in the amino acid sequence of wild-type IL-2 has been substituted with an amino acid residue having chemical reactivity that enables site-specific PEGylation of protein and then folding include a method described in U.S. Pat. No. 5,206,344 or International Publication No. WO 2012/065086. In addition, examples of PEGylation of the amino acid residue having chemical reactivity that enables site-specific PEGylation of protein in the peptide fragment include a method described in [Biomaterials 22 (2001) 405-417], [Int. J. Mol. Sci. 2015, 16, 25831-25864], or [J. Pharm. Sci., 105 (2016) 460-475].

Examples of the amino acid residue having chemical reactivity that enables site-specific PEGylation of protein include an amino acid residue comprising a thiol group and an amino acid residue comprising an azide group. Examples of the amino acid residue comprising a thiol group include cysteine, acetylcysteine and homocysteine, and are not limited thereto.

Examples of the amino acid residue comprising an azide group include an o-Az-Z-Lys residue, an m-Az-Z-Lys residue, $N^6$-azidolidine, and p-azidophenylalanine, and are not limited thereto. Other examples thereof may include non-natural amino acid residue described in International Publication No. WO 2017/030156, [Nature. 2017 Nov. 29; 551 (7682): 644-647.], International Publication No. WO 2013/068874, US Application Publication No. 2014/0046030, [Bioconj. Chem., 2014, 25 (2), pp 351-361], International Publication No. WO 2014/044872, [Bioconj. Chem. 2015 Nov. 18; 26 (11): 2249-60], International Publication No. WO 2014/124258, and [Proc Natl Acad Sci USA. 2011 Jun. 28; 108 (26): 10437-42]. The PEG and the non-natural amino acid residue may be bound to each other via a linker.

The linker is a hydrocarbon group comprising 1 to 20 carbon atoms, and the carbon may be modified with oxygen, nitrogen, sulfur, or the like, or the carbon may be substituted with oxygen, nitrogen, or sulfur. The linker can be appropriately changed depending on the type of the PEG or the non-natural amino acid residue.

Specific example of the chemical synthesis method include a method in which PEG is introduced into the IL-2 variant obtained by chemically synthesizing the peptide in which an amino acid residue at a PEGylation site in an amino acid sequence of wild-type IL-2 has been substituted with an amino acid residue comprising a thiol group, such as cysteine and/or an amino acid residue comprising an azide group, such as o-Az-Z-Lys residue and then folding to produce the PEGylated IL-2 variant. Examples of the method of PEGylation of an IL-2 variant into which a cysteine residue has been introduced include a method described in U.S. Pat. No. 5,206,344.

In addition, specific examples include a method in which PEG is introduced into the IL-2 variant obtained by chemically synthesizing the peptide in which an amino acid residue at a PEGylation site in an amino acid sequence of wild-type IL-2 has been substituted with cysteine or non-natural amino acid residue and then folding to produce the PEGylated IL-2 variant.

A PEG reagent represented by (Formula XX2) can be used for the synthesis of the PEGylated IL-2 variant.

[Chem. 89]

X-(Linker)$_n$-PEG-Me                              (Formula XX2)

In the formula, X represents a functional group reactive with a thiol group, a functional group reactive with an azide group, or a functional group selectively reacting with an N-terminal amino group.

Specific examples of the functional group having reactivity with thiol include a thiol group, a maleimide group, an acryl group, an iodoacetyl group, a bromoacetyl group, and a chloroacetyl group, and the iodoacetyl group and the maleimide group are favorable.

Specific examples of the functional group reactive with azide include an acetylene group, a DBCO group, a DBN group, and a cycloalkyne comprising a hetero atom on a medium ring structure (Angew. Chem. Int. Ed. 2015, 54, 1190-1194), and a thioester group, and DBCO is preferred.

Specific examples of the functional group selectively reacting with the N-terminal amino group include aldehyde.

In the formula, as "Linker", a hydrocarbon group comprising 1 to 20 carbon atoms may be used. The carbon may be modified with oxygen, nitrogen, sulfur, or the like, and the carbon may be substituted with oxygen, nitrogen, or sulfur.

In the formula, n represents 0 or 1.

In the formula, the "PEG" is a poly (ethylene glycol) molecule that is a water-soluble polymer comprising a structure in which ethylene glycol represented by "—$(CH_2CH_2O)_m$—" (m is 2 or more) is polymerized. Examples of a molecular weight of the PEG include PEG4, an average molecular weight of 20 kDa, 30 kDa, 40 kDa, 50 kDa, 60 kDa, 70 kDa, 80 kDa, 90 kDa, 100 kDa, or 200 kDa, but are not particularly limited. In addition, a shape of PEG may be linear or branched, but is not limited thereto.

Depending on the PEG reagent to be used, stereoisomers, optical isomers, geometric isomers, and the like may be formed in some cases, and these isomers may be separated and used by a known method, or may be used as a mixture. Since the obtained IL-2 variant is a macromolecule, it is considered that the structural difference between the isomers of these partial structures has almost no effect.

As the PEG reagent, in addition to a commercially available PEG reagent, a PEG reagent prepared from a commercially available PEG reagent can also be used. For example, it is possible to prepare a PEG reagent by condensing a PEG reagent comprising a carboxylic acid equivalent such as a carboxyl group or N-hydroxysuccinimide ester at the terminal with an amine having reactivity with a thiol group or a azide group. In addition, the PEG reagent can also be synthesized by condensing a PEG reagent comprising an amino group at a terminal with a carboxylic acid equivalent such as a carboxyl group or N-hydroxysuccinimide ester having reactivity with a thiol group or an azide group. However, the present invention is not limited thereto.

(Production of PEGylated IL-2 Variant by Expression Method)

Examples of a method for producing a PEGylated IL-2 variant by the expression method include a method in which after IL-2 variant in which an amino acid residue at a PEGylation site in an amino acid sequence of wild-type IL-2 is substituted with an amino acid residue having chemical reactivity that enables site-specific PEGylation of protein is expressed by a host cell such as *Escherichia coli*, and then PEG is bound to the amino acid residue in the IL-2 variant by chemical modification to produce the PEGylated IL-2 variant.

Specific examples thereof include, in the same manner as in the method described above in the section (Production of glycosylated IL-2 variant by expression method), a method in which an expression cassette containing a nucleotide sequence encoding an amino acid sequence to which substitution with an amino acid residue having chemical reactivity that enables site-specific PEGylation of protein is introduced into a PEGylation position in an amino acid sequence of wild-type IL-2 is incorporated an appropriate expression vector, and the expression vector is introduced into host cells such as *Escherichia coli* to obtain a transformant, the IL-2 variant is expressed on the transformant, and PEG is bound to a cysteine residue or a non-natural amino acid residue of the IL-2 variant by chemical modification, whereby it is possible to obtain the PEGylated IL-2 variant.

In a case where the *Escherichia coli* is used as the host cell, for the purpose of expression efficiency, purification of the produced protein, or the like, a linker may be introduced into the N-terminal of the wild-type IL-2 to form the expression cassette. Examples of the linker include a methionine residue, eight polyhistidines, and eight polyhistidines containing a methionine residue.

Examples of a method for preparing the IL-2 variant in which an amino acid residue of IL-2 is substituted with a cysteine residue include methods described in U.S. Pat. No. 5,206,344 and International Publication No. WO 2016/025385.

Examples of a method for preparing the IL-2 variant in which the amino acid residue of IL-2 is substituted with a non-natural amino acid residue having chemical reactivity that enables site-specific PEGylation of a protein include methods described in International Publication No. WO 2017/No. 030156, [Nature. 2017 Nov. 29; 551 (7682): 644-647.], International Publication No. WO 2013/068874, U.S. Patent Application Publication 2014/0046030, [Bioconj. Chem., 2014, 25 (2), pp 351-361], International Publication No. WO 2014/044872, [Bioconj. Chem. 2015 Nov. 18; 26 (11): 2249-60], International Publication No. WO 2014/124258, [Proc Natl Acad Sci US A. 2011 Jun. 28; 108 (26): 10437-42].

In addition, examples of a method for producing a IL-2 variant in which the amino acid residue of IL-2 is substituted with an o-Az-Z-Lys residue, an m-Az-Z-Lys residue, or an o-Az-Z-Lys residue and a method for PEGylation of the IL-2 variant include a method described in International Publication WO 2017/030156.

As a method for PEGylation of the IL-2 variant in which the amino acid residue at the PEGylation site in the amino acid sequence of IL-2 is substituted with an amino acid residue having chemical reactivity that enables site-specific PEGylation of protein, PEG can be introduced by methods described in Japanese Patent No. 5206344, International Publication No. 2012/065086, International Publication No. WO 2017/030156, [Nature. 2017 Nov. 29; 551 (7682): 644-647.], International Publication No. WO 2013/068874, US Application Publication No. 2014/0046030, [Bioconj. Chem., 2014, 25 (2), pp 351-361], International Publication No. WO 2014/044872, [Bioconj. Chem. 2015 Nov. 18; 26 (11): 2249-60], International Publication No. WO 2014/124258, and [Proc Natl Acad Sci USA. 2011 Jun. 28; 108 (26): 10437-42].

[Method for Producing IL-2 Variant in which PEG or Saccharide is Further Bound to Glycosylated IL-2 Variant or PEGylated IL-2 Variant, and Method for Producing the Same]

The glycosylated IL-2 variants described above may further have PEG thereto. In addition, the PEGylated IL-2 variants described above may further have a saccharide thereto. These IL-2 variants can be produced by combining the [Method for producing glycosylated IL-2 variant] and [Method for producing PEGylated IL-2 variant]. In addition, PEG can also be selectively introduced into an N-terminal amino group in accordance with International Publication No. WO2012/065086.

In a case where a saccharide is further introduced into the PEGylated IL-2 variant, an IL-2 variant comprising an amino acid sequence in which a saccharide is bound to at least one amino acid residue selected from the group consisting of amino acid residues at positions 11, 12, 13, 15, 16, 18, 19, 20, 84, 87, 88, 91, 92, 108, 115, 119, 122, 123, and 130 in an amino acid sequence of wild-type IL-2 is preferred, and an IL-2 variant in which the saccharide is bound to at least one amino acid residue selected from the group consisting of amino acid residues at positions 12, 115, 119 in the amino acid sequence is more preferred.

In a case where PEG is further introduced into the glycosylated IL-2 variant, an IL-2 variant comprising an amino acid sequence in which at least one amino acid residue selected from the group consisting of amino acid residues at positions 1, 3, 4, 5, 6, 7, 8, 51, 60, 78, 79, 99, 100, 101, and 129 in an amino acid sequence of wild-type IL-2 is substituted with the PEGylated amino acid residue is preferred, and an IL-2 variant comprising an amino acid sequence in which at least one amino acid residue selected from the group consisting of amino acid residues at positions 1, 3, 51, and 78 in the amino acid sequence is substituted with the PEGylated amino acid residue is more preferred.

Examples of the PEGylated amino acid residue include a PEGylated group derived from a cysteine residue, a PEGylated group derived from the N-terminal amino acid residue, and a PEGylated non-natural amino acid residue.

Examples of the group derived from a cysteine residue or a group derived from an N-terminal amino acid residue refers to a group in which PEG is bound to a side chain thiol group of the cysteine residue or a main chain amino group of the N-terminal amino acid residue by chemical modification or the like. The PEG and the group derived from the cysteine residue or the group derived from the N-terminal amino acid residue may be bound to each other via a linker. The linker can be appropriately changed depending on the type of the PEG or the non-natural amino acid residue.

Examples of the PEGylated non-natural amino acid residue include a group in which PEG is bound to a group derived from an amino acid residue comprising a thiol group or a group derived from an amino acid residue comprising an azide group, by chemical modification or the like. Examples of the group derived from an amino acid residue comprising a thiol group include a PEGylated group derived from an acetylcysteine residue and a PEGylated group derived from a homocysteine residue, but are not limited thereto.

Examples of the PEGylated group derived from an amino acid residue comprising an azide group include a PEGylated group derived from an o-Az-Z-Lys residue, a PEGylated group derived from an m-Az-Z-Lys residue, a PEGylated group derived from an N$^6$-diazolidine residue, and a PEGylated group derived from a p-azidophenylalanine residue, but are not limited thereto.

Other examples of the non-natural amino acid residue may include non-natural amino acid residue described in International Publication No. WO 2017/030156, [Nature. 2017 Nov. 29; 551 (7682): 644-647.], International Publication No. WO 2013/068874, US Application Publication No. 2014-0046030, [Bioconj. Chem., 2014, 25 (2), pp 351-361], International Publication No. WO 2014/044872, [Bioconj. Chem. 2015 Nov. 18; 26 (11): 2249-60], International Publication No. WO 2014/124258, [Proc Natl Acad Sci US A. 2011 Jun. 28; 108 (26): 10437-42] and the like. The PEG and the non-natural amino acid residue may be bound to each other via a linker. The linker can be appropriately changed depending on the type of the PEG or the non-natural amino acid residue.

In a case where an amino acid residue at position 1 in an amino acid sequence of wild-type IL-2 is substituted with a PEGylated amino acid residue, a PEGylated group derived from an N-terminal amino acid residue, a PEGylated group derived from a cysteine residue, a PEGylated group derived from an acetylcysteine residue, a PEGylated group derived from an o-Az-Z-Lys residue, and a PEGylated group derived from an m-Az-Z-Lys residue are preferred, and the PEGylated group derived from an N-terminal amino acid residue and the PEGylated group derived from an acetylcysteine residue are more preferred.

In a case where at least one amino acid residue selected from the group consisting of amino acid residues at positions 3, 4, 5, 6, 7, 8, 51, 60, 78, 79, 99, 100, 101, and 129 in an amino acid sequence of wild-type IL-2 is substituted with a PEGylated amino acid residue, the PEGylated group derived from a cysteine residue, the PEGylated group derived from an o-Az-Z-Lys residue, and PEGylated group derived from an m-Az-Z-Lys residue are preferred, and the PEGylated group derived from a cysteine residue is more preferred.

Examples of the PEGylated group derived from an N-terminal amino acid residue include a structure represented by (Formula Z0) below, in which PEG is bound to a main chain amino group of an alanine residue via a linker formed by reacting an aldehyde.

[Chem. 90]

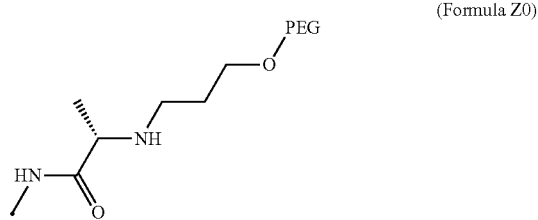

(Formula Z0)

Specific examples of the PEG in the formula include a structure represented by (Formula X00) below in a case where an average molecular weight is 20 kDa, but are not limited thereto.

[Chem. 91]

(Formula X00)

Specific examples of the PEGylated group derived from a cysteine residue include a structure represented by (Formula X4) below in which PEG is bound to a side chain thiol group of the cysteine residue via a linker formed by reacting a haloacetyl group, or a structure represented by (Formula X5), and/or (Formula X6), and/or (Formula X7) in which PEG is bound thereto via a linker formed by reacting maleimide.

[Chem. 92]

(Formula X4)

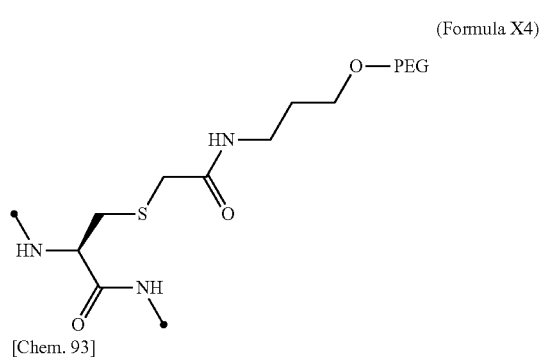

[Chem. 93]

(Formula X5)

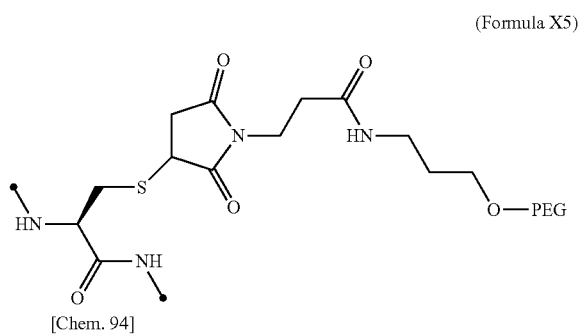

[Chem. 94]

(Formula X6)

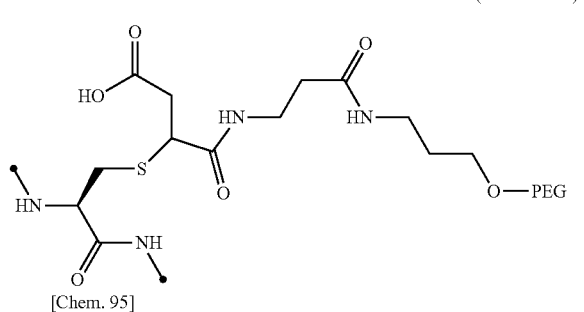

[Chem. 95]

(Formula X7)

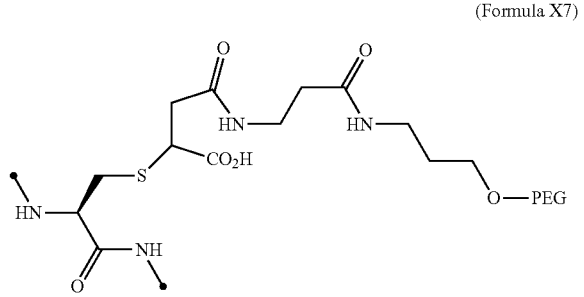

Specific examples of the PEG in the formula include a structure represented by (Formula X11) below in a case where an average molecular weight is 20 kDa, (Formula X11) below in a case where an average molecular weight is 40 kDa, (Formula X13) below in a case where an average molecular weight is 40 kDa, (Formula X13) below in a case where an average molecular weight is 80 kDa, (Formula X14) below in a case where an average molecular weight is 40 kDa, (Formula X14) below in a case where an average molecular weight is 80 kDa, or (Formula X15) below in a case where an average molecular weight is 50 kDa, but are not limited thereto.

[Chem. 96]

(Formula X11)

[Chem. 97]

(Formula X13)

[Chem. 98]

(Formula X14)

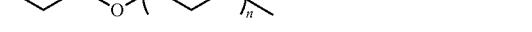

[Chem. 99]

(Formula X15)

Specific examples of the PEGylated group derived from an acetylcysteine residue include a structure represented by (Formula XX3) below in which PEG is bound to a side chain thiol group of the acetylcysteine residue via a linker formed by reacting a haloacetyl group, or a structure represented by (Formula X8), and/or (Formula X9), and/or (Formula X10) in which PEG is bound thereto via a linker formed by reacting maleimide.

[Chem. 100]

(Formula XX3)

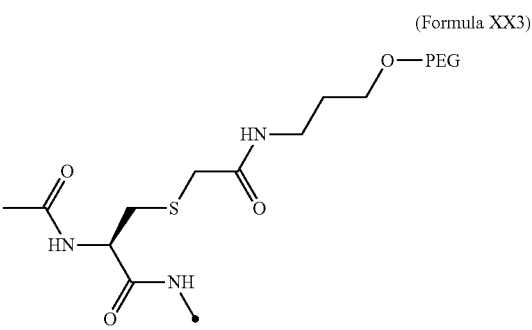

-continued

[Chem. 101]

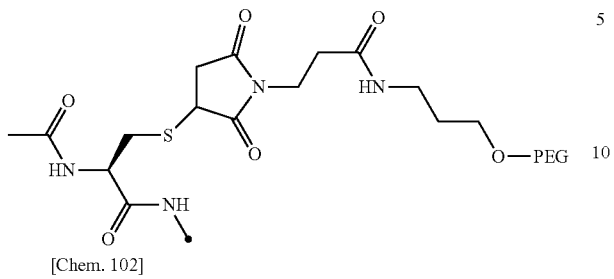

(Formula X8)

[Chem. 102]

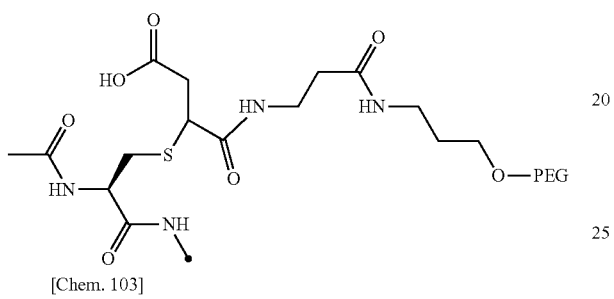

(Formula X9)

[Chem. 103]

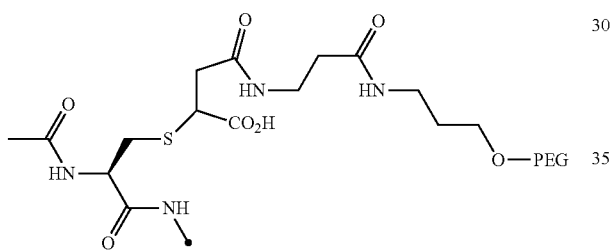

(Formula X10)

Specific examples of the PEG in the formula include a structure represented by (Formula X11) above in a case where an average molecular weight is 40 kDa, (Formula X13) above in a case where an average molecular weight is 40 kDa, (Formula X13) above in a case where an average molecular weight is 80 kDa, (Formula X14) above in a case where an average molecular weight is 80 kDa, or (Formula X15) above in a case where an average molecular weight is 50 kDa, but are not limited thereto.

As the IL-2 variant according to one embodiment of the present invention, IL-2 variants to be described below are preferred.

- An IL-2 variant in which an amino acid residue at position 11 in an amino acid sequence of wild-type IL-2 is substituted with a glycosylated amino acid residue, and an amino acid residue at position 1 is substituted with a PEGylated amino acid residue.
- An IL-2 variant in which an amino acid residue at position 12 in an amino acid sequence of wild-type IL-2 is substituted with a glycosylated amino acid residue, and an amino acid residue at position 1 is substituted with a PEGylated amino acid residue.
- An IL-2 variant in which an amino acid residue at position 19 in an amino acid sequence of wild-type IL-2 is substituted with a glycosylated amino acid residue, and the amino acid residue at position 1 is substituted with a PEGylated amino acid residue.
- An IL-2 variant in which an amino acid residue at position 38 in an amino acid sequence of wild-type IL-2 is substituted with a glycosylated amino acid residue, and an amino acid residue at position 1 is substituted with a PEGylated amino acid residue.
- An IL-2 variant in which an amino acid residue at position 91 in an amino acid sequence of wild-type IL-2 is substituted with a glycosylated amino acid residue, and an amino acid residue at position 1 is substituted with a PEGylated amino acid residue.
- An IL-2 variant in which amino acid residues at positions 12 and 91 in an amino acid sequence of wild-type IL-2 are substituted with a glycosylated amino acid residue, and an amino acid residue at position 1 is substituted with a PEGylated amino acid residue.
- An IL-2 variant in which amino acid residues at positions 91 and 119 in an amino acid sequence of wild-type IL-2 are substituted with a glycosylated amino acid residue, and an amino acid residue at position 1 is substituted with a PEGylated amino acid residue.
- An IL-2 variant in which amino acid residues at positions 12 and 91 in an amino acid sequence of wild-type IL-2 are substituted with a glycosylated amino acid residue, and an amino acid residue at position 3 is substituted with a PEGylated amino acid residue.
- An IL-2 variant in which an amino acid residue at position 15 in an amino acid sequence of wild-type IL-2 is substituted with a glycosylated amino acid residue, and an amino acid residue at position 3 is substituted with a PEGylated amino acid residue.
- An IL-2 variant in which amino acid residues at positions 12 and 119 in an amino acid sequence of wild-type IL-2 are substituted with a glycosylated amino acid residue, and an amino acid residue at position 3 is substituted with a PEGylated amino acid residue.
- An IL-2 variant in which amino acid residues at positions 12 and 91 in an amino acid sequence of wild-type IL-2 are substituted with a glycosylated amino acid residue, and an amino acid residue at position 51 is substituted with a PEGylated amino acid residue.
- An IL-2 variant in which an amino acid residue at position 12 in an amino acid sequence of wild-type IL-2 is substituted with a glycosylated amino acid residue, and an amino acid residue at position 78 is substituted with a PEGylated amino acid residue.
- An IL-2 variant in which amino acid residues at positions 12 and 119 in an amino acid sequence of wild-type IL-2 are substituted with a glycosylated amino acid residue, and an amino acid residue at position 78 is substituted with a PEGylated amino acid residue.
- An IL-2 variant in which an amino acid residue at position 15 in an amino acid sequence of wild-type IL-2 is substituted with a glycosylated amino acid residue, and an amino acid residue at position 78 is substituted with a PEGylated amino acid residue.

As the saccharides or PEGs to be bound to the PEGylated or glycosylated IL-2 variants described above of the present invention, various types thereof can be used in combination.

- An IL-2 variant in which an amino acid residue at position 11 in an amino acid sequence of wild-type IL-2 is substituted with the glycosylated group shown in (Formula 1) derived from a cysteine residue, a structure of Saccharide in (Formula 1) is a structure represented by (Formula 7), an amino acid residue at position 1 in the amino acid sequence is substituted with the PEGylated group shown in (Formula X0) derived from an N-terminal amino acid residue, and a structure of PEG in (Formula X0) is a structure represented by (Formula X00) in a case where an average molecular weight is 20 kDa.

An IL-2 variant in which an amino acid residue at position 12 in an amino acid sequence of wild-type IL-2 is substituted with the glycosylated group shown in (Formula 1) derived from a cysteine residue, a structure of Saccharide in (Formula 1) is a structure represented by (Formula 7), an amino acid residue at position 1 in the amino acid sequence is substituted with the PEGylated group shown in (Formula X0) derived from an N-terminal amino acid residue, and a structure of PEG in (Formula X0) is a structure represented by (Formula X00) in a case where an average molecular weight is 20 kDa.

An IL-2 variant in which an amino acid residue at position 38 in an amino acid sequence of wild-type IL-2 is substituted with the glycosylated group shown in (Formula 1) derived from a cysteine residue, a structure of Saccharide in (Formula 1) is a structure represented by (Formula 7), an amino acid residue at position 1 in the amino acid sequence is substituted with the PEGylated group shown in (Formula X0) derived from an N-terminal amino acid residue, and a structure of PEG in (Formula X0) is a structure represented by (Formula X00) in a case where an average molecular weight is 20 kDa.

An IL-2 variant in which an amino acid residue at position 91 in an amino acid sequence of wild-type IL-2 is substituted with the glycosylated group shown in (Formula 1) derived from a cysteine residue, a structure of Saccharide in (Formula 1) is a structure represented by (Formula 7), an amino acid residue at position 1 in the amino acid sequence is substituted with the PEGylated group shown in (Formula X0) derived from an N-terminal amino acid residue, and a structure of PEG in (Formula X0) is a structure represented by (Formula X00) in a case where an average molecular weight is 20 kDa.

An IL-2 variant in which an amino acid residue at position 12 and an amino acid residue at position 91 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 1 in the amino acid sequence is substituted with the PEGylated group represented by (Formula XX3) derived from an acetylcysteine acid residue, and a structure of PEG in (Formula XX3) is a structure represented by (Formula X13) in a case where an average molecular weight is 40 kDa or (Formula X15) in a case where an average molecular weight is 50 kDa.

An IL-2 variant in which an amino acid residue at position 12 and an amino acid residue at position 91 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 1 in the amino acid sequence is substituted with the PEGylated group represented by (Formula X8), (Formula X9), and/or (Formula X10) derived from an acetylcysteine residue, and a structure of PEG in (Formula X8), (Formula X9), and/or (Formula X10) is a structure represented by (Formula X13) in a case where an average molecular weight is 80 kDa, (Formula X15) in a case where an average molecular weight is 50 kDa, or (Formula X14) in a case where an average molecular weight is 80 kDa.

An IL-2 variant in which an amino acid residue at position 19 in an amino acid sequence of wild-type IL-2 is substituted with the glycosylated group shown in (Formula 1) derived from a cysteine residue, a structure of Saccharide in (Formula 1) is a structure represented by (Formula 8), an amino acid residue at position 1 in the amino acid sequence is substituted with the PEGylated group represented by (Formula XX3) derived from an acetylcysteine residue, and a structure of PEG in (Formula XX3) is a structure represented by (Formula X15) in a case where an average molecular weight is 50 kDa or (Formula X13) in a case where an average molecular weight is 40 kDa.

An IL-2 variant in which amino acid residues at position 91 and 119 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 1 in the amino acid sequence is substituted with the PEGylated group represented by (Formula XX3) derived from an acetylcysteine residue, and a structure of PEG in (Formula XX3) is a structure represented by (Formula X15) in a case where an average molecular weight is 50 kDa.

An IL-2 variant in which an amino acid residue at position 12 and an amino acid residue at position 91 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 3 in the amino acid sequence is substituted with the PEGylated group represented by (Formula X4) derived from a cysteine residue, and a structure of PEG in (Formula X4) is a structure represented by (Formula X11) in a case where an average molecular weight is 20 kDa, (Formula X11) in a case where an average molecular weight is 40 kDa, (Formula X13) in a case where an average molecular weight is 40 kDa, (Formula X14) in a case where an average molecular weight is 40 kDa, or (Formula X15) in a case where an average molecular weight is 50 kDa.

An IL-2 variant in which an amino acid residue at position 12 and an amino acid residue at position 91 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 3 in the amino acid sequence is substituted with the PEGylated group represented by (Formula X5), (Formula X6), and/or (Formula X7) derived from a cysteine acid residue, and a structure of PEG in (Formula X5), (Formula X6), and/or (Formula X7) is a structure represented by (Formula X15) in a case where an average molecular weight is 50 kDa.

An IL-2 variant in which an amino acid residue at position 12 in an amino acid sequence of wild-type IL-2 is substituted with the glycosylated group shown in (Formula 1) derived from a cysteine residue, a structure of Saccharide in (Formula 1) is a structure represented by (Formula 8), an amino acid residue at position 91 in the amino acid sequence is substituted with the glycosylated group represented by (Formula 1) derived from a cysteine residue, a structure of Saccharide in (Formula 1) is a structure represented by (Formula 4), an amino acid residue at position 3 in the amino acid sequence is substituted with the PEGylated group represented by (Formula X5), (Formula X6), and/or (Formula X7) derived from a cysteine residue, and a structure of PEG in (Formula X5), (Formula X6), and/or (Formula X7) is a structure represented by (Formula X14) in a case where an average molecular weight is 80 kDa.

An IL-2 variant in which an amino acid residue at position 12 in an amino acid sequence of wild-type IL-2 is substituted with the glycosylated group shown in (Formula 1) derived from a cysteine residue, a structure of Saccharide in (Formula 1) is a structure represented by (Formula 8), an amino acid residue at position 91 in the amino acid sequence is substituted with the glycosylated group represented by (Formula 1) derived from a cysteine residue, a structure of Saccharide in (Formula 1) is a structure represented by (Formula 4), an amino acid residue at position 3 in the amino acid sequence is substituted with the PEGylated group represented by (Formula X4) derived from a cysteine residue, and a structure of PEG in (Formula X4) is a structure represented by (Formula X15) in a case where an average molecular weight is 50 kDa.

An IL-2 variant in which an amino acid residue at position 15 in an amino acid sequence of wild-type IL-2 is substituted with the glycosylated group shown in (Formula 1) derived from a cysteine residue, a structure of Saccharide in (Formula 1) is a structure represented by (Formula 8), an amino acid residue at position 3 in the amino acid sequence is substituted with the PEGylated group represented by (Formula X4) derived from a cysteine residue, and a structure of PEG in (Formula X4) is a structure represented by (Formula X13) in a case where an average molecular weight is 40 kDa or (Formula X15) in a case where an average molecular weight is 50 kDa.

An IL-2 variant in which an amino acid residue at position 15 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 3 in the amino acid sequence is substituted with the PEGylated group represented by (Formula X5), (Formula X6), and/or (Formula X7) derived from a cysteine acid residue, and a structure of PEG in (Formula X5), (Formula X6), and/or (Formula X7) is a structure represented by (Formula X13) in a case where an average molecular weight is 80 kDa.

An IL-2 variant in which an amino acid residue at position 12 and an amino acid residue at position 119 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 3 in the amino acid sequence is substituted with the PEGylated group represented by (Formula X5), (Formula X6), and/or (Formula X7) derived from a cysteine acid residue, and a structure of PEG in (Formula X5), (Formula X6), and/or (Formula X7) is a structure represented by (Formula X13) in a case where an average molecular weight is 80 kDa or (Formula X14) in a case where an average molecular weight is 80 kDa.

An IL-2 variant in which an amino acid residue at position 12 and an amino acid residue at position 119 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 3 in the amino acid sequence is substituted with the PEGylated group represented by (Formula X4) derived from a cysteine residue, and a structure of PEG in (Formula X4) is a structure represented by (Formula X15) in a case where an average molecular weight is 50 kDa.

An IL-2 variant in which an amino acid residue at position 12 and an amino acid residue at position 91 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 51 in the amino acid sequence is substituted with the PEGylated group represented by (Formula X4) derived from a cysteine acid residue, and a structure of PEG in (Formula X4) is a structure represented by (Formula X11) in a case where an average molecular weight is 40 kDa or (Formula X15) in a case where an average molecular weight is 50 kDa.

An IL-2 variant in which an amino acid residue at position 12 in an amino acid sequence of wild-type IL-2 is substituted with the glycosylated group shown in (Formula 1) derived from a cysteine residue, a structure of Saccharide in (Formula 1) is a structure represented by (Formula 8), an amino acid residue at position 78 in the amino acid sequence is substituted with the PEGylated group represented by (Formula X4) derived from a cysteine residue, and a structure of PEG in (Formula X4) is a structure represented by (Formula X11) in a case where an average molecular weight is 40 kDa or (Formula X13) in a case where an average molecular weight is 40 kDa.

An IL-2 variant in which an amino acid residue at position 12 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 78 in the amino acid sequence is substituted with the PEGylated group represented by (Formula X5), (Formula X6), and/or (Formula X7) derived from a cysteine acid residue, and a structure of PEG in (Formula X5), (Formula X6), and/or (Formula X7) is a structure represented by (Formula X13) in a case where an average molecular weight is 40 kDa or 80 kDa or (Formula X14) in a case where an average molecular weight is 80 kDa.

An IL-2 variant in which amino acid residues at position 12 and 119 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 78 in the amino acid sequence is substituted with the PEGylated group represented by (Formula X4) derived from an cysteine residue, and a structure of PEG in (Formula X4) is a structure represented by (Formula X13) in a case where an average molecular weight is 40 kDa.

An IL-2 variant in which amino acid residues at positions 12 and 119 in an amino acid sequence of wild-type IL-2 are substituted with the glycosylated group shown in (Formula 1) derived from a cysteine residue, a structure of Saccharide in (Formula 1) is a structure represented by (Formula 8), an amino acid residue at position 78 in the amino acid sequence is substituted with the PEGylated group represented by (Formula X5), (Formula X6), and/or (Formula X7) derived from a cysteine acid residue, and a structure of PEG in (Formula X5), (Formula X6), and/or (Formula X7) is a structure represented by (Formula X13) in a case where an average molecular weight is 80 kDa or (Formula X14) in a case where an average molecular weight is 80 kDa.

An IL-2 variant in which an amino acid residue at position 15 in an amino acid sequence of wild-type IL-2 is substituted with the glycosylated group shown in (Formula 1) derived from a cysteine residue, a structure of Saccharide in (Formula 1) is a structure represented by (Formula 8), an amino acid residue at position 78 in the amino acid sequence is substituted with the PEGylated group represented by (Formula X4) derived from an cysteine residue, and a structure of PEG in (Formula X4) is a structure represented by (Formula X12) in a case where an average molecular weight is 40 kDa.

In the present embodiment, as the amino acid sequence of wild-type IL-2, an amino acid sequence represented by SEQ ID NO: 1, an amino acid sequence in which a methionine residue is bound to the N-terminal of the amino acid sequence represented by SEQ ID NO: 1, an amino acid sequence in which the N-terminal alanine residue of the amino acid sequence represented by SEQ ID NO: 1 has been deleted, an amino acid sequence in which the N-terminal alanine residue of the amino acid sequence represented by SEQ ID NO: 1 has been deleted and a methionine residue has been bound, or the amino acid sequence represented by SEQ ID NO: 1, the amino acid sequence in which a methionine residue is bound to the N-terminal of the amino acid sequence represented by SEQ ID NO: 1, the amino acid sequence in which the N-terminal alanine residue of the amino acid sequence represented by SEQ ID NO: 1 has been deleted, or the amino acid sequence in which the N-terminal alanine residue of the amino acid sequence represented by SEQ ID NO: 1 has been deleted and a methionine residue has been bound, wherein an amino acid residue at position 125 of these amino acid sequences, is substituted with a serine residue or an alanine residue is preferred.

When a kinetic improving element known to improve pharmacokinetics is bound to the IL-2 variant of the present invention, it is possible to control half-life in blood. Examples of the kinetic improving element include a saccharide, a peptide, protein, and lipid, and a method described in [Therapeutic Proteins (edited by Roland Kontermann, Wiley Blackwell, 2012)] can be used in combination. Specifically, in order not to affect the selectivity of the Treg cell proliferation activity of the IL-2 variant of the present invention, the half-life in blood can be controlled by a method such as sialylation, HESylation, O-glycosylation, fusion of peptides and proteins as PEG mimics, fusion of the constant region or the Fc region of the antibody, fusion with serum proteins such as albumin (including methods for introducing lipids and fusing with albumin), or binding to phospholipids, nanoparticles, during sealing to nanoparticles.

[Evaluation of Biological Activity of IL-2 Variant]

A biological activity of the IL-2 variant can be evaluated by any suitable method known in the related art. Evaluation methods include those described in Examples to be described later. Specific examples of a method for evaluating the biological activity of the IL-2 variant include methods (a) to (e) below. These methods can also be used to determine therapeutic effect, efficacy, and pharmacodynamic properties of the IL-2 variants.

(a) Method for Measuring Proliferation Activity of Treg Cells Stimulated by IL-2 Variant Treg cells are cultured in a medium supplemented with an IL-2 variant or wild-type IL-2, and a proliferation rate of the Treg cells is measured. Examples of other methods for measuring the proliferation activity of the Treg cells include a method for measuring an increase in the number of Treg cells in a mixed cell population and a method for measuring an abundance ratio of $CD4^+$ $CD25^+$ $FOXP3^+$ marker phenotype or $CD4^+$ $CD25^+$ $CD127^{low}$ marker phenotype, by flow cytometry; a method of measuring incorporation of tritiated thymidine into separated Treg cells; a method for measuring an increase in expression of a cell cycle protein related to proliferation, such as Ki-67, in Treg cells; and a method for measuring the cell division-related dilution of a biofluorescent dye such as carboxyfluorescein succinimidyl ester (CFSE) in Treg cells by flow cytometry.

(b) Method for Measuring Proliferation Activity of NK Cells Stimulated by IL-2 Variant NK cells are cultured in a medium supplemented with an IL-2 variant or wild-type IL-2, and a proliferation rate of the NK cells is measured. Examples of other methods for measuring the proliferation activity of NK cells include a method for measuring an increase in the number of NK cells in a mixed cell population and a method for measuring an abundance ratio of $CD56^+$ marker phenotype, by flow cytometry; a method of measuring incorporation of tritiated thymidine into separated NK cells; a method for measuring an increase in expression of a cell cycle protein related to proliferation, such as Ki-67, in NK cells; and a method for measuring the cell division-related dilution of a biofluorescent dye such as CFSE in NK cells by flow cytometry.

It is preferable that the IL-2 variant of the present invention has a high Treg proliferation activity and/or a low NK cell proliferation activity, as compared with those of wild-type IL-2. Instead of the wild-type IL-2, an IL-2 variant having Treg proliferation activity and/or NK cell proliferation activity equivalent to those of the wild-type IL-2 may be used.

(c) Method for Measuring Inhibitory Activity of Tregs Stimulated by IL-2 Variant on Responder T cells (Tresp) proliferation Tregs were cultured in a medium supplemented with an IL-2 variant or wild-type IL-2. A proliferation rate of Tresp when co-cultured with Tresp ($CD4^+$ Tresp, $CD8^+$ Tresp) in the presence of appropriate TCR stimulation was measured. A rate of inhibition of the proliferation of Tresp by the IL-2 variant is evaluated in comparison with that of wild-type IL-2. It is preferable that the IL-2 variant of the present invention proliferates Tregs having at least the same inhibitory activity on Tresp proliferation as compared with that of wild-type IL-2. Instead of the wild-type IL-2, an IL-2 variant that proliferates Tregs having the same inhibitory activity on Tresp proliferation as that of the wild-type IL-2 may be used.

(d) Ex Vivo Assay

For inflammatory cytokines such as IL-4, IL-6, IFNγ, or TNFα, which is a functional effector molecule of Teff and NK cells, PBMCs are cultured in a medium supplemented with a IL-2 variant or wild-type IL-2. A production amount of cytokines in a culture supernatant is measured. In addition, the production amount of the anti-inflammatory cytokines may be measured by the same method. It is preferable that the IL-2 variant of the present invention reduces the production amount of inflammatory cytokines and/or increases the production amount of anti-inflammatory cytokines as compared with a case of wild-type IL-2. Instead of the wild-type IL-2, an IL-2 variant that produces inflammatory cytokines and/or anti-inflammatory cytokines equivalent to those of wild-type IL-2 may be used.

(e) Measurement of Treg/Teff Ratio

PMBC cultured in a medium supplemented with an IL-2 variant or wild-type IL-2 is reacted with an anti-human CD4 antibody, an anti-human CD25 antibody, and an anti-human Foxp3 antibody. Among the CD4-positive fractions by flow cytometry, a $CD25^+$ $FOXP3^{high}$ fraction is defined as Treg, and a $CD25^+$ $FOXP3^{low}$ fraction is defined as effector T cells (Teff). An abundance ratio [Treg (%)/Teff (%)] (Treg/Teff ratio) is calculated. The data is analyzed using commercially available data analysis software (For example, FlowJo, version 7.6.5, manufactured by TreeStar). It is preferable that the IL-2 variant of the present invention has an improved Treg/Teff ratio as compared with that of the wild-type IL-2. Instead of the wild-type IL-2, an IL-2 variant having a Treg/Teff ratio equivalent to that of the wild-type IL-2 may be used.

[Composition]

According to one embodiment of the present invention, there is provided a composition containing an effective amount of the IL-2 variant of the present invention. Examples of a composition form include pharmaceutical compositions and reagents.

As shown in Examples to be described later, since the IL-2 variant of the present invention selectively activates Tregs, the composition containing the IL-2 variant of the present invention can be suitably used a composition having an immunosuppressive effect. In addition, as one embodiment of the present invention, there is provided a therapeutic agent for an immune disease, containing the IL-2 variant of the present invention.

Examples of a pathological condition or a disease for which the composition of the present invention is used include systemic lupus erythematosus, psoriasis, chronic graft-versus-host disease, acute graft-versus-host disease, Crohn's disease, ulcerative colitis, inflammatory bowel disease, multiple sclerosis, celiac disease, idiopathic thrombotic thrombocytopenic purpura, myasthenia gravis, Sjogren's syndrome, scleroderma, asthma, uveitis, epidermal hyperplasia, alopecia areata, Behcet's disease, Takayasu's arteritis, cartilage inflammation, bone breakdown, arthritis, juvenile arthritis, juvenile rheumatoid arthritis, oligoarticular juvenile rheumatoid arthritis, polyarticular juvenile rheumatoid arthritis, systemic onset juvenile rheumatoid arthritis, juvenile ankylosing spondylitis, juvenile enteropathy arthritis, juvenile reactive arthritis, juvenile lighter syndrome, sea syndrome (seronegative, tendon attachment, arthropathy syndrome), juvenile dermatomyositis, juvenile psoriatic arthritis, juvenile scleroderma, juvenile systemic lupus erythematosus, juvenile vasculitis, oligoarticular rheumatism, articulated rheumatoid arthritis, systemic onset rheumatoid arthritis, ankylosing spondylitis, enteric arthritis, reactive arthritis, Reiter's syndrome, dermatomyositis, psoriatic arthritis, vasculitis, myositis, polymyositis, dermatomyositis, osteoarthritis, polyarteritis nodosa, Wegener's granulomatosis, arteritis, rheumatic polymyalgia, sarcoidosis, sclerosis, primary biliary cirrhosis, sclerosing cholangitis, dermatitis, atopic dermatitis, atherosclerosis, Still's disease, chronic obstructive pulmonary disease, guillain-barre syndrome, type 1 diabetes, Graves' disease, Addison's disease, Raynaud's phenomenon, autoimmune hepatitis, inflammatory diseases such as Wiskott-Aldrich syndrome, autoimmune diseases, and allergic disease.

The composition of the present invention can be formulated by a known pharmaceutical method. For example, as a capsule, a tablet, a pill, a liquid, a powder, granules, fine granules, a film coating agent, pellets, lozenges, sublingual, a chewing agent, buccals, paste, syrup, suspension, elixirs, emulsion, coating agent, ointments, plasters, cataplasm, transdermal preparations, lotion, a suction agent, aerosol, injections, suppository, and the like, the composition can be used orally or parenterally.

In these formulations, pharmacologically acceptable carriers, specifically, for example, sterile water or normal saline solution, vegetable oil, a solvent, a base, an emulsifier, a suspension, a surfactant, a stabilizer, a flavoring agent, aromatics, excipients, vehicle, preservative, binder, diluent, a tonicity agent, a soothing agent, a bulking agent, a disintegrant, buffer, a coating agent, a lubricant, a colorant, sweetener, thickener, a corrigent, dissolution aid, or other additives can be appropriately combined with the composition.

In addition, syringe may be used for administration of the composition of the present invention, and other devices may be used. Examples of the device include an injector pen, an auto injector device, a needleless device, and subcutaneous patch device.

The composition of the present invention can be used for animals including humans, but there is no particular limitation on animals other than humans. The composition can be used for various livestock, poultry, pets, laboratory animals, and the like. Specific examples include pig, cow, horse, sheep, goat, chicken, duck, ostrich, duck, dog, cat, rabbit, hamster, mouse, rat, monkey, and the like, and are not limited thereto. In addition, these may be in a healthy state or an affected state. However, in a case where the composition of the present invention is a pharmaceutical composition, the composition is used for animals in affected state.

The effective amount of the IL-2 variant in the composition will depend, for example, on a state and a purpose of treatment. An appropriate dosage can be adjusted depending on an indication for which the IL-2 variant is to be used, a route of administration, and a size (body weight, body or organ size) and/or a condition (age and health) of a subject to be administered.

For example, a single dose or intake is generally 1 ng/kg body weight to 100 mg/kg body weight, and preferably 0.01 µg/kg body weight to 1 mg/kg body weight.

A product (pharmaceutical or reagent) of the composition of the present invention or a description thereof may be provided with a label meaning that it is used for suppressing immunity or the like. Here, "product or description provided with a label" means that the label is attached to the product body, a container, packaging, or the like, or a label such as manuals, package inserts, advertising materials, and other printed materials that disclose product information is attached.

[Selectivity for IL-2R]

According to one embodiment of the present invention, there is provided a method for improving selectivity of IL-2 for IL-2$R_{\alpha\beta\gamma}$. In the present embodiment, the selectivity of IL-2 for IL-2$R_{\alpha\beta\gamma}$ can be improved by modification by binding a saccharide or PEG to IL-2 by the method described above.

When IL-2 has the improved selectivity for IL-2$R_{\alpha\beta\gamma}$, there may be cases where an affinity of the IL-2 variant for a IL-2Rα subunit is higher than an affinity of wild-type IL-2 and an affinity of the variant IL-2 for at least one of IL-2Rβ subunit and IL-2Rγ subunit is lower than an affinity of wild-type IL-2.

According to one embodiment of the present invention, there is provided a method for improving an affinity of IL-2 for an IL-2Rα subunit. The expression "improving an affinity of IL-2 for IL-2Rα subunit" means that the IL-2 variant has an improved affinity for an IL-2Rα subunit compared with that of the wild-type IL-2. In the present embodiment, when modifying the IL-2 by binding a saccharide or PEG thereto by the method described above, a produced IL-2 variant has improved affinity for an IL-2Rα subunit compared with that of the wild-type IL-2, and the selectivity of IL-2 for $IL\text{-}2R_{\alpha\beta\gamma}$ can be improved.

The affinity of IL-2 for an IL-2Rα subunit can be evaluated by measuring the binding of IL-2 to $IL\text{-}2R_{\alpha}$ (CD25) using a Biacore and determining a dissociation constant $K_D$ using a steady state model. The binding of IL-2 to IL-2Rα by Biacore can be measured by a method to be described later in Examples. In the present embodiment, the $K_D$ of the IL-2 variant to IL-2Rα is preferably lower than that of a variant of the wild-type IL-2. Instead of the wild-type IL-2, an IL-2 variant having the same affinity for $IL\text{-}2R_{\alpha}$ as that of the wild-type IL-2 may be used.

According to one embodiment of the present invention, there is provided a method of reducing an affinity of IL-2 for at least one of IL-2Rβ subunit and IL-2Rγ subunit. The expression "reducing an affinity of IL-2 for at least one of IL-2Rβ subunit and IL-2Rγ subunit" refers to that an affinity of the IL-2 variant for at least one of the IL-2Rβ subunit and IL-2Rγ subunit is reduced as compared with that of the wild-type IL-2. In the present embodiment, when modifying the IL-2 by binding a saccharide or PEG thereto by the method described above, a produced IL-2 variant has lowered affinity for at least one of the IL-2Rβ subunit and IL-2Rγ subunit, compared with that of the wild-type IL-2, and the selectivity of IL-2 for $IL\text{-}2R_{\alpha\beta\gamma}$ can be improved.

For example, the affinity of IL-2 for IL-2Rβγ subunit can be evaluated by measuring the binding of IL-2 to $IL\text{-}2R_{\beta\gamma}$ by Biacore and determining a dissociation constant $K_D$ using a 1:1 binding model. The binding of IL-2 to $IL\text{-}2R_{\beta\gamma}$ by Biacore can be measured by a method to be described later in Examples. In the present embodiment, the $K_D$ of IL-2 for the $IL\text{-}2R_{\beta\gamma}$ is preferably higher than that of the wild-type IL-2. Instead of the wild-type IL-2, an IL-2 variant having the same affinity for the IL-2Rβγ subunit as that of the wild-type IL-2 can be used.

[Method for Selectively Activating Regulatory T Cells]

According to one embodiment of the present invention, there is provided a method for selectively activating regulatory T cells using the IL-2 variant of the present invention. In the present embodiment, the IL-2 variant of the present invention can be administered to a test subject to selectively activate the regulatory T cells.

EXAMPLES

Hereinafter, the present invention will be described more specifically based on Examples, but the present invention is not limited to Examples below.

Example 1

Synthesis of Glycosylated IL-2 Variant

Various IL-2 variants shown in Tables 1 to 5 were prepared by methods described below.

TABLE 1

| Produced glycosylated IL-2 variant | | | | |
|---|---|---|---|---|
| Name of variant | Glycosylation site | Amino acid residue before substitution | Amino acid residue after substitution | Mutation at position 125 |
| T3C-2 | 3 | T | C-lactose | — |
| T3C-9 | 3 | T | C-asialo | — |
| T3C-11 | 3 | T | C-disialo | — |
| S4C-2 | 4 | S | C-lactose | — |
| S4C-9 | 4 | S | C-asialo | — |
| S4C-11 | 4 | S | C-disialo | — |
| S5C-2 | 5 | S | C-lactose | — |
| S5C-9 | 5 | S | C-asialo | — |
| S5C-11 | 5 | S | C-disialo | — |
| Q11C-2 | 11 | Q | C-lactose | — |
| Q11C-9 | 11 | Q | C-asialo | — |
| Q11C-11 | 11 | Q | C-disialo | — |
| L12C-2 | 12 | L | C-lactose | — |
| L12C-9 | 12 | L | C-asialo | — |
| L12C-11 | 12 | L | C-disialo | — |
| Q13C-2 | 13 | Q | C-lactose | S |
| Q13C-11 | 13 | Q | C-disialo | S |
| EI5C-2 | 15 | E | C-lactose | S |
| E15C-11 | 15 | E | C-disialo | S |
| E15C-17 | 15 | E | C-tetrasialo | S |
| H16C-2 | 16 | H | C-lactose | — |
| H16C-3 | 16 | H | C-trisaccharide | S |
| H16C-5 | 16 | H | C-pentasaccharide | S |
| H16C-9 | 16 | H | C-asialo | — |
| H16C-11 | 16 | H | C-disialo | — |
| L18C-2 | 18 | L | C-lactose | — |
| LI8C-9 | 18 | L | C-asialo | — |
| L18C-11 | 18 | L | C-disialo | — |
| L19C-2 | 19 | L | C-lactose | — |
| L19C-9 | 19 | L | C-asialo | — |
| L19C-11 | 19 | L | C-disialo | — |
| L19C-11* | 19 | L | C-disialo | S |
| L19N-11 | 19 | L | N-disialo | S |
| L19C-17 | 19 | L | C-tetrasialo | S |

TABLE 2

| Produced glycosylated IL-2 variant | | | | |
|---|---|---|---|---|
| Name of variant | Glycosylation site | Amino acid residue before substitution | Amino acid residue after substitution | Mutation at position 125 |
| D20C-2 | 20 | D | C-lactose | S |
| D20C-11 | 20 | D | C-disialo | S |
| R38C-2 | 38 | R | C-lactose | — |
| R38C-9 | 38 | R | C-asialo | — |
| R38C-11 | 38 | R | C-disialo | — |
| D84C-2 | 84 | D | C-lactose | S |
| D84C-11 | 84 | D | C-disialo | S |
| S87C-2 | 87 | S | C-lactose | S |
| S87C-11 | 87 | S | C-disialo | S |
| N88C-2 | 88 | N | C-lactose | — |
| N88C-9 | 88 | N | C-asialo | — |
| N88C-11 | 88 | N | C-disialo | — |
| N88C-1 | 88 | N | C-GlcNAc | S |
| N88C-1* | 88 | N | C-glucose | S |
| N88-1 | 88 | N | N-GlcNAc | S |
| V91C-2 | 91 | V | C-lactose | — |
| V91C-9 | 91 | V | C-asialo | — |
| V91C-11 | 91 | V | C-disialo | — |
| I92C-2 | 92 | I | C-lactose | S |
| I92C-11 | 92 | I | C-disialo | S |
| E95C-2 | 95 | E | C-lactose | S |
| Al08C-2 | 108 | A | C-lactose | S |
| Al08C-9 | 108 | A | C-asialo | S |
| V115C-2 | 115 | V | C-lactose | S |
| V115C-9 | 115 | V | C-asialo | S |
| N119C-2 | 119 | N | C-lactose | S |
| N119C-9 | 119 | N | C-asialo | S |
| NU9C-11 | 119 | N | C-disialo | S |

TABLE 2-continued Produced glycosylated IL-2 variant

| Name of variant | Glyco-sylation site | Amino acid residue before substitution | Amino acid residue after substitution | Mutation at position 125 |
|---|---|---|---|---|
| I122C-2 | 122 | I | C-lactose | S |
| I122C-9 | 122 | I | C-asialo | S |
| T123C-11 | 123 | T | C-disialo | S |
| S127C-11 | 127 | S | C-disialo | S |
| S130C-2 | 130 | S | C-lactose | S |
| S130C-9 | 130 | S | C-asialo | S |

TABLE 3

Produced glycosylated IL-2 variant

| Name of variant | Glycosylation site 1 | | | Glycosylation site 2 | | | Glycosylation site 3 | | | Mutation at position 125 |
|---|---|---|---|---|---|---|---|---|---|---|
| | Glyco-sylation site | Amino acid residue before substitution | Amino acid residue after substitution | Glyco-sylation site | Amino acid residue before substitution | Amino acid residue after substitution | Glyco-sylation site | Amino acid residue before substitution | Amino acid residue after substitution | |
| K8C-11/L19C-11 | 8 | K | C-disialo | 19 | L | C-disialo | — | — | — | S |
| L12C-11/H16C-2 | 12 | L | C-disialo | 16 | H | C-lactose | — | — | — | S |
| L12C-11/H16C-2/L19C-11 | 12 | L | C-disialo | 16 | H | C-lactose | 19 | L | C-disialo | S |
| L12C-11/L19C-11 | 12 | L | C-disialo | 19 | L | C-disialo | — | — | — | S |
| L12C-11/N88C-2 | 12 | L | C-disialo | 88 | N | C-lactose | — | — | — | S |
| L12C-11/V91C-11 | 12 | L | C-disialo | 91 | V | C-disialo | — | — | — | S |
| L12N-11/V91N-11 | 12 | L | N-disialo | 91 | V | N-disialo | — | — | — | S |
| L12C-11/V115C-11 | 12 | L | C-disialo | 115 | V | C-disialo | — | — | — | S |
| L12C-11/N119C-11 | 12 | L | C-disialo | 119 | N | C-disialo | — | — | — | S |
| Q13C-11/V91C-11 | 13 | Q | C-disialo | 91 | V | C-disialo | — | — | — | S |
| Q13C-11/V115C-11 | 13 | Q | C-disialo | 115 | V | C-disialo | — | — | — | S |
| Q13C-11/N119C-11 | 13 | Q | C-disialo | 119 | N | C-disialo | — | — | — | S |
| E15C-11/V91C-11 | 15 | E | C-disialo | 91 | V | C-disialo | — | — | — | S |
| E15C-11/N119C-11 | 15 | E | C-disialo | 119 | N | C-disialo | — | — | — | S |
| E15C-11/T123C-11 | 15 | E | C-disialo | 123 | T | C-disialo | — | — | — | S |
| H16C-2/L19C-11 | 16 | H | C-lactose | 19 | L | C-disialo | — | — | — | S |
| H16C-2/V91C-11 | 16 | H | C-lactose | 91 | V | C-disialo | — | — | — | S |
| L19C-11/M23C-11 | 19 | L | C-disialo | 23 | M | C-disialo | — | — | — | S |
| L19C-11/V91C-11 | 19 | L | C-disialo | 91 | V | C-disialo | — | — | — | S |
| L19C-11/V115C-11 | 19 | L | C-disialo | 115 | V | C-disialo | — | — | — | S |
| V91C-11/V115C-11 | 91 | V | C-disialo | 115 | V | C-disialo | — | — | — | S |
| V91C-11/N119C-11 | 91 | V | C-disialo | 119 | N | C-disialo | — | — | — | S |

TABLE 4

Produced glycosylated IL-2 variant

| Name of variant | Glycosylation site 1 | | Glycosylation site 2 | | Glycosylation site 3 | | Glycosylation site 4 | | Glycosylation site 5 | | Amino acid residue after substitution | Mutation at position 125 |
|---|---|---|---|---|---|---|---|---|---|---|---|---|
| | Glyco-syl-ation site | Amino acid residue before sub-stitution | Glyco-syl-ation site | Amino acid residue before sub-stitution | Glyco-syl-ation site | Amino acid residue before sub-stitution | Glyco-syl-ation site | Amino acid residue before sub-stitution | Glyco-syl-ation site | Amino acid residue before sub-stitution | | |
| A1C-11/T3C-11/S5C-11/L12C-11/V91C-11 | 1 | A | 3 | T | 5 | S | 12 | L | 91 | V | C-disialo | S |
| T3C-11/L12C-11/T51C-11/V91C-11/E100C-11 | 3 | T | 12 | L | 51 | T | 91 | V | 100 | E | C-disialo | S |
| T3C-11/L12C-11/K76C-11/V91C-11/E100C-11 | 3 | T | 12 | L | 76 | K | 91 | V | 100 | E | C-disialo | S |

TABLE 4-continued

Produced glycosylated IL-2 variant

| Name of variant | Glycosylation site 1 Glycosylation site | Amino acid residue before substitution | Glycosylation site 2 Glycosylation site | Amino acid residue before substitution | Glycosylation site 3 Glycosylation site | Amino acid residue before substitution | Glycosylation site 4 Glycosylation site | Amino acid residue before substitution | Glycosylation site 5 Glycosylation site | Amino acid residue before substitution | Amino acid residue after substitution | Mutation at position 125 |
|---|---|---|---|---|---|---|---|---|---|---|---|---|
| T3C-11/ L12C-11/ K32C-11/ K76C-11/ V91C-11 | 3 | T | 12 | L | 32 | K | 76 | K | 91 | V | C-disialo | S |
| L12C-11/ V91C-11/ E100C-11/ T102C-11/ M104C-11 | 12 | L | 91 | V | 100 | E | 102 | T | 104 | M | C-disialo | S |

TABLE 5

Produced glycosylated IL-2 variant

| Name of variant | Glycosylation site 1 Glycosylation site | Amino acid residue before substitution | Amino acid residue after substitution | Glycosylation site 2 Glycosylation site | Amino acid residue before substitution | Amino acid residue after substitution | Cys mutation site | Amino acid residue before substitution | Amino acid residue after substitution | Mutation at position 125 |
|---|---|---|---|---|---|---|---|---|---|---|
| A1C/L12C-11/ V91C-11 | 12 | L | C-disialo | 91 | V | C-disialo | 1 | A | AcC | S |
| A1C/E15C-11 | 15 | E | C-disialo | — | — | C-disialo | 1 | A | AcC | S |
| A1C/L19C-11 | 19 | L | C-disialo | — | — | C-disialo | 1 | A | AcC | S |
| A1C/V91C-11/ N119C-11 | 91 | V | C-disialo | 119 | N | C-disialo | 1 | A | AcC | S |
| T3C/ L12C-11/ V91C-11 | 12 | L | C-disialo | 91 | V | C-disialo | 3 | T | C | S |
| T3C/L12C-X1/ V91C-2 | 12 | L | C-disialo | 91 | V | C-disialo | 3 | T | C | S |
| T3C/L12C-11/ N119C-11 | 12 | L | C-disialo | 119 | N | C-disialo | 3 | T | C | S |
| T3C/L19C-11 | 19 | L | C-disialo | — | — | C-disialo | 3 | T | C | S |
| T51C/L12C-11/ V91C-X1 | 12 | L | C-disialo | 91 | V | C-disialo | 51 | T | C | S |
| F78C/L12C-11 | 12 | L | C-disialo | — | — | C-disialo | 78 | F | C | S |
| F78C/L12C-11/ V91C-11 | 12 | L | C-disialo | 91 | V | C-disialo | 78 | F | C | S |
| F78C/E15C-11 | 15 | E | C-disialo | — | — | C-disialo | 78 | F | C | S |

<Description of Tables 1 to 5>

Glycosylation site: Position from the N-terminal of the amino acid sequence of wild-type mature human IL-2 (SEQ ID NO: 1) (hereinafter, also simply referred to as wild-type IL-2)

Cys mutation site: Position from the N-terminal of the amino acid sequence represented by SEQ ID NO: 1

Mutation at position 125: Indicating presence or absence of a mutation of amino acid residue at position 125 from the N-terminal of the amino acid sequence represented by SEQ ID NO:

1. A case where no mutation is introduced is described as "–" and a case where a mutation that substitutes an amino acid residue from cysteine to serine is introduced, is described as "S".

In the tables, structures described in the column "Amino acid residues after substitution" in "Glycosylation site" are shown below.

C-Saccharide (GlcNAc, glucose, lactose, trisaccharide, pentasaccharide, asialo, disialo, or tetrasialo) indicates a structure represented by (Formula 1) below in which a saccharide is introduced into a side chain thiol of cysteine via a $CH_2CONH$ linker.

[Chem. 104]

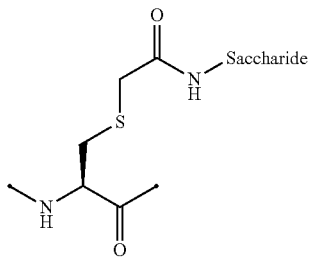

(Formula 1)

In (Formula 1) above, Saccharide indicates a saccharide.

N-Saccharide (GlcNAc or disialo) indicates a structure represented by (Formula 2) below in which saccharide is introduced into a side chain amide of asparagine.

[Chem. 105]

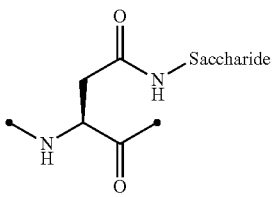

(Formula 2)

In (Formula 2) above, Saccharide indicates a saccharide.

GlcNAc indicates a structure represented by (Formula Y1) below.

[Chem. 106]

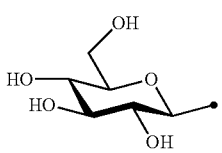

(Formula Y1)

Glucose indicates a structure represented by (Formula Y2) below.

[Chem. 107]

(Formula Y2)

Lactose indicates a structure represented by (Formula 4) below.

[Chem. 108]

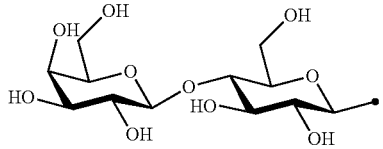

(Formula 4)

Trisaccharide indicates a structure represented by (Formula 5) below.

[Chem. 109]

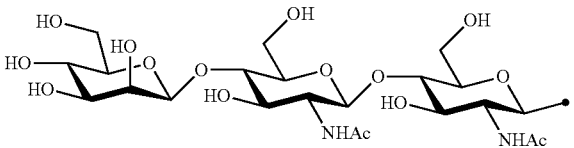

(Formula 5)

Pentasaccharide indicates a structure represented by (Formula 6) below.

[Chem. 110]

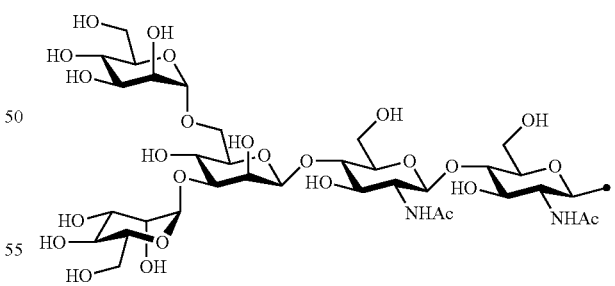

(Formula 6)

Asialo indicates a structure represented by (Formula 7) below.

[Chem. 111]
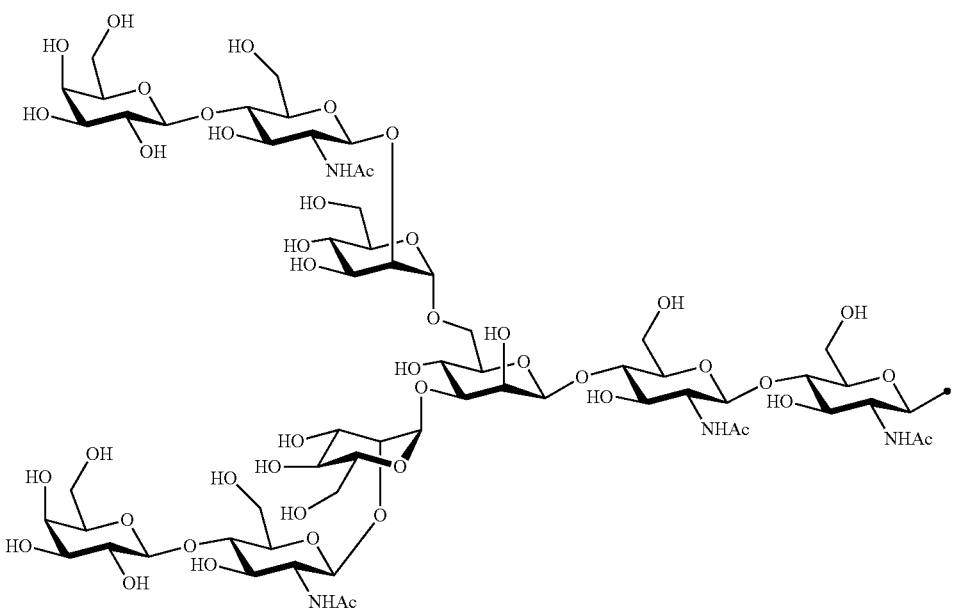
(Formula 7)
Disialo indicates a structure represented by (Formula 8) below.
[Chem. 112]
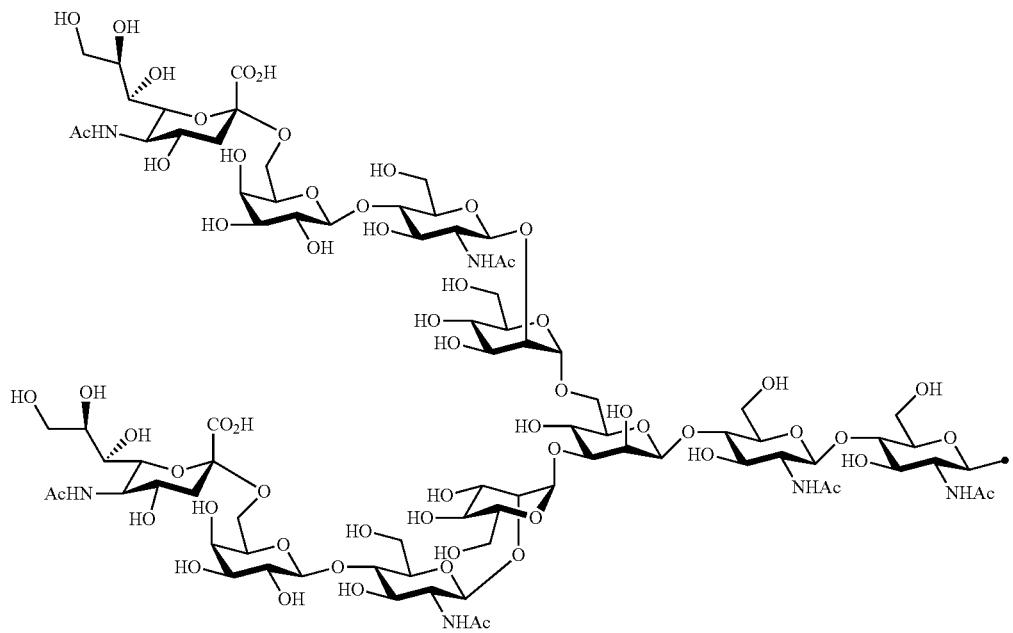
(Formula 8)
Tetrasialo indicates a structure represented by (Formula Y3) below.

[Chem. 113]

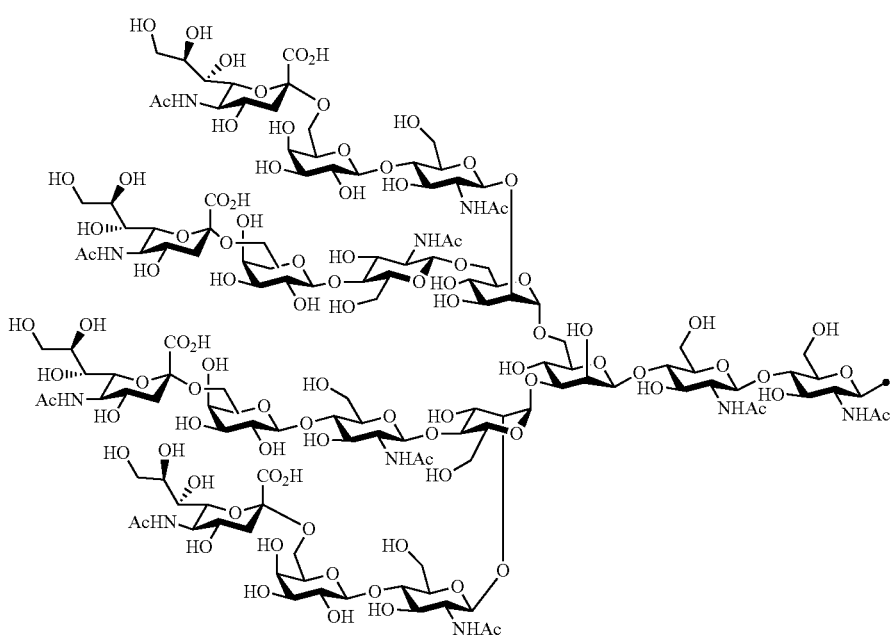

(Formula Y3)

In the table, AcC described in the column "Amino acid residue after substitution" in "Cys mutation site" indicates a structure represented by (Formula XXX) below.

In the table, C-acetamide described in the column "Amino acid residue after substitution" indicates a structure represented by (Formula 9) below.

[Chem. 114]

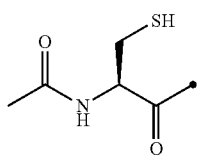

(Formula XXX)

[Chem. 115]

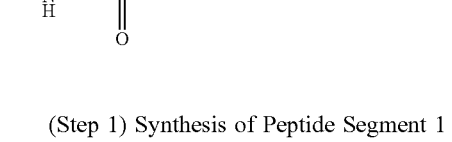

(Formula 9)

TABLE 6

| | Produced IL-2 or IL-2 variant | | | |
|---|---|---|---|---|
| Name of IL-2 or IL-2 variant | Mutation site | Amino acid residue before substitution | Amino acid residue after substitution | Mutation at position 125 |
| Wild-type IL-2 | — | — | — | — |
| L19C | 19 | L | C | S |
| L19C-acetamide | 19 | L | C-acetamide | S |
| L19N | 19 | L | N | S |
| N88C-acetamide | 88 | N | C-acetamide | S |

<Description of Table 6>
Mutation site: Position from the N-terminal of the amino acid sequence represented by SEQ ID NO: 1
Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".

(Step 1) Synthesis of Peptide Segment 1

Peptide thioesters or a glycosylated peptide thioesters of IL-2 amino acid sequence, 1 to 57 were prepared by the method below.

(Step 1-1a-1) Synthesis of Peptide Hydrazide

A first amino acid residue was loaded to tritylhydrazine resin obtained by a method described in [Angew. Chem. Int. Ed. 2014, 53, 6978-6981] using Fmoc-Gln (Trt)-OH (5 equiv), 1-hydroxybenzotriazole (5 equiv), and N,N'-diisopropylcarbodiimide (5 equiv) in DMF. According to a conventional method, elongation of amino acid using Fmoc amino acids (5.3 equiv), HCTU (5 equiv), N-methylmorpholine (5 equiv), or 2,4,6-trimethylpyridine (5 equiv) in DMF and deprotection with a 20% piperidine-DMF solution were repeated to extend second and subsequent amino acids.

The extended peptide was cleaved from the resin using trifluoroacetic acid (TFA), triisopropylsilane (TIPS) and water to remove side-chain protecting groups, and then dropped into ice-cooled ether. The resulting precipitate was collected by centrifugation. Purification was performed using a reversed-phase HPLC column [Proteonavi (trade name), manufactured by Shiseido Co., Ltd.] to synthesize the peptide hydrazide.

In this case, in the case of cysteine glycosylation, peptide hydrazide in which a glycosylation site was mutated to cysteine was prepared. In addition, in the case of introducing two types of saccharide, peptide hydrazide in which one was mutated to cysteine and the other was mutated to S-acetamidomethylcysteine was prepared.

In addition, when preparing an IL-2 variant in which amino acid sequence, position 3 or 51 is mutated to cysteine, the peptide hydrazide in which the position for introducing a saccharide is mutated to cysteine and position 3 or 51 in the amino acid sequence is mutated to S-acetamidomethylcysteine was prepared.

In addition, when preparing an analog in which amino acid sequence, position 1 was mutated to acetylcysteine, a peptide in which the position for introducing a saccharide is mutated to cysteine, amino acid sequence, position 1 is mutated to S-acetamidomethylcysteine, is extended on the resin, then an N-terminal amino group is acetylated using acetic anhydride and pyridine, and cleavage from the resin, removal of side-chain protecting groups, and purification were performed according to the method described above, and a peptide hydrazide in which the position 1 was mutated to acetylcysteine was prepared.

(Step 1-1a-2) Synthesis of Cys-Glycosylated Peptide Hydrazide or Cys-Acetamide-Bound Peptide Hydrazide The glycosylation using a bromoacetyl saccharide (prepared according to the method described in International Publication No. WO 2005/010053) to the peptide hydrazide obtained in (Step 1-1a-1) was carried out by a method described in [Tetrahedron Lett., 2004, 45, 3287-3290, Carbohydr. Res. 2009, 344, 762-770] to synthesize a targeted glycosylated peptide hydrazide.

A Cys-acetamide-bound peptide hydrazide was synthesized using bromoacetamide instead of the bromoacetyl saccharide, in the same manner as above.

(Step 1-1b) Synthesis of Asn-Glycosylated Peptide Hydrazide

A first amino acid residue was loaded to tritylhydrazine resin obtained by a method described in [Angew. Chem. Int. Ed. 2014, 53, 6978-6981] using Fmoc-Gln (Trt)-OH (5 equiv), 1-hydroxybenzotriazole (5 equiv), and N,N'-diisopropylcarbodiimide (5 equiv) in DMF. According to a conventional method, elongation of amino acid using Fmoc amino acids (5.3 equiv), HCTU (5 equiv) or N-methylmorpholine (5 equiv) in DMF and deprotection with a 20% piperidine-DMF solution were repeated to extend second and subsequent amino acids other than glycosylated Asn.

The glycosylated Asn (prepared according to a method described in International Publication WO 2004/005330) was extended by the method described in WO 2004/005330. The extended peptide was cleaved from the resin using trifluoroacetic acid (TFA), triisopropylsilane (TIPS) and water to remove side-chain protecting groups, and then dropped into ice-cooled ether. The resulting precipitate was collected by centrifugation. Purification was performed using a reversed-phase HPLC column [Proteonavi (trade name), manufactured by Shiseido Co., Ltd.] to synthesize the Asn-glycosylated peptide hydrazide.

(Step 1-2a) Synthesis of Peptide Thioester or Glycosylated Peptide Thioester

The peptide hydrazide obtained in (Step 1-1a-1), the Cys-glycosylated peptide hydrazide or the Cys-acetamide-bound peptide hydrazide obtained in (Step 1-1a-2) or Asn-glycosylated peptide hydrazide obtained in (Step 1-1b) is dissolved in 6 mol/L guanidine hydrochloride and 200 mmol/L phosphate buffer (pH 3), cooled to $-20°$ C., and then 200 mmol/L sodium nitrite, 6 mol/L guanidine hydrochloride and 200 mmol/L phosphate buffer (pH 7) were added thereto and stirred for 5 minutes. 400 mmol/L sodium 2-mercaptoethanesulfonate, 6 mol/L guanidine hydrochloride and 200 mmol/L phosphate buffer (pH 6) were added thereto, and stirred at $-15°$ C. for 1.5 hours. Then, purification was performed using a reversed-phase HPLC column [Proteonavi (trade name), manufactured by Shiseido Co., Ltd.] to obtain a peptide thioester or a glycosylated peptide thioester.

(Step 1-2b) Synthesis of Peptide Thioester to which Two Types of Saccharides were Bound When two types of saccharides are introduced, silver acetate suspended in acetic acid was added to a reaction solution of the glycosylated peptide hydrazide obtained in (Step 1-1a-2), the mixture was stirred for 6 hours, for the removal of S-acetamide methyl group. After adding dithiothreitol, the supernatant obtained by centrifugation was solvent-exchanged to 4 mol/L guanidine hydrochloride, 5 mmol/L phosphate buffer (pH 5) by gel filtration (Superdex G-75). 6 mol/L guanidine hydrochloride and 200 mmol/L phosphate buffer (pH 3) were added to eluate, and the pH was adjusted to 3 using 2 mol/L hydrochloric acid, and then the solution was cooled to $-15°$ C.

After 6 mol/L guanidine hydrochloride, 200 mmol/L sodium nitrite and 50 mmol/L phosphate buffer (pH 7) were added thereto and stirred at $-15°$ C. for 5 minutes, 6 mol/L guanidine hydrochloride, 400 mmol/L Sodium 2-mercaptoethanesulfonate and 200 mmol/L phosphate buffer (pH 6) were added thereto, and stirred at $-15°$ C. for 1.5 hours. Purification was performed by a reverse-phase HPLC column [Proteonavi (trade name), manufactured by Shiseido Co., Ltd.] to obtain the glycosylated peptide thioester.

A second kind of saccharide was introduced into the obtained glycosylated peptide thioester according to the method described in (Step 1-1a-2), and purification was performed by a reverse-phase HPLC column [Proteonavi (trade name), manufactured by Shiseido Co., Ltd.] to obtain a peptide thioester to which two types of saccharides were bound.

(Step 2) Synthesis of Peptide Segment 2

Peptide hydrazide or glycosylated peptide hydrazide of IL-2 amino acid sequence, 58 to 104 were prepared by the method below.

(Step 2-1a-1) Synthesis of Peptide Hydrazide

A first amino acid residue was loaded to tritylhydrazine resin obtained by a method described in [Angew. Chem. Int.

Ed. 2014, 53, 6978-6981] using Fmoc-Met-OH (5 equiv), 1-hydroxybenzotriazole (5 equiv), and N,N'-diisopropylcarbodiimide (5 equiv) in DMF.

According to a conventional method, elongation of amino acid using Fmoc amino acids (5.3 equiv), HCTU (5 equiv), N-methylmorpholine (5 equiv), or 2,4,6-trimethylpyridine (5 equiv) in DMF and deprotection with a 20% piperidine-DMF solution were repeated to extend second and subsequent amino acids.

The extended peptide was cleaved from the resin using trifluoroacetic acid (TFA), triisopropylsilane (TIPS) and water to remove side-chain protecting groups, and then dropped into ice-cooled ether. The resulting precipitate was collected by centrifugation. Purification was performed using a reversed-phase HPLC column [Proteonavi (trade name), manufactured by Shiseido Co., Ltd.] to synthesize the peptide hydrazide.

In this case, in a case of introducing a saccharide, a peptide hydrazide in which a glycosylation site was mutated to cysteine, and amino acid sequence, 58 was mutated to thioproline was prepared. When preparing an analog in which the amino acid sequence at position 78 was mutated to cysteine, a peptide hydrazide in which the amino acid sequence at position 78 was mutated to cysteine was prepared. When preparing an analog in which a saccharide was introduced into the amino acid sequence, 91 and the amino acid sequence, 78 was mutated to cysteine, a peptide hydrazide in which the amino acid sequence at position 91 was mutated to cysteine and the amino acid sequence at position 78 was mutated to S-acetamidomethylcysteine was prepared.

(Step 2-1a-2) Synthesis of Cys-Glycosylated Peptide Hydrazide or Cys-Acetamide-Bound Peptide Hydrazide After 10 equivalents of sodium 2-mercaptoethanesulfonate to the bromoacetyl saccharide, 8 mol/L guanidine hydrochloride aqueous solution, 2 mol/L hydrochloric acid and methoxyamine hydrochloride were added to the reaction solution in which the glycosylation using a bromoacetyl saccharide (prepared according to the method described in International Publication No. WO 2005/010053) to the peptide hydrazide obtained in (Step 2-1a-1) was carried out by the method described in [Tetrahedron Lett., 2004, 45, 3287-3290, Carbohydr. Res. 2009, 344, 762-770], pH was adjusted to 4, and reaction was performed at room temperature for 20 minutes. Purification was performed using a reversed-phase HPLC column [Proteonavi (trade name), manufactured by Shiseido Co., Ltd.] to synthesize the Cys-glycosylated peptide hydrazide.

Cys-bromoacetamide-bound peptide hydrazide was synthesized using bromoacetamide instead of the bromoacetyl saccharide, in the same manner as above.

(Step 2-1b) Synthesis of Asn-Glycosylated Peptide Hydrazide

Asn-glycosylated peptide hydrazide was prepared in the same manner as in (Step 1-1b).

(Step 3) Synthesis of Peptide Segment 3

The peptide or a glycosylated peptide of IL-2 amino acid sequence, 105 to 133 was prepared by the method below.

(Step 3-1) Adjustment of Solubilization Tag (H—C(Npys)RRRRR—NH$_2$)

Elongation of amino acid using Fmoc amino acids (5.3 equiv), HCTU (5 equiv), or N-methylmorpholine (5 equiv) in DMF on Rink-amide resin and deprotection with a 20% piperidine-DMF solution were repeated to extend amino acids. The extended peptide was cleaved from the resin using trifluoroacetic acid (TFA), triisopropylsilane (TIPS) and water to remove side-chain protecting groups, and then dropped into ice-cooled ether. The resulting precipitate was collected by centrifugation. The solubilization tag (H—C(Npys)RRRRR—NH$_2$) was prepared.

(Step 3-2) Synthesis of Solubilization Tag-Introduced Peptide

Peptides of IL-2 amino acid sequence, 105 to 133 were prepared by the method below.

A first amino acid residue was loaded to HMPB-ChemMatrix resin, using Fmoc-Thr (tBu)-OH (5 equiv), 1-(mesitylene-2-sulfonyl)-3-nitro-1,2,4-triazole (5 equiv), and 1-methylimidazole (3.5 equiv). According to the conventional method, elongation of amino acid using Fmoc amino acids (5.3 equiv), HCTU (5 equiv), N-methylmorpholine (5 equiv), or 2,4,6-trimethylpyridine (5 equiv) in DMF and deprotection with a 20% piperidine-DMF solution were repeated to extend second and subsequent amino acids.

The extended peptide was cleaved from the resin using trifluoroacetic acid (TFA), triisopropylsilane (TIPS) and water to remove side-chain protecting groups, and then dropped into ice-cooled ether. The resulting precipitate was collected by centrifugation to obtain a crude purified peptide. In a case of the glycosylation to cysteine, a peptide in which glycosylation site was mutated to cysteine, and amino acid sequence 105 was mutated to thioproline was prepared.

The solubilization tag (3 equivalents to the crude peptide product) obtained in (Step 3-1) was dissolved in 6.8 mol/L guanidine hydrochloride and 310 mmol/L phosphate buffer (pH 7), and 5 equivalents acetic anhydride was added thereto and stirred at room temperature for 1 hour. After adding 10 equivalents of arginine hydrochloride, the peptide crude product dissolved in 8 mol/L guanidine hydrochloride and 250 mmol/L trishydroxymethylaminomethane hydrochloride aqueous solution (pH 8) was added thereto, and stirred at room temperature for 1 hour. Purification was performed using a reversed-phase HPLC column [Proteonavi (trade name), manufactured by Shiseido Co., Ltd.] to synthesize the solubilization tag-introduced peptide.

(Step 3-3) Glycosylation of Solubilization Tag-Introduced Peptide

The solubilization tag-introduced peptide obtained in (Step 3-2) was dissolved in 8 mol/L guanidine hydrochloride, 5 mmol/L tris (2-carboxyethyl) phosphine and 200 mmol/L phosphate buffer (pH 6), a solution of 6 mol/L guanidine hydrochloride of bromoacetyl saccharide (5 equiv, prepared by the method described in International Publication No. WO 2005/010053) and 200 mmol/L phosphate buffer (pH 7) was added thereto and reacted for 5 hours.

After adding 4 equivalents of sodium 2-mercaptoethanesulfonate to the bromoacetyl saccharide and stirring for 1 hour, methoxyamine hydrochloride (300 equiv) dissolved in 6 mol/L guanidine hydrochloride and 200 mmol/L phosphate buffer (pH 7) was added thereto. The mixture was adjusted to have pH 4 using 2 mol/L hydrochloric acid and reacted for 1 hour. Purification was performed using a reversed-phase HPLC column [Proteonavi (trade name), manufactured by Shiseido Co., Ltd.] to synthesize the glycosylated peptide.

(Step 4) Synthesis of IL-2 Variant and Glycosylated IL-2 Variant (Step 4-1) Ligation Reaction of Peptide Segments 1 and 2

The peptide segment 1 obtained in (Step 1) above and the peptide segment 2 obtained in (Step 2) above (1.1 equiv) were dissolved in 8 mol/L guanidine hydrochloride, 100 mM tris(2-carboxyethyl) phosphine, 100 mM ascorbic acid, 50 mmol/L 4-mercaptophenylacetic acid and 200 mmol/L phosphate buffer (pH 7) and reacted. Thereafter, purification was performed using a reversed-phase HPLC column [Proteonavi (trade name), manufactured by Shiseido Co., Ltd.] to synthesize a conjugate of the peptide segments 1 and 2.

(Step 4-2) Thioesterification of Conjugate of Peptide Segments 1 and 2

The conjugate of the peptide segments 1 and 2 obtained in (Step 4-1) was thioesterified in the same manner as in (Step 1-2a).

(Step 4-3) Ligation with Peptide Segment 3

The peptide thioester obtained in (Step 4-2) above and the peptide segment 3 (1 equiv) obtained in (Step 3) above were dissolved in 8 mol/L guanidine hydrochloride, 100 mM tris(2-carboxyethyl) phosphine, 100 mM ascorbic acid, 50 mmol/L 4-mercaptophenylacetic acid and 200 mmol/L phosphate buffer (pH 7) and reacted. Thereafter, purification was performed using a reversed-phase HPLC column [Proteonavi (trade name), manufactured by Shiseido Co., Ltd.] to synthesize a conjugate of the peptide segments 1, 2, and 3.

(Step 4-4) Deprotection of Acetamide Methyl Group

In the case where the cysteine in the conjugate of the peptide segments 1, 2, and 3 obtained in (Step 4-3) above was protected with an acetamide methyl group, the acetamide methyl group was removed by the method below.

The conjugate of the peptide segments 1, 2, and 3 was dissolved in 6 mol/L urea and 5 mmol/L phosphate buffer (pH 5) and silver acetate (420 equivalents) suspended in acetic acid was added thereto and stirred for 5 hours. After adding an excess amount of dithiothreitol, the supernatant obtained by centrifugation was purified by a reversed-phase HPLC column [Proteonavi (trade name), manufactured by Shiseido Co., Ltd.] to obtain a de-acetamide-methyl product.

(Step 4-5) Deprotection of Sialic Acid Benzyl Ester

In a case where sialic acid side chain carboxylic acids on the saccharide of the conjugate of the peptide segments 1, 2, and 3 obtained in (Step 4-3) above are protected with benzyl groups, the benzyl groups were removed according to the method described in International Publication No. WO2004/005330. Thereafter, purification was performed using a reversed-phase HPLC column [Proteonavi (trade name), manufactured by Shiseido Co., Ltd.] to obtain the debenzylated product.

(Step 4-6) Synthesis of IL-2 Variant and Glycosylated IL-2 Variant

The conjugate of the peptide segments 1, 2, and 3 synthesized in (Step 4-3), (Step 4-4), or (Step 4-5) was dissolved in 6 mol/L guanidine hydrochloride and 100 mmol/L trishydroxymethylaminomethane hydrochloride (pH 8), and then 100 mmol/L trishydroxymethylaminomethane hydrochloride, 10 mmol/L reduced glutathione and 1 mmol/L oxidized glutathione (pH 8) were added thereto, and stirred at room temperature for 18 hours. Purification was performed using a reversed-phase HPLC column [Proteonavi (trade name), manufactured by Shiseido Co., Ltd.] to obtain the IL-2 variant and the glycosylated IL-2 variant.

The obtained IL-2 variant and the glycosylated IL-2 variant was confirmed that there was no problem in quality and purity, from the points that a calculated value and a measured value match in mass spectrometry, the CD spectrum matches that of the wild-type IL-2, and/or a band detected by SDS-PAGE was at a position of the band having an assumed molecular weight.

Example 2

Synthesis of N-Terminal PEGylated and Glycosylated IL-2 Variant

N-terminal PEGylated and glycosylated IL-2 shown in Table 7 were produced by a method described below.

TABLE 7

Produced N-terminal PEGylated and glycosylated IL-2 variant

| | PEGylation site | | | Glycosylation site | | | |
| --- | --- | --- | --- | --- | --- | --- | --- |
| Name of variant | PEGylation site | Amino acid residue before substitution | Amino acid residue after substitution | Glycosylation site | Amino acid residue before substitution | Amino acid residue after substitution | Mutation at position 125 |
| A1-Li20 (CHO)/Q11C-9 | 1 | A | A-Li20 (CHO) | 11 | Q | C-asialo | — |
| A1-Li20 (CHO)/L12C-9 | 1 | A | A-Li20 (CHO) | 12 | L | C-asialo | — |
| A1-Li20 (CHO)/R38C-9 | 1 | A | A-Li20 (CHO) | 38 | R | C-asialo | — |
| A1-Li20 (CHO)/V91C-9 | 1 | A | A-Li20 (CHO) | 91 | V | C-asialo | — |

<Description of Table 7>
Glycosylation site and PEGylation site: Position from the N-terminal of the amino acid sequence of wild-type mature human IL-2 (SEQ ID NO: 1) (hereinafter, also simply referred to as wild-type IL-2)

Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".

In the tables, structures described in the column "Amino acid residues after substitution" in "Glycosylation site" are shown below.

C-saccharide (asialo) indicates a structure represented by (Formula 1) below in which a saccharide is introduced into a side chain thiol of cysteine via a CH$_2$CONH linker.

[Chem. 116]

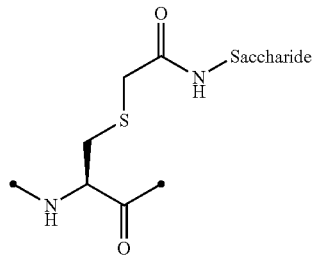

(Formula 1)

In (Formula X1) above, Saccharide indicates a saccharide.

Asialo indicates a structure represented by (Formula 7) below.

[Chem. 117]

In the table, structures described in the column "Amino acid residues after substitution" in "PEGylation site" are shown below.

Al-PEG(CHO)[Li20(CHO)] indicates a structure represented by (Formula Z0) below in which PEG is introduced into an alanine main chain amino group via a (CH$_2$)$_3$ linker.

[Chem. 118]

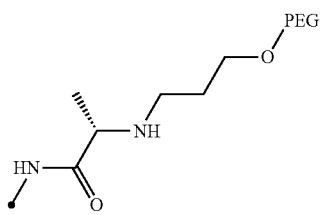

(Formula Z0)

Li20 indicates that, in (Formula Z0) above, PEG is a structure represented by (Formula X00) below in a case of an average molecular weight of about 20 kDa.

[Chem. 119]

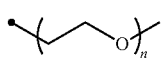

(Formula X00)

20 mmol of phosphate buffer (pH 5.5) of PEG-aldehyde (10 equiv, PJK-241; Creative PEG Works) was added to 1 mM EDTA and 20 mmol/L phosphate buffer (pH 5.5) of the glycosylated IL-2 variant at room temperature, and stirred at room temperature for 30 minutes. Thereafter, NaBH$_3$(CN) (1000 equiv) was added thereto, and stirred for 3 hours.

A solvent was replaced by 0.05% trifluoroacetic acid and 2% acetonitrile aqueous solution by ultrafiltration using (Formula 7)

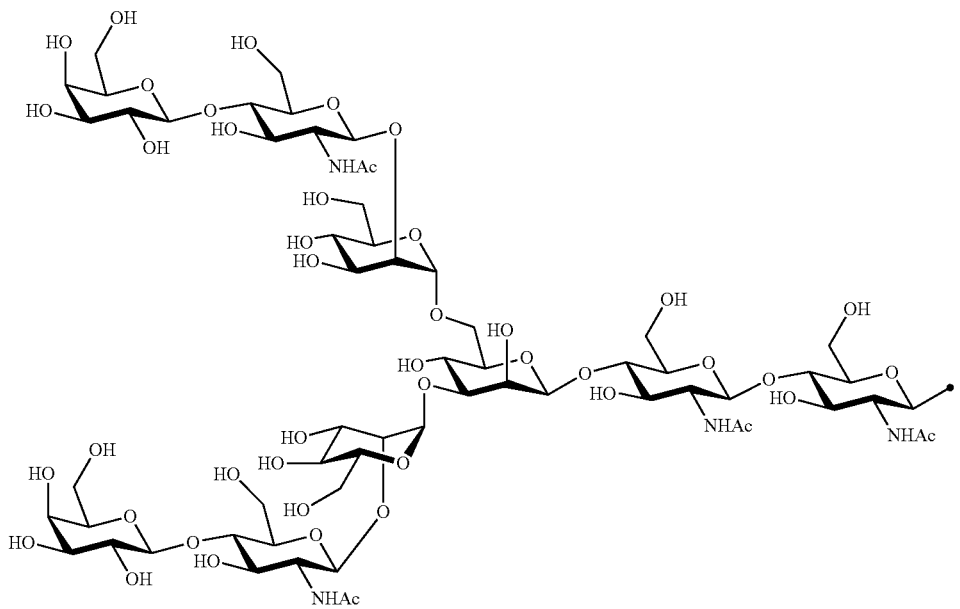

Amicon Ultra-0.5 (10 kDa), followed by purification in size exclusion chromatography (column; manufactured by Waters, connecting)(Bridge BEH450A, 3.5 μm, 7.8×150 mm and XBridge BEH200A, 3.5 μm, 7.8×150 mm), to synthesize an N-terminal PEGylated and glycosylated IL-2 variant.

A purity of the purified N-terminal PEGylated and glycosylated IL-2 variant was confirmed by SDS-PAGE. As a result, in all the variants, a single band in which a molecular weight of PEG was increased was confirmed, and it was confirmed that highly purified N-terminal PEGylated and glycosylated IL-2 variants were obtained.

Example 3

Synthesis of Cys-PEGylated and Glycosylated IL-2 Variant

Cys-PEGylated and glycosylated IL-2 shown in Table 8 were produced by a method described below.

TABLE 8

| | Produced Cys-PEGylated and glycosylated IL-2 variant | | | | | | | | | |
|---|---|---|---|---|---|---|---|---|---|---|
| | PEGylation site | | | Glycosylation site 1 | | | Glycosylation site 2 | | | |
| Name of variant | PEGylation site | Amino acid residue before substitution | Amino acid residue after substitution | Glycosylation site | Amino acid residue before substitution | Amino acid residue after substitution | Glycosylation site | Amino acid residue before substitution | Amino acid residue after substitution | Mutation at position 125 |
| A1C-Li40 (IAc)/L12C-11/V91C-11 | 1 | A | AcC-Li40 (IAc) | 12 | L | C-disialo | 91 | V | C-disialo | S |
| A1C-Y80 (Mal)/L12C-11/V91C-11 | 1 | A | AcC-V80 (Mal) | 12 | L | C-disialo | 91 | V | C-disialo | S |
| A1C-Y50 (IAc)/L12C-L1/V91C-11 | 1 | A | AcC-Y50 (IAc) | 12 | L | C-disialo | 91 | V | C-disialo | S |
| A1C-Y50 (Mal)/L12C-11/V91C-11 | 1 | A | AcC-Y50 (Mal) | 12 | L | C-disialo | 91 | V | C-disialo | S |
| A1C-W80 (Mal)/L12C-L1/V91C-1L | 1 | A | AcC-W80 (Mal) | 12 | L | C-disialo | 91 | V | C-disialo | S |
| A1C-Y50 (IAc)/L19C-11 | 1 | A | AcC-Y50 (IAc) | 19 | L | C-disialo | — | — | — | S |
| A1C-V40 (IAc)/L19C-11 | 1 | A | AcC-V40 (IAc) | 19 | L | C-disialo | — | — | — | S |
| A1C-Y50 (IAc)/V91C-11/N119C-11 | 1 | A | AcC-Y50 (IAc) | 91 | V | C-disialo | 119 | N | C-disialo | S |
| T3C-W80 (Mal)/LL2C-11/V91C-2 | 3 | T | C-W80 (Mal) | 12 | L | C-disialo | 91 | V | C-lactose | S |
| T3C-Li2O (IAc)/L12C-11/V91C-11 | 3 | T | C-L120 (IAc) | 12 | L | C-disialo | 91 | V | C-disialo | S |
| T3C-Li40 (IAc)/L12C-LL/V91C-11 | 3 | T | C-Li40 (IAc) | 12 | L | C-disialo | 91 | V | C-disialo | S |
| T3C-V40 (IAc)/LI2C-1L/V91C-1L | 3 | T | C-V40 (IAc) | 12 | L | C-disialo | 91 | V | C-disialo | S |
| T3C-W40 (IAc)/L12C-1L/V91C-11 | 3 | T | C-IY40 (IAc) | 12 | L | C-disialo | 91 | V | C-disialo | S |
| T3C-Y50 (IAc)/L12C-11/V91C-2 | 3 | T | C-Y50 (IAc) | 12 | L | C-disialo | 91 | V | C-lactose | S |
| T3C-Y50 (IAc)/L12C-11/V91C-11 | 3 | T | C-Y50 (IAc) | 12 | L | C-disialo | 91 | V | C-disialo | S |
| T3C-Y50 (Mal)/L12C-11/V91C-11 | 3 | T | C-Y50 (Mal) | 12 | L | C-disialo | 91 | V | C-disialo | S |
| T3C-V40 (IAc)/El5C-11 | 3 | T | C-V4D (IAc) | 15 | E | C-disialo | — | — | — | S |
| T3C-V80 (Mai)/El6C-11 | 3 | T | C-V80 (Mal) | 15 | E | C-disialo | — | — | — | S |
| T3C-Y50 (IAc)/El5C-11 | 3 | T | C-Y50 (IAc) | 15 | E | C-disialo | — | — | — | S |
| T3C-V80 (Mal)/L12C-11/N119C-11 | 3 | T | C-V80 (Mal) | 12 | L | C-disialo | 119 | N | C-disialo | S |
| T3C-W80 (Mal)/L12C-11/N119C-11 | 3 | T | C-W80 (Mal) | 12 | L | C-disialo | 119 | N | C-disialo | S |
| T3C-Y50 (IAc)/L12C-11/N119C-11 | 3 | T | C-Y50 (IAc) | 12 | L | C-disialo | 119 | N | C-disialo | S |
| T51C-Li40 (IAc)/L12C-11/V91C-11 | 51 | T | C-Li40 (IAc) | 12 | L | C-disialo | 91 | V | C-disialo | S |
| T51C-V40 (IAc)/L12C-11/V91C-11 | 51 | T | C-V10 (IAc) | 12 | L | C-disialo | 91 | V | C-disialo | S |
| T51C-W40 (IAc)/L12C-11/V91C-11 | 51 | T | C-W40 (IAc) | 12 | L | C-disialo | 91 | V | C-disialo | S |
| T51C-Y50 (lAc)/L12C-11/V91C-11 | 51 | T | C-Y50 (IAc) | 12 | L | C-disialo | 91 | V | C-disialo | S |
| F78C-Li40 (IAc)/ | | | | | | | | | | |

TABLE 8-continued

Produced Cys-PEGylated and glycosylated IL-2 variant

| | PEGylation site | | | Glycosylation site 1 | | | Glycosylation site 2 | | | Mutation at position 125 |
|---|---|---|---|---|---|---|---|---|---|---|
| Name of variant | PEGylation site | Amino acid residue before substitution | Amino acid residue after substitution | Glycosylation site | Amino acid residue before substitution | Amino acid residue after substitution | Glycosylation site | Amino acid residue before substitution | Amino acid residue after substitution | |
| L12C-11 | 78 | F | C-Li40 (IAc) | 12 | L | C-disialo | — | — | — | S |
| F78C-V40 (IAc)/ L12C-11 | 78 | F | C-V40 (IAc) | 12 | L | C-disialo | — | — | — | S |
| F78C-V40 (Mal)/ L12C-11 | 78 | F | C-V40 (Mal) | 12 | L | C-disialo | — | — | — | S |
| F78C-V80 (Mal)/ L12C-11 | 78 | F | C-V80 (Mal) | 12 | L | C-disialo | — | — | — | S |
| F78C-W80 (Mal)/ L12C-11 | 78 | F | C-W80 (Mal) | 12 | L | C-disialo | — | — | — | S |
| F78C-V40 (IAc)/ L12C-11/N119C-11 | 78 | F | C-V40 (IAc) | 12 | L | C-disialo | 119 | N | C-disialo | S |
| F78C-V80 (Mal)/ L12C-11/N119C-11 | 78 | F | C-V80 (Mal) | 12 | L | C-disialo | 119 | N | C-disialo | S |
| F78C-W80 (Mal)/ L12C-11/N119C-11 | 78 | F | C-W80 (Mal) | 12 | L | C-disialo | 119 | N | C-disialo | S |
| F78C-Li40 (IAc)/ E15C-11 | 78 | F | C-Li40 (IAc) | 15 | E | C-disialo | — | — | — | S |

<Description of Table 8>

PEGylation site and Glycosylation sites 1 and 2: Position from the N-terminal of the amino acid sequence of wild-type mature human IL-2 (SEQ ID NO: 1) (hereinafter, also simply referred to as wild-type IL-2)

Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".

In the tables, structures described in the column "Amino acid residues after substitution" in "Glycosylation site" are shown below.

C-Saccharide (lactose, disialo) indicates a structure represented by (Formula 1) below in which a saccharide is introduced into a side chain thiol of cysteine via a $CH_2CONH$ linker.

[Chem. 120]

(Formula 1)

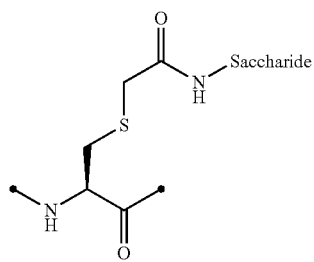

In (Formula 1) above, Saccharide indicates a saccharide.

Lactose indicates a structure represented by (Formula 4) below.

[Chem. 121]

(Formula 4)

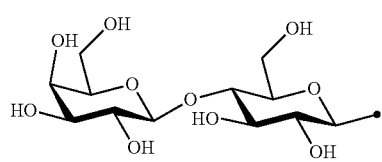

Disialo indicates a structure represented by (Formula 8) below.

[Chem. 122]

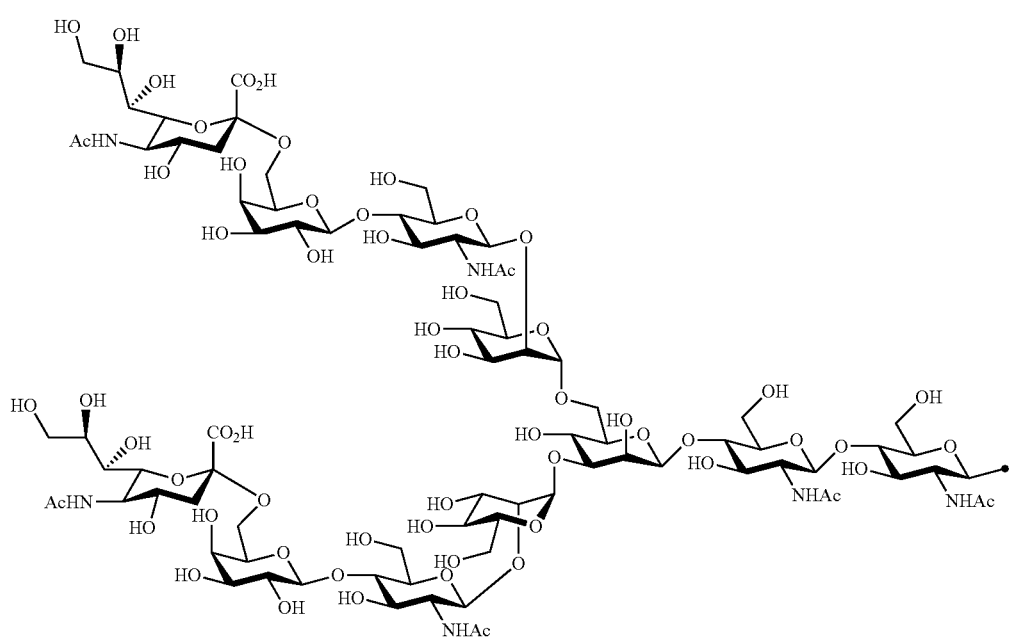

(Formula 8)

In the table, structures described in the column "Amino acid residues after substitution" in "PEGylation site" are shown below.

C-PEG(IAc) [Li20(IAc), Li40(IAc), V40(IAc), W40(IAc), Y50(IAc)] indicates a structure represented by (Formula X4) in which PEG is introduced into a cysteine side chain via a $CH_2CONH(CH_2)_3O$ linker.

[Chem. 123]

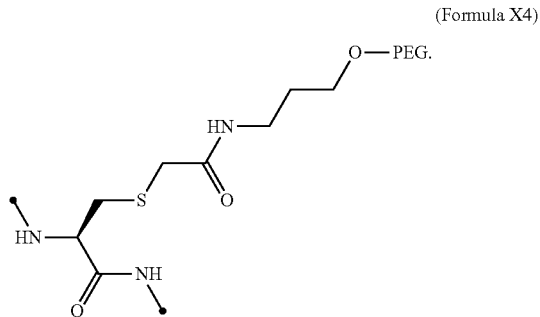

(Formula X4)

C-PEG(Mal) [V40(Mal), V80(Mal), W80(Mal), Y50(Mal)] indicates a structure represented by (Formula X5) below in which PEG is introduced into a cysteine side chain via a 3-(3-thio-2,5-dioxopyrrolidin-1-yl)-propyloxy linker. In this case, C-PEG(Mal) may indicate a structure represented by (Formula X6) or (Formula X7) in which a dioxopyrrolidine ring is opened.

[Chem. 124]

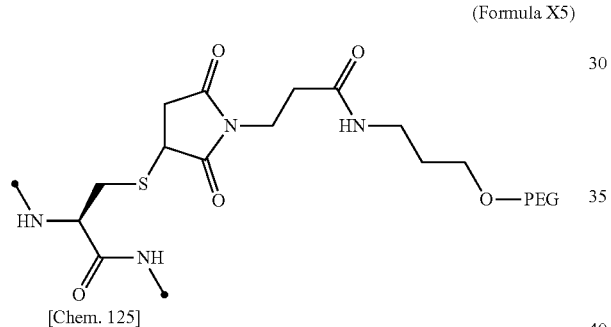

(Formula X5)

[Chem. 125]

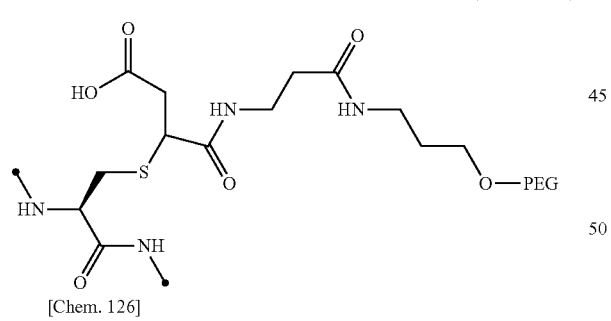

(Formula X6)

[Chem. 126]

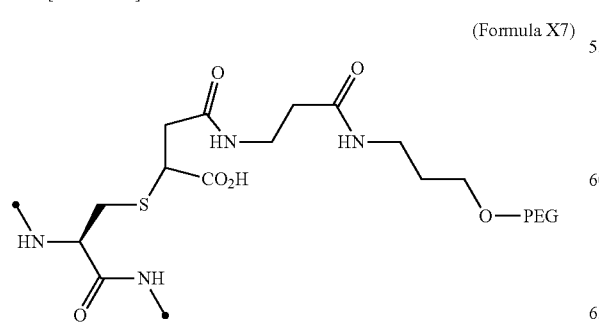

(Formula X7)

AcC-PEG(IAc) [Li40(IAc), Y50(IAc)] indicates a structure represented by (Formula XX3) below in which PEG is introduced into an acetylcysteine side chain via a $CH_2CONH(CH_2)_3O$ linker.

[Chem. 127]

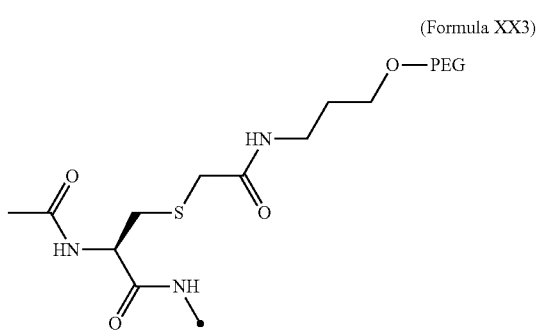

(Formula XX3)

AcC-PEG(Mal) [V80(Mal), W80(Mal), Y50(Mal)] indicates a structure represented by (Formula X8) below in which PEG is introduced into an N-acetylcysteine side chain via a 3-(3-thio-2,5-dioxopyrrolidin-1-yl)-propyloxy linker. In this case, AcC-PEG(Mal) may indicate a structure represented by (Formula X9) or (Formula X10) in which a dioxopyrrolidine ring is opened.

[Chem. 128]

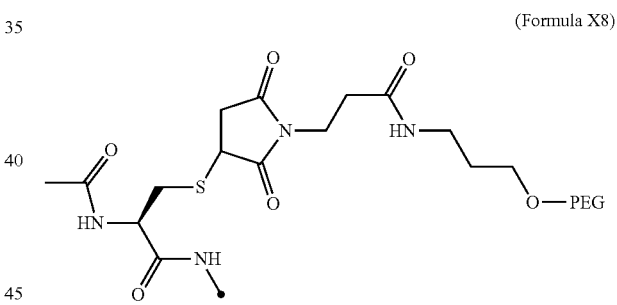

(Formula X8)

[Chem. 129]

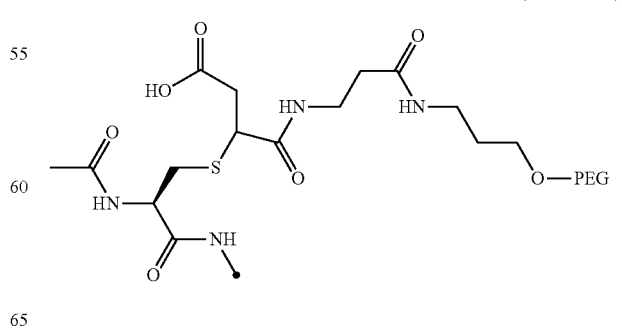

(Formula X9)

[Chem. 130]

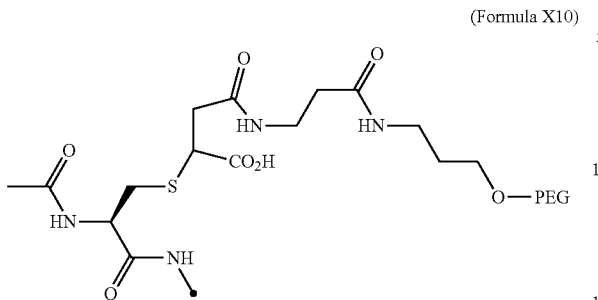

(Formula X10)

Li20 indicates that, in (Formula X4) to (Formula X10) above, PEG is a structure represented by (Formula X11) below in a case of an average molecular weight of about 20 kDa.

[Chem. 131]

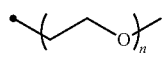

(Formula X11)

Li40 indicates that, in (Formula X4) to (Formula X10) above, PEG is a structure represented by (Formula X11) above in a case of an average molecular weight of about 40 kDa.

V40 indicates that, in (Formula X4) to (Formula X10) above, PEG is a structure represented by (Formula X13) below in a case of an average molecular weight of about 40 kDa.

[Chem. 132]

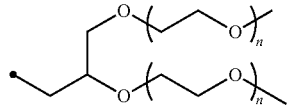

(Formula X13)

V80 indicates that, in (Formula X4) to (Formula X10) above, PEG is a structure represented by (Formula X13) above in a case of an average molecular weight of about 80 kDa.

W40 indicates that, in (Formula X4) to (Formula X10) above, PEG is a structure represented by (Formula X14) below in a case where an average molecular weight of $(CH_2CH_2O)_m$ is 5 kDa and an average molecular weight of $(CH_2CH_2O)_n$ is 7.5 kDa.

[Chem. 133]

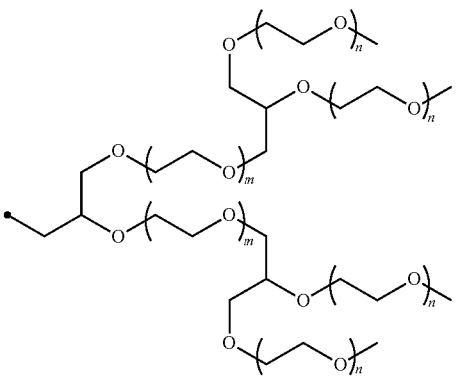

(Formula X14)

W80 indicates that, in (Formula X4) to (Formula X10) above, PEG is a structure represented by (Formula X14) above in a case where an average molecular weight of $(CH_2CH_2O)_m$ is 5 kDa and an average molecular weight of $(CH_2CH_2O)_n$ is 17.5 kDa.

Y50 indicates that, in (Formula X4) to (Formula X10) above, PEG is a structure represented by (Formula X15) below in a case where an average molecular weight of $(CH_2CH_2O)_m$ is 10 kDa and an average molecular weight of $(CH_2CH_2O)_n$ is 20 kDa.

[Chem. 134]

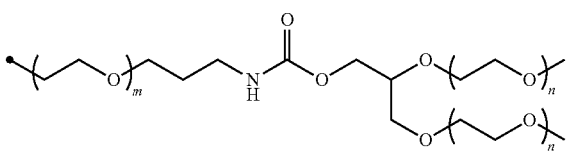

(Formula X15)

(Step 1) Preparation of PEG-Haloacetyl

PEG-amine (SUNBRIGHT GL2-400 PA; NOF CORPORATION, SUNBRIGHT GL3-400 PA100 U; NOF CORPORATION, or SUNBRIGHT GL4-400 PA; NOF CORPORATION) is dissolved in chloroform, and 1-Ethyl-3-(3-dimethylaminopropyl)carbodiimide Hydrochloride (5 equiv), 4-dimethylaminopyridine (5 equiv), and iodoacetic acid (5 equiv) were added thereto, and stirred at room temperature for 90 hours. Ether/isopropanol=1/1 was added, and precipitated solid was collected by filtration. The residue was dissolved in water, iodoacetic acid was removed by ultrafiltration using Amicon Ultra-0.5 (10 kDa), and lyophilization was performed to synthesize PEG-IAc.

[Step 2] Synthesis of Cys-PEGylated and Glycosylated IL-2 Variant 1 mmol/L EDTA and 20 mmol/L phosphate buffer (pH 5.5) of PEG-haloacetyl (5 equiv, the compound synthesized in Step 1 above or SUNBRIGHT ME-200IA; NOF CORPORATION, or SUNBRIGHT ME-4001A; NOF CORPORATION) or PEG-maleimide (5.0 nmol, SUNBRIGHT GL2-800MA; NOF CORPORATION, SUNBRIGHT GL4-400 MA100 U; NOF CORPORATION, or SUNBRIGHT GL4-800 MA; NOF CORPORATION) were added to 1 mmol/L EDTA and 20 mmol/L phosphate buffer (pH 5.5) of the glycosylated IL-2 variant shown in Table 5 at room temperature. The mixture was adjusted to have pH 7.2 to 7.4 using a 0.1 mol/L sodium hydroxide aqueous solution and stirred for 2 hours. Purification was performed in size exclusion chromatography (column; manufactured by Waters, connecting)(Bridge BEH450A, 3.5 7.8×150 mm and)(Bridge BEH200A, 3.5 7.8×150 mm) to synthesize the Cys-PEGylated and glycosylated IL-2 variant.

A purity of the purified Cys-PEGylated and glycosylated IL-2 variant was confirmed by SDS-PAGE. As a result, in all the variants, a single band in which a molecular weight of PEG was increased was confirmed, and it was confirmed that highly purified Cys-PEGylated and glycosylated IL-2 variants were obtained.

Example 4

Preparation of Expression Vectors for 8his-IL-2 for *Escherichia coli*, o-Az-Z-Lys-Introduced Human IL-2, and m-Az-Z-Lys-Introduced 8his-IL-2

8His-IL-2 expression vector for *Escherichia coli*, o-Az-Z-Lys-introduced 8His-IL-2 expression vector, and m-Az-Z-Lys-introduced 8His-IL-2 expression vector shown in Table 9 were produced by a method below.

TABLE 9

Produced 8His-IL-2 expression vector for *Escherichia coli*, o-Az-Z-Lys-introduced 8His-IL-2 expression vector, and m-Az-Z-Lys-introduced 8His-IL-2 expression vector

| Variant name | Az-Z-Lys introduction position | Amino acid residue before substitution | Amino acid residue after substitution | Modification at position 1 | Mutation at position 125 | Nucleotide sequence |
|---|---|---|---|---|---|---|
| 8His-IL-2 | — | — | — | MHHHHHHHHA | S | SEQ ID NO: 3 |
| 8His-S4 (oAzZK) | 4 | S | o-Az-Z-Lys | MHHHHHHHHA | S | SEQ ID NO: 4 |
| 8His-S5 (oAzZK) | 5 | S | o-Az-Z-Lys | MHHHHHHHHA | S | SEQ ID NO: 5 |
| 8His-S6 (oAzZK) | 6 | S | o-Az-Z-Lys | MHHHHHHHHA | S | SEQ ID NO: 6 |
| 8His-T7 (oAzZK) | 7 | T | o-Az-Z-Lys | MHHHHHHHHA | S | SEQ ID NO: 7 |
| 8His-K8 (oAzZK) | 8 | K | o-Az-Z-Lys | MHHHHHHHHA | S | SEQ ID NO: 8 |
| 8His-E60 (oAzZK) | 60 | E | o-Az-Z-Lys | MHHHHHHHHA | S | SEQ ID NO: 9 |
| 8His-F78 (oAzZK) | 78 | F | o-Az-Z-Lys | MHHHHHHHHA | S | SEQ ID NO: 10 |
| 8His-H79 (oAzZK) | 79 | F | o-Az-Z-Lys | MHHHHHHHHA | S | SEQ ID NO: 11 |
| 8His-R81 (oAzZK) | 81 | R | o-Az-Z-Lys | MHHHHHHHHA | S | SEQ ID NO: 12 |
| 8His-L94 (oAzZK) | 94 | L | o-Az-Z-Lys | MHHHHHHHHA | S | SEQ ID NO: 13 |
| 8His-S99 (oAzZK) | 99 | S | o-Az-Z-Lys | MHHHHHHHHA | S | SEQ ID NO: 14 |
| 8His-E100 (oAzZK) | 100 | E | o-Az-Z-Lys | MHHHHHHHHA | S | SEQ ID NO: 15 |
| 8His-T101 (oAzZK) | 101 | T | o-Az-Z-Lys | MHHHHHHHHA | S | SEQ ID NO: 16 |
| 8His-Q126 (oAzZK) | 126 | Q | o-Az-Z-Lys | MHHHHHHHHA | S | SEQ ID NO: 17 |
| 8His-I129 (oAzZK) | 129 | I | o-Az-Z-Lys | MHHHHHHHHA | S | SEQ ID NO: 18 |
| 8His-I129 (mAzZK) | 129 | I | m-Az-Z-Lys | MHHHHHHHHA | S | SEQ ID NO: 18 |
| 8His-S4 (oAzZK)/F78 (oAzZK) | 4, 78 | S, F | o-Az-Z-Lys | MHHHHHHHHA | S | SEQ ID NO: 27 |
| 8His-S5 (oAzZK)/F78 (oAzZK) | 5, 78 | S, F | o-Az-Z-Lys | MHHHHHHHHA | S | SEQ ID NO: 28 |
| 8His-K8 (oAzZK)/F78 (oAzZK) | 8, 78 | K, F | o-Az-Z-Lys | MHHHHHHHHA | S | SEQ ID NO: 29 |
| 8His-F78 (oAzZK)/H79 (oAzZK) | 78, 79 | F, H | o-Az-Z-Lys | MHHHHHHHHA | S | SEQ ID NO: 30 |
| 8His-F78 (oAzZK)/S99 (oAzZK) | 78, 99 | F, S | o-Az-Z-Lys | MHHHHHHHHA | S | SEQ ID NO: 31 |
| 8His-F78 (oAzZK)/I129 (oAzZK) | 78, 129 | F, I | o-Az-Z-Lys | MHHHHHHHHA | S | SEQ ID NO: 32 |
| 8His-S4 (oAzZK)/I129 (oAzZK) | 4, 129 | S, I | o-Az-Z-Lys | MHHHHHHHHA | S | SEQ ID NO: 33 |
| 8His-S5 (oAzZK)/I129 (oAzZK) | 5, 129 | S, I | o-Az-Z-Lys | MHHHHHHHHA | S | SEQ ID NO: 34 |
| 8His-K8 (oAzZK)/I129 (oAzZK) | 8, 129 | K, I | o-Az-Z-Lys | MHHHHHHHHA | S | SEQ ID NO: 35 |
| 8His-H79 (oAzZK)/I129 (oAzZK) | 79, 129 | H, I | o-Az-Z-Lys | MHHHHHHHHA | S | SEQ ID NO: 36 |
| 8His-S99 (oAzZK)/I129 (oAzZK) | 99, 129 | S, I | o-Az-Z-Lys | MHHHHHHHHA | S | SEQ ID NO: 37 |

<Description of Table 9>

Az-Z-Lys introduction position: Position from the N-terminal of the amino acid sequence represented by SEQ ID NO: 1

Modification at position 1: Indicates modification of alanine residue at position1 from the N-terminal in the amino acid sequence represented by SEQ ID NO: 1 MHHHHHHHHA indicates that a methionine and polyhistidine sequence (HHHHHHHH) tag are bound to an N-terminal alanine residue.

Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".

In the table, o-Az-Z-Lys described in the column "Amino acid residue after substitution" indicates a structure represented by (Formula 10) below.

[Chem. 135]

(Formula 10)

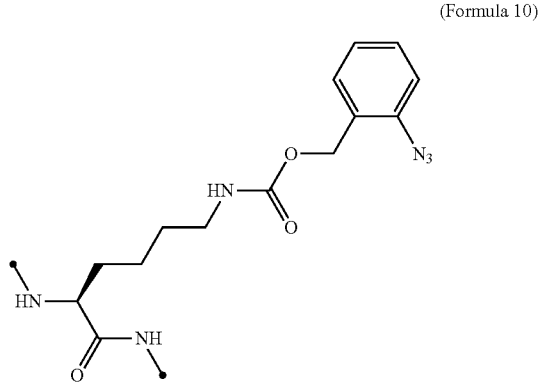

m-Az-Z-Lys indicates a structure represented by (Formula XX1) below.

[Chem. 136]

(Formula XX1)

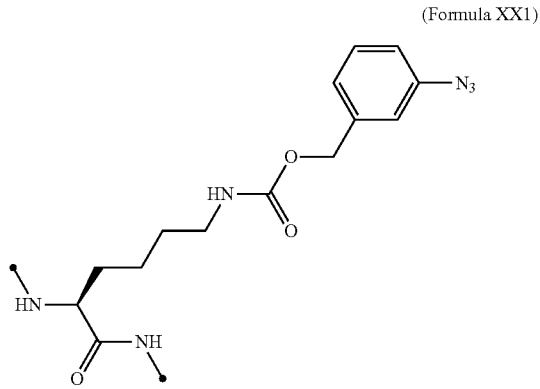

The expression vectors were produced based on 8His-IL-2 (amino acid sequence: SEQ ID NO: 2, nucleotide sequence encoding the amino acid sequence: SEQ ID NO: 3) consisting of amino acid residues in which an amino acid residue at position 125 in wild-type mature human IL-2 amino acid sequence represented by SEQ ID NO: 1 is substituted with cysteine to serine, and a methionine and polyhistidine sequence (HHHHHHHH) tag are bound to the N-terminal, as IL-2.

An 8His-IL-2 expression vector for *Escherichia coli* (hereinafter, referred to as pFLAG-CTS-Pyl TS_8His-hIL-2) was produced by inserting a nucleotide sequence (SEQ ID NO: 3) encoding 8His-IL-2 between an NdeI restriction enzyme site and a SalI restriction enzyme site of pFLAG-CTS-Pyl TS (International Publication No. WO 2017/030156) in which a nucleotide sequence of pyrrolidine RNA and a nucleotide sequence encoding pyrrolidyl tRNA synthetase enzyme (hereinafter, also referred to as Pyl tRNA or tRNA$^{Pyl}$) were inserted, immediately downstream of lac repressor gene lad of pFLAG-CTS (manufactured by SIGMA).

Based on the nucleotide sequence of 8His-IL-2, nucleotide sequences (SEQ ID NO: 4 to 18 and 27 to 37) in which a codon corresponding to a site for introducing o-Az-Z-Lys or m-Az-Z-Lys was substituted with an amber (TAG) codon were produced by a PCR method or an artificial gene synthesis (Nippon Genewith Co., Ltd.). The obtained nucleotide sequences were substituted with a nucleotide sequence of 8His-IL-2 of pFLAG-CTS-Pyl TS-8His-hIL-2.

Example 5

Preparation of 8His-IL-2, o-Az-Z-Lys-Introduced IL-2, and m-Az-Z-Lys-Introduced 8His-IL-2

8His-IL-2 and o-Az-Z-Lys-introduced 8His-IL-2 and m-Az-Z-Lys-introduced 8His-IL-2 shown in Table 10 were produced by the following method.

TABLE 10

Produced 8His-IL-2, o-Az-Z-Lys-introduced IL-2, and m-Az-Z-Lys-introduced 8His-IL-2

| Variant name | Az-Z-Lys introduction position | Amino acid residue before substitution | Amino acid residue after substitution | Modification at position 1 | Mutation at position 125 |
|---|---|---|---|---|---|
| 8His-IL-2 | — | — | — | MHHHHHHHHA | S |
| 8His-S4 (oAzZK) | 4 | S | o-Az-Z-Lys | MHHHHHHHHA | S |
| 8His-S5 (oAzZK) | 5 | S | o-Az-Z-Lys | MHHHHHHHHA | S |
| 8His-S6 (oAzZK) | 6 | S | o-Az-Z-Lys | MHHHHHHHHA | S |
| 8His-T7 (oAzZK) | 7 | T | o-Az-Z-Lys | MHHHHHHHHA | S |
| 8His-K8 (oAzZK) | 8 | K | o-Az-Z-Lys | MHHHHHHHHA | S |
| 8His-E60 (oAzZK) | 160 | E | o-Az-Z-Lys | MHHHHHHHHA | S |
| 8His-F78 (oAzZK) | 78 | F | o-Az-Z-Lys | MHHHHHHHHA | S |
| 8His-H79 (oAzZK) | 79 | F | o-Az-Z-Lys | MHHHHHHHHA | S |
| 8His-R81 (oAzZK) | 81 | R | o-Az-Z-Lys | MHHHHHHHHA | S |
| 8His-L94 (oAzZK) | 94 | L | o-Az-Z-Lys | MHHHHHHHHA | S |
| 8His-S99 (oAzZK) | 99 | S | o-Az-Z-Lys | MHHHHHHHHA | S |
| 8His-E100 (oAzZK) | 100 | E | o-Az-Z-Lys | MHHHHHHHHA | S |
| 8His-T101 (oAzZK) | 101 | T | o-Az-Z-Lys | MHHHHHHHHA | S |
| 8His-Q126 (oAzZK) | 126 | Q | o-Az-Z-Lys | MHHHHHHHHA | S |
| 8His-I129 (oAzZK) | 129 | I | o-Az-Z-Lys | MHHHHHHHHA | S |
| 8His-I129 (mAzZK) | 129 | I | m-Az-Z-Lys | MHHHHHHHHA | S |
| 8His-S4 (oAzZK)/F78 (oAzZK) | 4, 78 | S, F | o-Az-Z-Lys | MHHHHHHHHA | S |
| 8His-S5 (oAzZK)/F78 (oAzZK) | 5, 78 | S, F | o-Az-Z-Lys | MHHHHHHHHA | S |
| 8His-K8 (oAzZK)/F78 (oAzZK) | 8, 78 | K, F | o-Az-Z-Lys | MHHHHHHHHA | S |
| 8His-F78 (oAzZK)/H79 (oAzZK) | 78, 79 | F, H | o-Az-Z-Lys | MHHHHHHHHA | S |

TABLE 10-continued

Produced 8His-IL-2, o-Az-Z-Lys-introduced IL-2, and m-Az-Z-Lys-introduced 8His-IL-2

| Variant name | Az-Z-Lys introduction position | Amino acid residue before substitution | Amino acid residue after substitution | Modification at position 1 | Mutation at position 125 |
|---|---|---|---|---|---|
| 8His-F78 (oAzZK)/S99 (oAzZK) | 78, 99 | F, S | o-Az-Z-Lys | MHHHHHHHHA | S |
| 8His-F78 (oAzZK)/I129 (oAzZK) | 78, 129 | F, I | o-Az-Z-Lys | MHHHHHHHHA | S |
| 8His-S4 (oAzZK)/I129 (oAzZK) | 4, 129 | S, I | o-Az-Z-Lys | MHHHHHHHHA | S |
| 8His-S5 (oAzZK)/I129 (oAzZK) | 5, 129 | S, I | o-Az-Z-Lys | MHHHHHHHHA | S |
| 8His-K8 (oAzZK)/I129 (oAzZK) | 18, 129 | K, I | o-Az-Z-Lys | MHHHHHHHHA | S |
| 8His-H79 (oAzZK)/I129 (oAzZK) | 79, 129 | H, I | o-Az-Z-Lys | MHHHHHHHHA | S |
| 8His-S99 (oAzZK)/I129 (oAzZK) | 99, 129 | S, I | o-Az-Z-Lys | MHHHHHHHHA | S |

<Description of Table 10>
  Az-Z-Lys introduction position: Position from the N-terminal of the amino acid sequence represented by SEQ ID NO: 1
  Modification at position 1: Indicates modification of alanine residue at position1 from the N-terminal in the amino acid sequence represented by SEQ ID NO: 1 MHHHHHHHHA indicates that a methionine and polyhistidine sequence (HHHHHHHH) tag are bound to an N-terminal alanine residue.
  Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".

In the table, o-Az-Z-Lys described in the column "Amino acid residue after substitution" indicates a structure represented by (Formula 10) below.

[Chem. 137]

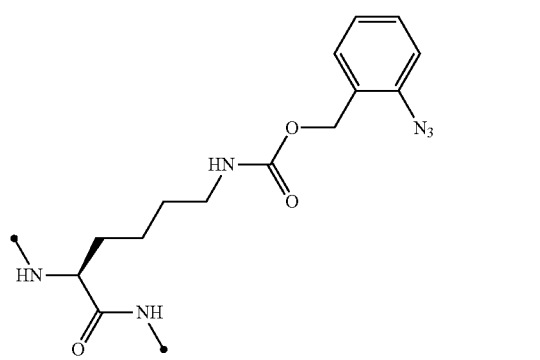

(Formula 10)

m-Az-Z-Lys indicates a structure represented by (Formula XX1) below.

[Chem. 138]

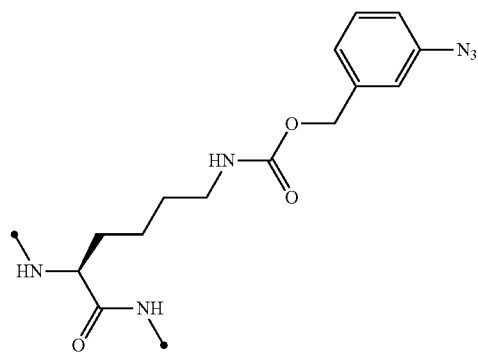

(Formula XX1)

The 8His-IL-2 expression vector for *Escherichia coli* and the o-Az-Z-Lys-introduced 8His-IL-2 expression vector or the m-Az-Z-Lys-introduced 8His-IL-2 expression vector prepared in Example 4 were introduced into *Escherichia coli* B-95. delA [Sci Rep, 2015. 5 (9699)]. 100 ng of the 8His-IL-2 expression vector and the o-Az-Z-Lys-introduced 8His-IL-2 expression vector or the m-Az-Z-Lys-introduced 8His-IL-2 expression vector were added to 100 µL of competent cells, and mixed gently. The mixture was allowed to stand on ice for 30 minutes.

Subsequently, the mixture was heated in a warm bath at 42° C. for 30 seconds, and allowed to stand again on ice for 2 minutes. After shaking culture was performed for 60 minutes in an incubator set at 37° C. with addition of 500 µL of an LB medium, the whole amount thereof was plated on an LB plate (1.5 w/v % agarose) containing ampicillin (manufactured by Wako Pure Chemical Industries, Ltd.) having a final concentration of 100 µg/mL. After overnight culture in an incubator set at 37° C., *Escherichia coli* growing on the plate was selected as a transgenic strain.

The total amount of the obtained transgenic strain was collected, and 800 mL of Super Broth [MOPS (manufactured by Nacalai Tesque, Inc.) 1 w/v %, Tryptone (manufactured by DIFCO) 3 w/v %, Yeast Extract (manufactured by DIFCO) 2 w/v %] to which final concentration 1 mM of o-Az-Z-Lys or m-A-z-Z-Lys (synthesized by GVK Biosciences according to a method described in International Publication No. 2017/030156) and final concentration 100 µg/mL of ampicillin were added was seeded with the transgenic strain. Shaking culture at 165 rpm was performed in an incubator set at 37° C.

At a stage in which a value of an absorbance at 600 nm of a microbial cell solution reached 1.5 to 2.0, isopropyl-β-thiogalactopyranoside (IPTG) (manufactured by Nacalai Tesque, Inc.) having a final concentration of 1.0 mmol/L was added, and shaking culture at 165 rpm was performed for 3 hours in an incubator set at 42° C. to express each human IL-2.

Microbial cells of *Escherichia coli* were collected by centrifuging [CR21E (manufactured by Hitachi, Ltd.), 7000 rpm, 4° C., 5 minutes] the microbial cell solution after the culture, and then 40 mL of B-PER Bacterial Protein Extraction Reagent (manufactured by Thermo Scientific) was added thereto to lyse the cells, followed by centrifugation (12000×4° C., 5 minutes) to obtain inclusion bodies.

The obtained inclusion body was dissolved in 32 mL of Inclusion Body Solubilization Reagent (manufactured by Thermo Scientific), followed by centrifugation again (12000×4° C., 30 minutes), and a supernatant was collected.

After diluting the inclusion body solubilized solution to 3 volumes with a 100 mmol/L Tris-HCl buffer (manufactured by Wako Pure Chemical Industries, Ltd.) (pH 8.0) containing 6 mol/L guanidine hydrochloride (manufactured by Wako Pure Chemical Industries, Ltd.), sample was added to TALON Metal Affinity Resin (manufactured by Clontech). After washing the mixture with a 100 mmol/L Tris-HCl buffer (pH 8.0) containing 6 mol/L guanidine hydrochloride, elution was performed with a 100 mmol/L Tris-HCl buffer (pH 8.0) containing 250 mmol/L imidazole and 6 mol/L guanidine hydrochloride. A protein concentration of the eluate was measured by measuring the absorbance at 280 nm.

The eluate was diluted 3-fold with a refolding buffer [100 mmol/L Tris-HCl buffer (pH 8.0) containing 1 mmol/L oxidized glutathione (manufactured by Sigma-Aldrich)] and allowed to stand at 4° C. overnight. Thereafter, the eluate was concentrated with Amicon Ultra-4 (3 kDa) (manufactured by Merck Millipore).

Superdex 75/10/300GL (manufactured by GE Healthcare) was connected to AKTA FPLC (manufactured by GE Healthcare), and 100 mmol/L Tris-HCl buffer (pH 8.0) containing 2 mol/L guanidine hydrochloride was sent as a mobile phase. The concentrate was added to a SEC column, and a monomer fraction was collected.

The obtained fraction was diluted 2-fold with D-PBS (manufactured by Nacalai Tesque, Inc.), allowed to stand at room temperature for 6 hours, and then subjected to ultrafiltration using Amicon Ultra-4 (3 kDa) to substitute the buffer with D-PBS.

It was confirmed that all of the produced o-Az-Z-Lys-introduced 8His-IL-2 and m-Az-Z-Lys-introduced 8His-IL-2 are in a band having the same molecular weight as 8His-IL-2 using SDS-PAGE.

Example 6

Preparation of o-Az-Z-Lys-Introduced IL-2 Expression Vector for *Escherichia coli*

An o-Az-Z-Lys-introduced IL-2 expression vector for *Escherichia coli* shown in Table 11 was prepared by a method below.

TABLE 11

Produced o-Az-Z-Lys-introduced 8His-IL-2 expression vector forr *Escherichia coli*

| Variant name | Az-Z-Lys introduction position | Amino acid residue before substitution | Amino acid residue after substitution | Modification at position 1 | Mutation at position 125 | Nucleotide sequence |
|---|---|---|---|---|---|---|
| F78 (oAzZK) | 78 | F | o-Az-Z-Lys | MA | S | SEQ ID NO: 42 |
| I129 (oAzZK) | 129 | I | o-Az-Z-Lys | MA | S | SEQ ID NO: 43 |
| desAla-I129 (oAzZK) | 129 | I | o-Az-Z-Lys | M | S | SEQ ID NO: 44 |
| S4 (oAzZK)/F78 (oAzZK) | 4, 78 | S, F | o-Az-Z-Lys | MA | S | SEQ ID NO: 45 |
| S5 (oAzZK)/F78 (oAzZK) | 5, 78 | S, F | o-Az-Z-Lys | MA | S | SEQ ID NO: 46 |
| K8 (oAzZK)/F78 (oAzZK) | 8, 78 | K, F | o-Az-Z-Lys | MA | S | SEQ ID NO: 47 |
| S4 (oAzZK)/I129 (oAzZK) | 4, 129 | S, I | o-Az-Z-Lys | MA | S | SEQ ID NO: 48 |
| S5 (oAzZK)/I129 (oAzZK) | 5, 129 | S, I | o-Az-Z-Lys | MA | S | SEQ ID NO: 49 |
| K8 (oAzZK)/I129 (oAzZK) | 8, 129 | K, I | o-Az-Z-Lys | MA | S | SEQ ID NO: 50 |

<Description of Table 11>

Az-Z-Lys introduction position: Position from the N-terminal of the amino acid sequence represented by SEQ ID NO: 1

Modification at position 1: Indicates modification of alanine residue at position1 from the N-terminal in the amino acid sequence represented by SEQ ID NO: 1 MA indicates that methionine is bound to the N-terminal alanine residue. M indicates that a mutation that substitutes an amino acid residue from alanine to methionine is introduced.

Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".

In the table, o-Az-Z-Lys described in the column "Amino acid residue after substitution" indicates a structure represented by (Formula 10) below.

[Chem. 139]

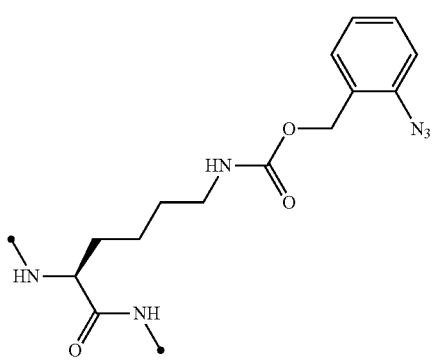

(Formula 10)

The expression vector was produced based on IL-2 consisting of amino acid sequence (amino acid sequence: SEQ ID NO: 38, nucleotide sequence encoding the amino acid sequence: SEQ ID NO: 39) in which an amino acid residue at position 125 in the wild-type mature human IL-2 amino acid sequence represented by SEQ ID NO: 1 is substituted from cysteine to serine and methionine is bound to the N-terminal, or IL-2 consisting of amino acid sequence (amino acid sequence: SEQ ID NO: 40, nucleotide sequence encoding the amino acid sequence: SEQ ID NO: 41) in which the amino acid residue at position 125 in the wild-type mature human IL-2 amino acid residue represented by SEQ ID NO: 1 is substituted from cysteine to serine, an alanine residue at position 1 is deleted, and methionine is bound to the N-terminal, as IL-2.

A nucleotide sequence (SEQ ID NO: 42 to 50) in which a codon corresponding to a site for introducing o-Az-Z-Lys was substituted with an amber (TAG) codon were inserted between the NdeI restriction enzyme site and the SalI restriction enzyme site of pFLAG-CTS-Pyl TS to produce various o-Az-Z-Lys-introduced IL-2 expression vectors for *Escherichia coli* (hereinafter, referred to as pFLAG-CTS-Pyl TS_hIL-2).

Example 7

Preparation of o-Az-Z-Lys-introduced IL-2

An o-Az-Z-Lys-introduced IL-2 in which any amino acid residue of IL-2 shown in Table 12 was substituted with an o-Az-Z-Lys residue was produced by a method below.

<Description of Table 12>
o-Az-Z-LysK introduction position: Position from the N-terminal of the amino acid sequence represented by SEQ ID NO: 1
Modification at position 1: Indicates modification of alanine residue at position1 from the N-terminal in the amino acid sequence represented by SEQ ID NO: 1 MA indicates that methionine is bound to the N-terminal alanine residue. M indicates that a mutation that substitutes an amino acid residue from alanine to methionine is introduced.
Mutation at position 125: Indicating presence or absence of a mutation of amino acid residue at position 125 from the N-terminal of the amino acid sequence represented by SEQ ID NO: 1. A case where no mutation is introduced is described as "–" and a case where a mutation that substitutes an amino acid residue from cysteine to serine is introduced, is described as "S".
In the table, o-Az-Z-Lys described in the column "Amino acid residue after substitution" indicates a structure represented by (Formula 10) below.

[Chem. 140]

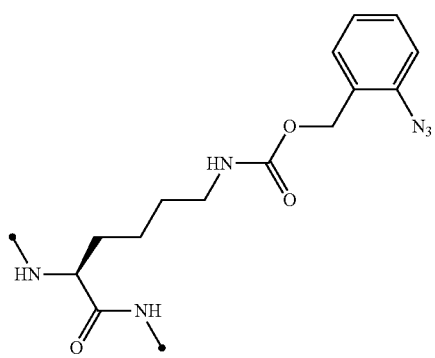

(Formula 10)

The o-Az-Z-Lys-introduced IL-2 expression vector for *Escherichia coli* produced in Example 6 was introduced into *Escherichia coli* B-95. delA [Sci Rep, 2015. 5 (9699)], and an inclusion body solubilized solution was prepared by the method described in Example 5.

HiPrep 26/60 Sephacryl S-100 HR (manufactured by GE Healthcare) was connected to AKTA FPLC, and 100 mmol/L Tris-HCl buffer (pH 8.0) containing 2 mol/L guanidine hydrochloride was sent as a mobile phase. The

TABLE 12

Produced o-Az-Z-Lys-introduced IL-2

| Variant name | oAzZK introduction position | Amino acid residue before substitution | Amino acid residue after substitution | Modification at position 1 | Mutation at position 125 |
|---|---|---|---|---|---|
| F78 (oAzZK) | 78 | F | o-Az-Z-Lys | MA | S |
| I129 (oAzZK) | 129 | I | o-Az-Z-Lys | MA | S |
| desAla-I129 (oAzZK) | 129 | I | o-Az-Z-Lys | M | S |
| S4 (oAzZK)/F78 (oAzZK) | 4, 78 | S, F | o-Az-Z-Lys | MA | S |
| S5 (oAzZK)/F78 (oAzZK) | 5, 78 | S, F | o-Az-Z-Lys | MA | S |
| K8 (oAzZK)/F78 (oAzZK) | 8, 78 | K, F | o-Az-Z-Lys | MA | S |
| S4 (oAzZK)/I129 (oAzZK) | 4, 129 | S, I | o-Az-Z-Lys | MA | S |
| S5 (oAzZK)/I129 (oAzZK) | 5, 129 | S, I | o-Az-Z-Lys | MA | S |
| K8 (oAzZK)/I129 (oAzZK) | 8, 129 | K, I | o-Az-Z-Lys | MA | S | inclusion body solubilized solution was added to a SEC column, and a monomer fraction was collected.

Oxidized glutathione was added to have a concentration of 2 mmol/L, and the mixture was allowed to stand at 4° C. overnight. Thereafter, the mixture was concentrated with Amicon Ultra-4 (3 kDa) (manufactured by Merck Millipore), and was buffer-substituted with a 10 mmol/L acetate buffer (pH 4.5) containing 0.4 mol/L arginine hydrochloride and 5 w/v % trehalose using an NAP column (manufactured by GE Healthcare).

It was confirmed that the produced o-Az-Z-Lys-introduced IL-2 had a molecular weight expected from the amino acid sequence, by SDS-PAGE.

Example 8

PEGylation of o-Az-Z-Lys-Introduced 8his-IL-2, m-Az-Z-Lys-Introduced 8his-IL-2, or o-Az-Z-Lys-Introduced IL-2

As shown in Tables 13 to 15, a PEGylated form of o-Az-Z-Lys-introduced 8His-IL-2, m-Az-Z-Lys-introduced 8His-IL-2, or o-Az-Z-Lys-introduced IL-2 (hereinafter, referred to as a PEGylated IL-2 variant) was prepared by a method below.

TABLE 13

Produced PEGylated IL-2 variant

| Variant name | PEGylation site | Amino acid residue before substitution | Amino acid residue after substitution | Modification at position 1 | Mutation at position 125 |
| --- | --- | --- | --- | --- | --- |
| 8His-S4 (oAzZK)-PEG4 | 4 | S | (oAzZK)-PEG4 | MHHHHHHHHA | S |
| 8His-S4 (oAzZK)-Li20 | 4 | S | (oAzZK)-Li20 | MHHHHHHHHA | S |
| 8His-S4 (oAzZK)-Li30 | 4 | S | (oAzZK)-Li30 | MHHHHHHHHA | S |
| 8His-S5 (oAzZK)-PEG4 | 5 | S | (oAzZK)-PEG4 | MHHHHHHHHA | S |
| 8His-S5 (oAzZK)-Li20 | 5 | S | (oAzZK)-Li20 | MHHHHHHHHA | S |
| 8His-S5 (oAzZK)-Li30 | 5 | S | (oAzZK)-Li30 | MHHHHHHHHA | S |
| 8His-S6 (oAzZK)-PEG4 | 6 | S | (oAzZK)-PEG4 | MHHHHHHHHA | S |
| 8His-S6 (oAzZK)-Li20 | 6 | S | (oAzZK)-Li20 | MHHHHHHHHA | S |
| 8His-S6 (oAzZK)-Li30 | 6 | S | (oAzZK)-Li30 | MHHHHHHHHA | S |
| 8His-T7 (oAzZK)-PEG4 | 7 | T | (oAzZK)-PEG4 | MHHHHHHHHA | S |
| 8His-T7 (oAzZK)-Li20 | 7 | T | (oAzZK)-Li20 | MHHHHHHHHA | S |
| 8His-T7 (oAzZK)-Li30 | 7 | T | (oAzZK)-Li30 | MHHHHHHHHA | S |
| 8His-K8 (oAzZK)-PEG4 | 8 | K | (oAzZK)-PEG4 | MHHHHHHHHA | S |
| 8His-K8 (oAzZK)-Li20 | 8 | K | (oAzZK)-Li20 | MHHHHHHHHA | S |
| 8His-K8 (oAzZK)-Li30 | 8 | K | (oAzZK)-Li30 | MHHHHHHHHA | S |
| 8His-E60 (oAzZK)-PEG4 | 60 | E | (oAzZK)-PEG4 | MHHHHHHHHA | S |
| 8His-E60 (oAzZK)-Li20 | 60 | E | (oAzZK)-Li20 | MHHHHHHHHA | S |
| 8His-E60 (oAzZK)-Li30 | 60 | E | (oAzZK)-Li30 | MHHHHHHHHA | S |
| 8His-F78 (oAzZK)-PEG4 | 78 | F | (oAzZK)-PEG4 | MHHHHHHHHA | S |
| 8His-F78 (oAzZK)-Li20 | 78 | F | (oAzZK)-Li20 | MHHHHHHHHA | S |
| 8His-F78 (oAzZK)-Li30 | 78 | F | (oAzZK)-Li30 | MHHHHHHHHA | S |
| 8His-F78 (oAzZK)-Li40 | 78 | F | (oAzZK)-Li40 | MHHHHHHHHA | S |
| 8His-F78 (oAzZK)-Y50 | 78 | F | (oAzZK)-Y50 | MHHHHHHHHA | S |
| 8His-F78 (oAzZK)-V40 | 78 | F | (oAzZK)-V40 | MHHHHHHHHA | S |
| 8His-F78 (oAzZK)-W40 | 78 | F | (oAzZK)-W40 | MHHHHHHHHA | S |
| F78 (oAzZK)-IIII40 | 78 | F | (oAzZK)-IIII40 | MA | S |
| F78 (oAzZK)-Li40 | 78 | F | (oAzZK)-Li40 | MA | S |
| F78 (oAzZK)-V40 | 78 | F | (oAzZK)-V40 | MA | S |
| F78 (oAzZK)-V80 | 78 | F | (oAzZK)-V80 | MA | S |
| F78 (oAzZK)-W40 | 78 | F | (oAzZK)-W40 | MA | S |
| F78 (oAzZK)-W80 | 78 | F | (oAzZK)-W80 | MA | S |
| 8His-H79 (oAzZK)-PEG4 | 79 | F | (oAzZK)-PEG4 | MHHHHHHHHA | S |
| 8His-H79 (oAzZK)-Li20 | 79 | F | (oAzZK)-Li20 | MHHHHHHHHA | S |
| 8His-H79 (oAzZK)-Li30 | 79 | F | (oAzZK)-LI30 | MHHHHHHHHA | S |

TABLE 14

Produced PEGylated IL-2 variant

| Variant name | PEGylation site | Amino acid residue before substitution | Amino acid residue after substitution | Modification at position 1 | Mutation at position 125 |
| --- | --- | --- | --- | --- | --- |
| 8His-R81(oAzZK)-PEG4 | 81 | R | (oAzZK)-PEG4 | MHHHHHHHHA | S |
| 8His-R81(oAzZK)-Li20 | 81 | R | (oAzZK)-Li20 | MHHHHHHHHA | S |
| 8His-R81(oAzZK)-Li30 | 81 | R | (oAzZK)-Li30 | MHHHHHHHHA | S |
| 8His-L94 (oAzZK)-PEG4 | 94 | L | (oAzZK)-PEG4 | MHHHHHHHHA | S |
| 8His-L94(oAzZK)-Li20 | 94 | L | (oAzZK)-Li20 | MHHHHHHHHA | S |
| 8His-L94(oAzZK)-Li30 | 94 | L | (oAzZK)-Li30 | MHHHHHHHHA | S |
| 8His-S99(oAzZK)-PEG4 | 99 | S | (oAzZK)-PEG4 | MHHHHHHHHA | S |
| 8His-S99(oAzZK)-Li20 | 99 | S | (oAzZK)-Li20 | MHHHHHHHHA | S |
| 8His-S99(oAzZK)-Li30 | 99 | S | (oAzZK)-Li30 | MHHHHHHHHA | S |
| 8His-E100(oAzZK)-PEG4 | 100 | E | (oAzZK)-PEG4 | MHHHHHHHHA | S |
| 8His-E100(oAzZK)-Li20 | 100 | E | (oAzZK)-Li20 | MHHHHHHHHA | S |

TABLE 14-continued

Produced PEGylated IL-2 variant

| Variant name | PEGylation site | Amino acid residue before substitution | Amino acid residue after substitution | Modification at position 1 | Mutation at position 125 |
|---|---|---|---|---|---|
| 8His-E100(oAzZK)-Li30 | 100 | E | (oAzZK)-Li30 | MHHHHHHHHA | S |
| 8His-T101(oAzZK)-PEG4 | 101 | T | (oAzZK)-PEG4 | MHHHHHHHHA | S |
| 8His-T101(oAzZK)-Li20 | 101 | T | (oAzZK)-Li20 | MHHHHHHHHA | S |
| 8His-T101(oAzZK)-Li30 | 101 | T | (oAzZK)-Li30 | MHHHHHHHHA | S |
| 8His-Q126 (oAzZK)-PEG4 | 126 | Q | (oAzZK)-PEG4 | MHHHHHHHHA | S |
| 8His-Q126(oAzZK)-Li20 | 126 | Q | (oAzZK)-Li20 | MHHHHHHHHA | S |
| 8His-Q126(oAzZK)-Li30 | 126 | Q | (oAzZK)-Li30 | MHHHHHHHHA | S |
| 8His-I129(oAzZK)-PEG4 | 129 | I | (oAzZK)-PEG4 | MHHHHHHHHA | S |
| 8His-I129(oAzZK)-Li20 | 129 | I | (oAzZK)-Li20 | MHHHHHHHHA | S |
| 8His-I129(oAzZK)-Li30 | 129 | I | (oAzZK)-Li30 | MHHHHHHHHA | S |
| 8His-I129(oAzZK)-Li40 | 129 | I | (oAzZK)-Li40 | MHHHHHHHHA | S |
| 8His-I129(oAzZK)-V40 | 129 | I | (oAzZK)-V40 | MHHHHHHHHA | S |
| 8His-I129(mAzZK)-V40 | 129 | I | (mAzZK)-V40 | MHHHHHHHHA | S |
| 8His-I129(oAzZK)-W40 | 129 | I | (oAzZK)-W40 | MHHHHHHHHA | S |
| 8His-I129(oAzZK)-Y50 | 129 | I | (oAzZK)-Y50 | MHHHHHHHHA | S |
| I129(oAzZK)-IIII40 | 129 | I | (oAzZK)-IIII40 | MA | S |
| I129(oAzZK)-Li30 | 129 | I | (oAzZK)-Li30 | MA | S |
| I129(oAzZK)-Li40 | 129 | I | (oAzZK)-Li40 | MA | S |
| I129(oAzZK)-V40 | 129 | I | (oAzZK)-V40 | MA | S |
| I129(oAzZK)-V80 | 129 | I | (oAzZK)-V80 | MA | S |
| I129(oAzZK)-W40 | 129 | I | (oAzZK)-W40 | MA | S |
| I129(oAzZK)-W80 | 129 | I | (oAzZK)-W80 | MA | S |
| desAla-I129(oAzZK)-V40 | 129 | I | (oAzZK)-V40 | M | S |
| desAla-I129(oAzZK)-W80 | 129 | I | (oAzZK)-W80 | M | S |
| desAla-I129(oAzZK)-V80 | 129 | I | (oAzZK)-V80 | M | S |

TABLE 15

Produced PEGylated IL-2 variant

| Variant name | PEGylation site 1 | | PEGylation site 2 | | | | Mutation at position 125 |
| | PEGylation site | Amino acid residue before substitution | PEGylation site | Amino acid residue before substitution | Amino acid residue after substitution | Modification at position 1 | |
|---|---|---|---|---|---|---|---|
| 8His-S4(oAzZK)-Li30/F78(oAzZK)-Li30 | 4 | S | 78 | F | (oAzZK)-Li30 | MHHHHHHHHA | S |
| S4(oAzZK)-Li40/F78(oAzZK)-Li40 | 4 | S | 78 | F | (oAzZK)-Li40 | MA | S |
| S4(oAzZK)-Y50/F78(oAzZK)-Y50 | 4 | S | 78 | F | (oAzZK)-Y50 | MA | S |
| 8His-S5(oAzZK)-Li30/F78(oAzZK)-Li30 | 5 | S | 78 | F | (oAzZK)-Li30 | MHHHHHHHHA | S |
| S5(oAzZK)-Li40/F78(oAzZK)-Li40 | 5 | S | 78 | F | (oAzZK)-Li40 | MA | S |
| 8His-K8(oAzZK)-Li30/F78(oAzZK)-Li30 | 8 | K | 78 | F | (oAzZK)-Li30 | MHHHHHHHHA | S |
| K8(oAzZK)-Li40/F78(oAzZK)-Li40 | 8 | K | 78 | F | (oAzZK)-Li40 | MA | S |
| 8His-F78(oAzZK)-Li30/H79(oAzZK)-Li30 | 78 | F | 79 | H | (oAzZK)-Li30 | MHHHHHHHHA | S |
| 8His-F78(oAzZK)-Li30/S99(oAzZK)-Li30 | 78 | F | 99 | S | (oAzZK)-Li30 | MHHHHHHHHA | S |
| 8His-F78(oAzZK)-Li30/I129(oAzZK)-Li30 | 78 | F | 129 | I | (oAzZK)-Li30 | MHHHHHHHHA | S |
| 8His-S4(oAzZK)-Li30/I129(oAzZK)-Li30 | 4 | S | 129 | I | (oAzZK)-Li30 | MHHHHHHHHA | S |
| 8His-S4(oAzZK)-Y50/I129(oAzZK)-Y50 | 4 | S | 129 | I | (oAzZK)-Y50 | MHHHHHHHHA | S |
| S4(oAzZK)-Li40/I129(oAzZK)-Li40 | 4 | S | 129 | I | (oAzZK)-Li40 | MA | S |
| S4(oAzZK)-Y50/I129(oAzZK)-Y50 | 4 | S | 129 | I | (oAzZK)-Y50 | MA | S |
| 8His-S5(oAzZK)-Li30/I129(oAzZK)-Li30 | 5 | S | 129 | T | (oAzZK)-Li30 | MHHHHHHHHA | S |
| S5(oAzZK)-Li40/I129(oAzZK)-Li40 | 5 | S | 129 | I | (oAzZK)-Li40 | MA | S |
| S5(oAzZK)-Y50/I129(oAzZK)-Y50 | 5 | S | 129 | I | (oAzZK)-Y50 | MA | S |
| 8His-K8(oAzZK)-Li30/I129(oAzZK)-Li30 | 8 | K | 129 | I | (oAzZK)-Li30 | MHHHHHHHHA | S |

TABLE 15-continued

| | Produced PEGylated IL-2 variant | | | | | | Mutation |
|---|---|---|---|---|---|---|---|
| | PEGylation site 1 | | PEGylation site 2 | | | | |
| Variant name | PEGylation site | Amino acid residue before substitution | PEGylation site | Amino acid residue before substitution | Amino acid residue after substitution | Modification at position 1 | at position 125 |
| 8His-K8(oAzZK)-Y50/ I129(oAzZK)-Y50 | 8 | K | 129 | I | (oAzZK)-Y50 | MHHHHHHHHA | S |
| K8(oAzZK)-Li40/ I129(oAzZK)-Li40 | 8 | K | 129 | I | (oAzZK)-Li40 | MA | S |
| K8(oAzZK)-Y50/ I129(oAzZK)-Y50 | 8 | K | 129 | I | (oAzZK)-Y50 | MA | S |
| 8His-H79(oAzZK)-Li30/ I129(oAzZK)-Li30 | 79 | H | 129 | I | (oAzZK)-Li30 | MHHHHHHHHA | S |
| 8His-S99(oAzZK)-Li30/ I129(oAzZK)-Li30 | 99 | S | 129 | I | (oAzZK)-Li30 | MHHHHHHHHA | S |

<Description of Tables 13, 14, and 15>
PEGylation site: Position from the N-terminal of SEQ ID NO: 1
Modification at position 1: Indicates modification of alanine residue at position1 from the N-terminal in the amino acid sequence represented by SEQ ID NO: 1 MA indicates that methionine is bound to the N-terminal alanine residue, and MHHHHHHHHA indicates that a methionine and polyhistidine sequence (HHHHHHHH) tag are bound to an N-terminal alanine residue.
Mutation at position 125: Indicating presence or absence of a mutation of amino acid residue at position 125 from the N-terminal of the amino acid sequence represented by SEQ ID NO: 1. A case where no mutation of the amino acid residue is introduced is described as "–" and a case where a mutation that substitutes an amino acid residue from cysteine to serine is introduced, is described as "S".

In the table, the structures described in the column of "Amino acid residues after substitution" are shown below.
(oAzZK)-PEG (PEG4, Li20, Li30, Li40, V40, V80, W40, W80, Y50, IIII40) indicates a structure represented by (Formula 11) or Formula (12) below in which PEG is introduced into a side chain amino group of lysine via a linker.

[Chem. 141]

(Formula 11)

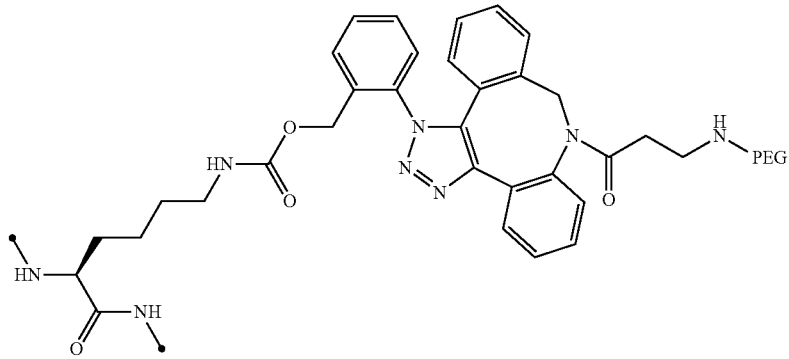

[Chem. 142]
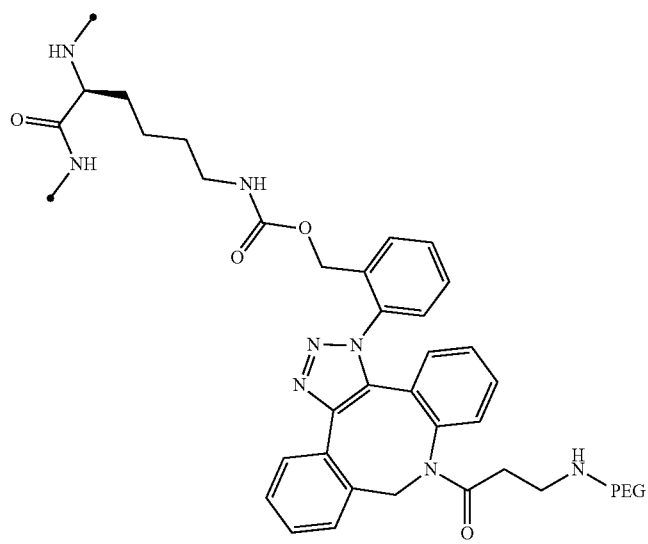
(Formula 12)
(mAzZK)-PEG (V40) indicates a structure represented by (Formula XX4) or (Formula XX5) below in which PEG is introduced into a side chain amino group of lysine via a linker.
[Chem. 143]
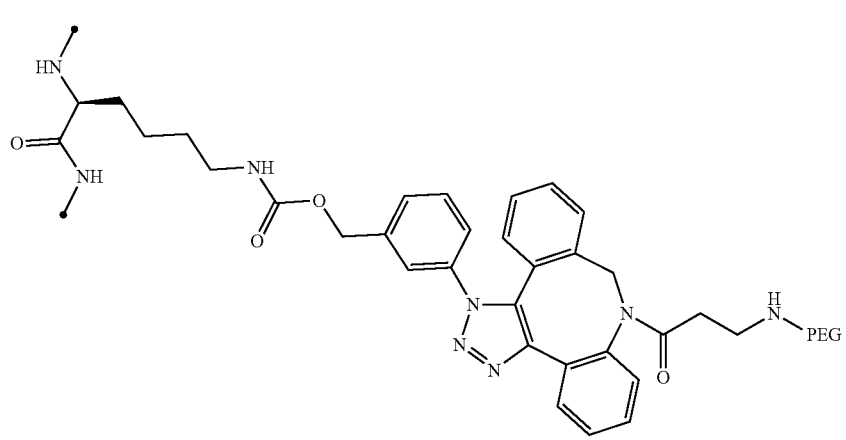
(Formula XX4)

[Chem. 144]

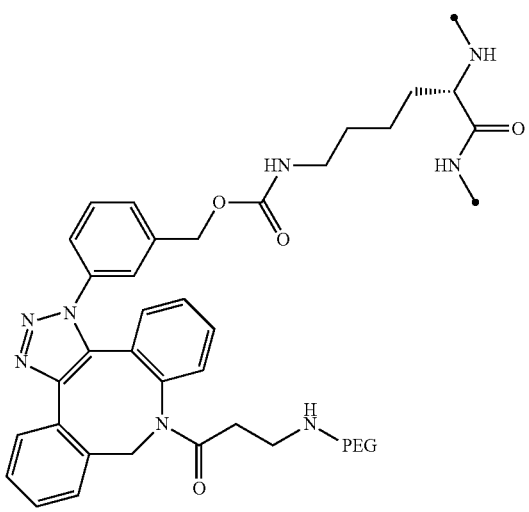

(Formula XX5)

PEG4 indicates a structure represented by (Formula 13) below.

[Chem. 145]

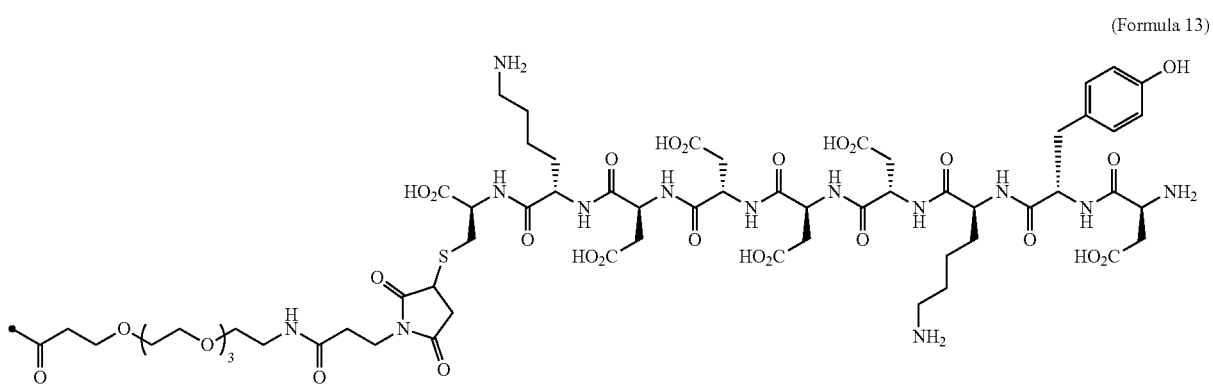

(Formula 13)

Li20 indicates a structure represented by (Formula 15) below in a case where an average molecular weight is about 20 kDa.

[Chem. 146]

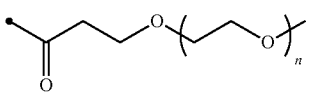

(Formula 15)

Li30 indicates a structure represented by (Formula 15) above in a case where an average molecular weight is about 30 kDa.

Li40 indicates a structure represented by (Formula X105) in a case where an average molecular weight is about 40 kDa.

[Chem. 147]

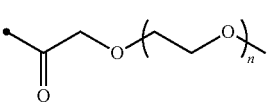

(Formula X105)

Y50 indicates a structure represented by (Formula X107) below in which an average molecular weight of $(CH_2CH_2O)_m$ is 10 kDa and an average molecular weight of $(CH_2CH_2O)_n$ is 20 kDa.

[Chem. 148]

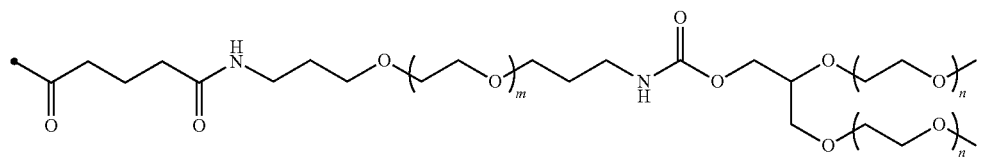

(Formula X107)

V40 indicates a structure represented by (Formula X109) below in which an average molecular weight is 40 kDa.

[Chem. 149]

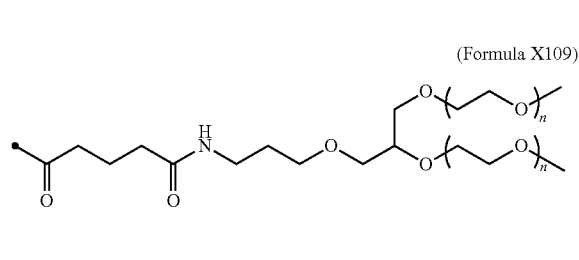

(Formula X109)

V80 indicates a structure represented by (Formula X109) above in which an average molecular weight is 80 kDa.

W40 indicates a structure represented by (Formula X111) below in which an average molecular weight of $(CH_2CH_2O)_m$ is 5 kDa and an average molecular weight of $(CH_2CH_2O)_n$ is 7.5 kDa.

[Chem. 150]

W80 indicates a structure represented by (Formula X112) below in which an average molecular weight of $(CH_2CH_2O)_m$ is 5 kDa and an average molecular weight of $(CH_2CH_2O)_n$ is 17.5 kDa.

[Chem. 151]

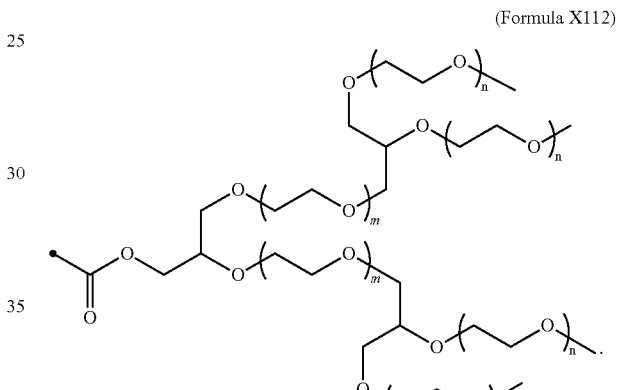

(Formula X112)

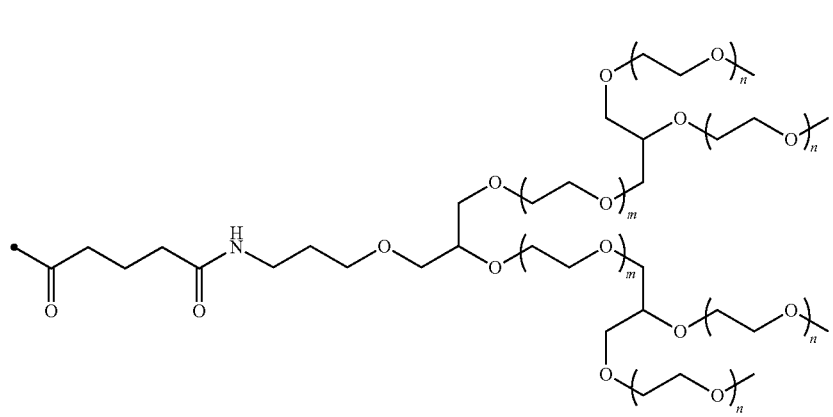

(Formula X111)

IIII40 indicates a structure represented by (Formula X113) below in which an average molecular weight is 40 kDa.

[Chem. 152]

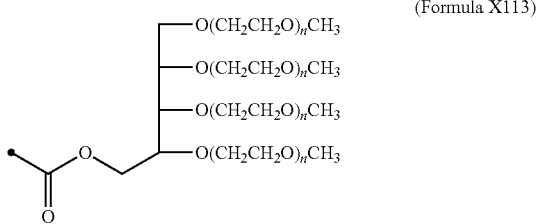

(Formula X113)

(Step 1a) Preparation 1 of PEG-DBCO

PEG-carboxylic acid (mPEG-AA 40K; manufactured by Creative PEG Works) was dissolved in chloroform, and 1-Ethyl-3-(3-dimethylaminopropyl) carbodiimide Hydrochloride (5 equiv), 4-dimethylaminopyridine (5 equiv), and Dibenzocyclooctyne-amine (5 equiv, A2763; Tokyo Chemical Industry) were added thereto, and stirred at room temperature for 3 hours. Ether/isopropanol=1/1 was added, and precipitated solid was collected by filtration to obtain PEG-DBCO.

(Step 1b) Synthesis 2 of PEG-DBCO

PEG-NHS (SUNBRIGHT GL2-400GS2; NOF CORPORATION, SUNBRIGHT GL2-800GS2; NOF CORPORATION, SUNBRIGHT GL4-400GS2; NOF CORPORATION, SUNBRIGHTGL4-800TS; NOF CORPORATION, SUNBRIGHT100GL2-400GS100U; NOF CORPORATION, or SUNBRIGHT XY4-400TS; NOF CORPORATION) were dissolved in chloroform, and Dibenzocyclooctyne-amine (5 equiv, A2763; Tokyo Chemical Industry) was added thereto, and stirred at room temperature for 3 hours. Ether/Isopropanol=1/1 was added, and precipitated solid was collected by filtration to synthesize PEG-DBCO.

(Step 2) Preparation of PEGylated IL-2 Variant

PEG-DBCO (DBCO-PEG4-FLAG (DYKDDDDK) (manufactured by Jena Bioscience), DBCO-PEG 20 kDa (manufactured by Click Chemistry Tools), DBCO-PEG 30 kDa (manufactured by Click Chemistry Tools), or the PEG-DBCO prepared in Step 1a or Step 1b was dissolved in D-PBS, and 20 mol equivalents thereof was added to the o-Az-Z-Lys-introduced 8His-IL-2, the m-Az-Z-Lys-introduced 8His-IL-2, or the o-Az-Z-Lys-introduced IL-2, and allowed to stand at room temperature overnight.

In the PEGylated IL-2 variant to which DBCO-PEG4-FLAG was bound, target protein was purified using ANTI-FLAG M2 Affinity Agarose Gel (manufactured by Sigma-Aldrich) according to a procedure described in a manufacturer's manual.

From the PEGylated IL-2 variant to which PEG other than the DBCO-PEG4-FLAG was bonded, first, unreacted PEG was removed by cation exchange chromatography using MonoS 5/50GL (manufactured by GE Healthcare). For the mobile phase, a 50 mmol/L phosphate buffer (pH 3.0) was used. Next, the PEGylated IL-2 variant was fractionated by size exclusion chromatography using Superrose 6 increase 10/300GL (manufactured by GE Healthcare). For the mobile phase, a 100 mmol/L Tris-HCl buffer (pH 8.0) containing 2 mol/L guanidine hydrochloride was used.

The obtained PEGylated IL-2 variant was subjected to ultrafiltration using Amicon Ultra-4 (3 kDa), or D-PBS or 10 mM acetate buffer (pH 4.5) containing 5 w/v % trehalose or 10 mM acetate buffer (pH 4.5) containing 0.4 mol/L arginine hydrochloride and 5 w/v % trehalose, by an NAP column.

A purity of the purified PEGylated IL-2 variant was confirmed by SDS-PAGE. As a result, in all the PEGylated IL-2 variants, a single band, in which a molecular weight was increased as much as PEG attached with respect to the o-Az-Z-Lys-introduced 8His-IL-2, the m-Az-Z-Lys-introduced 8His-IL-2, or the o-Az-Z-Lys-introduced IL-2, was confirmed, and it was confirmed that highly purified PEGylated IL-2 variants were obtained.

Example 9

Preparation of I129C Mutant IL-2 Expression Vector

The expression vector was produced based on IL-2 (amino acid sequence: SEQ ID NO: 51, nucleotide sequence encoding the amino acid sequence: SEQ ID NO: 52, hereinafter, referred to as IL-2_I129C) consisting of amino acid sequences in which alanine at position 1 in the wild-type mature human IL-2 represented by SEQ ID NO: 1 was deleted, an amino acid residue at position 125 was substituted from cysteine to serine, an amino acid residue at position 129 was substituted from isoleucine to cysteine, and methionine was bound to the N-terminal.

The nucleotide sequence of IL-2 I129C (SEQ ID NO: 52) was prepared by artificial gene synthesis (Ragass Japan), and inserted between the NdeI restriction enzyme site and a BamHI restriction enzyme sites of pET-22b (+) (manufactured by Novagen) to produce an IL-2I129C expression vector for *Escherichia coli* (hereinafter, referred to as pET-22b (+)-hIL-2I129C).

TABLE 16

Produced Cys-substituted IL-2 expression vector

| Variant name | Cys substitution position | Amino acid residue before substitution | Modification at position 1 | Mutation at position 125 | nucleotide sequence |
|---|---|---|---|---|---|
| I129C | 129 | I | M | S | SEQ ID NO: 52 |

<Description of Table 16>
 Cys mutation position: Position from the N-terminal of SEQ ID NO: 1
 Modification at position 1: Indicates modification of alanine residue at position1 from the N-terminal in the amino acid sequence represented by SEQ ID NO: 1 M indicates that an amino acid residue is substituted from alanine to methionine.
 Mutation at position 125: Indicating presence or absence of a mutation of amino acid residue at position 125 from the N-terminal of the amino acid sequence represented by SEQ ID NO: 1. A case where no mutation of the amino acid residue is introduced is described as "–" and a case where a mutation that substitutes an amino acid residue from cysteine to serine is introduced, is described as "S".

Example 10

Preparation of IL-2I129C

The IL-2 I129C was produced by a method described below. The pET-22b (+)-hIL-2_I129C for *Escherichia coli* prepared in Example 9 was introduced into *Escherichia coli* BL21 (DE3) (manufactured by Novagen), and an inclusion body was obtained by the method described in Example 5.

The obtained inclusion body was dissolved in 15 mL of 100 mmol/L Tris-HCl buffer (pH 8.0) containing 6 mol/L guanidine hydrochloride, 5 mmol/L DTT, and 5 mmol/L EDTA, and then heated at 60° C. for 30 minutes. A supernatant was collected by centrifugation (19000×g, 4° C., 30 minutes) (inclusion body solubilized solution).

15 mL of 100 mmol/L Tris-HCl buffer (pH 8.0) was added to the inclusion body solubilized solution, and allowed to stand at room temperature for 10 minutes, and then a precipitate was collected by centrifugation (19000×g, 4° C., 30 minutes).

The obtained precipitate was dissolved again in a 100 mmol/L Tris-HCl buffer (pH 8.0) containing 6 mol/L guanidine hydrochloride, 5 mmol/L DTT, and 5 mmol/L EDTA (precipitate solubilized solution).

HiPrep 26/60 Sephacryl S-100HR (manufactured by GE Healthcare) was connected to AKTAFPLC, and 100 mmol/L Tris-HCl buffer (pH 8.0) containing 6 mol/L guanidine hydrochloride, 5 mmol/L DTT, and 5 mmol/L EDTA was sent thereto as a mobile phase. The precipitate solubilized solution was added to a SEC column, and a monomer fraction was collected.

Refolding was performed by a method below. The prepared monomer IL-2I129C was buffer-exchanged to a 100 mmol/L Tris-HCl buffer (pH 8.0) containing 6 mol/L guanidine hydrochloride, using a NAP column, then changed to a 100 mmol/L Tris-HCl buffer (pH 8.0) containing 2 mol/L guanidine hydrochloride, 10 vol % glycerol, 6.9 mmol/L reduced glutathione, and 0.7 mmol/L oxidized glutathione, and allowed to stand at room temperature overnight. Thereafter, a refolding fraction was collected by reverse phase HPLC using Proteovavi (manufactured by Shiseido Co., Ltd.) and lyophilized.

A purity of the produced IL-2_I129C was confirmed by SDS-PAGE. As a result, a single band having a molecular weight expected from the amino acid sequence was confirmed.

Example 11

PEGylation of IL-2_I129C

A PEGylated form of IL-2_I129C shown in Table 17 (hereinafter, referred to as PEGylated IL-2 variant) was prepared by a method below.

TABLE 17

| | Produced PEGylated IL-2 variant | | | |
|---|---|---|---|---|
| Variant name | PEGylation site | Amino acid residue before substitution | Amino acid residue after substitution | Modification at position 1 | Mutation at position 125 |
| I129C-V40(Mal) | 129 | I | C-V40(Mal) | M | S |
| I129C-V80(Mal) | 129 | I | C-V80(Mal) | M | S |
| I129C-W80(Mal) | 129 | I | C-W80(Mal) | M | S |

<Description of Table 17>

PEGylation site: Position from the N-terminal of SEQ ID NO: 1

Modification at position 1: Indicates modification of alanine residue at position1 from the N-terminal in the amino acid sequence represented by SEQ ID NO: 1 M indicates that an amino acid residue is substituted from alanine to methionine.

Position at 125: Indicating presence or absence of a mutation of amino acid residue at position 125 from the N-terminal of SEQ ID NO: 1 A case where no mutation of the amino acid residue is introduced is described as "−" and a case where a mutation that substitutes an amino acid residue from cysteine to serine is introduced, is described as "S".

In the table, the structures described in the column of "Amino acid residues after substitution" are shown below.

C-PEG(Mal) (V40, V80, W80) indicates a structure represented by (Formula X119) below in which PEG is introduced into a cysteine side chain via a 3-(3-thio-2,5-dioxopyrrolidin-1-yl)-propyloxy linker. In this case, C-PEG(Mal) may indicate a structure represented by (Formula X120) or (Formula X121) in which a dioxopyrrolidine ring is opened.

[Chem. 153]

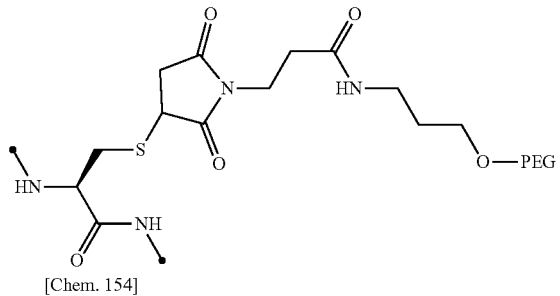

(Formula X119)

[Chem. 154]

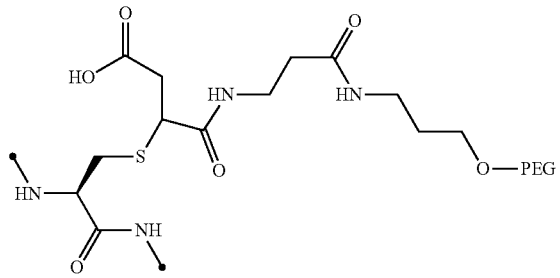

(Formula X120)

[Chem. 155]

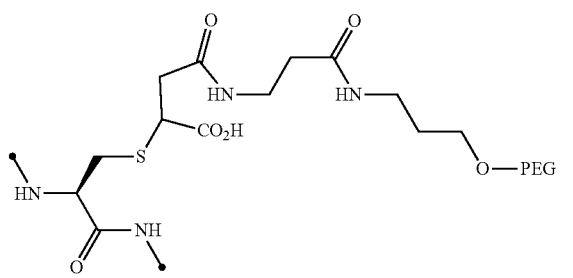

(Formula X121)

V40 indicates that, in (Formula X119) to (Formula X121) above, PEG is a structure represented by (Formula X122) below in a case of an average molecular weight of about 40 kDa.

[Chem. 156]

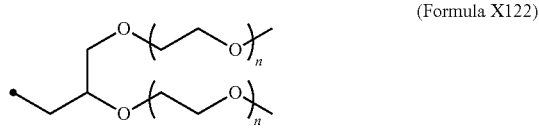

(Formula X122)

V80 indicates that, in (Formula X119) to (Formula X121) above, PEG is a structure represented by (Formula X122) above in a case of an average molecular weight of about 80 kDa.

W80 indicates that, in (Formula X119) to (Formula X121) above, PEG is a structure represented by (Formula X128) below in a case where an average molecular weight of $(CH_2CH_2O)_m$ is 5 kDa and an average molecular weight of $(CH_2CH_2O)_n$ is 17.5 kDa.

[Chem. 157]

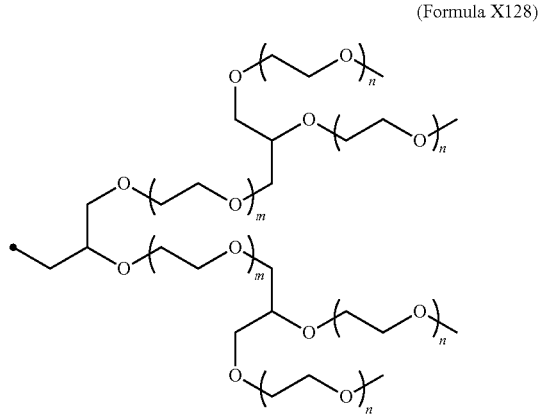

(Formula X128)

The lyophilized product of the IL-2_I129C prepared in Example 10 was dissolved in a 20 mmol/L Tris-HCl buffer (pH 7.0) containing 2 mol/L guanidine hydrochloride and 1 mmol/L EDTA. PEG-maleimide (SUNBRIGHT GL2-400MA; NOF CORPORATION, SUNBRIGHT GL2-800MA; NOF CORPORATION, or SUNBRIGHT GL4-800MA; NOF CORPORATION) is dissolved in D-PBS, and 20 mol equivalents thereof was added to the IL-2_I129C and allowed to stand at room temperature overnight. PEGylated IL-2_I129C was purified by the method described in Example 8. The obtained PEGylated IL-2_I129C was buffer-substituted with a 10 mM acetate buffer (pH 4.5) containing 0.4 mol/L arginine hydrochloride, and 5 w/v % trehalose, using an NAP column.

A purity of the purified PEGylated IL-2 variant was confirmed by SDS-PAGE. As a result, in all the PEGylated IL-2 variants, a single band in which the molecular weight was increased as much as PEG attached with respect to the IL-2_I129C was confirmed, and it was confirmed that highly purified PEGylated IL-2 variants were obtained.

Example 12

Evaluation of IL-2R$_{\alpha\beta\gamma}$ Selectivity

A selectivity of the produced IL-2 variant for human IL-2R$_{\alpha\beta\gamma}$ was evaluated by a method below.

Human IL-2R$_{\alpha\beta\gamma}$ or human IL-2R$_{\beta\gamma}$ was expressed in a mouse pro B cell line Ba/F3 (RCB0805) to produce a human IL-2-dependent survival cell line. Each cell was obtained by gene transfer of p DELTA vector comprising a genetic sequence (SEQ ID NO: 20) encoding an amino acid sequence (SEQ ID NO: 19) of human IL-2R$_{\alpha\beta\gamma}$-Azami green fusion in which human CD25, human CD122, human CD132, and monomeric Azami-Green were fused via furin cleavage sequence (RAKR) and foot-and-mouth-disease virus-derived 2A peptide sequence (APVKQTLNFDLLKLAGDVESNPGP) or a genetic sequence (SEQ ID NO: 22) encoding an amino acid sequence (SEQ ID NO: 21) of human IL-2R$_{\beta\gamma}$-Azami green fusion in which human CD122, human CD132, and monomer azami-Green were fused via a furin cleavage sequence and a foot-and-mouth-disease virus-derived 2A peptide sequence to Ba/F3, by using Nucleofector 2b (manufactured by Lonza), and selecting a clone exhibiting human IL-2 dependency. The obtained cells were named Ba/F3-hIL-2R$_{\alpha\beta\gamma}$ and Ba/F3-hIL-2R$_{\beta\gamma}$, respectively.

Ba/F3-hIL-2R$_{\alpha\beta\gamma}$ and Ba/F3-hIL-2R$_{\beta\gamma}$ were collected in a centrifuge tube, centrifuged at 1200 rpm for 3 minutes, and then a supernatant thereof was removed by suction. After washing the resulting product 4 times with D-PBS, and the cells were suspended at $5.0 \times 10^4$ cells/mL in an assay medium [medium in which 50 mL of Inactivated FBS (manufactured by GIBCO) and 5 mL of penicillin-streptomycin mixed solution (manufactured by Nacalai Tesque, Inc.) were added to 500 mL of RPMI 1640 medium (manufactured by Nacalai Tesque, Inc.)], and a 96-well white flat bottom plate (manufactured by Sumitomo Bakelite) was seeded with the suspended cells at 100 μL/well.

An assay medium (0% control), a commercially available IL-2 solution (final concentration 65 nmol/L, 100% control) diluted to 390 nmol/L in an assay medium, IL-2 (manufactured by peprotech) which is commercially available IL-2 diluted to 6-fold a final concentration in an assay medium [hereinafter, referred to as IL-2(P)], and IL-2 (manufactured by Thermo Fisher Scientific) [hereinafter, referred to as IL-2(T)], or various glycosylated IL-2 solutions (maximum final concentration 65 nM, 9 conditions in 10-fold dilution series) were added at 20 μL/well and cultured at 37° C. under 5% $CO_2$ for 24 to 48 hours.

A Celltiter-Glo solution (manufactured by Promega) was added at 80 μL/well, and allowed to stand at room temperature for 10 minutes, and then a luminescence value was measured using a multimode plate reader ARVO (manufactured by Perkin Elmer).

Assuming that a relative fluorescence units (RLU) value of wells to which IL-2 (P) or IL-2 (T) was added at a final concentration of 65 nmol/mL was 100% and the RLU value of wells to which a medium without IL-2 was added was 0%, the IL-2-dependent cell proliferation rates of various variants (% of IL-2-dependent proliferation) were calculated. An $EC_{50}$ value was calculated using statistical analysis software XLfit5 version 5.3.1.3 (manufactured by IBDS), based on the obtained data.

For the IL-2 (P) or the IL-2 (T), and various glycosylated IL-2 variants, a ratio ($EC50_{\beta\gamma}/EC50\alpha\beta\gamma$) between the $EC_{50}$ value for Ba/F3-hIL-2R$_{\alpha\beta\gamma}$ ($EC_{50\alpha\beta\gamma}$) and the $EC_{50}$ value for Ba/F3-hIL-2R$_{\beta\gamma}$ ($EC50_{\beta\gamma}$) was defined as an $EC_{50}$ ratio value, and used as an index of IL-2R$_{\alpha\beta\gamma}$ selectivity.

The $EC_{50}$ ratio values of the various glycosylated IL-2 variants when the $EC_{50}$ ratio value of the IL-2 (P) or the IL-2 (T) was set as 1 are shown as "Standardized $EC_{50}$ ratio value" in Tables 18 to 20.

TABLE 18

Standardized EC50 ratio value of glycosylated IL-2 variant

| Standardized EC50 ratio value | Variant |
| --- | --- |
| <5 | T3C-2, T3C-9, T3C-11, S4C-2, S4C-9, S4C-11, S5C-2, S5C-9, SSC-11, Q11C-2, Q11C-9, L12C-2, H16C-11, L18C-9, L19N-11, R38C-2, R38C-9, R38C-11, N88-1, N88C-1, I92C-11, V115C-9, N119C-11, I122C-9, S127C-11 |
| 5~30 | Q11C-11, L12C-9, L12C-11, L18C-2, L18C-11, D20C-2, D20C-11, D84C-2, S87C-2, S87C-11, N88C-9, N88C-11, |

TABLE 18-continued

Standardized EC50 ratio value of glycosylated IL-2 variant

| Standardized EC50 ratio value | Variant |
| --- | --- |
| >30 | V91C-2, V91C-9, V91C-11, Al08C-2, Al08C-9, V115C-2, N119C-2, N119C-9, I122C-2, T123C-11 Q13C-2, Q13C-11, E15C-2, E15C-11, H16C-2, H16C-3, H16C-5, H16C-9, L19C-2, L19C-9, L19C-11, L19C-11*, N88C-2, I92C-2, S130C-2, S130C-9 |

TABLE 19

Standardized EC50 ratio value of glycosylated IL-2 variant

| Standardized EC50 ratio value | Variant |
| --- | --- |
| <5 | D84C-11, E95C-2, L12C-11/H16C-2/L19C-11, L12C-11/L19C-11, L12C-11/N88C-2, L12N-11/V91N-11, E15C-11/V91C-11, E15C-11/T123C-11, H16C-2/L19C-11, H16C-2/V91C-11, L19C-11/V91C-11 |
| 5 to 30 | K8C-11/L19C-11, L12C-11/H16C-2, E15C-11/N119C-11, L19C-11/M23C-11, T3C-11/L12C-11/K32C-11/K76C-11/V91C-11 |
| >30 | E15C-17, L19C-17, L12C-11/V91C-11, L12C-11/V115C-11, L12C-11/N119C-11, Q13C-11/V91C-11, Q13C-11/V115C-11, Q13C-11/N119C-11, L19C-11/V115C-11, V91C-11/V115C-11, V91C-11/N119C-11, AlC-11/T3C-11/S5C-11/L12C-11/V91C-11, T3C-11/L12C-11/T51C-11/V91C-11/E100C-11, T3C-11/L12C-11/K76C-11/V91C-11/E100C-11, L12C-11/V91C-11/E100C-11/T102C-11/M104C-11 |

TABLE 20

Standardized EC50 ratio values of N-terminal PEGylated and glycosylated IL-2 variant and Cys-PEGylated and glycosylated IL-2 variant

| Standardized EC50 ratio value | Variant |
| --- | --- |
| <5 | T51C-V40 (IAc)/L12C-11/V91C-11, T51C-W40 (IAc)/L12C-11/V91C-11 |
| 5 to 30 | T3C-V40 (IAc)/L12C-11/V91C-11, T3C-W40 (IAc)/L12C-11/V91C-11, T3C-W80 (Mal)/L12C-11/V91C-2, T3C-V80 (Mal)/L12C-11 /N119C-11, T3C-W80 (Mal)/L12C-11 /N119C-11, T3C-Y50 (IAc)/L12C-11/N119C-11, T51C-Li40 (IAc)/L12C-11/V91C-11, T51C-Y50 (IAc)/L12C-11/V91C-11, F78C-V40 (IAc)/L12C-11 /N119C-11, F78C-V80 (Mal)/L12C-11 /N119C-11, F78C-W80 (Mal)/L12C-11 /N119C-11 |
| >30 | Al-Li20 (CH0)/Q11C-9, Al-Li20 (CH0)/L12C-9, Al-Li20 (CH0)/R38C-9, Al-Li20 (CH0)/V91C-9, AlC-Li40 (IAc)/L12C-11/V91C-11, AlC-V80 (Mal)/L12C-11/V91C-11, AlC-Y50 (IAc)/L12C-11/V91C-11, AlC-Y50 (Mal)/L12C-11/V91C-11, AlC-W80 (Mal)/L12C-11/V91C-11, AlC-Y50 (IAc)/L19C-11, AlC-V40 (IAc)/L19C-11, AlC-Y50 (IAc)/V91C-11 /N119C-11, T3C-Li20 (IAc)/L12C-11/V91C-11, T3C-Li40 (IAc)/L12C-11/V91C-11, T3C-Y50 (IAc)/L12C-11/V91C-2, T3C-Y50 (IAc)/L12C-11/V91C-11, T3C-Y50 (Mal)/L12C-11/V91C-11 T3C-V40 (IAc)/E15C-11, T3C-V80 (Mal)/E15C-11, T3C-Y50 (IAc)/E15C-11, F78C-Li40 (IAc)/L12C-11, |

TABLE 20-continued

Standardized EC50 ratio values of N-terminal PEGylated and glycosylated IL-2 variant and Cys-PEGylated and glycosylated IL-2 variant

| Standardized EC50 ratio value | Variant |
|---|---|
| | F78C-V40 (IAc)/L12C-11, F78C-V40(Mal)/L12C-11, F78C-V80 (Mal)/L12C-11, F78C-W80 (Mal)/L12C-11, F78C-Li40 (IAc)/E15C-11 |

In Tables 18 to 20, in the control, a glycosylated IL-2 variant, N-terminal PEGylated and glycosylated IL-2, and Cys-PEGylated and glycosylated IL-2 which have a standardized $EC_{50}$ ratio value of 5 or more, were determined as variants having higher selectivity for IL-2$R_{\alpha\beta\gamma}$ than that of the IL-2 (P) or the IL-2 (T) as control.

As shown in Tables 18 to 20, it was confirmed that a number of glycosylated IL-2 variants, N-terminal PEGylated and glycosylated IL-2, and Cys-PEGylated and glycosylated IL-2 were the variants having higher selectivity for IL-2$R_{\alpha\beta\gamma}$ than that of the IL-2 (P) or the IL-2 (T). Furthermore, it was found that Q13C-2, Q13C-11, E15C-2, E15C-11, H16C-2, H16C-3, H16C-5, H16C-9, L19C-2, L19C-9, L19C-11, L19C-11*, N88C-2, I92C-2, S130C-2, S130C-9, E15C-17, L19C-17, L12C-11/V91C-11, L12C-11/V115C-11, L12C-11/N119C-11, Q13C-11/V91C-11, Q13C-11/V115C-11, Q13C-11/N119C-11, L19C-11/V115C-11, V91C-11/V115C-11, V91C-11/N119C-11, A1C-11/T3C-11/S5C-11/L12C-11/V91C-11, T3C-11/L12C-11/T51C-11/V91C-11/E100C-11, T3C-11/L12C-11/K76C-11/V91C-11/E100C-11, L12C-11/V91C-11/E100C-11/T102C-11/M104C-11, A1-Li20(CHO)/Q11C-9, A1-Li20(CHO)/L12C-9, A1-Li20(CHO)/R38C-9, A1-Li20(CHO)/V91C-9, A1C-Li40(IAc)/L12C-11/V91C-11, A1C-V80(Mal)/L12C-11/V91C-11, A1C-Y50(IAc)/L12C-11/V91C-11, A1C-Y50 (Mal)/L12C-11/V91C-11, A1C-W80(Mal)/L12C-11/V91C-11, A1C-Y50(IAc)/L19C-11, A1C-V40(IAc)/L19C-11, A1C-Y50(IAc)/V91C-11/N119C-11, T3C-Li20(IAc)/L12C-11/V91C-11, T3C-Li40(IAc)/L12C-11/V91C-11, T3C-Y50(IAc)/L12C-11/V91C-2, T3C-Y50(IAc)/L12C-11/V91C-11, T3C-Y50(Mal)/L12C-11/V91C-11, T3C-V40(IAc)/E15C-11, T3C-V80(Mal)/E15C-11, T3C-Y50(IAc)/E15C-11, F78C-Li40(IAc)/L12C-11, F78C-V40(IAc)/L12C-11, F78C-V40(Mal)/L12C-11, F78C-V80(Mal)/L12C-11, F78C-W80(Mal)/L12C-11, F78C-Li40(IAc)/E15C-11 had a standardized $EC_{50}$ ratio value of greater than 30, and were a glycosylated IL-2 variant, N-terminal PEGylated and glycosylated IL-2, and Cys-PEGylated and glycosylated IL-2 which have extremely higher selectivity for IL-2$R_{\alpha\beta\gamma}$ than that of the IL-2 (P) or the IL-2 (T) as control.

Table 21 and Table 22 show results obtained by measuring the IL-2-dependent cell proliferation rate of the various PEGylated IL-2 variants and calculating the standardized $EC_{50}$ ratio values, in the same manner. However, the control of the glycosylated IL-2 variant was IL-2 (P) or IL-2 (T), whereas the control of the PEGylated IL-2 variant was IL-2 (P) or 8His-IL-2 was used.

TABLE 21

Standardized $EC_{50}$ ratio value of PEGylated IL-2 variant

| Standardized EC50 ratio value | Variant |
|---|---|
| <5 | 8His-S4 (oAzZK)-PEG4, 8His-S5 (oAzZK)-PEG4, 8His-S6 (oAzZK)-PEG4, 8His-T7 (oAzZK)-PEG4, 8His-T7 (oAzZK)-Li20, 8His-K8 (oAzZK)-PEG4, 8His-E60 (oAzZK)-PEG4, 8His-E60 (oAzZK)-Li20, 8His-F78 (oAzZK)-PEG4, 8His-H79 (oAzZK)-PEG4, 8His-R81 (oAzZK)-PEG4, 8His-R81 (oAzZK)-Li20, 8His-R81 (oAzZK)-Li30, 8His-L94 (oAzZK)-PEG4, 8His-L94 (oAzZK)-Li20, 8His-L94 (oAzZK)-Li30, 8His-S99 (oAzZK)-PEG4, 8His-S99 (oAzZK)-Li20, 8His-E100 (oAzZK)-PEG4, 8His-E100 (oAzZK)-Li30, 8His-T101 (oAzZK)-PEG4, 8His-Q126 (oAzZK)-PEG4, 8His-Q126 (oAzZK)-Li20 |
| 5 to 30 | 8His-S4 (oAzZK)-Li20, 8His-S4 (oAzZK)-Li30, 8His-S5 (oAzZK)-Li20, 8His-S5 (oAzZK)-Li30, 8His-S6 (oAzZK)-Li20, 8His-S6 (oAzZK)-Li30, 8His-T7 (oAzZK)-Li30, 8His-K8 (oAzZK)-Li20, 8His-K8 (oAzZK)-Li30, 8His-E60 (oAzZK)-Li30, 8His-F78 (oAzZK)-Li20, 8His-H79 (oAzZK)-Li20, 8His-H79 (oAzZK)-Li30, 8His-S99 (oAzZK)-Li30, 8His-E100 (oAzZK)-Li20, 8His-T101 (oAzZK)-Li20, 8His-T101 (oAzZK)-Li30, 8His-Q126 (oAzZK)-Li30, 8His-I129 (oAzZK)-PEG4, 8His-I129 (oAzZK)-Li20 |
| >30 | 8His-F78 (oAzZK)-Li30, 8His-I129 (oAzZK)-Li30 |

TABLE 22

Standardized $EC_{50}$ ratio value of PEGylated IL-2 variant

| Standardized EC50 ratio value | Variant |
|---|---|
| <5 | — |
| 5 to 30 | — |
| >30 | 8His-F78 (oAzZK)-Li40, 8His-F78 (oAzZK)-V40, 8His-F78 (oAzZK)-W40, 8His-F78 (oAzZK)-Y50, F78 (oAzZK)-Li40, F78 (oAzZK)-V40, F78 (oAzZK)-W40, F78 (oAzZK)-IlI40, F78 (oAzZK)-V80, F78 (oAzZK)-W80, 8His-I129 (oAzZK)-Li40, 8His-I129 (oAzZK)-V40, 8His-I129 (mAzZK)-V40, 8His-I129 (oAzZK)-Y50, I129 (oAzZK)-Li30, I129 (oAzZK)-Li40, I129 (oAzZK)-V40, I129 (oAzZK)-W40, I129 (oAzZK)-IlI40, I129 (oAzZK)-V80, I129 (oAzZK)-W80, desAla-I129 (oAzZK)-V40, desAla-I129 (oAzZK)-W80, desAla-I129 (oAzZK)-Y80, I129C-V40 (Mal), I129C-V80 (Mal), I129C-W80 (Mal), 8His-S4 (oAzZK)-Li30/F78 (oAzZK)-Li30, S4 (oAzZK)-Li40/F78 (oAzZK)-Li40, S4 (oAzZK)-Y50/F78 (oAzZK)-Y50, 8His-S5 (oAzZK)-Li30/F78 (oAzZK)-Li30, S5 (oAzZK)-Li40/F78 (oAzZK)-Li40, 8His-K8 (oAzZK)-Li30/F78 (oAzZK)-Li30, K8 (oAzZK)-Li40/F78 (oAzZK)-Li40, 8His-F78 (oAzZK)-Li30/H79 (oAzZK)-Li30, 8His-F78 (oAzZK)-Li30/S99 (oAzZK)-Li30, 8His-F78 (oAzZK)-Li30 /I129 (oAzZK)-Li30, 8His-54 (oAzZK)-Li30/I129 (oAzZK)-Li30, 8His-54 (oAzZK)-Y50/I129 (oAzZK)-Y50, |

TABLE 22-continued

Standardized EC$_{50}$ ratio value of PEGylated IL-2 variant

| Standardized EC$_{50}$ ratio value | Variant |
|---|---|
| | S4 (oAzZK)-Li40/I129 (oAzZK)-Li40, |
| | S4 (oAzZK)-Y50/I129 (oAzZK)-Y50, |
| | 8His-S5 (oAzZK)-Li30 /I129 (oAzZK)-Li30, |
| | S5 (oAzZK)-Li40/I129 (oAzZK)-Li40, |
| | S5 (oAzZK)-Y50/I129 (oAzZK)-Y50, |
| | 8His-K8 (oAzZK)-Li30/I129 (oAzZK)-Li30, |
| | 8His-K8 (oAzZK)-Y50/I129 (oAzZK)-Y50, |
| | K8 (oAzZK)-Li40/I129 (oAzZK)-Li40, |
| | K8 (oAzZK)-Y50/I129 (oAzZK)-Y50, |
| | 8His-H79 (oAzZK)-Li30/I129 (oAzZK)-Li30, |
| | 8His-S99 (oAzZK)-Li30/I129 (oAzZK)-Li30 |

In Tables 21 and 22, a PEGylated IL-2 variant having a standardized EC$_{50}$ ratio value of 5 or more was determined as a variant having higher selectivity for IL-2R$_{\alpha\beta\gamma}$ than that of the 8His-IL-2 as control.
As shown in Tables 21 and 22, it was confirmed that a number of PEGylated IL-2 variants were variants having higher selectivity for IL-2R$_{\alpha\beta\gamma}$ than that of the 8His-IL-2. Furthermore, 8His-F78(oAzZK)-Li30, 8His-F78(oAzZK)-Li40, 8His-F78(oAzZK)-V40, 8His-F78(oAzZK)-W40, 8His-F78(oAzZK)-Y50, F78(oAzZK)-Li40, F78(oAzZK)-V40, F78(oAzZK)-W40, F78(oAzZK)-IIII40, F78(oAzZK)-V80, F78(oAzZK)-W80, 8His-I129(oAzZK)-Li30, 8His-I129(oAzZK)-Li40, 8His-I129(oAzZK)-V40, 8His-I129(mAzZK)-V40, 8His-I129(oAzZK)-W40, 8His-I129(oAzZK)-Y50, I129(oAzZK)-Li30, I129(oAzZK)-Li40, I129(oAzZK)-V40, I129(oAzZK)-W40, I129(oAzZK)-IIII40, I129(oAzZK)-V80, I129(oAzZK)-W80, desAla-I129(oAzZK)-V40, desAla-I129(oAzZK)-W80, desAla-I129(oAzZK)-V80, I129C-V40(Mal), I129C-V80(Mal), I129C-W80(Mal), 8His-S4(oAzZK)-Li30/F78(oAzZK)-Li30, S4(oAzZK)-Li40/F78(oAzZK)-Li40, S4(oAzZK)-Y50/F78(oAzZK)-Y50, 8His-S5(oAzZK)-Li30/F78(oAzZK)-Li30, S5(oAzZK)-Li40/F78(oAzZK)-Li40, 8His-K8(oAzZK)-Li30/F78(oAzZK)-Li30, K8(oAzZK)-Li40/F78(oAzZK)-Li40, 8His-F78(oAzZK)-Li30/H79(oAzZK)-Li30, 8His-F78(oAzZK)-Li30/S99(oAzZK)-Li30, 8His-F78(oAzZK)-Li30/I129(oAzZK)-Li30, 8His-S4(oAzZK)-Li304129(oAzZK)-Li30, 8His-S4(oAzZK)-Y50/I129(oAzZK)-Y50, S4(oAzZK)-Li404129(oAzZK)-Li40, S4(oAzZK)-Y50/I129(oAzZK)-Y50, 8His-S5(oAzZK)-Li304129(oAzZK)-Li30, S5(oAzZK)-Li404129(oAzZK)-Li40, S5(oAzZK)-Y50/I129(oAzZK)-Y50, 8His-K8(oAzZK)-Li30/I129(oAzZK)-Li30, 8His-K8(oAzZK)-Y50/I129(oAzZK)-Y50, K8(oAzZK)-Li404129(oAzZK)-Li40, K8(oAzZK)-Y50/I129(oAzZK)-Y50, 8His-H79(oAzZK)-Li30/I129(oAzZK)-Li30, and 8His-S99(oAzZK)-Li30/I129(oAzZK)-Li30 had a standardized EC$_{50}$ ratio value of greater than 30, and were a PEGylated IL-2 variant having extremely higher selectivity for IL-2R$_{\alpha\beta\gamma}$ than that of the IL-2 (P) or the 8His-IL-2 as control.

In experiments above, it was confirmed that the EC$_{50}$ ratio values of the IL-2 (P), the IL-2 (T), wild-type IL-2, and the 8His-IL-2 are comparable. Therefore, the glycosylated IL-2 variants and the PEGylated and glycosylated IL-2 variants having a standardized EC$_{50}$ ratio value of 5 or more in Tables 18 to 20, and the PEGylated IL-2 variants having the standardized EC$_{50}$ ratio values of 5 or more in Tables 21 and 22 are variants having higher selectivity for IL-2R$_{\alpha\beta\gamma}$ than that of wild-type IL-2.

Example 13

Treg Proliferation Activity

Cell proliferation activities of human Tregs by various IL-2 were measured by a method below. For the various IL-2, H16C-2, E15C-11, L19C-9, L19C-11, N88C-2, L12C-11/V91C-11, V91C-11/V115C-11, V91C-11/N119C-11, and A1C-11/T3C-11/S5C-11/L12C-11/V91C-11 were used as the glycosylated IL-2 variants; A1C-Y50(IAc)/L12C-11/V91C-11, T3C-Li20(IAc)/L12C-11/V91C-11, T3C-Y50(IAc)/L12C-11/V91C-11, T3C-Y50(IAc)/E15C-11, T3C-V40(IAc)/E15C-11, T3C-V80(Mal)/E15C-11, and F78C-V40(IAc)/L12C-11 were used as Cys-PEGylated and glycosylated IL-2 variants; 8His-S4(oAzZK)-Li20, 8His-S5(oAzZK)-Li20, 8His-S6(oAzZK)-Li20, 8His-T7(oAzZK)-Li20, 8His-K8(oAzZK)-Li20, 8His-E60(oAzZK)-Li20, 8His-F78(oAzZK)-Li20, 8His-F78(oAzZK)-V40, 8His-F78(oAzZK)-W40, 8His-H79(oAzZK)-Li20, 8His-R81(oAzZK)-Li20, 8His-L94(oAzZK)-Li20, 8His-S99(oAzZK)-Li20, 8His-E100(oAzZK)-Li20, 8His-T101(oAzZK)-Li20, 8His-Q126(oAzZK)-Li20, 8His-I129(oAzZK)-Li20, 8His-I129(oAzZK)-Li40, 8His-I129(oAzZK)-V40, 8His-I129(oAzZK)-W40, 8His-I129(oAzZK)-Y50, I129(oAzZK)-V40, I129(oAzZK)-W80, I129C-V40(Mal), 8His-S4(oAzZK)-Li30/F78(oAzZK)-Li30, 8His-S5(oAzZK)-Li30/F78(oAzZK)-Li30, 8His-K8(oAzZK)-Li30/F78(oAzZK)-Li30, 8His-F78(oAzZK)-Li30/H79(oAzZK)-Li30, 8His-F78(oAzZK)-Li30/S99(oAzZK)-Li30, 8His-F78(oAzZK)-Li304129(oAzZK)-Li30, 8His-S4(oAzZK)-Li30/I129(oAzZK)-Li30, S4(oAzZK)-Y504129(oAzZK)-Y50, 8His-S5(oAzZK)-Li30/I129(oAzZK)-Li30, S5(oAzZK)-Y50/I129(oAzZK)-Y50, 8His-K8(oAzZK)-Li30/I129(oAzZK)-Li30, K8(oAzZK)-Y50/I129(oAzZK)-Y50, 8His-H79(oAzZK)-Li30/I129(oAzZK)-Li30, and 8His-S99(oAzZK)-Li30/I129(oAzZK)-Li30 were used as PEGylated IL-2 variants; and the IL-2 (P) and the 8His-IL-2 were used as control.

After human frozen peripheral blood mononuclear cells (PBMCs) (manufactured by AllCells) were melted in a warm bath at 37° C., the cells were suspended in 10 mL of a culture medium [X-vivo15 SFM (manufactured by Lonza) 1000 mL, heat-inactivated human AB serum (manufactured by SIGMA) 150 mL], and a T-75 flask for adhesion (manufactured by greiner bio-one) was seeded the cells, and allowed to stand for 24 hours to culture the cells (37° C., under conditions of 95 vol % air/5 vol % CO$_2$). A total amount of cells was collected, and CD4$^+$ T cells were enriched using EasySep Human CD4$^+$ Tcells Enrichment kit (manufactured by STEMCELL Technologies).

After staining (on ice, 30 minutes) with Anti-human CD4-Alexa 488 (manufactured by Biolegend), anti-human CD25-PE (manufactured by BD Pharmingen), and anti-human CD127-BV421 (manufactured by Biolegend), a CD4$^+$ CD25$^+$ CD127$^{low}$ fraction (Treg) was separated using a cell sorter SH800 (manufactured by SONY Biotechnology).

The separated Treg and CD3/CD28 Dynabeads (manufactured by Thermo Fischer SCIENTIFIC) washed three times with the culture medium were mixed with each other, and suspended in a culture medium at 3.4×10$^4$ cells/mL, respectively, and a 96-well U bottom plate (manufactured by Corning) was seeded with at 150 μL/well. Various IL-2 solutions diluted to 4-fold the final concentration with a culture medium were added at 50 μL/well, and culture was started at 37° C. under 5% CO$_2$.

After culturing for 5 to 7 days, 50 μL of a total volume of each well was transferred to a 96-well white plate. A Celltiter-Glo solution was added at 50 μL/well, and the mixture was allowed to stand at room temperature for 10 minutes, and then a luminescence value was measured using a luminometer (manufactured by TURNER BIOSYSTEMS).

Assuming that the RLU value of a well to which IL-2 (P) or 8His-IL-2 as control was added at a final concentration of 65 nmol/L was 100% and the RLU value of a well to which a medium without containing IL-2 was added was 0%, the Treg proliferation rates of various IL-2 were calculated.

Results obtained are shown in FIGS. 1A to 1J. As shown in FIGS. 1A to 1C, IL-2 (P) exhibited an IL-2-dependent cell proliferation rate of 80% or higher at an IL-2 concentration of 650 pmol/L, whereas H16C-2, E15C-11, L19C-9, L19C-11*, N88C-2, L12C-11/V91C-11, V91C-11/V115C-11, and V91C-11/N119C-11 as the glycosylated IL-2 variants and T3C-Y50(IAc)/E15C-11 as the Cys-PEGylated and glycosylated IL-2 variant exhibited an IL-2-dependent cell proliferation rate of 80% or higher at an IL-2 concentration of 650 to 6500 pmol/L.

In addition, L12C-11/F78C-V40(IAc) as the Cys-PEGylated and glycosylated IL-2 variant exhibited an IL-2-dependent cell proliferation rate of 80% or higher at an IL-2 concentration of 65 nmol/L. A1C-11/T3C-11/S5C-11/L12C-11/V91C-11 as the glycosylated IL-2 variant, and A1C-Y50(IAc)/L12C-11/V91C-11, T3C-Li20(IAc)/L12C-11/V91C-11, T3C-Y50(IAc)/L12C-11/V91C-11, T3C-V40(IAc)/E15C-11, and T3C-V80(Mal)/E15C-11 as the Cys-PEGylated and glycosylated IL-2 variant had an IL-2-dependent cell proliferation rate of 80% or lower even at an IL-2 concentration of 65 nmol/L.

As shown in FIGS. 1D to 1J, 8His-IL-2 as a control exhibited an IL-2-dependent cell proliferation rate of 80% or higher at an IL-2 concentration of 6500 pmol/L, whereas 8His-S4(oAzZK)-Li20, 8His-S5(oAzZK)-Li20, 8His-S6(oAzZK)-Li20, 8His-T7(oAzZK)-Li20, 8His-K8(oAzZK)-Li20, 8His-E60(oAzZK)-Li20, 8His-F78(oAzZK)-Li20, 8His-F78(oAzZK)-V40, 8His-F78(oAzZK)-W40, 8His-H79(oAzZK)-Li20, 8His-R81(oAzZK)-Li20, 8His-L94(oAzZK)-Li20, 8His-S99(oAzZK)-Li20, 8His-E100(oAzZK)-Li20, 8His-T101(oAzZK)-Li20, 8His-Q126(oAzZK)-Li20, 8His-I129(oAzZK)-Li20, 8His-I129(oAzZK)-Li40, 8His-I129(oAzZK)-V40, 8His-I129(oAzZK)-W40, 8His-I129(oAzZK)-Y50, I129(oAzZK)-V40, I129C-V40(Mal), 8His-S4(oAzZK)-Li30/F78(oAzZK)-Li30, 8His-S5(oAzZK)-Li30/F78(oAzZK)-Li30, 8His-K8(oAzZK)-Li30/F78(oAzZK)-Li30, 8His-F78(oAzZK)-Li30/S99(oAzZK)-Li30, 8His-S4(oAzZK)-Li30/I129(oAzZK)-Li30, 8His-S5(oAzZK)-Li30/I129(oAzZK)-Li30, 8His-K8(oAzZK)-Li30/I129(oAzZK)-Li30, and 8His-S99(oAzZK)-Li30/I129(oAzZK)-Li30 as the PEGylated IL-2 variant exhibited an IL-2-dependent cell proliferation rate of 80% or higher at an IL-2 concentration of 650 to 6500 pmol/L.

In addition, I129(oAzZK)-W80, 8His-F78(oAzZK)-Li30/H79(oAzZK)-Li30, 8His-F78(oAzZK)-Li30/I129(oAzZK)-Li30, S4(oAzZK)-Y50/I129(oAzZK)-Y50, S5(oAzZK)-Y504129(oAzZK)-Y50, K8(oAzZK)-Y50/I129(oAzZK)-Y50, and 8His-H79(oAzZK)-Li304129(oAzZK)-Li30 as the PEGylated IL-2 variant exhibited an IL-2-dependent cell proliferation rate of 80% or higher at an IL-2 concentration of 65 nmol/L.

From results above, it was confirmed that all the evaluated IL-2 variants had Treg cell proliferation activity. In addition, in various IL-2 variants, H16C-2, E15C-11, L19C-9, L19C-11*, N88C-2, L12C-11/V91C-11, V91C-11/V115C-11, and V91C-11N119C-11 as the glycosylated IL-2 variant, T3C-Y50(IAc)/E15C-11 as the Cys-PEGylated and glycosylated IL-2 variant, and 8His-S4(oAzZK)-Li20, 8His-S5(oAzZK)-Li20, 8His-S6(oAzZK)-Li20, 8His-T7(oAzZK)-Li20, 8His-K8(oAzZK)-Li20, 8His-E60(oAzZK)-Li20, 8His-F78(oAzZK)-Li20, 8His-F78(oAzZK)-V40, 8His-F78(oAzZK)-W40, 8His-H79(oAzZK)-Li20, 8His-R81(oAzZK)-Li20, 8His-L94(oAzZK)-Li20, 8His-S99(oAzZK)-Li20, 8His-E100(oAzZK)-Li20, 8His-T101(oAzZK)-Li20, 8His-Q126(oAzZK)-Li20, 8His-I129(oAzZK)-Li20, 8His-I129(oAzZK)-Li40, 8His-I129(oAzZK)-V40, 8His-I129(oAzZK)-W40, 8His-I129(oAzZK)-Y50, I129(oAzZK)-V40, I129C-V40(Mal), 8His-S4(oAzZK)-Li30/F78(oAzZK)-Li30, 8His-S5(oAzZK)-Li30/F78(oAzZK)-Li30, 8His-K8(oAzZK)-Li30/F78(oAzZK)-Li30, 8His-F78(oAzZK)-Li30/S99(oAzZK)-Li30, 8His-S4(oAzZK)-Li30/I129(oAzZK)-Li30, 8His-S5(oAzZK)-Li30/I129(oAzZK)-Li30, 8His-K8(oAzZK)-Li30/I129(oAzZK)-Li30, and 8His-S99(oAzZK)-Li30/I129(oAzZK)-Li30 as the PEGylated IL-2 variant had maintained Treg proliferation activity with respect to IL-2 (P) or 8His-IL-2 (P) as control.

In addition, in various IL-2 variants, A1C-11/T3C-11/S5C-11/L12C-11/V91C-11 as the glycosylated IL-2 variant, A1C-Y50(IAc)/L12C-11/V91C-11, T3C-Li20(IAc)/L12C-11/V91C-11, T3C-Y50(IAc)/L12C-11/V91C-11, T3C-V40(IAc)/E15C-11, T3C-V80(Mal)/E15C-11, and F78C-V40(IAc)/L12C-11 as the Cys-PEGylated and glycosylated IL-2 variant, and I129(oAzZK)-W80, 8His-F78(oAzZK)-Li30/H79(oAzZK)-Li30, 8His-F78(oAzZK)-Li30/I129(oAzZK)-Li30, S4(oAzZK)-Y50/I129(oAzZK)-Y50, S5(oAzZK)-Y50/I129(oAzZK)-Y50, K8(oAzZK)-Y50/I129(oAzZK)-Y50, and 8His-H79(oAzZK)-Li30/I129(oAzZK)-Li30 as the PEGylated IL-2 variant had lowered Treg proliferation activity, with respect to IL-2 (P) or 8His-IL-2 (P) as control.

Example 14

NK Cell Proliferation Activity

The cell proliferation activity of human NK cells of various IL-2 was measured by a method below. For the various IL-2 variants, H16C-2, E15C-11, L19C-9, L19C-11*, N88C-2, L12C-11/V91C-11, V91C-11/V115C-11, V91C-11/N119C-11, and A1C-11/T3C-11/S5C-11/L12C-11/V91C-11 were used as the glycosylated IL-2 variants; A1C-Y50(IAc)/L12C-11/V91C-11, T3C-Li20(IAc)/L12C-11/V91C-11, T3C-Y50(IAc)/L12C-11N91C-11, T3C-Y50(IAc)/E15C-11, T3C-V40(IAc)/E15C-11, T3C-V80(Mal)/E15C-11, and F78C-V40(IAc)/L12C-11 were used as Cys-PEGylated and glycosylated IL-2 variants; 8His-S4(oAzZK)-Li20, 8His-S5(oAzZK)-Li20, 8His-S6(oAzZK)-Li20, 8His-T7(oAzZK)-Li20, 8His-K8(oAzZK)-Li20, 8His-E60(oAzZK)-Li20, 8His-F78(oAzZK)-Li20, 8His-F78(oAzZK)-V40, 8His-F78(oAzZK)-W40, 8His-H79(oAzZK)-Li20, 8His-R81(oAzZK)-Li20, 8His-L94(oAzZK)-Li20, 8His-S99(oAzZK)-Li20, 8His-E100(oAzZK)-Li20, 8His-T101(oAzZK)-Li20, 8His-Q126(oAzZK)-Li20, 8His-I129(oAzZK)-Li20, 8His-I129(oAzZK)-Li40, 8His-I129(oAzZK)-V40, 8His-I129(oAzZK)-W40, 8His-I129(oAzZK)-Y50, I129(oAzZK)-V40, I129(oAzZK)-W80, I129C-V40(Mal), 8His-S4(oAzZK)-Li30/F78(oAzZK)-Li30, 8His-S5(oAzZK)-Li30/F78(oAzZK)-Li30, 8His-K8(oAzZK)-Li30/F78(oAzZK)-Li30, 8His-F78(oAzZK)-Li30/H79(oAzZK)-Li30, 8His-F78(oAzZK)-Li30/S99(oAzZK)-Li30, 8His-F78(oAzZK)-

Li30/I129(oAzZK)-Li30, 8His-S4(oAzZK)-Li30/I129 (oAzZK)-Li30, S4(oAzZK)-Y50/I129(oAzZK)-Y50, 8His-S5(oAzZK)-Li30/I129(oAzZK)-Li30, S5(oAzZK)-Y50/I129(oAzZK)-Y50, 8His-K8(oAzZK)-Li30/I129(oAzZK)-Li30, K8(oAzZK)-Y50/I129(oAzZK)-Y50, 8His-H79 (oAzZK)-Li30/I129(oAzZK)-Li30, and 8His-S99(oAzZK)-Li30/I129(oAzZK)-Li30 were used as PEGylated IL-2 variants; and the IL-2 (P) and the 8His-IL-2 were used as control.

A separation of NK cells from human PBMC was performed by a method below. Frozen human PBMC was thawed according to the method described in Example 13, and CD56+ NK cells were separated using NK Cell Isolation Kit human (manufactured by Miltenyi Biotech). The separated cells were washed three times with a culture medium (1500 rpm, room temperature, 5 minutes) and then subjected to a proliferation assay below.

The separated NK cells were suspended in a culture medium or X-vivo 10 SFM (manufactured by Lonza) to be $1.3 \times 10^5$ cells/mL, and a 96-well U-bottom plate was seeded with the cells at 150 μL/well ($2 \times 10^4$ cells/well). An IL-2 solution diluted to 4-fold a final concentration with the culture medium or the X-vivo 10 SFM was added at 50 μL/well, and the cells were cultured at 37° C. under 5% $CO_2$ for 4 to 6 days. Thereafter, the NK cell proliferation rates of various IL-2 were calculated by the method described in Example 13.

FIGS. 2A to 2H show results obtained using a proliferation medium, and FIGS. 2I to 2K show results obtained using the X-vivo 10 SFM.

As shown in FIGS. 2A, 2H, and 2K, in the proliferation medium, IL-2 (P) exhibited an IL-2-dependent cell proliferation rate of 80% or higher at an IL-2 concentration of 6500 pmol/L, whereas H16C-2 and L19C-9 as the glycosylated IL-2 variant exhibited an IL-2-dependent cell proliferation rate of 20% or higher and lower than 80% even at an IL-2 concentration of 65 nmol/L, and N88C-2 and L12C-11/V91C-11 as the glycosylated IL-2 variant and A1C-Y50(IAc)/L12C-11/V91C-11, T3C-Li20(IAc)/L12C-11/V91C-11, T3C-Y50(IAc)/L12C-11/V91C-11, T3C-Y50(IAc)/E15C-11, T3C-V40(IAc)/E15C-11, T3C-V80(Mal)/E15C-11, and L12C-11/F78C-V40(IAc) as the Cys-PEGylated and glycosylated IL-2 variant exhibited an IL-2-dependent cell proliferation rate of lower than 20% even at an IL-2 concentration of 65 nmol/L.

In addition, in X-vivo 10 SFM, IL-2 (P) exhibited an IL-2-dependent cell proliferation rate of 80% or higher at an IL-2 concentration of 65 pmol/L, whereas E15C-11 as the glycosylated IL-2 variant exhibited an IL-2-dependent cell proliferation rate of 80% or higher at an IL-2 concentration of 6500 pmol/L, L19C-11*, V91C-11/V115C-11, and V91C-11/N119C-11 as the glycosylated IL-2 variant exhibited an IL-2-dependent cell proliferation rate of 80% or higher at an IL-2 concentration of 65 nmol/L, and A1C-11/T3C-11/S5C-11/L12C-11/V91C-11 as the glycosylated IL-2 variant had an IL-2-dependent cell proliferation rate of 20% or lower even at an IL-2 concentration of 65 nmol/L.

Then, as shown in FIGS. 2B to 2G, 2I, and 2J, in the proliferation medium, 8His-IL-2 exhibited an IL-2-dependent cell proliferation rate of 80% or higher at an IL-2 concentration of 6500 pmol/L as in IL-2 (P), whereas 8His-S4(oAzZK)-Li20, 8His-S5(oAzZK)-Li20, 8His-S6(oAzZK)-Li20, 8His-T7(oAzZK)-Li20, 8His-K8(oAzZK)-Li20, 8His-E60(oAzZK)-Li20, 8His-F78(oAzZK)-Li20, 8His-H79(oAzZK)-Li20, 8His-R81(oAzZK)-Li20, 8His-L94(oAzZK)-Li20, 8His-S99(oAzZK)-Li20, 8His-E100(oAzZK)-Li20, 8His-T101(oAzZK)-Li20, and 8His-Q126(oAzZK)-Li20 as the PEGylated IL-2 variant exhibited an IL-2-dependent cell proliferation rate of 80% or higher at an IL-2 concentration of 65 nmol/L, 8His-I129(oAzZK)-Li20, 8His-F78(oAzZK)-V40, 8His-F78(oAzZK)-W40, 8His-I129(oAzZK)-Li40, 8His-I129(oAzZK)-V40, 8His-I129(oAzZK)-W40, and 8His-I129(oAzZK)-Y50 as the PEGylated IL-2 variant had an IL-2-dependent cell proliferation rate of 20% or higher and lower than 80% at an IL-2 concentration of 65 nmol/L, and I129(oAzZK)-W80, I129C-V40(Mal), 8His-S4(oAzZK)-Li30/I129(oAzZK)-Li30, S4(oAzZK)-Y50/I129(oAzZK)-Y50, 8His-S5(oAzZK)-Li30/I129(oAzZK)-Li30, S5(oAzZK)-Y50/I129(oAzZK)-Y50, 8His-K8(oAzZK)-Li30/I129(oAzZK)-Li30, and K8(oAzZK)-Y50/I129(oAzZK)-Y50 as the PEGylated IL-2 variant had an IL-2-dependent cell proliferation rate of lower than 20% at an IL-2 concentration of 65 nmol/L. In addition, in the X-vivo 10 SFM, IL-2 (P) exhibited an IL-2-dependent cell proliferation rate of 80% or higher at an IL-2 concentration of 65 pmol/L, whereas I129(oAzZK)-V40, 8His-S5(oAzZK)-Li30/F78(oAzZK)-Li30, and 8His-F78(oAzZK)-Li30/S99(oAzZK)-Li30 as the PEGylated IL-2 variant exhibited an IL-2-dependent cell proliferation rate of 80% or higher at an IL-2 concentration of 65 nmol/L, 8His-S4(oAzZK)-Li30/F78(oAzZK)-Li30, 8His-K8(oAzZK)-Li30/F78(oAzZK)-Li30, 8His-F78(oAzZK)-Li30/H79(oAzZK)-Li30, 8His-F78(oAzZK)-Li304129(oAzZK)-Li30, and 8His-H79(oAzZK)-Li30/I129(oAzZK)-Li30 as the PEGylated IL-2 variant had an IL-2-dependent cell proliferation rate of 20% or higher and lower than 80% even at an IL-2 concentration of 65 nmol/L. 8His-S99(oAzZK)-Li30/I129(oAzZK)-Li30 had an IL-2-dependent cell proliferation rate of 30% at a maximum addition concentration of 6500 pmol/L.

From results above, it was confirmed that all evaluated IL-2 variants had reduced cell proliferation activity on NK cells. In particular, it was confirmed that H16C-2, E15C-11, L19C-9, L19C-11*, N88C-2, L12C-11/V91C-11, V91C-11/V115C-11, V91C-11/N119C-11, and A1C-11/T3C-11/S5C-11/L12C-11N91C-11 as the glycosylated IL-2 variant, A1C-Y50(IAc)/L12C-11N91C-11, T3C-Li20(IAc)/L12C-11/V91C-11, T3C-Y50(IAc)/L12C-11/V91C-11, T3C-Y50(IAc)/E15C-11, T3C-V40(IAc)/E15C-11, T3C-V80(Mal)/E15C-11, and L12C-11/F78C-V40(IAc) as the Cys-PEGylated and glycosylated IL-2 variant, and 8His-F78(oAzZK)-V40, 8His-F78(oAzZK)-W40, 8His-I129(oAzZK)-Li20, 8His-I129(oAzZK)-Li40, 8His-I129(oAzZK)-V40, 8His-I129(oAzZK)-W40, 8His-I129(oAzZK)-Y50, I129(oAzZK)-V40, I129(oAzZK)-W80, I129C-V40(Mal), 8His-S4(oAzZK)-Li30/F78(oAzZK)-Li30, 8His-S5(oAzZK)-Li30/F78(oAzZK)-Li30, 8His-K8(oAzZK)-Li30/F78(oAzZK)-Li30, 8His-F78(oAzZK)-Li30/H79(oAzZK)-Li30, 8His-F78(oAzZK)-Li30/S99(oAzZK)-Li30, 8His-F78(oAzZK)-Li30/I129(oAzZK)-Li30, 8His-S4(oAzZK)-Li30/I129(oAzZK)-Li30, S4(oAzZK)-Y50/I129(oAzZK)-Y50, 8His-S5(oAzZK)-Li30/I129(oAzZK)-Li30, S5(oAzZK)-Y50/I129(oAzZK)-Y50, 8His-K8(oAzZK)-Li30/I129(oAzZK)-Li30, K8(oAzZK)-Y50/I129(oAzZK)-Y50, 8His-H79(oAzZK)-Li30/I129(oAzZK)-Li30, and 8His-S99(oAzZK)-Li30/I129(oAzZK)-Li30 as the PEGylated IL-2 variant had a greatly reduced cell proliferation activity than those of the IL-2 (P) and 8His-IL-2 as controls.

Tregs express IL-2$R_{\alpha\beta\gamma}$, and NK cells express IL-2$R_{\beta\gamma}$. From results of Examples 13 and 14, it was found that all evaluated IL-2 variants selectively proliferated Tregs expressing IL-2$R_{\alpha\beta\gamma}$ but not NK cells expressing IL-2$R_{\beta\gamma}$.

Example 15

Inhibitory Activity of IL-2-Stimulated Tregs on Tresp Proliferation

The inhibitory activity of Tregs proliferated by being stimulated by various IL-2 on human Tresp proliferation was measured by a method described below. All cells were separated from each other by the same lot of frozen human PBMC. For the various IL-2, the glycosylated IL-2 variants H16C-2, L19C-9, and N88C-2 were used, and IL-2 (P) as control were used.

Seven days before the assay, Tregs were separated from the frozen human PBMCs as described in Example 13. The obtained Tregs were cultured for 7 days in the presence of CD3/CD28 Dynabeads (Tregs:beads=1:1) and various IL-2 (final concentration: 65 nM). The obtained cells were used as IL-2-stimulated Tregs.

The cell preparation on the day of test was performed as follows. Tregs were separated from the frozen human PBMC by the method described in Example 13 and used as unstimulated Tregs. After $CD3^+CD25^-$ T cells were separated from the frozen human PBMC, by using EasySep Human T Cell Enrichment Kit (manufactured by STEM-CELL Technologies) and EasySep Human Pan-CD25 Positive Selection and Depletion Kit (manufactured by STEM-CELL Technologies), the cells were labeled by reacting Celltrace violet (manufactured by Thermo Fischer SCIENTIFIC) diluted to 40 μmol/L with a 10% FBS-containing RPMI1640 medium, at room temperature for 5 minutes.

The obtained cells were used as responder T cells (Tresp). HLA-DR+ cells were separated from frozen human PBMCs using Anti-HLA-DR MicroBeads, human (manufactured by Miltenyi Biotec). The obtained cells were used as Antigen presenting cell (APC).

After the obtained cells were suspended in X-vivo 15 SFM to which an anti-CD3 antibody OKT3 (manufactured by Biolegend) was added to obtain a final concentration of 0.5 μg/mL, a 96-well V-bottom plate (manufactured by Sumitomo Bakelite) was seeded with Tresp at $2 \times 10^4$ cells/well (50 μL), APC at $1 \times 10^5$ cells/well (50 μL), and Tregs at $1.6 \times 10^2$ to $5 \times 10^3$ cells/well (50 μL) (Tresp:Treg=4:1 to 128:1), and the cells were cultured at 37° C. under 5% $CO_2$ for 4 days.

Thereafter, the cells were stained with anti-human CD4-APC (manufactured by BD Pharmingen) and anti-human CD8-PE (manufactured by BD Pharmingen) (at room temperature for 15 minutes), and then various fluorescent intensities were measured by flow cytometer FACS Canto II (manufactured by BD Biosciences).

The obtained data was exported as FCS file, and then analyzed using data analysis software FLowJo (TreeStar, version 7.6.5) for a division index value, which is an average number of cell divisions in $CD4^+$ Tresp or $CD8^+$ Tresp.

APC and Tresp were added, and assuming that a division index value of the well without adding Treg was set as 100% control, and a division index value of the well with adding only Tresp was set as 0% control, a cell proliferation rate of Tresp when adding unstimulated Treg or IL-2 stimulated Treg was calculated. Results obtained are shown in FIGS. 3(A) and 3(B).

As shown in FIGS. 3(A) and 3(B), the cell proliferation of $CD4^+$ Tresp and $CD8^+$ Tresp was not inhibited, in a case of using the unstimulated Treg and also in a case of adding Tregs at a maximum amount of $5 \times 10^3$ cells/well (Tresp:Treg=4:1).

On the other hand, in cases of adding IL-2-stimulated Tregs which was stimulated by IL-2 (P), and the glycosylated IL-2 variants H16C-2, L19C-9, and N88C-2 and proliferated, the proliferation of Tresp was inhibited compared with a case of adding unstimulated Treg was added.

The proliferation of $CD4^+$ Tresp was inhibited by about 40% to 60% and the proliferation of $CD8^+$ Tresp was inhibited by up to about 30% to 40% by the IL-2 stimulated Tregs. The inhibition rate of Tresp proliferation was comparable between Treg stimulated with commercially available IL-2 and Treg stimulated with the glycosylated IL-2 variant.

From the results above, it was found that the produced glycosylated IL-2 variant enhanced the Treg inhibitory activity to the same extent as that of IL-2 (P).

Example 16

Ex Vivo Assay

Production amounts of various cytokines of human PBMC stimulated with various IL-2 were measured by a method below. As various IL-2, glycosylated IL-2 variants H16C-2, L19C-9, and N88C-2, and IL-2 (P) were used as positive control.

After dispensing human peripheral blood into a 15 mL centrifuge tube, the human peripheral blood was centrifuged at 2000 rpm for 10 minutes, and a supernatant thereof was collected to obtain human plasma. The obtained plasma was sterilized by filtration using a 0.22 μm filter. The same amount of PBS as the collected plasma was added to the peripheral blood and diluted, and then human PBMC was obtained by a density gradient centrifugation method using Ficoll Paque plus (manufactured by GE Healthcare).

The obtained human PBMC was suspended in autologous plasma at $5 \times 10^6$ cells/mL, and an anti-CD3 antibody OKT3 was added thereto to obtain a final concentration of 0.5 μg/mL. After seeding a 96-well U-bottom plate therewith at 180 μl/well, various IL-2 diluted to 10-fold the final concentration with 0.1% BSA-PBS were added at 20 μl/well. After culturing at 37° C. under 5% $CO_2$ for 5 days, the culture supernatant was collected, and a production amount of cytokine in the supernatant was quantified using Human Th1/2/17 CBA kit (manufactured by BD Biosciences).

In addition, using the obtained human PBMC, the Treg-selective proliferation activity of various IL-2 was measured by method described below. After reacting the human PBMC with Anti-human CD4-Alexa 488, cells were fixed and permeabilized with PerFix EXPOSE Buffer 1 and PerFix EXPOSE Buffer 2 of PerFix-EXPOSE Phospho Epitope Exposure Kit (manufactured by Beckman Coulter). Then, PerFix EXPOSE Buffer 3 containing anti-human CD25-PE (manufactured by BD Biosciences) and anti-human Foxp3 Alexa 647 (manufactured by Bioregend, Cat #320214) was added thereto and the cells were stained (shade, room temperature, 60 minutes).

Furthermore, after adding a PerFix EXPOSE Buffer 4 and washing the cells twice (centrifugation at 2500 rpm for 3 minutes), various fluorescence intensities were measured with a flow cytometer LSRFortessa (manufactured by BD Biosciences).

The obtained data was exported as FCS file, and then analyzed using data analysis software FLowJo (manufactured by TreeStar, version 7.6.5). Among the CD4 positive fractions, the $CD25^+$ $Foxp3^{high}$ fraction was defined as Treg, and the $CD25^+$ $Foxp3^{low}$ fraction was defined as effector T cells (Teff). An abundance ratio thereof [Treg (%)/Teff (%)] was calculated, and determined as an index of Treg-selective proliferation activity.

Results of the measured production amount of cytokine are shown in FIGS. 4(A) to 4(E). As shown in FIGS. 4(A) to 4(E), IL-2 (P) promoted the production of all cytokines of IL-4, IL-6, IL-10, IFNγ, and TNFα, among the measured cytokines.

On the other hand, in the glycosylated IL-2 variant, the production amounts of IL-6 and IL-10 were comparable as those of commercially available IL-2, but the production amounts of IL-4, IFNγ, and TNFα were decreased. The production of IL-17A was equal to or less than a detection limit under any culture conditions.

IL-10 is an anti-inflammatory cytokine, and IL-6, IL-4, IFNγ, and TNFα are inflammatory cytokines.

From the results above, it was confirmed that the produced glycosylated IL-2 variant had a significantly lower production activity of proinflammatory cytokines than that of IL-2 (P).

In addition, FIG. 4F shows the obtained Treg/Teff ratio. As shown in FIG. 4 (F), a Treg/Teff ratio in a case of stimulation with IL-2 (P) was about 0.2 to 0.3. On the other hand, the Treg/Teff ratio in a case of stimulation with the glycosylated IL-2 variants H16C-2, L19C-9, and N88C-2 was about 0.3 to 0.5.

From the results above, it was found that, under the culture conditions in which various immune cells close to an in vivo environment exist, the produced glycosylated IL-2 variants selectively proliferated Treg rather than Teff, as compared to IL-2 (P). Although both the Treg and the Teff express IL-2R$_{\alpha\beta\gamma}$, the IL-2 variant has a property of selectively proliferating the Treg rather than the Teff, and is a desirable IL-2 variant for relieving inflammation.

Example 17

Affinity Analysis

Affinities of various IL-2 for human CD25ECD-Fc and human IL-2R$_{\beta\gamma}$ECD-Fc were measured by a method below. For the various IL-2, the glycosylated IL-2 variants L12C-2, L12C-9, L12C-11, H16C-2, L19C-9, L12C-11, N88C-2, and V91C-11 were used, and wild-type IL-2, 8His-IL-2, and IL-2 (P) were used as control.

human CD25ECD-Fc and human IL-2R$_{\gamma\gamma}$ECD-Fc

Human CD25ECD-Fc-Avitag expression vector for mammalian cells was produced by inserting a nucleotide sequence (SEQ ID NO: 24) designed based on an amino acid sequence (SEQ ID NO: 23) of CD25ECD-Fc-Avitag consisting of an extracellular region of human CD25 and human IgG1-derived Fc comprising an Avitag sequence (GLNDIFEAQKIEWHE) at a C-terminal into a BglII restriction enzyme site and BamHI restriction enzyme site of INPEP4 vector.

In addition, human IL-2R$_{\beta\gamma}$ ECD-Fc expression vector for mammalian cells was produced by inserting a nucleotide sequence (SEQ ID NO: 26) designed based on an amino acid sequence (SEQ ID NO: 25) of human CD122 ECD-Fc-Avitag-8Hishuman CD132 ECD-Fc-FLAG in which CD122 ECD-Fc(knob)-Avitag-8His consisting of an extracellular region of human CD122 and human IgG1-derived Fc region comprising Y354C/T366W mutation and an Avitag sequence and a polyhistidine tag sequence (HHHHHHHH) at a C terminal and CD132 ECD-Fc (hole)-FLAG consisting of an extracellular region of human CD132, and human IgG1-derived Fc region comprising Y349C/T366S/L368A/Y407V mutation and FLAG tag sequence at a C-terminal were joined via a furin cleavage sequence and foot-and-mouth-disease virus-derived 2A peptide sequence to a BglII restriction enzyme site and a BamHI restriction enzyme site of INPEP4 vector.

Using the obtained plasmid and Expi293 Expression System (manufactured by Thermo Fisher SCIENTIFIC), various Fc fusion proteins were expressed in the culture supernatant. CD25ECD-Fc was roughly purified using Mabselect sure (manufactured by GE Healthcare), and then a monomer fraction was collected by size exclusion chromatography using Superdex 200 10/300 GL (manufactured by GE Healthcare) (mobile phase: D-PBS).

On the other hand, IL-2R$_{\beta\gamma}$ ECD-Fc was roughly purified using Mabselect sure, then a monomer fraction was collected by size exclusion chromatography (mobile phase: D-PBS) using Superdex 200 10/300 GL and further purification was performed using ANTI-FLAG M2 Affinity Agarose Gel.

A Series S Sensor chip CM5 (manufactured by GE Healthcare) was set on a Biacore T-100 (manufactured by GE Healthcare), and anti-human Fc was immobilized on a flow cell for affinity measurement and a flow cell for reference, using the Human Anti body Capture Kit (GE healthcare).

Next, after replacing a flow path with HBS-EP (+) buffer (manufactured by GE Healthcare), CD25ECD-Fc or IL-2R$_{\beta\gamma}$ECD-Fc diluted with HBS-EP (+) was added as ligand only to the flow cell for the affinity measurement (immobilized amount: 200 to 900 RU).

Thereafter, IL-2 (P) diluted to an optimum concentration with an HBS-EP (+) buffer was added to the affinity measurement flow cell and the reference flow cell as an analyte to obtain a sensorgram. 3 mol/L MgCl$_2$ was used for the regeneration reaction of the flow cell.

Biacore T-100 Evaluation software was used to calculate kinetic constants from the obtained sensorgrams. For the analysis of the binding to CD25ECD-Fc, the dissociation constant $K_D$ was determined using a steady state model. In the analysis of binding to IL-2R$_{\beta\gamma}$ ECD-Fc, a binding rate constant $k_a$, a dissociation rate constant $k_d$ and $K_D$ were determined using 1:1 binding model. Table 23 shows the obtained $K_D$.

TABLE 23

| | $K_D$ (M) | |
|---|---|---|
| Variant name | hCD25ECD-Fc | hIL-2R$_{\beta\gamma}$ECD-Fc |
| IL-2 (P) | 1.30 × 10$^{-8}$ | 2.09 × 10$^{-10}$ |
| 8His-IL-2 | 1.50 × 10$^{-8}$ | 2.09 × 10$^{-10}$ |
| Wild-type IL-2 | 3.32 × 10$^{-8}$ | 2.15 × 10$^{-10}$ |
| L12C-2 | 1.33 × 10$^{-8}$ | 3.67 × 10$^{-10}$ |
| L12C-9 | 1.46 × 10$^{-8}$ | 8.31 × 10$^{-10}$ |
| L12C-11 | 1.51 × 10$^{-8}$ | 7.40 × 10$^{-10}$ |
| H16C-2 | 1.25 × 10$^{-8}$ | 1.11 × 10$^{-8}$ |
| L19C-9 | 2.09 × 10$^{-8}$ | 2.10 × 10$^{-9}$ |
| L19C-11 | 1.98 × 10$^{-8}$ | 3.34 × 10$^{-9}$ |
| N88C-2 | 1.12 × 10$^{-8}$ | 4.39 × 10$^{-8}$ |
| V91C-11 | 1.35 × 10$^{-8}$ | 5.84 × 10$^{-10}$ |

As shown in Table 23, the $K_D$ value for CD25 was almost the same between the glycosylated IL-2 variant and IL-2 (P). On the other hand, the $K_D$ value for IL-2R$_{\beta\gamma}$ was higher in the glycosylated IL-2 variant than in IL-2 (P).

Combined with the results in Tables 18 to 20, it was confirmed that the higher the $K_D$ value for IL-2R$_{\beta\gamma}$, the higher the IL-2R$_{\alpha\beta\gamma}$ selectivity.

From the results above, it was considered that the glycosylated IL-2 variant maintained the affinity for CD25, while the affinity for IL-2R$_{\beta\gamma}$ was reduced, thereby improving the IL-2R$_{\alpha\beta\gamma}$ selectivity.

Example 18

Influence of Saccharide/PEG Structure

In order to evaluate an effect of amino acid modification to IL-2 or binding the saccharide or PEG on IL-2R$_{\alpha\beta\gamma}$ selectivity, the standardized EC$_{50}$ ratio values were measured for L19C, L19C-acetamide, and L19N produced in Example 1 and various o-Az-Z-Lys-introduced 8His-IL-2 produced Example 5, in the same manner as the method described in Example 12. Table 24 shows results obtained.

TABLE 24

| Standardized EC50 ratio value | Variant |
|---|---|
| <5 | 8His-S4 (oAzZK), 8His-S5 (oAzZK), 8His-S6 (oAzZK), 8His-T7 (oAzZK), 8His-K8 (oAzZK), 8His-E60 (oAzZK), 8His-F78 (oAzZK), 8His-H79 (oAzZK), 8His-R81 (oAzZK), 8His-L94 (oAzZK), 8His-S99 (oAzZK), 8His-E100 (oAzZK), 8His-T101 (oAzZK), 8His-I129 (oAzZK) |
| 5 to 30 | L19C, L19C-acetamide L19N, 8His-Q126 (oAzZK) |
| >30 | — |

As shown in Table 24, the standardized EC$_{50}$ ratio values of L19C, L19C-acetamide, and L19N were 5 to 30. As shown in Table 18, since the standardized EC$_{50}$ ratio values of L19C-2, L19C-9, L19C-11 and L19C-11* were 30 or more, it was found that L19C-2, L19C-9, L19C-11, and L19C-11* have improved selectivity for IL-2R$_{\alpha\beta\gamma}$ due to glycosylation.
In addition, as shown in Table 24, the standardized EC$_{50}$ ratio values of the o-Az-Z-Lys-introduced 8His-IL-2 variants other than 8His-Q126(oAzZK) were 5 or less. As shown in Tables 21 and 22, since the standardized EC$_{50}$ ratio values of 8His-S4(oAzZK)-Li20, 8His-S4(oAzZK)-Li30, 8His-S5 (oAzZK)-Li20, 8His-S5(oAzZK)-Li30, S6(oAzZK)-Li20, 8His-S6(oAzZK)-Li30, 8His-T7(oAzZK)-Li30, 8His-K8 (oAzZK)-Li20, 8His-K8(oAzZK)-Li30, 8His-E60(oAzZK)-Li30, 8His-F78(oAzZK)-Li20, 8His-F78(oAzZK)-Li30, 8His-F78(oAzZK)-Li40, 8His-F78(oAzZK)-V40, 8His-F78 (oAzZK)-W40, 8His-F78(oAzZK)-Y50, 8His-H79 (oAzZK)-Li20, 8His-H79(oAzZK)-Li30, 8His-S99 (oAzZK)-Li30, 8His-E100(oAzZK)-Li20, 8His-T101 (oAzZK)-Li20, 8His-T101(oAzZK)-Li30, 8His-I129 (oAzZK)-PEG4, 8His-I129(oAzZK)-Li20, 8His-I129 (oAzZK)-Li30, 8His-I129(oAzZK)-Li40, 8His-I129 (oAzZK)-V40, 8His-I129(oAzZK)-W40, and 8His-I129 (oAzZK)-Y50 were 5 or more, it was found that these PEGylated IL-2 variants have improved selectivity for IL-2R$_{\alpha\beta\gamma}$ due to PEG binding.
While the present invention has been described in detail and with reference to specific embodiments thereof, it will be apparent to one skill in the art that various changes and modifications can be made therein without departing from the spirit and scope thereof. This application is based on Japanese Patent Application (Japanese Patent Application No. 2017-252224) filed on Dec. 27, 2017, the entire contents of which are incorporated hereinto by reference.

SEQUENCE LISTING FREE TEXT

SEQ ID NO: 1: Amino acid sequence of wild-type mature human IL-2
SEQ ID NO: 2: Amino acid sequence of 8His-IL-2
SEQ ID NO: 3: nucleotide sequence of 8His-IL-2
SEQ ID NO: 4: nucleotide sequence of 8His-S4(oAzZK)
SEQ ID NO: 5: nucleotide sequence of 8His-S5(oAzZK)
SEQ ID NO: 6: nucleotide sequence of 8His-S6(oAzZK)
SEQ ID NO: 7: nucleotide sequence of 8His-T7(oAzZK)
SEQ ID NO: 8: nucleotide sequence of 8His-K8(oAzZK)
SEQ ID NO: 9: nucleotide sequence of 8His-E60(oAzZK)
SEQ ID NO: 10: nucleotide sequence of 8His-F78 (oAzZK)
SEQ ID NO: 11: nucleotide sequence of 8His-H79 (oAzZK)
SEQ ID NO: 12: nucleotide sequence of 8His-R81 (oAzZK)
SEQ ID NO: 13: nucleotide sequence of 8His-L94 (oAzZK)
SEQ ID NO: 14: nucleotide sequence of 8His-S99 (oAzZK)
SEQ ID NO: 15: nucleotide sequence of 8His-E100 (oAzZK)
SEQ ID NO: 16: nucleotide sequence of 8His-T101 (oAzZK)
SEQ ID NO: 17: nucleotide sequence of 8His-Q126 (oAzZK)
SEQ ID NO: 18: nucleotide sequences of 8His-I129 (oAzZK) and 8His-I129(mAzZK)
SEQ ID NO: 19: Amino acid sequence of human IL-2R$_{\beta\gamma}$-Azami green fusion
SEQ ID NO: 20: nucleotide sequence of human IL-2R$_{\alpha\beta\gamma}$-Azami green fusion
SEQ ID NO: 21: Amino acid sequence of human IL-2R$_{\beta\gamma}$-Azami green fusion
SEQ ID NO: 22: nucleotide sequence of human IL-2R$_{\beta\gamma}$-Azami green fusion
SEQ ID NO: 23: Amino acid sequence of human CD25 ECD-Fc-Avitag
SEQ ID NO: 24: nucleotide sequence of human CD25 ECD-Fc-Avitag
SEQ ID NO: 25: Amino acid sequence of human CD122 ECD-Fc-Avitag-8Hishuman CD132 ECD-Fc-FLAG
SEQ ID NO: 26: nucleotide sequence of human CD122 ECD-Fc-Avitag-8Hishuman CD132 ECD-Fc-FLAG
SEQ ID NO: 27: nucleotide sequence of 8His-S4 (oAzZK)/F78(oAzZK)
SEQ ID NO: 28: nucleotide sequence of 8His-S5 (oAzZK)/F78(oAzZK)
SEQ ID NO: 29: nucleotide sequence of 8His-K8 (oAzZK)/F78(oAzZK)
SEQ ID NO: 30: nucleotide sequence of 8His-F78 (oAzZK)/H79(oAzZK)
SEQ ID NO: 31: nucleotide sequence of 8His-F78 (oAzZK)/S99(oAzZK)
SEQ ID NO: 32: nucleotide sequence of 8His-F78 (oAzZK)/I129(oAzZK)
SEQ ID NO: 33: nucleotide sequence of 8His-S4 (oAzZK)/I129(oAzZK)

SEQ ID NO: 34: nucleotide sequence of 8His-S5 (oAzZK)/I129(oAzZK)
SEQ ID NO: 35: nucleotide sequence of 8His-K8 (oAzZK)/I129(oAzZK)
SEQ ID NO: 36: nucleotide sequence of 8His-H79 (oAzZK)/I129(oAzZK)
SEQ ID NO: 37: nucleotide sequence of 8His-S99 (oAzZK)/I129(oAzZK)
SEQ ID NO: 38: Amino acid sequence of N-terminal methionine-added IL-2 C125S
SEQ ID NO: 39: nucleotide sequence of N-terminal methionine-added IL-2 C125S
SEQ ID NO: 40: Amino acid sequence of desAla_IL-2 C125S
SEQ ID NO: 41: nucleotide sequence of desAla_IL-2 C125S
SEQ ID NO: 42: nucleotide sequence of F78(oAzZK)
SEQ ID NO: 43: nucleotide sequence of I129(oAzZK)
SEQ ID NO: 44: nucleotide sequence of desAla_I129 (oAzZK)
SEQ ID NO: 45: nucleotide sequence of S4(oAzZK)/F78 (oAzZK)
SEQ ID NO: 46: nucleotide sequence of S5(oAzZK)/F78 (oAzZK)
SEQ ID NO: 47: nucleotide sequence of K8(oAzZK)/F78 (oAzZK)
SEQ ID NO: 48: nucleotide sequence of S4(oAzZK)/I129 (oAzZK)
SEQ ID NO: 49: nucleotide sequence of S5(oAzZK)/I129 (oAzZK)
SEQ ID NO: 50: nucleotide sequence of K8(oAzZK)/ I129(oAzZK)
SEQ ID NO: 51: Amino acid sequence of I129C
SEQ ID NO: 52: nucleotide sequence of I129C

The invention claimed is:

1. An Interleukin-2 (IL-2) variant having improved selectivity for an IL-2 receptor (IL-2R)$_{\alpha\beta\gamma}$, wherein the IL-2 variant is a polyethylene glycol (PEG)-bound IL-2 variant comprising an amino acid sequence in which amino acid residues at one or more of positions 4, 5, 6, 7, 8, 60, 78, 79, 99, 100, 101, and 129 in the amino acid sequence represented by SEQ ID NO: 1 are substituted with a PEGylated non-natural amino acid residue derived from an $N^6$-[{(o-azidobenzyl) oxy}carbonyl]-L-lysine (o-Az-Z-Lys) residue or derived from an $N^6$-[{(m-azidobenzyl)oxy}carbonyl]-L-lysine (m-Az-Z-Lys) residue.

2. The IL-2 variant according to claim 1, wherein the amino acid sequence is further substituted at position 125 in the amino acid sequence represented by SEQ ID NO: 1 with a serine residue.

3. The IL-2 variant according to claim 1, wherein the PEGylated residue derived from an o-Az-Z-Lys residue comprises a structure represented by (Formula 11) and/or (Formula 12)

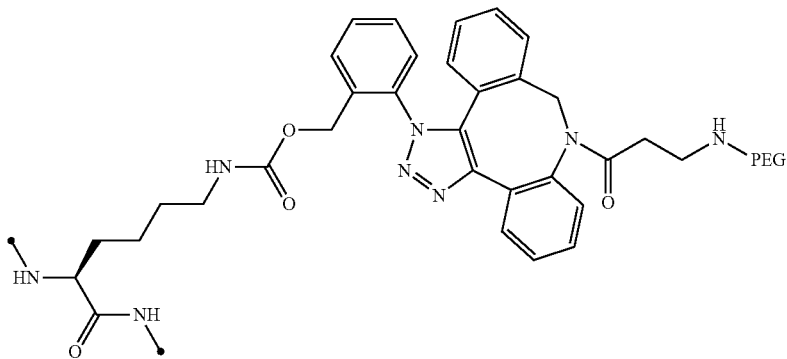

(Formula 11)

-continued
(Formula 12)
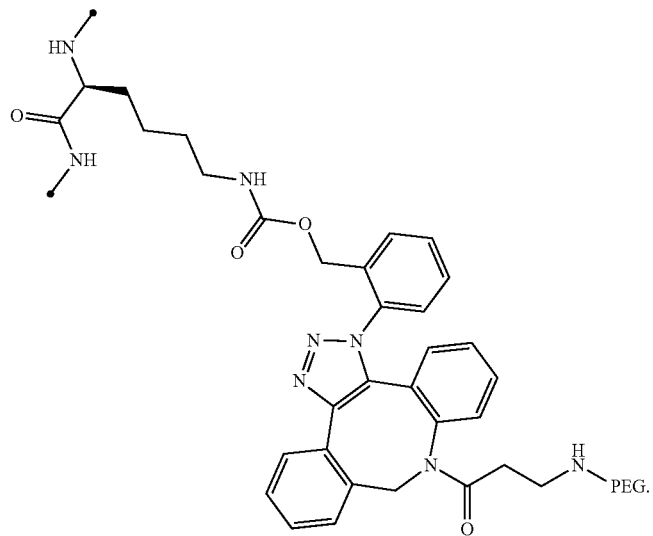
wherein "-" represents a bond between the PEGylated residue and an adjacent amino acid residue in the IL-2 variant.
4. The IL-2 variant according to claim 1, wherein the PEGylated residue derived from an m-Az-Z-Lys residue comprises a structure represented by (Formula Y4) and/or (Formula Y5)
(Formula Y4)
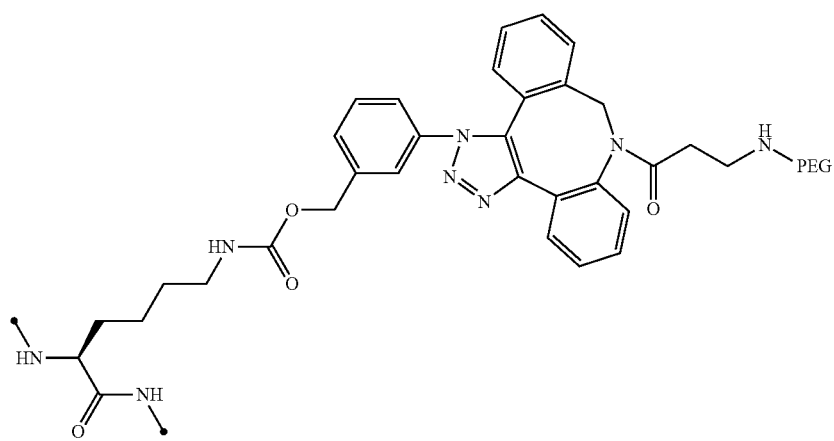

(Formula Y5)

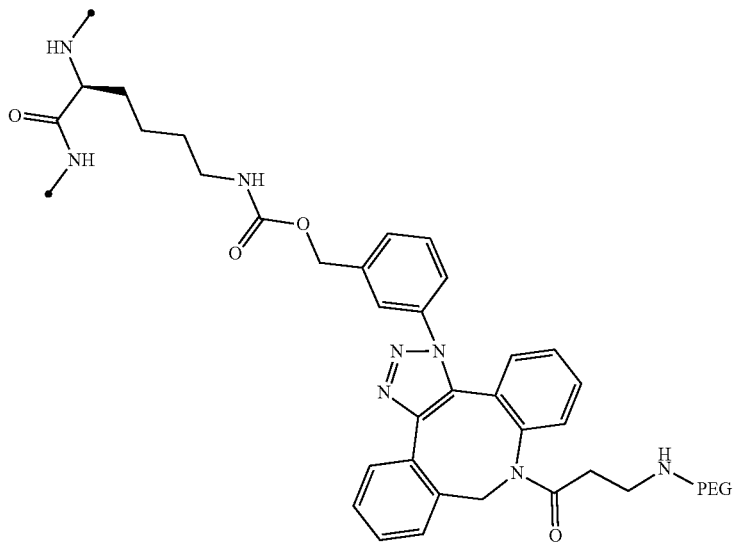

wherein "-" represents a bond between the PEGylated residue and an adjacent amino acid residue in the IL-2 variant.

5. The IL-2 variant according to claim 1, wherein the PEG is linear.

6. The IL-2 variant according to claim 1, wherein the PEG is branched.

7. The IL-2 variant according to claim 1, wherein the PEG has an average molecular weight of 10 kDa or more.

8. The IL-2 variant according to claim 1, wherein the PEG has an average molecular weight of 10 kDa, 20 kDa, 30 kDa, 40 kDa, 50 kDa, 60 kDa, 70 kDa, or 80 kDa.

9. The IL-2 variant according to claim 4, wherein the PEG comprises a structure represented by at least one formula of (Formula 13), (Formula 14), (Formula 15), (Formula 16), (Formula X7), (Formula X8), (Formula X9), (Formula X10), (Formula X11), (Formula X13), (Formula X14), or (Formula X15)

(Formula 13)

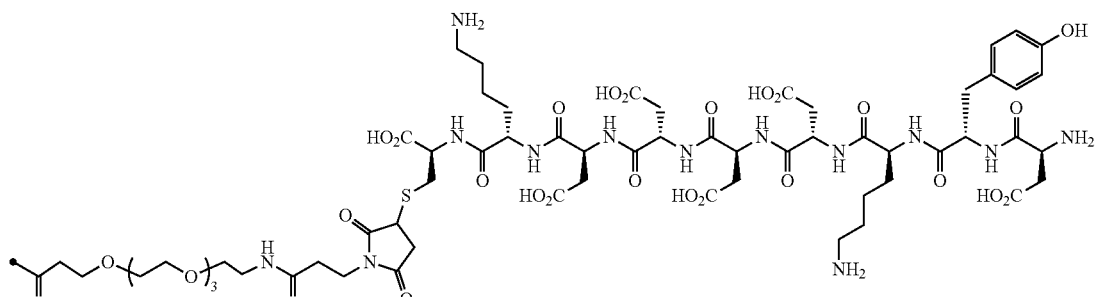

(Formula 14)

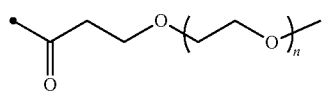

(Formula X7)

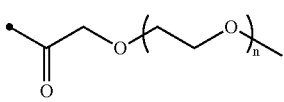

(Formula 15)

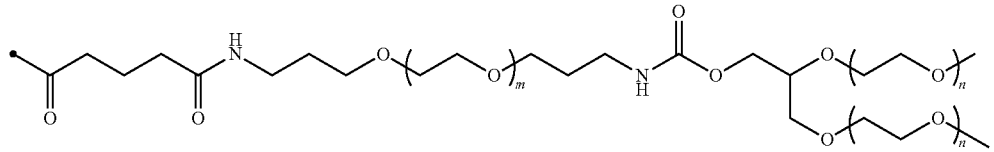

(Formula 16)

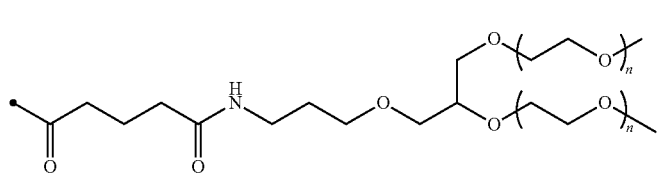

(Formula X8)
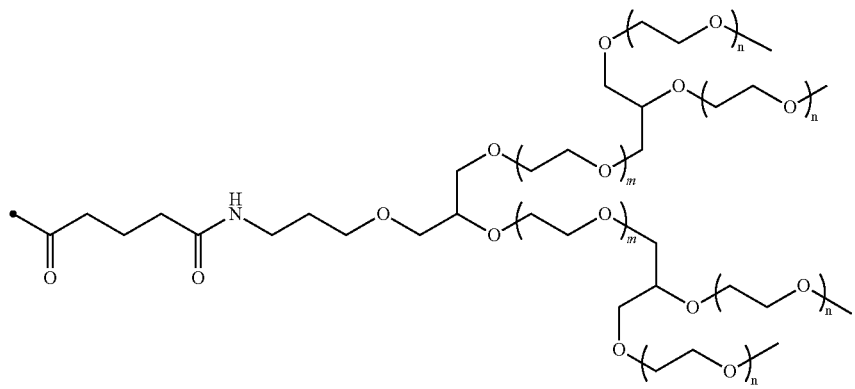
(Formula X9)
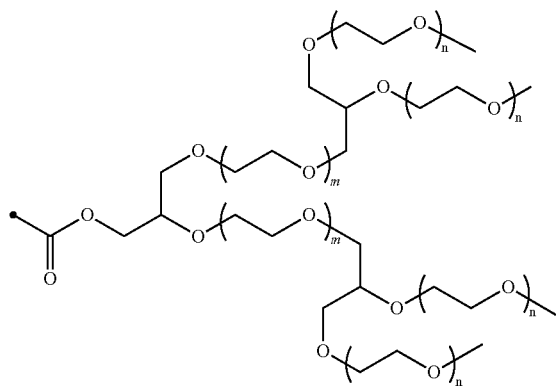
(Formula X10)
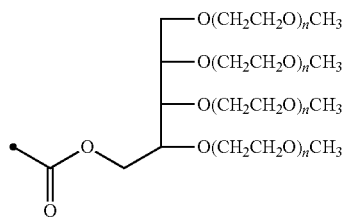
(Formula X13)
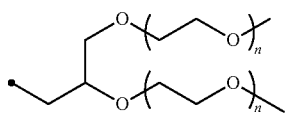
(Formula X14)
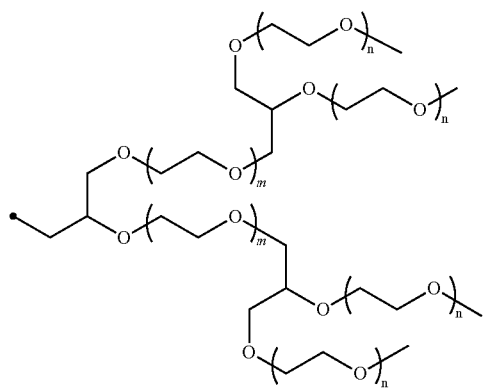
(Formula X11)
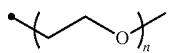

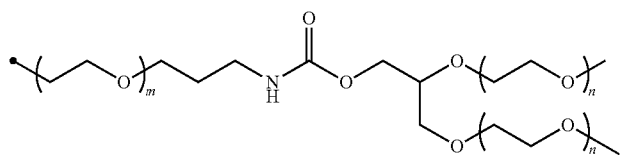

(Formula X15)

wherein "-" represents a bond between PEG and the nitrogen atom in N-PEG of (Formula Y4) or (Formula Y5), and wherein m and n are independently 2 or more.

10. The IL-2 variant according to claim 1, wherein a methionine residue is bound to an N-terminal of IL-2.

11. The IL-2 variant according to claim 1, wherein N-terminal alanine of IL-2 is deleted.

12. A pharmaceutical composition comprising the IL-2 variant according to claim 1 and a pharmacologically acceptable carrier.

13. The IL-2 variant according to claim 1, comprising an amino acid sequence in which the amino acid residue at position 129 in the amino acid sequence represented by SEQ ID NO: 1 is substituted with a PEGylated non-natural amino acid residue, and wherein the amino acid sequence is optionally further substituted at position 125 in the amino acid sequence represented by SEQ ID NO: 1 with a serine residue, wherein the PEGylated non-natural amino acid residue comprises a structure represented by Formula 11 or Formula 12:

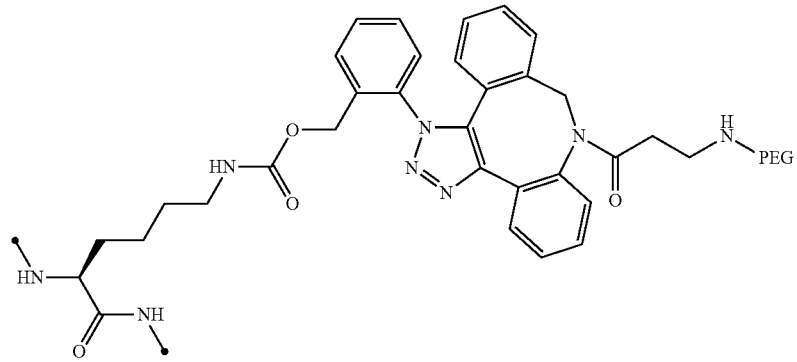

(Formula 11)

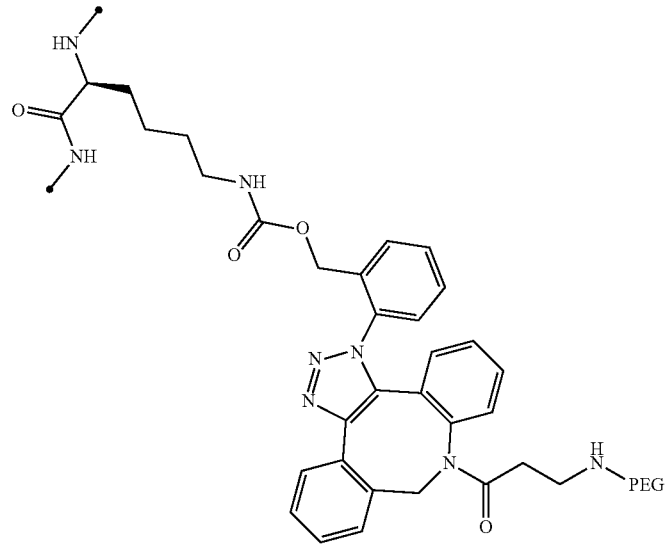

(Formula 12)

wherein "-" represents a bond between the PEGylated non-natural amino acid residue and an adjacent amino acid residue in the IL-2 variant, wherein PEG has an average molecular weight of 80 kDa, wherein PEG comprises a structure represented by Formula 16 or Formula X9:

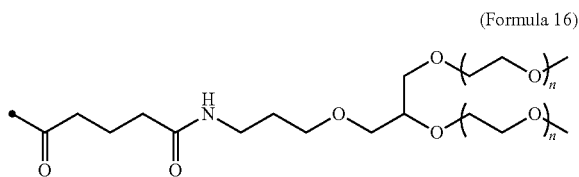
(Formula 16)

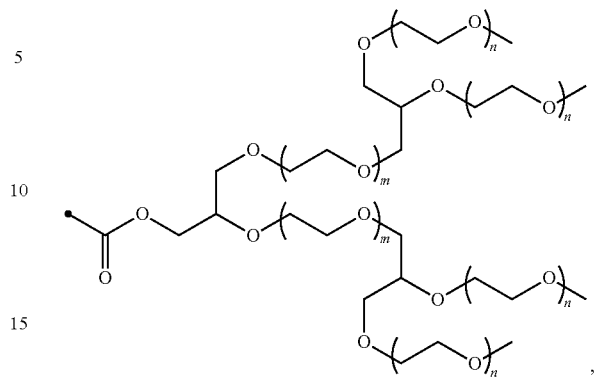
(Formula X9)

wherein "-" represents a bond between PEG and the nitrogen atom in N-PEG of (Formula 11) or (Formula 12), wherein m and n are independently 2 or more, and wherein N-terminal alanine of IL-2 is deleted.

* * * * *